US010751385B2

(12) United States Patent
Petit et al.

(10) Patent No.: US 10,751,385 B2
(45) Date of Patent: Aug. 25, 2020

(54) PREVENTION AND/OR TREATMENT OF HEARING LOSS OR IMPAIRMENT

(71) Applicants: INSTITUT PASTEUR, Paris (FR); Centre National de la Recherche Scientifique (CNRS), Paris (FR); Sorbonne Université, Paris (FR); Université Clermont Auvergne, Clemont-Ferrand (FR)

(72) Inventors: Christine Petit, Paris (FR); Paul Avan, Clermont-Ferrand (FR); Sedigheh Delmaghani, Paris (FR); Jean Defourny, Paris (FR); Asadollah Aghaie, Paris (FR); Saaid Safieddine, Paris (FR); Alice Emptoz, Paris (FR)

(73) Assignees: Institut Pasteur, Paris (FR); Centre National de la Recherche Scientifique (CNRS), Paris (FR); Sorbonne Université, Paris (FR); Université Clermont Auvergne, Clermont-Ferrand (FR)

( * ) Notice: Subject to any disclaimer, the term of this patent is extended or adjusted under 35 U.S.C. 154(b) by 0 days.

(21) Appl. No.: 15/551,096

(22) PCT Filed: Feb. 19, 2016

(86) PCT No.: PCT/EP2016/053613
§ 371 (c)(1),
(2) Date: Aug. 15, 2017

(87) PCT Pub. No.: WO2016/131981
PCT Pub. Date: Aug. 25, 2016

(65) Prior Publication Data
US 2018/0055908 A1 Mar. 1, 2018

(30) Foreign Application Priority Data

Feb. 20, 2015 (EP) .................................... 15305270
Oct. 16, 2015 (EP) .................................... 15306664

(51) Int. Cl.
| A61K 38/17 | (2006.01) |
| A61K 8/64 | (2006.01) |
| A61K 9/00 | (2006.01) |
| A61Q 19/02 | (2006.01) |
| A61Q 19/08 | (2006.01) |
| A61K 48/00 | (2006.01) |
| A61K 35/761 | (2015.01) |
| C12N 15/86 | (2006.01) |
| C12N 7/00 | (2006.01) |
| C12N 15/113 | (2010.01) |

(52) U.S. Cl.
CPC ............ *A61K 38/1709* (2013.01); *A61K 8/64* (2013.01); *A61K 9/0019* (2013.01); *A61K 9/0046* (2013.01); *A61K 35/761* (2013.01); *A61K 38/17* (2013.01); *A61K 48/00* (2013.01); *A61K 48/005* (2013.01); *A61K 48/0075* (2013.01); *A61Q 19/02* (2013.01); *A61Q 19/08* (2013.01); *C12N 7/00* (2013.01); *C12N 15/113* (2013.01); *C12N 15/86* (2013.01); *A01K 2217/075* (2013.01); *A01K 2227/105* (2013.01); *A01K 2267/0306* (2013.01); *A61K 2800/91* (2013.01); *C12N 2310/14* (2013.01); *C12N 2310/531* (2013.01); *C12N 2710/10021* (2013.01); *C12N 2710/10043* (2013.01); *C12N 2750/14143* (2013.01)

(58) Field of Classification Search
None
See application file for complete search history.

(56) References Cited

FOREIGN PATENT DOCUMENTS

| CN | 1341652 A | * | 3/2002 | ............ C07K 14/47 |
| WO | 02/20606 A1 | | 3/2002 | |
| WO | 2011/028503 A1 | | 3/2011 | |
| WO | 2011/075838 A1 | | 6/2011 | |

OTHER PUBLICATIONS

Hergueta-Redondo et al., "Gasdermin-B Promotes Invasion and Metastasis in Breast Cancer Cells", PLOS One, 2014; pp. 1-15 (Year: 2014).*
Akil, O ., Seal, R.P., Burke, K., Wang, C., Alemi, A., During, M., Edwards, R.H., Lustig, L.R. (2012). Restoration of hearing in the VGLUT3 knockout mouse using virally mediated gene therapy. Neuron 75(2), 283-93.
Akino K, Toyota M, Suzuki H, Imai T, Maruyama R, Kusano M, Nishikawa N, Watanabe Y, SasakiY, Abe T, Yamamoto E, Tarasawa I, Sonoda T, Mori M, Imai K, Shinomura Y, Tokino T (2007). Identification of DFNA5as a target of epigenetic inactivation in gastric cancer. Cancer Sci. 98(1):88-95.
Angermuller, S., and Fahimi, H. D. (1981). Selective cytochemical localization of peroxidase, cytochrome oxidase and catalase in rat liver with 3,3'—diaminobenzidine. Histochemistry 71(1), 33-44.

(Continued)

*Primary Examiner* — Lianko G Garyu
(74) *Attorney, Agent, or Firm* — Arrigo, Lee, Guttman & Mouta-Bellum LLP

(57) ABSTRACT

The present invention relates to the use of gasdermin, in particular of gasdermin A, gasdermin B, gasdermin C, gasdermin D, DFNA5 or DFNB59 (or pejvakin), and more particularly pejvakin for modulating cellular redox homeostasis. A particularly preferred use of gasdermin, in particular of gasdermin A, gasdermin B, gasdermin C, gasdermin D, DFNA5 or DFNB59 (or pejvakin), and more particularly pejvakin in the context of the present invention is as an antioxidant. The present invention also concerns a virally-mediated gene therapy for restoring genetically-impaired auditory and vestibular functions in subjects suffering from an Usher syndrome. More precisely, this gene therapy takes advantage of an AAV2/8 vector expressing at least one USH1 gene product, preferably SANS.

7 Claims, 47 Drawing Sheets

Specification includes a Sequence Listing.

(56) References Cited

OTHER PUBLICATIONS

Basta, D., Tzschentke, B., and Ernst, A. (2005). Noise-induced cell death in the mouse medial geniculate body and primary auditory cortex. Neuroscience letters 381, 199-204.
Benjamini, Y., and Hochberg, Y. (1995). Controlling the false discovery rate: a practical and powerful approach to multiple testing. J. Roy. Statist. Soc. Ser. B. 57, 289-300.
Binder, C.J., Weiher, H., Exner, M., Kerjaschki, D. (1999). Glomerular overproduction of oxygen radicals in Mpv17 gene-inactivated mice causes podocyte foot process flattening and proteinuria: A model of steroid-resistant nephrosis sensitive to radical scavenger therapy. Am. J. Pathol. 154(4), 1067-75.
Bischoff AM, Luijendijk MW, Huygen PL, van Duijnhoven G, De Leenheer EM, Oudesluijs GG, Van Laer L, Cremers FP, Cremers CW, Kremer H (2004). A novel mutation identified in the DFNA5gene in a Dutch family: a clinical and genetic evaluation. Audiol Neurootol. 9(1):34-46.
Bolstad, B.M., Irizarry, R.A., Astrand, M., Speed, T.P. (2003). A comparison of normalization methods for high density oligonucleotide array data based on variance and bias. Bioinformatics 19(2), 185-93.
Bonekamp, N.A., Volkl, A., Fahimi, H.D., and Schrader, M. (2009). Reactive oxygen species and peroxisomes: struggling for balance. BioFactors 35, 346-355.
Borck, G., Rainshtein, L., Hellman-Aharony, S., Volk, A.E., Friedrich, K., Taub, E, Magal, N., Kanaan, M., Kubisch, C., Shohat, M., Basel-Vanagaite, L. (2012). High frequency of autosomal-recessive DFNB59 hearing loss in an isolated Arab population in Israel. Clin Genet . 82(3), 271-6.
Caberlotto, E., Michel, V., Foucher, I., Bahloul, A., Goodyear, R.J., Pepermans, E., Michalski, N., Perfettini, I., Alegria-Prevot, 0., Chardenoux, S., Do Cruzeiro, M., et al. (2011). Usher type 1G protein sansis a critical component of the tip—link complex, a structure controlling actin polymerization in stereocilia. Proc. Natl. Acad . Sci. USA 108(14), 5825-30.
Chai Y, Chen D, Wang X, Wu H, Yang T (2014). A novel splice site mutation in DFNA5 causes late-onset progressive non-syndromic hearing loss in a Chinese family. Int J Pediatr Otorhinolaryngol. 78(8): 1265-8.
Cheng J, Han DY, Dai P, Sun HJ, Tao R, Sun Q, Yan D, Qin W, Wang HY, Ouyang XM, Yang SZ, Cao JY, Feng GY, Du LL, Zhang YZ, Zhai SQ, Yang WY, Liu XZ, He L, Yuan HJ (2007). A novel DFNA5mutation, IVS8+4A>G, in the splice donor site of intron 8 causes late-onset non-syndromic hearing loss in a Chinese family. Clin Genet. 72(5):471-7.
Cody, A.R., and Johnstone, B.M. (1981). Acoustic trauma: Single neuron basis for the "half-octave shift". J. Acoust. Soc. Am. 70, 707-711.
Collin, R.W., Kalay, E., Oostrik, J., Caylan, R., Wollnik, B., Arslan, S., den Hollander, A.I., Birinci, Y., Lichtner, P., Strom, T.M. (2007). Involvement of DFNB59mutations in autosomal recessive nonsyndromic hearing impairment. Hum. Mutat. 28(7), 718-23.
Collins, T.J . (2007). ImageJ for microscopy. Biotechniques 43, 25-30.
Copper, L.B., Chan DK, Roediger FC, Shaffer BR, Fraser JF, Musatov S, Selesnick SH, Kaplitt MG. AAV-mediated delivery of the caspase inhibitor XIAP protects against cisplatin ototoxicity. Oto[ Neurotol. Jun. 2006;27(4):484-90.
Delille, H.K., Agricola, B., Guimaraes, S.C., Barta, H., Luers, G.H., Fransen, M., and Schrader, M. (2010). Pex11pbeta-mediated growth and division of mammalian peroxisomes follows a maturation pathway. Journal of cell science 123, 2750-2762.
Delmaghani, S., del Castillo, F.J., Michel, V., Leibovici, M., Aghaie, A., Ron, U., Van Laer, L., Ben-Tal, N., Van Camp, G., Weil, D., et al._(2006). Mutations in the gene encoding pejvakin, a newly identified protein of the afferent auditory pathway, cause DFNB59auditory neuropathy. Nat. Genet . 38, 770-8.

Diana, S., Liu, Z.W., Jeong, J.K., Dietrich, M.O., Ruan, H.B., Kim, E., Suyama, S., Kelly, K., Gyengesi, E., Arbiser, J.L., et al. (2011). Peroxisome proliferation—associated control of reactive oxygen species sets melanocortin tone and feeding in diet-induced obesity . Nat Med 17, 1121-1127.
Dobie, R.A. (2005) Audiometric Threshold Shift Definitions: Simulations and Suggestions, Ear and Hearing 26(1 ) 62-77.
Ebermann, I., Walger, M., Scholl, H.P., Charbel Issa, P., Luke, C., Nurnberg, G., Lang-Roth, R., Becker, C., Nurnberg, P., Bolz, H.J. (2007). Truncating mutation of the DFNB59 gene causes cochlear hearing impairment and central vestibular dysfunction. Hum. Mutat. 28(6), 571-7.
Ehret, G., and Riecke, S. (2002). Mice and humans perceive multiharmonic communication sounds in the same way. Proc. Natl. Acad. Sci. USA 99(1), 479-482.
Evans, P., and Halliwell, B. (1999). Free radicals and hearing. Cause, consequence, and criteria. Ann. NY Acad. Sci. 884, 19-40.
Fransen, M., Nordgren, M., Wang, B., and Apanasets, 0. (2012). Role of peroxisomes in ROS/RNS-metabolism: implications for human disease. Biochim Biophys Acta 1822, 1363-1373.
Han, C., and Someya, S. (2013). Mouse models of age-related mitochondrial neurosensory hearing loss. Molecular and cellular neurosciences 55, 95-100.
HashemzadehChaleshtori, M., Simpson,M.A., Farrokhi, E., Dolati, M., Hoghooghi Rad, L., Amani Geshnigani, S., Crosby, A.H. (2007). Novel mutations in the pejvakin gene are associated with autosomal recessive non-syndromic hearing loss in Iranian families. Clin. Genet. 72(3), 261-3.
He, W., Newman, J.C., Wang, M.Z., Ho, L., and Verdin, E. (2012). Mitochondrial sirtuins: regulators of protein acylation and metabolism. Trends in endocrinology and metabolism: TEM23, 467-476.
Henderson, D., Bielefeld, E.C., Harris, K.C., and Hu, B.H. (2006). The role of oxidative stress in noise-induced hearing loss. Ear and hearing 27, 1-19.
Housley, G.D., Morton-Jones, R., Vlajkovic, S.M., Telang, R.S., Paramananthasivam, V., Tadros, S.F., Wong, A.C., Froud, K.E., Cederholm, J.M., Sivakumaran, Y., et al. (2013). ATP-gated ion channels mediate adaptation to elevated sound levels. Proc Natl Acad Sci US A. 110(18), 7494-9.
Imig, T.J., and Durham, D. (2005). Effect of unilateral noise exposure on the tonotopic distribution of spontaneous activity in the cochlear nucleus and inferior colliculus in the cortically intact and decorticate rat. The Journal of comparative neurology 490, 391-413.
Jain, N., Thatte, J., Braciale, T., Ley K., O'Connell, M., Lee, J.K. (2003). Local-pooled-error test for identifying differentially expressed genes with a small number of replicated microarrays. Bioinformatics 19(15), 1945-51.
Janero, D.R. (1990). Malondialdehyde and thiobarbituric acid-reactivity as diagnostic indices of lipid peroxidation and peroxidative tissue injury. Free Radic. Biol. Med. 9(6), 515-40.
Kaplitt, M.G., Leone P, Samulski RJ, Xiao X, Pfaff DW, O'Malley KL, During MJ. Long-term gene expression and phenotypic correction using adeno-associated virus vectors in the mammalian brain. Nat Genet. Oct. 1994;8(2):148-54.
Kayagaki N, Stowe IB, Lee BL, O'Rourke K, Anderson K, Warming S, Cuellar T, Haley B, Roose-Girma M, Phung QT, Liu PS, Lill JR, Li H, Wu J, Kummerfeld S, Zhang J, Lee WP, Snipas SJ, Salvesen GS, Morris LX, Fitzgerald L, Zhang Y, Bertram EM, Goodnow CC, Dixit VM (2015). Caspase-11 cleaves gasdermin D for non-canonical inflammasome signaling. Nature. Sep. 16. doi: 10.1038/nature15541.
Kim MS, Lebron C, Nagpal JK, Chae YK, Chang X, Huang Y, Chuang T, Yamashita K, Trink B, Ratovitski EA, Califano JA, Sidransky D (2008). Methylation of the DFNA5 increases risk of lymph node metastasis in human breast cancer. Biochem Biophys ResCommun. 370(1):38-43.
Kim MS, Chang X, Yamashita K, Nagpal JK, Baek JH, Wu G, Trink B, Ratovitski EA, Mori M, Sidransky D (2008). Aberrant promoter methylation and tumor suppressive activity of the DFNA5gene in colorectal carcinoma. Oncogene. 27(25):3624-34.
Kemp, D.T. (2002). Otoacoustic emissions, their origin in cochlear function, and use. Br. Med. Bull. 63, 223-241.

(56) References Cited

OTHER PUBLICATIONS

Koch, J., Pranjic, K., Huber, A., Ellinger, A., Hartig, A., Kragler, F., and Brocard, C. (2010). PEX11 family members are membrane elongation factors that coordinate peroxisome proliferation and maintenance. Journal of cell science 123, 3389-3400.

Kress, C., Vandormael-Pournin, S., Baldacci, P., Cohen-Tannoudji, M., Babinet, C. (1998). Nonpermissiviness for mouse embryonic stem (ES) cell derivation circumvented by a single backcross to 129/Sv strain: establishment of EScell lines bearing the Omd conditional lethal mutation. Mamm. Genome 9,998-1001.

Kujawa, S.G., and Liberman, M.C. (2009). Adding insult to injury: cochlear nerve degeneration after "temporary" noise-induced hearing loss. The Journal of neuroscience : the official journal of the Society for Neuroscience 29, 14077-14085.

Lallemand, Y., Luria, V., Haffner-Krausz, R., Lanai, P. (1998). Maternally expressed PGK-cre transgene as a tool for early and uniform activation of the Cre site-specific recombinase. Transgenic Res. 7, 105-112.

Lay, D., Gorgas, K. and Just, W.W. (2006). Peroxisome biogenesis: where Arf and coatomer might be involved. Biochim Biophys Acta 1763, 1678-1687.

Lee, SP., Hwang, Y.S., Kim, Y.J., Kwon, K.S., Kim, H.J., Kim, K., Chae, H.Z. (2001). Cyclophilin A binds to peroxiredoxins and activates its peroxidase activity. J. Biol. Chem. 276(32), 29826-32.

Lee, J.N., Kim, S.G., Lim, J.Y., Kim, S.J., Choe, S.K., and Park, R. (2015). Proteasome inhibitors induce auditory hair cell death through peroxisome dysfunction. Biochemical and biophysical research communications 456, 269-274.

Li, X., Baumgart, E, Dong, G.X., Morrell, J.C., Jimenez-Sanchez, G., Valle, D., Smith, K.D., and Gould, S.J. (2002). PEX11alpha is required for peroxisome proliferation in response to 4-phenylbutyrate but is dispensable for peroxisome proliferator-activated receptor alpha-mediated peroxisome proliferation. Molecular and cellular biology 22, 8226-8240.

Li-Yang MN, Shen XF, Wei QJ, Yao J, Lu YJ, Cao X, Xing GQ (2015). IVS8+1DeIG, a Novel Splice Site Mutation Causing DFNA5Deafnessin a Chinese Family. Chin Med J (Engl). 128(18):2510-2515.

Lizana, L., Bauer, B., and Orwar, 0. (2008). Controlling the rates of biochemical reactions and signaling networks by shape and volume changes. Proceedings of the National Academy of Sciences of the United States of America 105, 4099-4104.

Lopez-Huertas, E., Charlton, W.L., Johnson, B., Graham, I.A., and Baker, A. (2000). Stress induces peroxisome biogenesis genes. TheEMBOjournal 19,6770-6777.

Matise, M.P., Auerbach, W., Joyner, A. (1999). Production of targeted embryonic stem cell clones. In: Joyner A, ed. Gene targeting. A practical approach . Oxford: Oxford University Press;p. 101-132.

Menuet, C., Cazals, Y., Gestreau, C., Borghgraef, P., Gielis, L., Dutschmann, M., Van Leuven, F., Hilaire, G. (2011). Age-Related Impairment of Ultrasonic Vocalization in Tau. P301L Mice: Possible Implication for Progressive Language Disorders . PloS One 6(10), e25770.

Meyer zum Gottesberge, A.M., Felix, H., Reuter, A., Weiher, H. (2001). Ultrastructural and physiological defects in the cochlea of the Mpv17 mouse strain. A comparison between young and old adult animals. Hear. Res. 156(1-2), 69-80.

Michard, Q., Commo, S., Belaidi, J.P., Alleaume, A.M., Michelet, J.F., Daronnat, E., Eilstein, J., Duche, D., Marrot, L., Bernard, B.A. (2008b). TRP-2 specifically decreases WM35cell sensitivity to oxidative stress. Free Radie. Biol. Med. 44(6), 1023-31.

Michard, Q., Commo, S., Rocchetti, J ., El Houari, F., Alleaume, A.M., Wakamatsu, K., Ito, S., Bernard, B.A. (2008a). TRP-2 expression protects HEK cells from dopamine- and hydroquinone-induced toxicity. Free Radie. Biol. Med. 45(7), 1002-10.

Motley, A.M., and Hettema, E.H. (2007). Yeast peroxisomes multiply by growth and division. J Cell Biol 178, 399-410.

Mujtaba, G., Bukhari, I., Fatima, A., Naz, S. (2012). A p.C343S missense mutation in PJVK causes progressive hearing loss. Gene 504(1 ), 98-101.

Needleman, S.B., and Wunsch, C.D. (1970). A general method applicable to the search for similaritis in the amino acid sequence of two proteins. J. Mot. Biol. 48(3), 443-453.

Nishio A, Noguchi Y, Sato T, Naruse TK, Kimura A, Takagi A, Kitamura K (2014) . A DFNA5 mutation identified in Japanese families with autosomal dominant hereditary hearing loss. Ann Hum Genet. 78(2):83-91.

Ohinata, Y., Miller, J.M., Altschuler , R.A., and Schacht, J. (2000) . Intense noise induces formation of vasoactive lipid peroxidation products in the cochlea. Brain research 878, 163-173.

Ohlemiller, K.K., McFadden, S.L., Ding, D.L., Flood, D.G., Reaume, A.G., Hoffman, E.K., Scott, R.W., Wright, J.S., Jutcha, G.V., and Salvi, R.J. (1999a). Targeted deletion of the cytosolic Cu/Zn-superoxide dismutase gene (Sod1) increases susceptibility to noise-induced hearing loss. Audiology & neuro-otology 4, 237-246.

Ohlemiller, K.K., Wright, J.S., and Dugan, L.L. (1999b). Early elevation of cochlear reactive oxygen species following noise exposure. Audiol Neurootol 4, 229-236.

Ohlemiller , K.K., McFadden, S.L., Ding, D.L., Lear, P.M., and Ho, Y.S. (2000). Targeted mutation of the gene for cellular glutathione peroxidase (Gpx1) increases noise-induced hearing loss in mice. Journal of the Association for Research in Otolaryngology : JARO1, 243-254.

Okatsu, K., Saisho, K., Shimanuki, M., Nakada, K., Shitara, H., Sou, Y.S., Kimura, M., Sato, S., Hattori, N., Komatsu, M., et al. (2010). p62/SQSTM1cooperates with Parkin for perinuclear clustering of depolari zed mitochondria . Genes to cells: devoted to molecular Etcellular mechanisms 15, 887-900.

Op de Beeck K, Van Camp G, Thys S, Cools N, Callebaut I, Vrijens K, Van Nassauw L, Van Tendeloo VF, Timmermans JP, Van Laer L (2011). The DFNA5 gene, responsible for hearing loss and involved in cancer, encodes a novel apoptosis-inducing protein. Eur J Hum Genet. 19(9):965-73.

Passreiter, M., Anton, M., Lay, D., Frank, R., Harter, C. , Wieland , F.T. , Gorgas, K., and Just, W.W. (1998). Peroxisome biogenesis: involvement of ARF and coatomer. J Cell Biol 141, 373-383.

Pienkowski, M., and Eggermont, J.J. (2009). Long-term, partially-reversible reorganization of frequency tuning in mature cat primary auditory cortex can be induced by passive exposure to moderate-level sounds. Hearing research 257, 24-40.

Rahman, I., Kode, A. , and Biswas, S.K. (2006). Assay for quantitative determination of glutathione and glutathione disulfide levels using enzymatic recycling method. Nat. Protoc . 1, 3159-3165.

Reddy, J.K., Azarnoff, D.L., and Hignite, C.E. (1980). Hypolipidaemic hepatic peroxisome proliferators form a novel class of chemical carcinogens. Nature 283, 397-398.

Robles, L., and Ruggero M.A. (2001). Mechanics of the mammalian cochlea. Physiol Rev. 81(3), 1305-52.

Roux, I., Safieddine, S., Nouvian, R., Grati, M., Simmler, M.C., Bahloul, A., Perfettini, I., Le Gall, M., Rostaing, P., Hamard, G., et al. (2006). Otoferlin, defective in a human deafness form, is essential for exocytosis at the auditory ribbon synapse . Cell 127(2), 277-89.

Roux, I., Hosie, S., Johnson, S.L., Bahloul, A., Cayet, N., Nouaille, S., Kros, C.J ., Petit, C., and Safieddine, S. (2009). Myosin VI is required for the proper maturation and function of inner hair cell ribbon synapses. Hum. Mol. Genet. 18, 4615-4628.

Roy, S., Ryals, M.M., Van den Bruele, A.B., Fitzgerald, T.S., Cunningham, L.L. (2013). Sound preconditioning therapy inhibits ototoxic hearing loss in mice. J. Clin. Invest. 123(11 ), 4945-9.

Sadanaga, M., and Morimitsu, T. (1995). Development of endocochlear potential and its negative component in mouse cochlea. Hearing research 89, 155-161.

Santos, M.J., Quintanilla, R.A., Toro, A., Grandy, R., Dinamarca, M.C., Godoy, J.A., and Inestrosa, N.C. (2005). Peroxisomal proliferation protects from beta-amyloid neurodegeneration. The Journal of biological chemistry 280, 41057-41068.

Schrader, M., and Fahimi, H.D. (2006). Peroxisomes and oxidative stress. Biochim Biophys Acta 1763, 1755-1766.

(56) References Cited

OTHER PUBLICATIONS

Schrader, M., Reuber, B.E., Morrell, J.C., Jimenez-Sanchez, G., Obie, C., Stroh, T.A., Valle, D., Schroer, T.A., and Gould, S.J. (1998). Expression of PEX11beta mediates peroxisome proliferation in the absence of extracellular stimuli. The Journal of biological chemistry 273, 29607-29614.

Schrader, M., Wodopia, R., and Fahimi, H.D. (1999). Induction of tubular peroxisomes by UV irradiation and reactive oxygen species in HepG2 cells. J Histochem Cytochem 47, 1141-1148.

Schwander, M., Sczaniecka, A., Grillet, N., Bailey, J.S., Avenarius, M., Najmabadi, H., Steffy, B.M., Federe, G.C., Lagler, E.A., Banan, R. (2007). A forward genetics screen in mice identifies recessive deafness traits and reveals that pejvakin is essential for outer hair cell function. J. Neurosci. 27(9), 2163-75.

Shi J, Zhao Y, Wang K, Shi X, Wang Y, Huang H, Zhuang Y, Cai T, Wang F, Shao F (2015). Cleavage of GSDMDby inflammatory caspases determines pyroptotic cell death. Sep. 16. doi: 10.1038/nature15514. [Epub ahead of print].

Shi P, Tang A, Xian L, Hou S, Zou D, Lv Y, Huang Z, Wang Q, SongA, Lin Z, Gao X (2015). Lossof conserved Gsdma3self-regulation causesautophagy and cell death . Biochem J. 468(2)325-36.

Smith, J.J ., and Aitchison, J.D. (2013). Peroxisomes take shape. Nat Rev Mot Cell Biol 14, 803-817.

Tang, X.D., Garcia, M.L., Heinemann, S.H., and Hoshi, T. (2004). Reactive oxygen species impair Slo1 BK channel function by altering cysteine—mediated calcium sensing. Nat. Struct. Mol. Biol. 11, 171-178.

Thelen, N., Breuskin, I., Malgrange, B., Thiry, M. (2009). Early identification of inner pillar cells during rat cochlear development. Cell Tissue Res. 337, 1-14.

Tran, C., Hewson, S., Steinberg, S.J., Mercimek-Mahmutoglu, S. (2014). Late-onset Zellweger spectrum disorder caused by PEX6mutations mimicking X-linked adrenoleukodystrophy. Pediatr Neural. 51(2), 262-5.

Van Laer L, Huizing EH, Verstreken M, van Zuijlen D, Wauters JG, Bossuyt PJ, Van de Heyning P, McGuirt WT, Smith RJ, Willems PJ, Legan PK, Richardson GP, Van Camp G (1998). Nonsyndromic hearing impairment is associated with a mutation in DFNA5.Nat Genet. 20(2):194-7.

Wang, Y., Hirose, K., and Liberman, M.G. (2002). Dynamics of noise-induced cellular injury and repair in the mouse cochlea. Journal of the Association for Research in Otolaryngology : JARO3, 248-268.

Wang CJ, Tang L, Shen DW, Wang C, Yuan QY, Gao W, Wang YK, Xu RH, Zhang H (2013). The expression and regulation of DFNA5 in human hepatocellular carcinoma DFNA5in hepatocellular carcinoma . Mol Biol Rep. 40(12):6525-31.

Yamane, H., Nakai, Y., Takayama, M., Iguchi, H., Nakagawa, T., and Kojima, A. (1995). Appearance of free radicals in the guinea pig inner ear after noise-induced acoustic trauma. Eur Arch Otorhinolaryngol 252, 504-508.

Yamashita, D., Jiang, H.Y., Schacht, J., and Miller, J.M. (2004). Delayed production of free radicals following noise exposure. Brain research 1019, 201-209.

Yu C, Meng X, Zhang S, Zhao G, Hu L, Kong X (2003). A 3-nucleotide deletion in the polypyrimidine tract of intron 7 of the DFNA5 gene causes nonsyndromic hearingimpairment inaChinesefamily.Genomics.82(5):575-9.

Zhang, Q.J., Lan, L., Li, N., Qi, Y., Zong, L., Shi, W., Yu, L., Wang, H., Yang, J., Xie, L.Y., et al. (2015). Identification of a novel mutation of PJVKin the Chinese non-syndromic hearing losspopulation with low prevalence of the PJVKmutations. Acta oto-laryngologica 135, 211-216.

Avan P, Bi.iki B, Petit C. (2013). Auditory distortions: origins and functions. Physiol Rev. Oct;93(4):1563-619.

Hardisty-Hughes RE, Parker A, Brown SD (2010). A hearing and vestibular phenotyping pipeline to identify mouse mutants with hearing impairment. Nat Protec., Jan;5(1):177-90.

Le Calvez S, Avan P, Gilain L, Romand R., (1998) Hear Res. Jun;120(1-2):37-50.

Michalski N, Michel V, Caberlotto E, Lefevre GM, van Aken AF, Tinevez JY, Bizard E, Houbron C, Weil D, Hardelin JP, Richardson GP, Kras CJ, Martin P, Petit C. . 2009, Harmonin-b, an actin-binding scaffold protein, is involved in the adaptation of mechanoelectrical transduction by sensory hair cells. Pflugers ArchNov;459(1 ): 115-30.

Mustapha et al., 2002. Hum. Genet. vol. 110, 348-350.

Weil et al., 2003. Human Molecular Genetics vol. 12, No. 5, 463-471.

European Search Report, Application No. EP 15305270, dated Sep. 2, 2015.

European Search Report, Application No. EP 15306664, dated Feb. 17, 2016.

International Search Report, Application No. PCT/EP2016/053613.

Database WPI Week 201307,Thomson Scientific, London, GB Oct. 2012.

Sedigheh Delmaghani, et al., Mutations in the gene encoding pejvakin, a newly identified protein of the afferent auditory pathway, cause DFNB59 auditory neuropathy.

Anna Rita Fetoni, et al., Noise-Induced Hearing Loss (NIHL) as a Target of Oxidative Stress-Mediated Damage: Cochlear and Cortical Responses after an Increase in Antioxidant Defense.

Marc Fransen, et al., Role of peroxisomes in ROS/RNS-metabolism: Implications for human disease.

Gwenaelle S. G. Geleoc, et al., "Sound Strategies for Hearing Restoration," Science, May 9, 2014; 344(6184).

William J. Kimberling, et al., "Localization of Usher Syndrome Type II to Chromosome 1q," Genomics, 7, 245-249 (1990).

Yukihide Maeda, et al., "The Therapeutic Regulation of Gene Expression in the Inner Ear using RNA Interference," Adv. Otorhinolaryngol., 2009; 66: 13-36.

Ghulam Mujtaba, et al., "A p.C343S missense mutation in PJVK causes progressive hearing loss," Gene 504 (2012) 98-101.

Su-Hua Sha, et al., "Antioxidants attenuate gentamicin-induced free radical formation in vitro and ototoxicity in vivo: d-methionine is a potential protectant," Hearing Research, vol. 142 (2000) 34-40.

Hong-Joon Park, et al., "Evidence for a founder mutation causing DFNA5 hearing loss in East Asians," J Hum Genet. Jan. 2010; 55(1): 59-62. doi:10.1038.jhg.2009.114.

Saeki and Sasaki, "Gasdermin Superfamily: A Novel Gene Family Functioning in Epitheliam Cells," In: Endothelium and Epithelium, Editors: J. Carrasco and m. Mota, pp. 193-211 (c) 2012 Nova Science Publishers, Inc.

\* cited by examiner

D

B

C    Treated Ush1g −/− mice

Ush1g +/− mice

PREVENTION AND/OR TREATMENT OF HEARING LOSS OR IMPAIRMENT

BACKGROUND OF THE INVENTION

The mammalian hearing organ, the cochlea, consists of a coiled, fluid filled membranous duct that contains the sensory epithelium responsive to sound. This sensory epithelium, termed the organ of Corti, comprises two different kinds of sensory cells, inner hair cells (IHCs) and outer hair cells (OHCs), which are surrounded by supporting cells. The apical specialization of hair cells, the hair bundle, houses the mechanotransduction machinery that transforms sound-induced mechanical stimuli into cell depolarization. This results in neurotransmitter release and the generation in spiral ganglion neurons (SGN) (auditory nerve) of action potentials that are relayed by the brainstem to the auditory cortex. Each class of sensory cells serves a different function. IHCs are the genuine sound receptors, whereas OHCs behave as active mechanical amplifiers that impart high sensitivity, sharp tuning and wide dynamic range to the cochlea. This functional difference is also evident in the afferent innervation of hair cells. Each single IHC is innervated by 15-20 type I spiral ganglion neurons that provide parallel channels for transmitting auditory information to the brain. In contrast, 30-60 OHCs are innervated by a single type II spiral ganglion neuron, thus integrating the sensory input from many different effector cells.

The basic auditory signal conveyed by spiral ganglion neurons is analysed, decoded and integrated along the afferent auditory pathway, which includes four major relays (cochlear nuclei, superior olive, inferior colliculus and medial geniculate body) before reaching the auditory cortex in the temporal lobe of the brain. Each level in the auditory pathway is tonotopically organized, paralleling the distribution of the range of sound frequencies perceived along the cochlear spiral, from base (high frequencies) to apex (low frequencies).

Most forms of inherited sensorineural hearing impairment are due to cochlear cell defects. However, a substantial proportion of cases, including up to 10% of all cases of permanent hearing impairment in children, are caused by a lesion located beyond the cochlea. Clinical tests for sensorineural hearing impairment include recording the auditory brainstem response (ABR), which measures the acoustic stimulus-evoked electrophysiological response of the auditory nerve and brainstem, and otoacoustic emissions (OAEs), which are low level sounds originating from the cochlea due to the mechanical activity of OHCs. Auditory neuropathy is a type of sensorineural hearing impairment in which the ABR is absent or severely distorted while OAEs are preserved. This suggests a primary lesion located in the IHC, in the auditory nerve or in the intervening synapse, but may also include damage to neuronal populations in the auditory pathway.

Age-related hearing loss (ARHL or presbycusis), which affects more than 30% people above 60 and overall, about 5 million people in France, is the result of a combination of factors, genetic and environmental (lifelong exposure to noise and to chemicals). Yet it has been shown in the 1950s that subjects who spend their lives in silent environments do not suffer from any hearing impairment even in their 80 s. This, and a huge body of evidence collected in subjects occupationally exposed to noise, leads to conclude that noise-induced hearing loss (NIHL) is the dominant cause of hearing impairment in ageing subjects. It is one of the most frequent conditions in workers, and an increasing matter of concern as exposure to loud sound during leisure has increased dramatically, particularly in younger subjects, with the development of inexpensive portable music players. Permanent hearing loss resulting from the loss of auditory hair cells (HCs) and spinal ganglion neurons (SGNs) is irreversible because the cells are terminally developed and cannot be replaced by mitosis. Although great efforts have been made to regenerate lost HCs and SGNs in mammals, these efforts have been largely unsuccessful so far.

The DFNB59 gene has been identified to underlie an autosomal recessive auditory neuropathy. The product of DFNB59, pejvakin, is known to be expressed in all the relays of the afferent auditory pathway, from the cochlea to the midbrain, and plays a critical role in the physiology of auditory neurons (Delmaghani S. et al, 2006). This first study was performed in patients affected by pure auditory neuropathies that consistently showed increased inter-wave delay of auditory brainstem responses (ABRs).

Since then, other DFNB59 patients have been reported, who display a cochlear dysfunction, as shown by the absence of OAEs. Because the latter patients were carrying truncating (nonsense or frame-shifting) PJVK mutations, whereas the former had missense mutations (p.T54I or p.R183W), the DFNB59 phenotypic variability has tentatively been ascribed to the difference in the mutations (Collin et al., 2007; Ebermann et al., 2007; Hashemzadeh Chaleshtori et al., 2007; Schwander et al., 2007; Borck et al., 2012; Mujtaba et al., 2012; Zhang et al., 2015). Subsequently-reported patients, who carried the p.R183W missense mutation but lacked OAEs unlike the first reported patients (Collin et al., 2007), called into question the existence of a straightforward connection between the nature of the PJVK mutation and the hearing phenotype.

The precise function of pejvakin is still unknown and its role in the hearing impairment aetiology remains to be elucidated in order to identify novel treatments and/or adapt conventional ones.

Pejvakin belongs to the family of molecules called gasdermins, expressed in the epithelial cells of several tissues and whose actual functions remain unknown. In humans, the sequences of DFNB59 and DFNA5 genes share at least 50% identity and the encoded proteins belong to the gasdermin family group of proteins, which also comprises the proteins encoded respectively by the GSDMA, GSDMB, GSDMC and GSDMD genes, as demonstrated by multiple sequence alignment and phylogenetic tree of all the gasdermin family of proteins (Shi et al., 2015, Saeki and Sasaki, 2011). Of note, DFNB59 and DFNA5 are also designated as gasdermin-related proteins.

In this aim, the present inventors studied Pjvk knock-out mice. This study revealed an unprecedented hypervulnerability to sound exposure and allowed them to identify what the target cells and the cellular mechanisms underlying the pejvakin defect are. More precisely, they found that pejvakin is a peroxisome-associated protein involved in the division of this organelle and playing a critical role in antioxidant metabolism.

Moreover, their results show that it is possible to alleviate the hair cells and neuronal cell defects of Pjvk$^{-/-}$ mice by treating them with antioxidant compounds, and to fully prevent the auditory defect by gene transfer in the cochlea. These findings have major therapeutic implications, as described below.

DETAILED DESCRIPTION OF THE INVENTION

The present Inventors identified the biochemical mechanisms involved in the congenital hearing impairment and sound vulnerability observed in pejvakin deficient mice.

More precisely, they have shown that these phenomena are due to a faulty homeostasis of reactive oxygen species (ROS) in the auditory system of Pjvk$^{-/-}$ mice. This was demonstrated by various means: (i) the expression of some antioxidant genes, CypA, Gpx2, c-Dct, and, Mpv17 was reduced in the Pjvk$^{-/-}$ mice. (ii) The reduced glutathione (GSH) content was decreased in Pjvk$^{-/-}$ cochlea whilst the oxidized glutathione (GSSG) content was increased. Therefore the ratio between GSH and GSSG was reduced in Pjvk$^{-/-}$ mice. The increase in GSSG as well as the decrease in GSH:GSSG ratio are well known as markers of oxidative stress in cells. Thus the lack of pejvakin increases oxidative stress in the Pjvk$^{-/-}$ cochlea. (iii) Lipids are natural targets of oxidation by ROS and the content of aldehydes that are the by-product of lipid peroxidation were shown to be increased in the cochlea of Pjvk$^{-/-}$, indicating Pjvk defect results in ROS cellular damage. (iv) Sound exposure is known to induce oxidative stress as the result of cellular hyperactivity, which is associated with an antioxidant protective response. The present Inventors herein showed that the expression levels of Pjvk and of some antioxidants increased in response to sound. In addition, the transcription rate of Pjvk increased in the physiological response to noise (sound preconditioning), indicating that it is likely involved in the immediate adaptive antioxidant response to noise.

In an aspect, the present invention relates to the use of a gasdermin, which designates a member of the gasdermin family of proteins, for modulating cellular redox homeostasis. Thus, the present invention concerns the use of a gasdermin as a redox modulator. A particularly preferred use of gasdermin in the context of the present invention is as an antioxidant. Accordingly, a gasdermin can be advantageously used as such in pharmaceutical compositions.

The terms "modulator of cellular redox homeostasis" or "redox modulator" as used herein refer to an agent or compound that modifies the redox status (or redox potential or redox state) in a cell. This agent or compound can (i) act indirectly by changing the balance of oxidants and antioxidants in a cell and/or (ii) act directly by increasing or decreasing the rate of generation or of elimination of ROS in a cell and/or by increasing or decreasing the amount of ROS in a cell.

The term "gasdermin" as used herein refers to any member of the gasdermin family of proteins or polypeptides, or any homolog of a member of the gasdermin family of proteins or polypeptides, in humans or non-human mammals such as primates, cats, dogs, swine, cattle, sheep, goats, horses, rabbits, rats, mice, and the like. In humans, members of the gasdermin family include, but are not limited to: gasdermin A, gasdermin B, gasdermin C, gasdermin D, DFNA5 and DFNB59 (or pejvakin) (Shi et al., 2015; Saeki and Sasaki, 2011).

In another embodiment, the term "gasdermin" also designates any fragment of a member of the gasdermin family of proteins or polypeptides, or any fragment of a homolog of a member of the gasdermin family of proteins or polypeptides, wherein said fragment retains at least one biological function that is of interest in the present context (Shi et al., 2015; Saeki and Sasaki, 2011).

In a particular embodiment, the present invention relates to the use of a gasdermin chosen among: gasdermin A, gasdermin B, gasdermin C, gasdermin D, DFNA5 and DFNB59 (or pejvakin), for modulating cellular redox homeostasis. The present invention therefore concerns the use of gasdermin A, gasdermin B, gasdermin C, gasdermin D, DFNA5 or DFNB59 (or pejvakin), as a redox modulator. A particularly preferred use of gasdermin A, gasdermin B, gasdermin C, gasdermin D, DFNA5 or DFNB59 (or pejvakin) in the context of the present invention is as an antioxidant. Accordingly, gasdermin A, gasdermin B, gasdermin C, gasdermin D, DFNA5 or DFNB59 (or pejvakin) can be advantageously used as such in pharmaceutical compositions.

In a more particular embodiment of this aspect, the present invention relates to the use of pejvakin for modulating cellular redox homeostasis. Thus, an embodiment of the present invention concerns the use of pejvakin as a redox modulator.

Regarding the role of pejvakin as a modulator of cellular redox homeostasis, the role here proposed is an indirect one, which involves an effect via an organelle, peroxisome. The glutathione is the major antioxidant within the cell and as shown by the present Inventors, the oxidized glutathione content increases in the cochlea of Pjvk$^{-/-}$ mice, whereas the reduced glutathione content decreases, showing an impaired anti-oxidant defence in the cochlea of these mice.

A particularly preferred use of pejvakin in the context of said particular embodiment of the present invention is as an antioxidant.

Accordingly, pejvakin can be advantageously used as such in pharmaceutical compositions.

The term "antioxidant" herein qualifies any molecule that is capable of modulating the redox homeostasis in a cell, preferably in an auditory cell. Such a molecule is involved in the subtly orchestrated balance of redox status in cells, or in the delicate balance between the ROS generation and elimination. Consequently, it is very important for the proper functioning of these cells. In a particular embodiment, "antioxidant molecules" herein designate any molecule that is capable of restoring the normal function of one or more organelles selected from peroxisomes, lysosomes, mitochondria, and endoplasmic reticulum in a cell, e.g., in an auditory cell.

An "antioxidant" compound may not be able to eliminate the Reactive Species (ROS or RNS) directly (e.g., by physical interaction). It is thus not a "RS inhibiting compound" as meant in the present invention (see below).

For example, said antioxidant compounds may be a gasdermin, and preferably a gasdermin-related protein chosen among: pejvakin (DFNB59), gasdermin A, gasdermin B, gasdermin C, gasdermin D, DFNA5, cyclophilin A, c-dopachrome tautomerase or Mpv17.

Pejvakin or autosomal recessive deafness type 59 protein or PJVK is a protein belonging to the gasdermin family. In human, it has the sequence SEQ ID NO:1 (NCBI Reference Sequence: NP_001036167.1). In mouse, it has the sequence SEQ ID NO:2 (NCBI Reference Sequence: NP_001074180). It is known to be expressed in all the relays of the afferent auditory pathway from the cochlea to the midbrain and is thought to play a critical role in the physiology of auditory neurons (Delmaghani S. et al, 2006). Several impairing mutations have been described (Collin et al., 2007; Ebermann et al., 2007; Hashemzadeh Chaleshtori et al., 2007; Schwander et al., 2007; Borck et al., 2012; Mujtaba et al., 2012; Zhang et al., 2015).

Human pejvakin is encoded by the DFNB59 gene of SEQ ID NO:3 in human (NCBI Reference Sequence: NM_001042702.3, the coding sequence being comprised between the nucleotides 357 and 1415). The mouse DFNB59 gene is of SEQ ID NO:4 (NCBI Reference Sequence: NM_001080711.2, the coding sequence being comprised between the nucleotides 150 and 1208).

In the context of the invention, the term "pejvakin" herein designates a polypeptide having the amino acid sequence SEQ ID NO:1 (human PJVK) or SEQ ID NO:2 (mouse PJVK) or an homologous sequence thereof. Said latter homologous sequence is for example the PJVK protein of another animal species, the polypeptide having said latter homologous sequence retains at least one biological function of human PJVK or mouse PJVK that is of interest in the present context. This latter homologous sequence shares preferably at least 50%, preferably at least 60%, more preferably at least 70%, more preferably at least 80%, and even more preferably at least 90% identity with SEQ ID NO:1 or SEQ ID NO:2. Preferably, the identity percentage between said homologous sequence and SEQ ID NO:1 or SEQ ID NO:2 is identified by a global alignment of the sequences in their entirety, this alignment being performed by means of an algorithm that is well known by the skilled person, such as the one disclosed in Needleman and Wunsch (1970). Accordingly, sequence comparisons between two amino acid sequences can be performed for example by using any software known by the skilled person, such as the "needle" software using the "Gap open" parameter of 10, the "Gap extend" parameter of 0.5 and the "Blosum 62" matrix.

In another embodiment, the term "pejvakin" also designates any polypeptide encoded by a DFNB59 gene. In a preferred embodiment, said DFNB59 gene is chosen in the group consisting of: SEQ ID NO:3, SEQ ID NO:4, or any homologous gene of another animal species, said homologous gene whose encoding protein shares at least 50%, similarity with SEQ ID NO:3 or SEQ ID NO:4 and more particularly preferably at least 50%, preferably at least 60%, more preferably at least 70%, more preferably at least 80%, and even more preferably at least 90% identity with SEQ ID NO:3 or SEQ ID NO:4.

In another embodiment, the term "pejvakin" also designates any fragment of human PJVK or mouse PJVK or any fragment of a polypeptide having a homologous sequence as defined above, wherein said fragment retains at least one biological function of human PJVK or mouse PJVK that is of interest in the present context. This fragment shares preferably at least 30%, preferably at least 40%, more preferably at least 50%, more preferably at least 60%, and even more preferably at least 70% identity with SEQ ID NO:1 or SEQ ID NO:2.

Gasdermin A is a protein which belongs to the gasdermin family. In human, it has the sequence SEQ ID NO:21 (NCBI Reference Sequence: NP_835465.2). In mouse, gasdermin A has the sequence SEQ ID NO:22 (NCBI Reference Sequence: NP_067322.1), gasdermin A2 has the sequence SEQ ID NO:23 (NCBI Reference Sequence: NP_084003.2) and gasdermin A3 has the sequence SEQ ID NO:24 (NCBI Reference Sequence: NP_001007462.1). It is known to be expressed predominantly in the gastrointestinal tract and in the skin. It was discovered as a potential tumour suppressor with a different expression pattern in normal stomach and human gastric cancer cells. Gasdermin A was reported as a target of LIM domain only 1 (LMO1) in human gastric epithelium and induced apoptosis in a transforming growth factor-β-dependent manner and mouse gasdermin A3 has been reported to cause autophagy followed by cell death (Shi P et al., 2015). Human gasdermin A is encoded by the mRNA of SEQ ID NO:25 (NCBI Reference Sequence: NM_178171.4). The mouse gasdermin A gene is of SEQ ID NO:26 (NCBI Reference Sequence: NM_021347.4), the gasdermin A2 gene is of SEQ ID NO:27 (NCBI Reference Sequence: NM_029727.2) and the gasdermin A3 gene is of SEQ ID NO:28 (NCBI Reference Sequence: NM_001007461.1).

In the context of the invention, the term "gasdermin A" herein designates a polypeptide having the amino acid sequence SEQ ID NO:21 (human gasdermin A) or SEQ ID NO:22, SEQ ID NO:23 or SEQ ID NO:24 (mouse gasdermin A, GSDM A2 and GSDM A3 respectively) or an homologous sequence thereof. Said latter homologous sequence is for example the gasdermin A protein of another animal species, the polypeptide having said latter homologous sequence retains at least one biological function of human gasdermin A or mouse gasdermin A, GSDM A2 or GSDM A3 that is of interest in the present context. This latter homologous sequence shares preferably at least 50%, preferably at least 60%, more preferably at least 70%, more preferably at least 80%, and even more preferably at least 90% identity with SEQ ID NO:21, SEQ ID NO:22, SEQ ID NO:23 or SEQ ID NO:24.

Preferably, the identity percentage between said homologous sequence and SEQ ID NO:21, SEQ ID NO:22, SEQ ID NO:23 or SEQ ID NO:24 is identified by a global alignment of the sequences in their entirety, this alignment being performed by means of an algorithm that is well known by the skilled person, such as the one disclosed in Needleman and Wunsch (1970). Accordingly, sequence comparisons between two amino acid sequences can be performed for example by using any software known by the skilled person, such as the "needle" software using the "Gap open" parameter of 10, the "Gap extend" parameter of 0.5 and the "Blosum 62" matrix.

In another embodiment, the term "gasdermin A" also designates any polypeptide encoded by a gasdermin A gene. In a preferred embodiment, said gasdermin A gene is chosen in the group consisting of: SEQ ID NO:25, SEQ ID NO:26, SEQ ID NO:27, SEQ ID NO:28 or any homologous gene of another animal species, said homologous gene sharing preferably at least 50%, more preferably at least 60%, more preferably at least 70%, more preferably at least 80%, and even more preferably at least 90% identity with SEQ ID NO:25, SEQ ID NO:26, SEQ ID NO:27 or SEQ ID NO:28.

In another embodiment, the term "gasdermin A" also designates any fragment of human gasdermin A or mouse gasdermin A, GSDM A2 or GSDM A3 or any fragment of a polypeptide having an homologous sequence as defined above, wherein said fragment retains at least one biological function of human gasdermin A or mouse gasdermin A, GSDM A2 or GSDM A3 that is of interest in the present context. This fragment shares preferably at least 30%, preferably at least 40%, more preferably at least 50%, more preferably at least 60%, and even more preferably at least 70% identity with SEQ ID NO:21, SEQ ID NO:22, SEQ ID NO:23 or SEQ ID NO:24.

Gasdermin B is a protein which belongs to the gasdermin family. In human, gasdermin B isoform 3 has the sequence SEQ ID NO:29 (NCBI Reference Sequence: NP_001159430.1). It is known to be expressed in oesophagus, stomach, liver, and colon. The function of gasdermin B is not known. The gene Gsdmb was not identified in mouse genome.

Human gasdermin B is encoded by the transcript variant 3 (mRNA) of SEQ ID NO:30 in human (NCBI Reference Sequence: NM_001165958.1).

In the context of the invention, the term "gasdermin B" herein designates a polypeptide having the amino acid sequence SEQ ID NO:29 (human gasdermin B) or an homologous sequence thereof. Said latter homologous sequence is for example the gasdermin B protein of another animal species, the polypeptide having said latter homologous sequence retains at least one biological function of human gasdermin B that is of interest in the present context. This homologous sequence shares preferably at least 50%, preferably at least 60%, more preferably at least 70%, more preferably at least 80%, and even more preferably at least 90% identity with SEQ ID NO:29.

Preferably, the identity percentage between said homologous sequence and SEQ ID NO:29 is identified by a global alignment of the sequences in their entirety, this alignment being performed by means of an algorithm that is well known by the skilled person.

In another embodiment, the term "gasdermin B" also designates any polypeptide encoded by a gasdermin B gene. In a preferred embodiment, said gasdermin B gene is chosen in the group consisting of: SEQ ID NO:30 or any homologous gene of another animal species, said homologous gene sharing preferably at least 50%, more preferably at least 60%, more preferably at least 70%, more preferably at least 80%, and even more preferably at least 90% identity with SEQ ID NO:30.

In another embodiment, the term "gasdermin B" also designates any fragment of human gasdermin B or any fragment of a polypeptide having a homologous sequence as defined above, wherein said fragment retains at least one biological function of human gasdermin B that is of interest in the present context. This fragment shares preferably at least 30%, preferably at least 40%, more preferably at least 50%, more preferably at least 60%, and even more preferably at least 70% identity with SEQ ID NO:29.

Gasdermin C is a protein which belongs to the gasdermin family. In human, it has the sequence SEQ ID NO:31 (NCBI Reference Sequence: NP_113603.1). In mouse, gasdermin C has the sequence SEQ ID NO:32 (NCBI Reference Sequence: NP_113555.1), gasdermin C2 has the sequence SEQ ID NO:33 (NCBI Reference Sequence: NP_001161746.1), gasdermin C3 has the sequence SEQ ID NO:34 (NCBI Reference Sequence: NP_899017.2). It is known to be expressed in oesophagus, stomach, trachea, spleen, and skin and its function is not known.

Human gasdermin C is encoded by the mRNA of SEQ ID NO:35 (NCBI Reference Sequence: NM_031415.2). The mouse gasdermin C gene is of SEQ ID NO:36 (NCBI Reference Sequence: NM_031378.3), the gasdermin C2 gene is of SEQ ID NO:37 (NCBI Reference Sequence: NM_001168274.1) and the gasdermin C3 gene is of SEQ ID NO:38 (NCBI Reference Sequence: NM_183194.3)

In the context of the invention, the term "gasdermin C" herein designates a polypeptide having the amino acid sequence SEQ ID NO:31 (human gasdermin C) or SEQ ID NO:32, SEQ ID NO:33, SEQ ID NO:34 (mouse gasdermin C, gasdermin C2 and gasdermin C3 respectively) or an homologous sequence thereof. Said latter homologous sequence is for example the gasdermin C protein of another animal species, the polypeptide having said latter homologous sequence retains at least one biological function of human gasdermin C or mouse gasdermin C, C2 or C3 that is of interest in the present context. This homologous sequence shares preferably at least 50%, preferably at least 60%, more preferably at least 70%, more preferably at least 80%, and even more preferably at least 90% identity with SEQ ID NO:31, SEQ ID NO:32, SEQ ID NO:33 or SEQ ID NO:34.

Preferably, the identity percentage between said homologous sequence and SEQ ID NO:31, SEQ ID NO:32, SEQ ID NO:33 or SEQ ID NO:34 is identified by a global alignment of the sequences in their entirety, this alignment being performed by means of an algorithm that is well known by the skilled person.

In another embodiment, the term "gasdermin C" also designates any polypeptide encoded by a gasdermin C gene. In a preferred embodiment, said gasdermin C gene is chosen in the group consisting of: SEQ ID NO:35, SEQ ID NO:36, SEQ ID NO:37, SEQ ID NO:38, or any homologous gene of another animal species, said homologous gene sharing preferably at least 50%, more preferably at least 60%, more preferably at least 70%, more preferably at least 80%, and even more preferably at least 90% identity with SEQ ID NO:35, SEQ ID NO:36, SEQ ID NO:37 or SEQ ID NO:38.

In another embodiment, the term "gasdermin C" also designates any fragment of human gasdermin C or mouse gasdermin C, C2 or C3 or any fragment of a polypeptide having a homologous sequence as defined above, wherein said fragment retains at least one biological function of human gasdermin C or mouse gasdermin C, C2 or C3 that is of interest in the present context. This fragment shares preferably at least 30%, preferably at least 40%, more preferably at least 50%, more preferably at least 60%, and even more preferably at least 70% identity with SEQ ID NO:31, SEQ ID NO:32, SEQ ID NO:33 or SEQ ID NO:34.

Gasdermin D is a protein belonging to the gasdermin family. In human, it has the sequence SEQ ID NO:39 (NCBI Reference Sequence: NP_001159709.1). In mouse, it has the sequence SEQ ID NO:40 (NCBI Reference Sequence: NP_081236.1). It is known to be expressed in oesophagus and stomach and is involved in pyroptotic cell death (Shi J et al., 2015; Kayagaki et al., 2015). This activity appears upon a cleavage of the protein by caspase-11.

Human gasdermin D is encoded by the mRNA of SEQ ID NO:41 in human (NCBI Reference Sequence: NM_001166237.1). The mouse gasdermin D gene is of SEQ ID NO:42 (NCBI Reference Sequence: NM_026960.4).

In the context of the invention, the term "gasdermin D" herein designates a polypeptide having the amino acid sequence SEQ ID NO:39 (human gasdermin D) or SEQ ID NO:40 (mouse gasdermin D) or an homologous sequence thereof. Said latter homologous sequence is for example the gasdermin D protein of another animal species, the polypeptide having said gasdermin D homologous sequence retains at least one biological function of human gasdermin D or mouse gasdermin D that is of interest in the present context. This homologous sequence shares preferably at least 50%, preferably at least 60%, more preferably at least 70%, more preferably at least 80%, and even more preferably at least 90% identity with SEQ ID NO:39 or SEQ ID NO:40.

Preferably, the identity percentage between said homologous sequence and SEQ ID NO:39 or SEQ ID NO:40 is identified by a global alignment of the sequences in their entirety, this alignment being performed by means of an algorithm that is well known by the skilled person.

In another embodiment, the term "gasdermin D" also designates any polypeptide encoded by a gasdermin D gene. In a preferred embodiment, said gasdermin D gene is chosen in the group consisting of: SEQ ID NO:41, SEQ ID NO:42, or any homologous gene of another animal species, said homologous gene sharing preferably at least 50%, more preferably at least 60%, more preferably at least 70%, more preferably at least 80%, and even more preferably at least 90% identity with SEQ ID NO:41 or SEQ ID NO:42.

In another embodiment, the term "gasdermin D" also designates any fragment of human gasdermin D or mouse gasdermin D or any fragment of a polypeptide having a homologous sequence as defined above, wherein said fragment retains at least one biological function of human gasdermin D or mouse gasdermin D that is of interest in the present context. This fragment shares preferably at least 30%, preferably at least 40%, more preferably at least 50%, more preferably at least 60%, and even more preferably at least 70% identity with SEQ ID NO:39 or SEQ ID NO:40.

DFNA5 is a protein which belongs to the gasdermin family. In human, it has the sequence SEQ ID NO:43 (NCBI Reference Sequence: NP_004394.1). In mouse, non-syndromic hearing impairment protein homolog has the sequence SEQ ID NO:44 (NCBI Reference Sequence: NP_061239.1). It is known to be expressed in placenta, brain, heart, kidney, lung, liver, skin, eye, and cochlea. The role of the protein is not yet known. However, the N-terminal of DFNA5 has been showed to induce apoptosis in transfected human cell lines (Op de Beeck et al., 2011). In addition, it has been shown that endogenous DFNA5 is epigenetically silenced by hypermethylation in several forms of cancer and it is considered as a tumour suppressor gene (Akino et al., 2007; Kim et al, 2008a,b; Wang et al., 2013). Several impairing mutations have been described. These mutations are located in either intron 7 or intron 8 of DFNA5 and resulted in skipping of exon 8 and premature termination of the encoded protein (Van Laer et al., 1998; Yu et al., 2003; Bischoff et al., 2004; Cheng et al., 2007; Park et al., 2010; Chai et al., 2014; Nishio et al., 2014; Li-Yang et al., 2015).

Human DFNA5 is encoded by the DFNA5 transcript variant 1 (mRNA) of SEQ ID NO:45 in human (NCBI Reference Sequence: NM_004403.2). The mouse DFNA5 gene is of SEQ ID NO:46 (NCBI Reference Sequence: NM_018769.3).

In the context of the invention, the term "DFNA5" herein designates a polypeptide having the amino acid sequence SEQ ID NO:43 (human DFNA5) or SEQ ID NO:44 (mouse DFNA5) or an homologous sequence thereof. Said latter homologous sequence is for example the DFNA5 protein of another animal species, the polypeptide having said DFNA5 homologous sequence retains at least one biological function of human DFNA5 or mouse DFNA5 that is of interest in the present context. This homologous sequence shares preferably at least 50%, preferably at least 60%, more preferably at least 70%, more preferably at least 80%, and even more preferably at least 90% identity with SEQ ID NO:43 or SEQ ID NO:44.

Preferably, the identity percentage between said homologous sequence and SEQ ID NO:43 or SEQ ID NO:44 is identified by a global alignment of the sequences in their entirety, this alignment being performed by means of an algorithm that is well known by the skilled person.

In another embodiment, the term "DFNA5" also designates any polypeptide encoded by a DFNA5 gene. In a preferred embodiment, said DFNA5 gene is chosen in the group consisting of: SEQ ID NO:45, SEQ ID NO:46, or any homologous gene of another animal species, said homologous gene sharing preferably at least 50%, more preferably at least 60%, more preferably at least 70%, more preferably at least 80%, and even more preferably at least 90% identity with SEQ ID NO:45 or SEQ ID NO:46.

In another embodiment, the term "DFNA5" also designates any fragment of human DFNA5 or mouse DFNA5 or any fragment of a polypeptide having a homologous sequence as defined above, wherein said fragment retains at least one biological function of human DFNA5 or mouse DFNA5 that is of interest in the present context. This fragment shares preferably at least 30%, preferably at least 40%, more preferably at least 50%, more preferably at least 60%, and even more preferably at least 70% identity with SEQ ID NO:43 or SEQ ID NO:44.

Besides (alternatively or additionally, depending on the embodiment under consideration) gasdermins, one can use other antioxidants compounds such as those described below.

Cyclophilin A is involved in the reduction of hydrogen peroxide ($H_2O_2$) into $H_2O$, indirectly via the activation of several peroxiredoxins (Lee et al., 2001; Evans and Halliwell, 1999).

c-dopachrome tautomerase decreases cell sensitivity to oxidative stress by increasing reduced glutathione (GSH) level, the major small antioxidant molecule of the cell (Michard et al., 2008a; 2008b).

Although Mpv17 has a yet unknown activity, Mpv17-defect in both human and mouse results in a hepatocerebral mitochondrial DNA depletion syndrome with profound deafness (Binder et al., 1999) reported in the mutant mice and reactive oxygen species (ROS) accumulation (Meyer zum Gottesberge et al., 2001).

With the present results, it is the first time that a gasdermin, pejvakin, is pinpointed as a key element in NIHL affecting outer hair cells, inner hair cells and neurons of the auditory pathways. Its role is of high importance to prevent ROS induced cellular damages in auditory cells.

In the aspect of the present invention yet described above, it is related to the use of a gasdermin for modulating cellular redox homeostasis. Thus, the present invention concerns the use of a gasdermin as a redox modulator.

In a particular embodiment of this aspect, the present invention relates to the use of a gasdermin chosen among: gasdermin A, gasdermin B, gasdermin C, gasdermin D, DFNA5 and DFNB59 (or pejvakin) for modulating cellular redox homeostasis. Thus, the present invention concerns the use of a gasdermin chosen among: gasdermin A, gasdermin B, gasdermin C, gasdermin D, DFNA5 and DFNB59 (or pejvakin), as a redox modulator.

In a preferred embodiment, a gasdermin, in a particular embodiment: gasdermin A, gasdermin B, gasdermin C, gasdermin D, DFNA5 or DFNB59 (or pejvakin) and in a more particular embodiment: pejvakin, is therefore used to prevent and/or reduce ROS-induced cellular damages, especially in cochlear hair cells, afferent auditory neurons and neurons of the auditory brainstem and auditory central pathway, in a subject in need thereof. In a preferred embodiment, a gasdermin, in a particular embodiment: gasdermin A, gasdermin B, gasdermin C, gasdermin D, DFNA5 or DFNB59 (or pejvakin), and in a more particular embodiment: pejvakin, is used to prevent and/or reduce ROS-induced cellular damages in Inner Hair Cells (IHC), Outer Hair Cells (OHC), or neurons of the auditory pathway.

More generally, a gasdermin, in a particular embodiment: gasdermin A, gasdermin B, gasdermin C, gasdermin D, DFNA5 or DFNB59 (or pejvakin), and in a more particular embodiment: PJVK, is likely to be a key element in preventing and/or treating the noise-induced damages affecting auditory cells such as cochlear hair cells, afferent auditory neurons and neurons of the auditory brainstem and auditory central pathway, in a subject in need thereof.

Although noise exposure is known to induce oxidative stress as the result of cellular hyperactivity, which is normally associated with an antioxidant protective response, it is herein reported for the first time that even exposure to low energy sound induces an antioxidant protective response.

In a preferred embodiment, a gasdermin, in a particular embodiment: gasdermin A, gasdermin B, gasdermin C, gasdermin D, DFNA5 or DFNB59 (or pejvakin), and in a more particular embodiment: pejvakin, is thus used to prevent and/or reduce ROS-induced cellular damages due to noise exposure. These ROS-induced cellular damages are for example diagnosed in subjects suffering from noise-induced hearing loss (NIHL). NIHL encompasses all types of permanent hearing losses resulting from excessive exposure to intense sounds, which induces mechanical deleterious effects (e.g., to stereocilia bundles and to the plasma membrane of auditory hair cells) and metabolic disturbances (e.g., leading to a swelling of the synaptic regions of IHCs and auditory neurons, in relation to the excitotoxicity of the neurotransmitter, glutamate).

Presbycusis, which affects more than 30% people above 60 and overall, about 5 million people in France, is the result of a combination of factors, genetic and environmental (lifelong exposure to noise and to chemicals). Yet it has been shown in the 1950s that subjects who spend their lives in silent environments do not suffer from any hearing loss even in their 80 s. This, and a huge body of evidence collected in subjects occupationally exposed to noise, leads to conclude that noise-induced hearing loss (NIHL) is the dominant cause of hearing impairment in ageing subjects.

In a more preferred embodiment, a gasdermin, in a particular embodiment: gasdermin A, gasdermin B, gasdermin C, gasdermin D, DFNA5 or DFNB59 (or pejvakin) and in a more particular embodiment: pejvakin, is used to prevent and/or treat presbycusis or age-related hearing impairment.

ROS-induced damages may also be due to an acoustic trauma, which may occur after a single, short exposure to extremely loud noise (>120 dB SPL). As a matter of fact, it is thought that, after such an acoustic trauma, subjects experience protracted worsening of their hearing lesions in relation to disrupted ROS metabolism and its consequences on cellular homeostasis, even when these subjects have a normal antioxidant equipment. Likely, their antioxidant defences can be easily overwhelmed by the after-effects of the acoustic trauma. A gasdermin, and in particular pejvakin could improve the way that these patients heal and recover hearing after a damaging exposure. Thus, in a more preferred embodiment, a gasdermin: gasdermin A, gasdermin B, gasdermin C, gasdermin D, DFNA5 or DFNB59 (or pejvakin) and, and in particular pejvakin, is used to prevent and/or treat sensorineural hearing losses due to an acoustic trauma.

In normal subjects exposed to loud sound, even below the legal limit, and who might suffer damage to their auditory structures (e.g., the so-called hidden hearing impairment reported by Kujawa and Liberman (2009), with loss of a specific population of auditory neurons which leads to poor understanding in noise and to hyperacusis and tinnitus despite the lack of elevation in hearing thresholds, shows that this situation is conceivable and possibly widespread), controlled intake of pejvakin should increase the level of protection of the auditory system and protect against 'hidden' forms of neuropathic presbycusis.

In a more preferred embodiment, a gasdermin, in a particular embodiment gasdermin A, gasdermin B, gasdermin C, gasdermin D, DFNA5 or DFNB59 (or pejvakin) and in a more particular embodiment: pejvakin, is therefore used to prevent and/or treat hearing impairment including, e.g., hearing loss and auditory threshold shift.

In addition to direct effects of noise exposure, other factors also involve ROS metabolism and increased oxidative stress, notably chemical substances known for their ototoxicity. A targeted application of a gasdermin, and in particular pejvakin, should be able to alleviate these side-effects, even when the initial insult that triggers ROS production is not mechanical, but chemical.

In a preferred embodiment, the present invention therefore targets a gasdermin, in a particular embodiment gasdermin A, gasdermin B, gasdermin C, gasdermin D, DFNA5 or DFNB59 (or pejvakin), and in a more particular embodiment PJVK, for use for preventing and/or treating auditory damages induced by exposure to ototoxic substances. Said ototoxic substances can be medication or chemical substances on which a subject has been unfortunately or voluntarily exposed.

There are more than 200 known ototoxic medications (prescription and over-the-counter) on the market today. These include medicines used to treat serious infections, cancer, and heart disease. Ototoxic medications known to cause permanent damage include certain aminoglycoside antibiotics, such as gentamicin, and cancer chemotherapy drugs, such as cisplatin and carboplatin.

Other medications may reversibly affect hearing. This includes some diuretics, aspirin and NSAIDs, and macrolide antibiotics. On Oct. 18, 2007, the U.S. Food and Drug Administration (FDA) announced that a warning about possible sudden hearing impairment would be added to drug labels of PDE5 inhibitors, which are used for erectile dysfunction.

In addition to medications, hearing impairment including hearing loss and auditory threshold shift may result from specific drugs, metals (such as lead, mercury, trimethyltin), solvents (such as toluene, for example found in crude oil, gasoline and automobile exhaust, styrene, xylene, n-hexane, ethyl benzene, white spirit, carbon disulfide, perchloroethylene, trichloroethylene, or p-xylene), pesticides/herbicides (organophosphates) and asphyxiating agents (carbon monoxide, hydrogen cyanide).

To conclude, a gasdermin, in a particular embodiment: gasdermin A, gasdermin B, gasdermin C, gasdermin D, DFNA5 or DFNB59 (or pejvakin) and in a more particular embodiment: PJVK may be used to prevent and/or treat acquired sensorineural hearing impairments that involve ROS metabolism and increased oxidative stress. These disorders may be due to direct effect of noise exposure (e.g. intense acoustic trauma, presbycusis) or to chemical substances that are known for their ototoxicity.

In a preferred embodiment, a gasdermin, in a particular embodiment: gasdermin A, gasdermin B, gasdermin C, gasdermin D, DFNA5 or DFNB59 (or pejvakin) and in a more particular embodiment: PJVK is thus used to prevent and/or treat presbycusis, noise-induced hearing loss or sudden sensorineural hearing impairment or auditory damages induced by acoustic trauma or ototoxic substances, in a subject in need thereof.

As used herein, the term "hearing impairment" refers to a hearing defect that can either be congenital or not.

As used herein, the term "hearing loss" refers to a hearing defect that develops in previously normal hearing individual. It can appear at any age.

As used herein the term "auditory threshold shift" is intended to mean any reduction in a subject's ability to detect sound. Auditory threshold shift is defined as a 10 decibel (dB) standard threshold shift or greater in hearing sensitivity for two of 6 frequencies ranging from 0.5-6.0 (0.5, 1, 2, 3, 4, and 6) kHz (cited in Dobie, R. A. (2005)). Auditory threshold shift can also be only high frequency, and in this case would be defined as 5 dB auditory threshold shift at two adjacent high frequencies (2-6 kHz), or 10 dB at any frequency above 2 kHz.

As used herein, the term "treating" is intended to mean the administration of a therapeutically effective amount of one of the antioxidant compound of the invention to a subject who is suffering from a disease, e.g., a loss or impairment of hearing, in order to minimize, reduce, or completely impair the symptoms of same, e.g., the loss of hearing. "Treatment" is also intended to designate the complete restoration of hearing function regardless of the cellular mechanisms involved.

In the context of the present invention, the term "preventing" a disease, e.g., presbycusis, herein designates impairing or delaying the development of the symptoms of said disease, e.g., delaying the impairment of hearing sensitivity within the aforesaid frequency range, particularly at the high frequency range above 3-4 kHz.

Some congenital hearing impairments are known to affect ROS homeostasis in the auditory system. These disorders are for example the Usher syndrome (USH), Alport syndrome (AS), Alstrom syndrome (ALMS), Bardet-Biedl syndrome (BBS), Cockayne syndrome (CS), spondyloepiphyseal dysplasia congenital (SED), Flynn-Aird syndrome, Hurler syndrome (MPS-1), Kearns-Sayre syndrome (CPEO), Norrie syndrome, and Albers-Schonberg disease (ADO II). Thus, in another embodiment a gasdermin: gasdermin A, gasdermin B, gasdermin C, gasdermin D, DFNA5 or DFNB59 (or pejvakin) and in a more particular embodiment: pejvakin may be used for restoring the auditory capacities in subjects suffering from these congenital hearing impairments.

As explained in the experimental part below, localization of pejvakin to peroxisomes, organelles that are major effectors in the response to oxidative stress, ultrastructural anomalies of this organelle in Pjvk$^{-/-}$ mice and transfection experiments suggested a role of pejvakin in stress-induced peroxisome proliferation. More generally, administration of a gasdermin: gasdermin A, gasdermin B, gasdermin C, gasdermin D, DFNA5 or DFNB59 (or pejvakin) and in a more particular embodiment: pejvakin, would help treating peroxisomal disorders.

In another embodiment, the present invention therefore relates to a gasdermin, in a particular embodiment: gasdermin A, gasdermin B, gasdermin C, gasdermin D, DFNA5 or DFNB59 (or pejvakin) and in a more particular embodiment: pejvakin, for use as antioxidant for treating subjects suffering from peroxisomal disorders or mitochondrial disorders leading to ROS production.

Said peroxisomal disorders are preferably chosen in the group consisting of: the Zellweger syndrome (ZS), the infantile Refsum disease (IRD), neonatal adrenoleukodystrophy (NALD) and the rhizomelic chondrodysplasia punctata type 1 (RCDP1). More precisely, pejvakin would improve the hearing capacity of subjects suffering from said peroxisomal disorders.

In a preferred embodiment, a gasdermin, in a particular embodiment: gasdermin A, gasdermin B, gasdermin C, gasdermin D, DFNA5 or DFNB59 (or pejvakin) and in a more particular embodiment: pejvakin, is used for restoring peroxisome and/or mitochondria-mediated homeostasis in auditory cells from said subjects.

Sensorineural hearing disorders were already reported as part of the picture of extremely severe diseases, which belong to the spectrum of Zellweger disease and occur when the biogenesis of peroxisomes is defective. In these cases, metabolism is impaired in many organs. The patients die in early childhood, except when they are affected by milder forms of this spectrum of diseases, notably those with late onset (e.g., in relation to PEX6 mutations, Tran et al., 2014). Presence of hearing impairment has been reported in most of these patients, and usually ascribed to abnormal neural conduction in relation to adrenoleukodystrophy-like dysfunctions.

In a particular embodiment, a gasdermin, in a particular embodiment: gasdermin A, gasdermin B, gasdermin C, gasdermin D, DFNA5 or DFNB59 (or pejvakin) and in a more particular embodiment pejvakin, is used as antioxidant for improving the hearing in subjects suffering from the Zellweger disease or from other peroxisomal disorders that come with hearing impairment.

Other severe conditions are thought to involve failure of ROS metabolism, which might be improved by the use of a gasdermin, in a particular embodiment: gasdermin A, gasdermin B, gasdermin C, gasdermin D, DFNA5 or DFNB59 (or pejvakin) and in a more particular embodiment: pejvakin, as it is able to activate important protective pathways much more specifically and powerfully than existing drugs. For example, it may be possible to use a gasdermin, and in particular pejvakin, to treat other neurodegenerative disorders involving peroxisomal defects, such as Parkinson's disease (PD), Alzheimer's disease (AD), Familial Amyotrophic Lateral Sclerosis (FALS), as well as other age-related disorders including age-related macular degeneration (ARMD), type 2 diabetes, atherosclerosis, arthritis, cataracts, osteoporosis, hypertension, skin aging, skin pigmentation, and cardiovascular diseases.

As previously mentioned, pejvakin belongs to gasdermins, whose actual functions remain unknown. Nonetheless, some gasdermins have been incriminated in oesophageal and gastric cancers, hepatocarcinomas and breast carcinomas. It is acknowledged that the redox status of cancer cells usually differs from that of normal cells, and that the regulation of oxidative stress and of the metabolism of ROS is a key element of tumour growth and of responses to anticancer therapies. The potent role of pejvakin in the protection of auditory structures against effects of oxidative stress suggests that this molecule could influence or modulate cancer development.

In a preferred embodiment, a gasdermin, in a particular embodiment: gasdermin A, gasdermin B, gasdermin C, gasdermin D, DFNA5 or DFNB59 (or pejvakin) and in a more particular embodiment: pejvakin, is thus used for treating subjects suffering from cancer, inflammatory diseases and ischemia-reperfusion injury.

Typically, said cancer is chosen in the group consisting of: breast cancer, head and neck cancer, lung cancer, ovarian cancer, pancreatic cancer, colorectal carcinoma, breast carcinoma, hepatocarcinoma, cervical cancer, sarcomas, brain tumours, renal cancer, prostate cancer, melanoma and skin cancers, oesophageal or gastric cancer, multiple myeloma, leukaemia or lymphoma.

In a preferred embodiment, said cancer is an oesophageal or a gastric cancer, a hepatocarcinoma or a breast carcinoma.

In another embodiment, gasdermin is used as a modulator of cellular redox homeostasis for preventing and/or reversing skin aging and/or skin pigmentation. Preferably, said gasdermin is pejvakin. Said gasdermin may be used in a subject normally expressing gasdermin.

Here, said gasdermin can be either therapeutically applied to treat and/or prevent pathological disorders, states, diseases, conditions, or cosmetically applied to attenuate, alleviate, slow down, remedy, reduce, overcome, reverse, delay, limit, and/or prevent aesthetic skin troubles due to normal aging.

In one embodiment, gasdermin is cosmetically used for preventing, delaying, attenuating, overcoming, reducing, slowing down, limiting, alleviating, and/or reversing skin aging and skin pigmentation. Said gasdermin may be used in a subject normally expressing gasdermin.

More generally, it would be possible to use a gasdermin, in a particular embodiment: gasdermin A, gasdermin B, gasdermin C, gasdermin D, DFNA5 or DFNB59 (or pejvakin) and in a more particular embodiment pejvakin, to treat all the diseases due to the failure of ROS metabolism, especially those that are age-related such as Parkinson's disease (PD), Alzheimer's disease (AD), Familial Amyotrophic Lateral Sclerosis (FALS), age-related macular degeneration (ARMD), type 2 diabetes, atherosclerosis, arthritis, cataracts, osteoporosis, hypertension, skin aging, skin pigmentation, and cardiovascular diseases.

As used herein, the term "subjects" is intended to mean humans or non-human mammals such as primates, cats, dogs, swine, cattle, sheep, goats, horses, rabbits, rats, mice and the like. In a preferred embodiment, said subjects are human subjects.

In another preferred embodiment, said subjects do not suffer from a hereditary hearing impairment.

In a more preferred embodiment, said subjects have a normal expression of endogenous gasdermin, in a particular embodiment: gasdermin A, gasdermin B, gasdermin C, gasdermin D, DFNA5 or DFNB59 (or pejvakin) and in a more particular embodiment: pejvakin.

By "normal expression of gasdermin" it is herein meant that gasdermin, and in particular the GSDMA, GSDMB, GSDMC, GSDMD, DFNA5 and DFNB59 genes are normally expressed in the treated subject (i.e., neither the GSDMA, GSDMB, GSDMC, GSDMD, DFNA5 and/or DFNB59 genes nor their transcription are altered as compared with healthy subjects), and that the endogenously encoded gasdermin polypeptides are normally expressed (i.e., they are functional and expressed at a normal level as compared with healthy subjects). As a matter of fact, the use of a gasdermin for restoring the auditory capacity of subjects having an altered expression level of a gasdermin is not encompassed within the scope of the present invention.

Expression of gasdermin, and in particular of pejvakin, in a subject may be assessed by any conventional means, such as RT-PCR or ELISA on a blood sample, in situ hybridization (ISH) and/or immunohistochemistry (IHC) on a tissue biopsy when available, or by clinical imaging.

In all of these applications, it is possible to combine the gasdermin, in a particular embodiment: gasdermin A, gasdermin B, gasdermin C, gasdermin D, DFNA5 or DFNB59 (or pejvakin) and in a more particular embodiment: PJVK treatment with another antioxidant treatment or with a RS inhibiting compound as defined below.

In Vivo Administration of Gasdermin, and in Particular Pejvakin: Vectors

The gasdermin, in a particular embodiment: gasdermin A, gasdermin B, gasdermin C, gasdermin D, DFNA5 or DFNB59 (or pejvakin) and in a more particular embodiment: pejvakin, polypeptide can be administered directly to the subject. In this case, the gasdermin, in a particular embodiment: gasdermin A, gasdermin B, gasdermin C, gasdermin D, DFNA5 or DFNB59 (or pejvakin) and in a more particular embodiment: pejvakin polypeptide is advantageously included in a pharmaceutical composition as disclosed below.

In a preferred embodiment, the gasdermin, in a particular embodiment: gasdermin A, gasdermin B, gasdermin C, gasdermin D, DFNA5 or DFNB59 (or pejvakin) and in a more particular embodiment: pejvakin polypeptide is produced in situ in the appropriate auditory cells by in vivo gene therapy.

Two alternative strategies for gene therapy can be contemplated for treating animal subjects. One strategy is to administer a vector encoding the gene of interest directly to the subject. The second is to use cells that have been i) removed from the target subject and ii) treated ex vivo with a vector expressing the gene of interest; these cells are then re-administered to the same subject.

Different methods for gene therapy are known in the art. These methods include, yet are not limited to, the use of DNA plasmid vectors as well as DNA and RNA viral vectors. In the present invention, such vectors may be used to express the pejvakin coding gene, DFNB59, in cells of the auditory pathway such as cochlear hair cells, afferent auditory neurons and neurons of the auditory brainstem pathway.

In another aspect, the present invention therefore relates to a vector encoding a gasdermin, in a particular embodiment: gasdermin A, gasdermin B, gasdermin C, gasdermin D, DFNA5 or DFNB59 (or pejvakin) and in a more particular embodiment the Pejvakin polypeptide, for use to prevent and/or treat noise-induced damages to auditory cells or peroxisomal disorders or cancer or inflammatory diseases or ischemia-reperfusion injury.

Preferably, said noise-induced damages lead to an acoustic trauma, presbycusis, noise-induced hearing loss (NIHL).

This vector may also be used to prevent and/or treat auditory damages due to ototoxic substance exposure.

Preferably, said peroxisomal disorders are chosen in the group consisting of: Zellweger syndrome (ZS), the infantile refsum disease (IRD), neonatal adrenoleukodystrophy (NALD) and the rhizomelic chondrodysplasia punctata type 1 (RCDP1).

Preferably, said cancer is chosen in the group consisting of: an esophageal, a gastric cancer, a hepatocarcinoma and a breast carcinoma.

In a preferred embodiment, said vector is a viral vector that is able to transfect the cells of the auditory pathway such as cochlear hair cells, afferent auditory neurons and neurons of the auditory brainstem pathway. These vectors are well-known in the art. They are for example lentiviruses, adenoviruses and Adeno-associated viruses (AAV).

The AAV vectors display several advantages such as i) a long lasting expression of synthesized genes (Cooper et al, 2006), ii) a low risk for pathogenic reactions (because they are artificially manufactured and not ototoxic), iii) they trigger low immunogenic response, and iv) they do not integrate the human genome (Kaplitt et al., 1994). AAV is therefore preferred to transfer the pejvakin coding gene in order to efficiently protect the auditory pathway.

In a more preferred embodiment, said vector is therefore an AAV vector.

The AAV vectors targeted by the present invention are any adeno-associated virus known in the art including, but not limited to AAV1, AAV2, AAV3, AAV4, AAV5, AAV6, AAV7, AAV8, AAV9, and AAV10.

In a more preferred embodiment, the serotype of said vector is AAV8, AAV5, or AAV1.

In order to increase the efficacy of gene expression, and prevent the unintended spread of the virus, genetic modifications of AAV can be performed. These genetic modifications include the deletion of the E1 region, deletion of the E1 region along with deletion of either the E2 or E4 region, or deletion of the entire adenovirus genome except the cis-acting inverted terminal repeats and a packaging signal. Such vectors are advantageously encompassed by the present invention.

Moreover, genetically modified AAV having a mutated capsid protein may be used so as to direct the gene expression towards a particular tissue type, e.g., to auditory cells. In this aim, modified serotype-2 and -8 AAV vectors in which tyrosine residues in the viral envelope are substituted for alanine residues can be used. In the case of tyrosine mutant serotype-2, tyrosine 444 can be substituted with alanine (AAV2-Y444A). In the case of serotype 8, tyrosine 733 can be substituted with an alanine reside (AAV8-Y733A).

Specific AAV vectors that would be able to carry a gasdermin, in particular the pejvakin, coding gene to auditory cells and methods to administer same are for example disclosed in WO 2011/075838. In the context of the invention, it would be for example possible to use the mutated tyrosine AAVs disclosed in WO 2011/075838 to deliver the pejvakin coding gene in auditory cells. These mutated vectors avoid degradation by the proteasome, and their transduction efficiency is significantly increased. Mutated tyrosine residues on the outer surface of the capsid proteins include, for example, but are not limited to, mutations of Tyr252 to Phe272 (Y252F), Tyr272 to Phe272 (Y272F), Tyr444 to Phe444 (Y444F), Tyr500 to Phe500 (Y500F), Tyr700 to Phe700 (Y700F), Tyr704 to Phe704 (Y704F), Tyr730 to Phe730 (Y730F) and Tyr733 to Phe733 (Y733F). These modified vectors facilitate penetration of the vector across the round window membranes, which allow for non-invasive delivery of the vectors to the hair cells/spiral ganglion neurons of the cochlea. For example, by using AAV2-Y444A or AAV8-Y733A, it is possible to increase gene transfer by up to 10,000 fold, decreasing the amount of AAV necessary to infect the sensory hair cells of the cochlea.

The skilled person would easily determine if it is required, prior to the administration of the vector of the invention, to enhance the permeability of the round window membrane as proposed in WO 2011/075838, depending on the target cell.

For instance, an appropriate vector in the context of the invention is an AAV8 vector. More particularly, it can be a vector having the nucleotide sequence of an AAV2 genome that is modified so as to encode AAV8 capsid proteins.

Another aspect of the present invention relates to a vector encoding pejvakin short hairpin RNA (shRNA), for use for treating cancer, inflammatory diseases or ischemia-reperfusion injury.

Use for Treating Congenital Hearing Impairment Due to Altered DFNB59 Gene Expression or Deficiency The present inventors studied for the first time the effect of antioxidants on the auditory function of Pjvk$^{-/-}$ mice.

A further aspect of the present invention concerns a Pjvk$^{-/-}$ mouse model, as described in detail in the Examples below.

N-acetyl L cysteine (NaC), and taurine, two antioxidant compounds, were administered to these mice. Their results show that these molecules have a protective effect on IHCs. Although the dose at which the molecules were administered was difficult to control, as mouse pups received the treatment via the milk delivered by their orally treated mother, in N-acetyl cysteine treated mice, the number of auditory neurons that responded to sound stimulation in synchrony was restored. Conversely, sound amplification by the cochlea and some aspects of neuronal conduction remained defective, unaffected by the treatment.

In another aspect, the present invention therefore relates to:
either a RS inhibiting compound and an antioxidant compound, such as N-acetyl cysteine or taurine or glutathione or a gasdermin, in a particular embodiment: gasdermin A or gasdermin B or gasdermin C or gas- dermin D or DFNA5 or pejvakin or cyclophilin A or c-dopachrome tautomerase or Mpv17, or
a RS inhibiting compound (such as N-acetyl cysteine or taurine or glutathione) or an antioxidant compound (with the exception of a gasdermin, and in particular with the exception of gasdermin A, gasdermin B, gasdermin C, gasdermin D, DFNA5, pejvakin) such as cyclophilin A or c-dopachrome tautomerase or Mpv17, for use (alone or in combination with one or more other active compounds) to treat subjects suffering from congenital hearing impairment due to altered DFNB59 gene expression or deficiency.

"Congenital hearing impairment due to altered DFNB59 gene expression or deficiency" herein designates the so-called "DFNB59 patients" described in the art. These patients exhibit an endogenous PJVK that is either truncated or mutated, and consequently not functional. These mutations are for example p.T54I, p.R183W, p.C343S, p.K41SfsX18, p.R167X and p.V330LfsX7 (Collin et al., 2007; Ebermann et al., 2007; Hashemzadeh Chaleshtori et al., 2007; Schwander et al., 2007; Borck et al., 2012; Mujtaba et al., 2012; Zhang et al., 2015).

A "RS inhibiting compound" herein designates any compound that is able to degrade/scavenge a Reactive Species such as ROS (Reactive Oxygen Species) or RNS (Reactive Nitrogen Species), namely superoxide, $H_2O_2$, hydroperoxide, lipid peroxide, lipoxygenase products, superoxide anion, hydroxyl- or alkoxyl-radicals. It is for example an enzyme (such as superoxide dismutase (SOD), catalase (CAT), Glutathione peroxidase (GPx), Glutathione reductase (GR)), or a metabolic compound (such as uric acid, creatine, cysteine, N-acetyl-cysteine, glutathione, 2-oxo-thiazolidine-4-carbixylate, and other thiol-delivering compounds, N-butyl-phenylnitrone, carnitine, lipoic acid, ubiquinone, or CoQ10) or a nutritional compound (such as Vitamin E, Vitamin C, selenium-containing compound ebselen, selenomethionine, and selenocysteine, polyphenols, flavonoids or a carotenoid). This definition applies to all aspects and embodiments of the invention.

Preferably, said RS inhibiting compound is neither gasdermin A, gasdermin B, gasdermin C, gasdermin D, DFNA5 or PJVK nor a vector encoding same.

More preferably, said RS inhibiting compound is chosen in the group consisting of: salicylate, N-acetyl cysteine, taurine, glutathione, and D-methionine.

In a preferred embodiment, said RS inhibiting compound is combined with an antioxidant compound of the invention. Said antioxidant compound is preferably, a gasdermin, and in particular gasdermin A, gasdermin B, gasdermin C, gasdermin D, DFNA5 or PJVK or a vector encoding same.

Other antioxidant compounds useful in the present invention are for example: cyclophilin A, glutathione peroxidase 2, c-dopachrome tautomerase, Mpv17, or any combination thereof.

In a particularly preferred embodiment, said antioxidant compound is a gasdermin, and in particular gasdermin A, gasdermin B, gasdermin C, gasdermin D, DFNA5 or PJVK, or a vector encoding same, which is combined with at least one other compound chosen in the group consisting of: cyclophilin A, glutathione peroxidase 2, c-dopachrome tautomerase, Mpv17, N-acetyl cysteine, or any combination thereof.

In another aspect, the present invention therefore targets a pharmaceutical composition comprising:
either an antioxidant compound (according to the present invention, including a gasdermin, and in particular gasdermin A, gasdermin B, gasdermin C, gasdermin D, DFNA5 or pejvakin) and at least one RS inhibiting compound (as defined above), or an antioxidant compound according to the present invention (with the exception of a gasdermin, and in particular with the exception of gasdermin A, gasdermin B, gasdermin C, gasdermin D, DFNA5 and pejvakin), or at least one RS inhibiting compound (as defined above), for use to treat subjects suffering from congenital hearing impairment due to altered DFNB59 gene expression or deficiency.

Use for Treating Hearing Impairments Other than Those Due to Altered DFNB59 Gene Expression or Deficiency Exposure to sound of high energy is known to induce oxidative stress as the result of cellular hyperactivity, which is associated with an antioxidant protective response. It is now shown that this also applies upon exposure to normally harmless sound energy.

A strong emphasis is now placed on the part played by ROS and oxidative stress as a possible common background to noise-induced damage to auditory sensory cells. For example it has been proposed that sound exposure results in an increased cytoplasmic concentration of $Ca^{2+}$, which may powerfully interact with mitochondrial metabolism and activate ROS production by mitochondria. When the amount of the produced ROS exceeds some limit, or when ROS homeostasis in the stimulated cells is inappropriate, pathophysiological responses may be triggered, which lead to increased cell damage and ultimately, cell death. Normally, the cells of the auditory system are thought to be abundantly equipped with molecules (e.g., melanin, glutathione) and pathways (e.g. superoxide dismutase) that keep their ROS metabolism under control. It is also widely thought that the abundance of these molecules in the cochlea bears some relationship with the metabolically demanding processes of hearing transduction.

In another aspect, the present invention therefore relates to an antioxidant compound for use to treat subjects suffering from hearing impairment, said hearing impairment being preferably due to noise (e.g., because of an acoustic trauma, presbycusis, or in case of hidden hearing impairment) or to ototoxic substances, with the exception of congenital hearing impairment due to altered DFNB59 gene expression or deficiency.

Said "antioxidant compound", as defined earlier, is capable of modulating the redox homeostasis of cells, preferably of auditory cells (for example by restoring the normal function of peroxisomes in auditory cells). In a preferred embodiment, it is not able to down-regulate Reactive Species (ROS or RNS) directly (e.g., by physical interaction leading to RS-degradation or scavenging).

In a preferred embodiment, said compound is any antioxidant compound capable of modulating the redox homeostasis of cells, including a gasdermin, and in particular gasdermin A, gasdermin B, gasdermin C, gasdermin D, DFNA5 or PJVK.

More preferably, said antioxidant compound is chosen in the group consisting of: gasdermins (and in particular among gasdermin A, gasdermin B, gasdermin C, gasdermin D, DFNA5, PJVK) cyclophilin A, glutathione peroxidase 2, c-dopachrome tautomerase, Mpv17 or combination thereof.

In another preferred embodiment, said subject has a normal expression of endogenous gasdermin A, gasdermin B, gasdermin C, gasdermin D, DFNA5 or pejvakin.

In a preferred embodiment, said antioxidant compound is combined with any of the RS inhibiting compound defined above. Said RS inhibiting compound is preferably chosen in the group consisting of: taurine, salicylate, N-acetyl cysteine, D-methionine and glutathione.

In another aspect, the present invention therefore targets a pharmaceutical composition comprising an antioxidant compound (according to the present invention) and optionally at least one RS inhibiting compound (as defined above), for use to treat subjects suffering from hearing impairment, such as a hearing loss preferably due to noise (e.g., because of an acoustic trauma, presbycusis, or in case of hidden hearing impairment) or to ototoxic substances, with the exception of congenital hearing impairment due to altered DFNB59 gene expression or deficiency.

In a preferred embodiment, said pharmaceutical composition contains a gasdermin, in a particular embodiment said pharmaceutical composition comprises gasdermin A, gasdermin B, gasdermin C, gasdermin D, DFNA5 or PJVK, or a vector encoding same, as an antioxidant compound.

Pharmaceutical Compositions

The antioxidant compounds (e.g., a gasdermin, in particular PJVK, or a vector encoding same, etc.) and/or RS inhibiting compounds of the invention are advantageously incorporated into pharmaceutical compositions suitable for an administration to a subject.

In another aspect, the present invention also relates to the use of the antioxidant compounds (e.g., gasdermin A, gasdermin B, gasdermin C, gasdermin D, DFNA5, PJVK or a vector encoding same, etc.) and/or RS inhibiting compounds of the invention for manufacturing pharmaceutical compositions intended to prevent and/or treat subjects suffering from the above-cited disorders.

More particularly, the present invention relates to the use of gasdermin A, gasdermin B, gasdermin C, gasdermin D, DFNA5, pejvakin, or a vector encoding same for manufacturing pharmaceutical compositions intended to treat subjects suffering from hearing impairment, from a peroxisomal disorder or from cancer. In a preferred embodiment, said hearing loss is due to noise or to ototoxic substances, as disclosed above, but not of genetic reasons (congenital hearing impairment due to DFNB59 deficiency being notably excluded). In another preferred embodiment, said peroxisomal disorders are chosen in the group consisting of: Zellweger syndrome (ZS), the infantile refsum disease (IRD), neonatal adrenoleukodystrophy (NALD) and the rhizomelic chondrodysplasia punctata type 1 (RCDP1). In another preferred embodiment, said cancer is an oesophageal or a gastric cancer, a hepatocarcinoma or a breast carcinoma.

Moreover, the present invention relates to the use of RS inhibiting compounds—other than gasdermin A, gasdermin B, gasdermin C, gasdermin D, DFNA5 or PJVK—for manufacturing pharmaceutical compositions intended to treat subjects suffering from congenital hearing impairment due to altered DFNB59 gene expression or deficiency.

The present invention also relates to pharmaceutical compositions comprising the antioxidant compounds and/or RS inhibiting compounds (chemical substances, polypeptides and/or vectors encoding same) described above, and a pharmaceutically acceptable carrier.

As used herein, "pharmaceutically acceptable carrier" includes any and all solvents, dispersion media, coatings, antibacterial and antifungal agents, isotonic and absorption delaying agents, and the like that are physiologically compatible. Examples of pharmaceutically acceptable carriers include one or more of water, saline, phosphate buffered saline, dextrose, glycerol, ethanol and the like, as well as combinations thereof. In many cases, it can be preferable to include isotonic agents, for example, sugars, polyalcohols such as mannitol, sorbitol, or sodium chloride in the composition. Pharmaceutically acceptable carriers can further comprise minor amounts of auxiliary substances such as wetting or emulsifying agents, preservatives or buffers, which enhance the shelf life or effectiveness of the antioxidant compounds or of the pharmaceutical compositions containing same.

The pharmaceutical compositions of the invention may be in a variety of forms. These include, for example, liquid, semi-solid and solid dosage forms, such as liquid solutions (e.g., injectable and infusible solutions), dispersions or suspensions, tablets, pills, powders, liposomes and suppositories. The form used depends on the intended mode of administration and therapeutic application. Typical compositions are in the form of injectable or infusible solutions, such as compositions similar to those used for passive immunization of humans.

In the context of the invention, the typical mode of administration of the composition of the invention is intratympanic (in the middle ear), intracochlear, or parenteral (e.g., intravenous, subcutaneous, intraperitoneal, intramuscular, intrathecal). In one example, the pharmaceutical composition of the invention is administered by intravenous infusion or injection. In another example, the pharmaceutical composition of the invention is administered by intramuscular or subcutaneous injection. In another example, the composition of the invention is administered perorally. In yet another example, the pharmaceutical composition of the invention is delivered to a specific location using stereostatic delivery, particularly through the tympanic membrane or mastoid into the middle ear.

Pharmaceutical compositions typically must be sterile and stable under the conditions of manufacture and storage. The pharmaceutical composition of the invention is preferably formulated as a solution, microemulsion, dispersion, liposome, or other ordered structure suitable to high drug concentration. Sterile injectable solutions can be prepared by incorporating the antioxidant compounds and/or RS inhibiting compounds of the invention in the required amount in an appropriate solvent optionally with one or a combination of ingredients enumerated above, as required, followed by filtered sterilization. Generally, dispersions are prepared by incorporating the antioxidant compounds and/or RS inhibiting compounds of the invention into a sterile vehicle that contains a basic dispersion medium and optionally other ingredients from those enumerated above, as required. In the case of sterile lyophilized powders for the preparation of sterile injectable solutions, the preferred methods of preparation are vacuum drying and spray-drying that yields a powder of the active ingredient plus any additional desired ingredient from a previously sterile-filtered solution thereof. The proper fluidity of a solution can be maintained, for example, by the use of a coating such as lecithin, by the maintenance of the required particle size in the case of dispersion and by the use of surfactants. Prolonged absorption of injectable compositions can be achieved by including an agent in the composition that delays absorption, for example, monostearate salts and gelatine.

The pharmaceutical composition of the invention can be administered by a variety of methods known in the art. As will be appreciated by the skilled artisan, the route and/or mode of administration will vary depending upon the desired results. In certain embodiments, the antioxidant compounds and/or RS inhibiting compounds of the invention may be prepared with a carrier that will protect same against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are generally known to those skilled in the art.

The pharmaceutical compositions of the invention include a "therapeutically effective amount" or a "prophylactically effective amount" of the antioxidant compounds and/or RS inhibiting compounds of the invention. A "therapeutically effective amount" refers to the amount of the antioxidant compounds and/or RS inhibiting compounds of the invention that is effective, at dosages and for periods of time necessary, to achieve the desired therapeutic result, in this case for both prophylaxis and treatment of hearing impairment or peroxisomal disorders or cancer without unacceptable toxicity or undesirable side effects.

A therapeutically effective amount of the antioxidant compounds and/or RS inhibiting compounds of the invention can vary according to factors such as the disease state, age, sex, and weight of the subject, and the ability of said compound to elicit a desired response in same. A therapeutically effective amount can also be one in which any toxic or detrimental effects of the claimed compounds are outweighed by the therapeutically beneficial effects. A "prophylactically effective amount" refers to an amount of the antioxidant compounds and/or RS inhibiting compounds of the invention that is effective, at dosages and for periods of time necessary, to achieve the desired prophylactic result. Typically, since a prophylactic dose can be used in subjects prior to or at an earlier stage of disease, the prophylactically effective amount is usually less than the therapeutically effective amount.

Dosage regimens can be adjusted to provide the optimum desired response (e.g., a therapeutic or prophylactic response). For example, a single bolus can be administered, several divided doses can be administered over time or the dose can be proportionally reduced or increased as indicated by the exigencies of the therapeutic situation. It can be especially advantageous to formulate parenteral compositions in dosage unit form for ease of administration and uniformity of dosage. Dosage unit form as used herein refers to physically discrete units suited as unitary dosages for the mammalian subjects to be treated; each unit containing a predetermined quantity of the antioxidant compound and/or RS inhibiting compounds of the invention calculated to produce the desired therapeutic effect in association with the required pharmaceutical carrier. The specification for the dosage unit forms can be dictated by and directly dependent on (a) the unique characteristics of the antioxidant compound and/or RS inhibiting compounds and the particular therapeutic or prophylactic effect to be achieved, and (b) the limitations inherent in the art of formulating such antioxidant compound and/or RS inhibiting compounds for treating or preventing hearing impairment or peroxisomal disorders in a subject.

Method to Diagnose and Treat a Hypervulnerability to Sound

Acoustic energy is the main factor that determines the damaging effects of exposure to loud sounds. To evaluate chronic exposure to sound, one uses the LEX index, the level of a stable sound which, presented over an eight-hour working shift, would deliver the same acoustic energy. This LEX calculates the energies delivered by sounds with different levels and time courses, and allows their detrimental potential to be compared. For occupational noise exposure, the LEX must not exceed a legally-fixed limit above which it is estimated that permanent hearing loss may occur if the exposure is a long-lasting one (e.g., an 8-h working shift, 5 days/week, 48 weeks/year, for 40 years). The legal limit for LEX in western countries varies from 80 to 90 dB (e.g., 80 dB in the European Community; 90 dB in the USA—OSHA—; A-weighted, i.e., measured through a filter which reproduces the frequency-dependence of human hearing sensitivity).

The present Inventors have discovered that mouse mutants in which pejvakin is defective or absent, and which, as a result, suffer from congenital sensorineural hearing impairment, are inordinately vulnerable to short exposure to loud sound, to the point that a single exposure to a LEX of 63 dB leads to about 30 dB hearing threshold elevation which persists more than a week. In comparison, a legally acceptable LEX of 80 dB for a whole life of work normally leads to no hearing threshold elevation at all (and in the USA law, it is assumed that 90 dB is equally tolerable). As the dB scale is a logarithmic one, a two-fold increase in power translates into a 3-dB increase, and a ten-fold increase in power, in a 10-dB increase. Thus the LEX, which damages hearing in Pjvk$^{-/-}$ mice, is several orders of magnitude lower than the normally harmless dose of loud sound. This has never been reported before. Up until this observation, the lowest LEX reported in mutant animals and able to produce hearing loss, was 73 dB (10 times more energetic than our exposures). Furthermore, this loss was temporary, with recovery within the next few tens of hours; it had to reach 99 dB for the hearing loss to fail to recover rapidly (these mice were defective for an ATP receptor (Housley et al., 2013), as against 63 dB in Pjvk$^{-/-}$ mice. Another report showing that noise exposure may result in permanent neuronal damage in the absence of hearing threshold elevation used LEXs of 94 dB (1,000 times more energetic than our exposures).

The Inventors furthermore observed that DFNB59 patients, who carry deleterious mutations in the Pjvk gene, display the same astonishing sensitivity to loud sound exposure as Pjvk$^{-/-}$ mice. This was proved by recording their auditory-evoked potentials in response to impulse sounds. At a LEX=57 dB, these sounds, routinely used for audiological diagnosis at much higher levels, induced in all tested patients large changes in their evoked responses, with an increase in latency of all identifiable waves, which often exceeded 0.5 ms for wave V, and a strong two- to three-fold decrease in intensity. Such changes were never observed in control subjects who could be exposed to at least four times as much acoustic energy without suffering any change in latency or amplitude of their auditory evoked potentials. These phenomena were therefore unique to DFNB59 patients, and, akin to auditory fatigue, were fortunately reversible after 10 min in silence.

In another aspect, the present invention relates to a method for diagnosing an acoustic hypervulnerability in a subject, comprising the steps of:
a) measuring the expression level of the pejvakin polypeptide in said subject, and/or
b) detecting the presence of inactivating mutations in the pejvakin polypeptide in said subject, and/or
c) clinically audiological testing for sensorineural hearing impairment, e.g., by recording the auditory brainstem response (ABR) and otoacoustic emissions (OAEs) in said subject.

As a matter of fact, if the expression level of the pejvakin polypeptide is decreased in said subject (as compared to healthy individuals) or if the pejvakin polypeptide is expressed in normal amounts but is biologically unfunctional in said subject, or if the auditory cells of said subject exhibit altered peroxisomes (as compared with those of healthy individuals), then said subject is likely to be highly susceptible to noise exposure.

As observed in DFNB59 patients, this may lead to irreversible deafness.

Preferably, steps a) and b) are performed on auditory cells of said subject, more precisely on cochlear hair cells, afferent auditory neurons and neurons of the auditory brainstem pathway. Alternatively, they may be performed on blood samples.

In the context of the invention, the "expression level of the pejvakin polypeptide is decreased" in a subject if the transcription and/or the translation of the endogenous DFNB59 gene is impaired. Accordingly, the amount of the pejvakin transcript or of the pejvakin polypeptide is diminished as compared with the level of pejvakin transcript or of the pejvakin polypeptide expressed in healthy individuals. The skilled person well knows how to measure the amount of the pejvakin transcript or of the pejvakin polypeptide in a subject, e.g., in blood samples.

"Biologically unfunctional" pejvakin may be produced when the endogenous DFNB59 gene contains nonsense mutations (leading to the generation of truncated pejvakin) or missense mutations. Some of them have already been disclosed (Collin et al., 2007; Ebermann et al., 2007; Hashemzadeh Chaleshtori et al., 2007; Schwander et al., 2007; Borck et al., 2012; Delmaghani et al., 2006; Mujtaba et al., 2012; Zhang et al., 2015). As shown in these articles, the skilled person well knows how to detect these mutations, e.g., in blood samples.

"Peroxisomal alteration" may be detected by any conventional technique. Examples thereof are disclosed in the experimental part below. Altered peroxisomes are observed for example when their size is significantly enlarged and/or when their density is significantly decreased as compared with control cells (that is, cells of the same category, but from healthy individuals).

Conventional intervention in case of sensorineural hearing impairment includes sound amplification by hearing aids and cochlear implant fitting, depending on the degree of impairment. However, conventional hearing aids, routinely used in severely hearing-impaired patients, might have harmful results in DFNB59 patients, as exposure to amplified sound is expected to lead to long-lasting damage to cochlear sensory cells and auditory neurons. Cochlear implant, an acoustico-electronic device that bypasses the cochlea and delivers a direct electrical stimulation to the primary auditory neurons, which is particularly beneficial for patients affected by profound deafness of cochlear origin, should similarly increase ROS in these neurons, thereby threatening their long-term survival. In both cases, specific protection against the production or the effects of the ROS is anticipated to be mandatory.

The case of pejvakin deficits, which induce a non-life-threatening impairment, is the first in which several potentially damaging effects of sound amplification on sensory cells and neurons emerge, at levels of sound energy-induced activity of auditory cells that are several orders of magnitude lower than normal in the absence of pejvakin.

Hence, when a subject has been diagnosed to suffer from noise hypervulnerability according to the above mentioned method, it is important not to use sound amplification by hearing aids or by cochlear implant fitting, unless irreversible ROS-induced damages may be induced.

For these patients, alternative treatments should therefore be contemplated. These treatments include administration of RS inhibiting compounds and/or antioxidant compounds, wherein, depending on the considered treatment, said antioxidant compounds are or are not gasdermin (in particular gasdermin A, gasdermin B, gasdermin C, gasdermin D, DFNA5, DFNB59 (or pejvakin)). Such antioxidant compound can advantageously be selected from: cyclophilin A, c-dopachrome tautomerase and Mpv17.

In a related aspect, the present invention therefore relates to a method for treating subjects in need thereof, comprising the steps of performing the above-mentioned diagnostic method and, if said subject is diagnosed to suffer from noise hypervulnerability, administering to said subject an RS inhibiting compound.

In a preferred embodiment, the present invention relates to a method for treating subjects in need thereof, comprising the step of:
a) administering to said subjects a therapeutic amount of a RS inhibiting compound (such as taurine or N-acetyl-cysteine) and/or of an antioxidant compound (such as a gasdermin, and in particular: gasdermin A, gasdermin B, gasdermin C, gasdermin D, DFNA5, pejvakin, or cyclophilin A, c-dopachrome tautomerase or Mpv17).

In particular, when said subjects suffer from congenital hearing impairment due to altered DFNB59 gene expression or deficiency, then step a) is for administering to said subjects a therapeutic amount of:
either a RS inhibiting compound (such as taurine or N-acetyl-cysteine) and an antioxidant compound (such as a gasdermin, and in particular: gasdermin A, gasdermin B, gasdermin C, gasdermin D, DFNA5, pejvakin, cyclophilin A, c-dopachrome tautomerase or Mpv17); or
a RS inhibiting compound (such as taurine or N-acetyl-cysteine) or an antioxidant compound (such as cyclophilin A, c-dopachrome tautomerase or Mpv17) with the exception of a gasdermin, and in particular with the exception of gasdermin A, gasdermin B, gasdermin C, gasdermin D, DFNA5 and pejvakin.

Yet in particular, when said subjects suffer from hearing impairments other than those due to altered DFNB59 gene expression or deficiency, then step a) is for administering to said subjects a therapeutic amount of a RS inhibiting compound (such as taurine or N-acetyl-cysteine) and/or of an antioxidant compound (such as a gasdermin, and in particular: gasdermin A, gasdermin B, gasdermin C, gasdermin D, DFNA5, pejvakin, cyclophilin A, c-dopachrome tautomerase or Mpv17).

In another preferred embodiment, the present invention relates to a method for treating subjects in need thereof, comprising the steps of:
a) measuring the expression level of the pejvakin polypeptide in said subjects, and/or
b) detecting the presence of inactivating mutations in the pejvakin polypeptide in said subjects, and/or
c) clinically audiological testing for sensorineural hearing impairment, e.g., by recording the auditory brainstem response (ABR) and otoacoustic emissions (OAEs) in said subjects; and
d) administering to said subjects a therapeutic amount of a gasdermin, and in particular: gasdermin A, gasdermin B, gasdermin C, gasdermin D, DFNA5, pejvakin, optionally along with other antioxidant compound and/or RS inhibiting compounds, as defined above.

In particular, when said subjects suffer from congenital hearing impairment due to altered DFNB59 gene expression or deficiency, then step d) is for administering to said subjects a therapeutic amount of:
either a RS inhibiting compound (such as taurine or N-acetyl-cysteine) and an antioxidant compound (such as a gasdermin, and in particular: gasdermin A, gasdermin B, gasdermin C, gasdermin D, DFNA5, pejvakin, cyclophilin A, c-dopachrome tautomerase or Mpv17); or
a RS inhibiting compound (such as taurine or N-acetyl-cysteine) or an antioxidant compound (such as cyclophilin A, c-dopachrome tautomerase or Mpv17) with the exception of a gasdermin, and in particular with the exception of gasdermin A, gasdermin B, gasdermin C, gasdermin D, DFNA5 and pejvakin.

Yet in particular, when said subjects suffer from hearing impairments other than those due to altered DFNB59 gene expression or deficiency, then step d) is for administering to said subjects a therapeutic amount of a RS inhibiting compound (such as taurine or N-acetyl-cysteine) and/or of an antioxidant compound (such as a gasdermin, and in particular: gasdermin A, gasdermin B, gasdermin C, gasdermin D, DFNA5, pejvakin, cyclophilin A, c-dopachrome tautomerase or Mpv17).

As used herein, the term "subjects" is intended to designate humans and non-human mammals such as primates, cats, dogs, swine, cattle, sheep, goats, horses, rabbits, rats, mice and the like. In a preferred embodiment, said subjects are human subjects.

EXAMPLES

Figure 1:
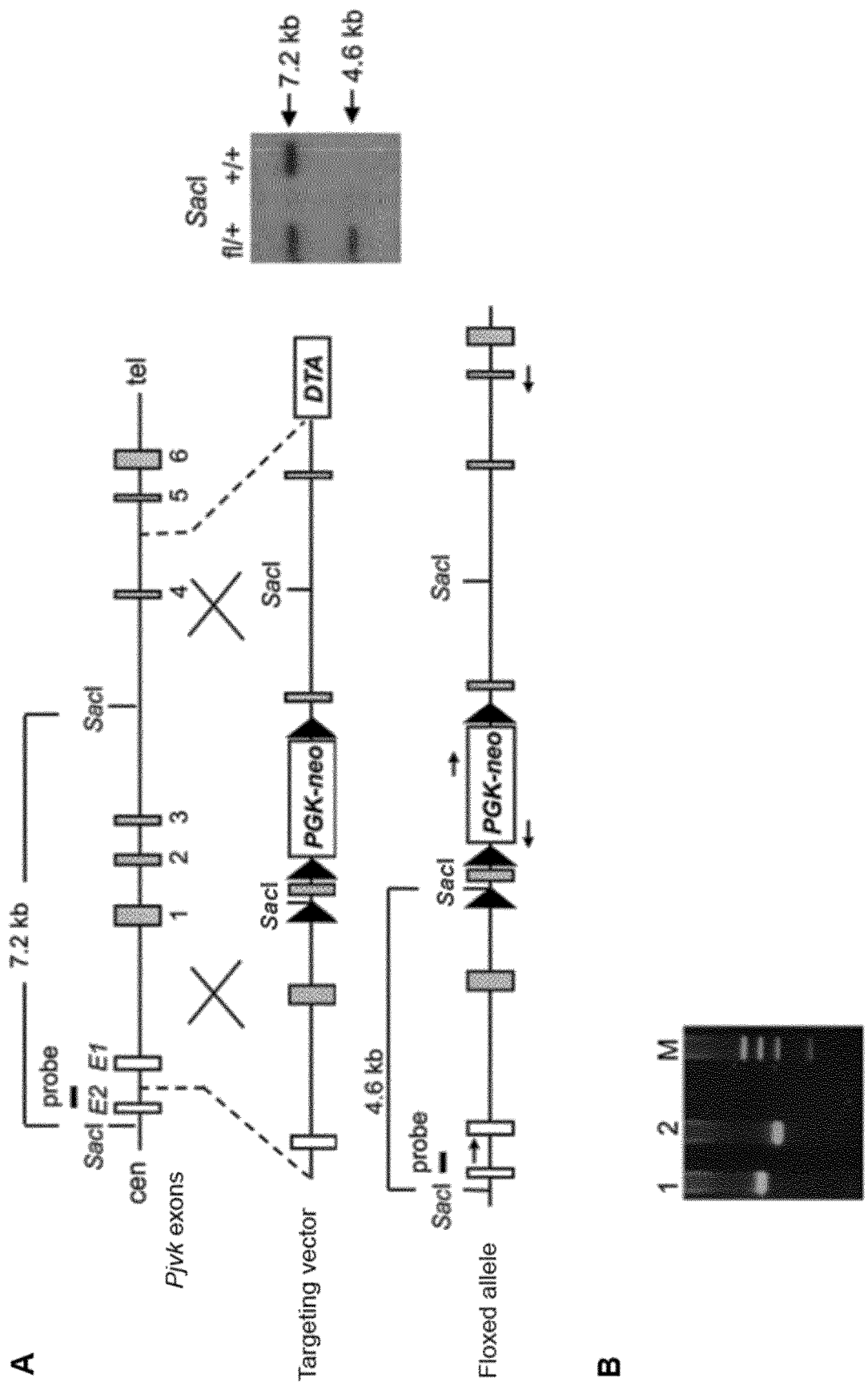
FIG. 1 describes the strategy for targeted replacement of the Pjvk wild-type allele with a floxed allele. (A) Schematic representation of the murine Pjvk gene and the targeting construct used to produce a floxed Pjvk allele ($Pjvk^{fl}$) with loxP sequences (triangles) flanking exon 2, followed by a PGK-neo cassette. DTA: diphtheria toxin A fragment. An additional SacI site was engineered before the first loxP site for Southern blot analysis. Small arrows indicate the positions of PCR primers used to screen recombinant ES cell clones. Right panel: Southern blot analysis of SacI-digested genomic DNA of wild-type (+/+) and $Pjvk^{fl/+}$ (fl/+) mice. Exon 2 of Prkra (a gene flanking Pjvk on the centromeric side) was used as the probe for Southern blot analysis. The probe hybridizes to a 4.6 kb fragment from the floxed allele and to a 7.2 kb fragment from the wild-type allele. (B) RT-PCR analysis of the Pjvk transcript in inner ears of $Pjvk^{+/+}$ and $Pjvk^{-/-}$ P7 mice. $Pjvk^{-/-}$ mice were obtained by crossing $Pjvk^{fl/fl}$ mice with transgenic mice carrying the cre recombinase under the control of the ubiquitous PGK promoter. The expected 1059 bp amplicon is seen in the $Pjvk^{+/+}$ mouse (lane 1), while a 963 bp fragment is detected in the $Pjvk^{-/-}$ mouse (lane 2), because of the deletion of exon 2. M, DNA size marker: φX174 DNA HaeIII digest.

I. Material and Methods
Animal Handling

Animals were housed in the Institut Pasteur animal facilities accredited by the French Ministry of Agriculture to perform experiments on live mice (accreditation 75-15-01, issued on Sep. 6, 2013 in appliance of the French and European regulations on care and protection of the Laboratory Animals (EC Directive 2010/63, French Law 2013-118, Feb. 6, 2013). The corresponding author confirms that protocols were approved by the veterinary staff of the Institut Pasteur animal facility, and were performed in compliance with the NIH Animal Welfare Insurance #

A5476-01 issued on 31 Jul. 2012. C57Bl/6 wild-type mice were obtained from Janvier laboratories.

Gene Targeting, Genotyping, and RT-PCR

A targeting vector was designed, in which exon 2 of Pjvk and the neomycin selection cassette were flanked with loxP sites. A negative selection cassette coding for diphtheria toxin A fragment (DTA) was inserted at the 3'-end of the targeting Pjvk sequence (FIG. 1A). CK35 embryonic stem (ES) cells (Kress et al., 1998), derived from a 129/Sv mouse embryo, were electroporated with the purified, linearized targeting vector, and plated on G418 selective medium as reported (Matise et al., 1999). Approximately 300 recombinant ES cell clones were obtained, of which 12 were correctly targeted. The homologous recombinant event was confirmed on the left and right sides by PCR, using the primers specific to the 5' and 3' genomic sequence, outside of the region used in the targeting vector, and specific to the neo sequence. The sequences of the PCR primers used to genotype the floxed Pjvk allele are available on request. Integration of the recombinant DNA construct was confirmed by Southern blot analysis and PCR amplification of genomic DNA extracted from the mouse tails. Two independent clones were used to create germ line-transmitting chimeric mice by injection into C57BL/6J blastocysts. Mating of male chimeras with C57BL/6J females produced heterozygous animals. Mice heterozygous for the floxed Pjvk allele were mated with PGK-Cre$^m$ deleter mice carrying the cre recombinase gene driven by the early acting ubiquitous phosphoglycerate kinase-1 gene promoter (Lallemand et al., 1998), to obtain Pjvk knock-out (Pjvk$^{-/-}$) mice. Targeted deletion of exon 2 was confirmed by PCR analysis.

To obtain Pjvk conditional knockout mice (Pjvk$^{fl/fl}$ Myo15-cre$^{+/-}$), in which expression of the deleted Pjvk was restricted to the inner ear sensory cells, mice carrying the floxed Pjvk allele were mated with transgenic mice expressing the cre-recombinase under the control of the myosin 15 gene promoter (Caberlotto et al., 2011). Analyses of the auditory function were performed in ubiquitous knock-out and conditional knockout mice. All studies were performed on mixed C57BL/6J-129/Sv genetic background.

For RT-PCR analysis of the Pjvk transcript, total RNA was extracted from inner ears of Pjvk$^{+/+}$ and Pjvk$^{-/-}$ P7 mice with NucleoSpin® RNA II (Macherey-Nagel). In the Pjvk$^{+/+}$ mice, a transcript of 1059 bp in length was detected, while in the Pjvk$^{-/-}$ mice a transcript of 963 bp lacking the exon 2 sequence was detected.

Audiological Studies in Mice

Auditory tests were performed in an anechoic room. They consisted of distortion-product otoacoustic emissions (DPOAEs), auditory brainstem responses (ABRs), electrically-evoked brainstem responses (EEBRs), and cochlear potentials. Mice were anesthetized with an intraperitoneal injection of a ketamine and levomepromazin mixture (100 mg/kg: 5 mg/kg) and their core temperature was kept at 37° C. with the help of a servo-controlled heating pad. The DPOAE at frequency $2f_1-f_2$ was recorded in response to two equal level primary tones, $f_1$ and $f_2$, with $f_2/f_1=1.20$ (Cub$^e$Dis system, Mimosa Acoustics; ER10B microphone, Etymotic Res.). Frequency $f_2$ was swept at $1/10^{th}$ octave steps from 4 to 20 kHz, and DPOAE level was plotted against frequency $f_2$ (primary tone levels increased from 20 to 70 dB SPL in 10 dB steps, then to 75 dB SPL). DPOAE threshold was defined as the smallest primary level giving rise to a detectable DPOAE. ABRs in response to calibrated short tone bursts in the 5-40 kHz range (repetition rate 17/s) were derived from the synchronous averaging of electroencephalograms recorded between subcutaneous stainless steel electrodes at the vertex and ipsilateral mastoid, with the help of a standard digital averaging system (CED1401+). A hundred responses to the tone bursts were averaged except within 10 dB of the ABR threshold (defined as the smallest tone-burst level giving rise to at least one repeatable wave above noise background level, 150 nV in an anesthetized animal), for which 300 tone bursts were used. Once ABR thresholds had been assessed, ABRs in response to 95 and 105 dB SPL tone bursts (100 averages) were collected for analysis of suprathreshold ABR waveforms, amplitudes and latencies. Controlled sound exposure was applied with the same acoustic probe used for ABRs without moving the sound system, so that pre- and post-exposure ABRs shared the same calibration. Intense stimuli were the same tone-bursts used for ABR measurements at 105 dB SPL, presented 1,000 times at the same repetition rate of 17/s.

Electrical stimulations of the eighth cranial nerve were delivered by a silver electrode placed in the round-window niche and excited by biphasic electrical impulses (neutral electrode in neck muscles; peak amplitude of electrical stimulus about 0.5 V; duration of the positive and negative phases 150 microseconds; adjustable repetition rate). EEBRs were extracted using the same setup as for ABRs (Roux et al., 2006), in response to 100 electrical impulses presented with alternating polarities (repetition rate 17 Hz). EEBR threshold was defined as the smallest electrical amplitude eliciting repeatable waves above noise background level (the same as for ABRs), labelled from E II to E IV in reference to their ABR equivalents II-IV. Controlled electrical stimulation was applied at 5 dB above EEBR detection threshold with a 200 Hz repetition rate. Occasionally, the silver electrode on the round window served for recording Compound Action Potentials (CAPs) in response to the same tone-bursts used for ABR studies (averages of 32 presentations, repetition rates 17/s), prior to EEBR data collection. These recordings served to check that CAP thresholds and ABR thresholds were within 2 dB of each other at all frequencies, and the exact position of ABR wave I could be ascertained form the larger wave N1, its equivalent on CAP recordings. This was particularly important in mice with abnormally small wave I to avoid incorrect identifications (when wave I was reduced to a very small flattened deflection resembling a summating potential, the slightly larger wave II might have been mistakenly labelled wave I on ABR recordings, while wave N1, even when small, kept its characteristic shape).

The round-window electrode also provided access to the cochlear microphonic potential (CM), with the same setting used for CAP measurements, except that the stimulus polarity was fixed for CM recordings, instead of alternating between rarefaction and condensation tone-bursts for CAP detection. CM is a far-field potential resulting from mechanoelectrical transduction currents through the OHCs at the basal end of the cochlea, near the collecting electrode, and is an oscillating change in electric potential at the stimulus frequency. Although its shape is closely similar to that of the stimulus that activates the sound-delivering earphone, it was easily separated from a possible electric artefact radiated by the earphone by its delay of about 0.5 ms after stimulus onset, in relation to sound propagation along the tubing system that connected the earphone to the ear canal of the mouse. Its peak-to-peak amplitude was measured for a stimulus of 5 kHz (a frequency much lower than the best frequency of the responding OHCs, so that CM was independent of their electromotility status) presented at 95 dB SPL.

Recording of Mouse Vocalizations

The protocol was adapted from the protocol described previously by Menuet et al. (2011). In brief, mice were placed in a polyethylene cage covered by a metal wire lid. A free field microphone (type 4192, ½-inch, Bruel & Kjaer) was placed 2 cm above the metal lid, in the centre of the cage. The microphone output was preamplified (Microphone power supply type 2801, Bruel & Kjaer) and digitized by the sound card of a computer (Dell D830; Dell Inc.) at the sampling rate of 192 kHz. Acoustic vocalizations in the 5-90 kHz frequency range were stored online by Adobe Audition 1.5 software. Their analysis was performed using software developed on Matlab (The MathWorks Inc., MA), allowing a spectrographic display of vocalizations in the time-frequency domain, from which the total time of vocalization, the average intensity of vocalizations, and the spectral complexity of vocalizations were determined.

Stabulation of Mice in an Acoustically Quiet Environment

Noting that most of the noise exposure of a young mouse comes from surrounding sound vocalizations (Ehret & Riecke, 2002), the pups were split from the same litters into three groups placed in isolated boxes. Separation was done before P10, that is several days before the onset of hearing in the mouse. Boxes were kept in quiet booths, shielded from the sound from other cages. In the first group, only 2 mice were kept in a cage with a foster mother; in the second group, 4 mice; and in the third group, the remaining (6 to 10) pups were left with their mother.

Audiological Tests and Controlled Sound Exposure in Patients

Informed consent was obtained from all the subjects included in the study. Clinical examination was carried out on the five affected subjects carrying the p.T54I mutation in PJVK, and 13 control patients with sensorineural hearing impairments of cochlear origin and matched auditory thresholds and extant otoacoustic emissions. Pure-tone audiometry was performed using air- and bone-transmitted tones. Hearing impairment was objectively assessed by means of ABRs and transient-evoked otoacoustic emissions (TEOAEs). To test the hearing hypervulnerability to sound in these patients, a minimal sound exposure eliciting ABRs was used. ABRs were first recorded in response to 250 impulse stimuli clicks (at a repetition rate of 20/s) at 99 dB above normal detection threshold (the maximum level with this equipment, a Vivosonic Integrity™ Version 4.50), that is, 20-30 dB above the ABR threshold in the tested ear. Then, averaging was extended to 500 and 1000 clicks, and the three averaged ABRs were compared as regards wave identification, amplitudes and latencies post click-onset. In control patients, averaging was prolonged until about 4000 responses to clicks had been collected. After a 10-min pause with no sound stimulus, the procedure was done all over again. TEOAEs were averaged just before the first ABR procedure, then just after, in response to 260 series of clicks presented at 40 dB above normal detection threshold (i.e., they were inaudible in patients). The so-called nonlinear TEOAE recording procedure was used (derived from the ILO88 system, Kemp, 2002), allowing genuine TEOAEs to be extracted from linear reflection artefacts from the middle ear and background noise to be evaluated. TEOAE responses were analysed in 1-kHz-wide bands centred on 1, 2, 3 and 4 kHz.

Acoustic Overexposure for Quantification of Cochlear Transcripts in Mice

Three-week old C57Bl/6 wild-type mice were used. The sound stimulation episode to which the animals were exposed consisted, in a first set of experiments, of a 1-hour pure tone overstimulation at 5-20 kHz with an intensity of 105 dB SPL. In the second set of experiments, the mice were submitted to a so-called "preconditioning sound exposure" that consisted of a bandpass-filtered white noise (BPWN) whose spectrum covered the interval 5-20 kHz, with a lower intensity of 90 dB SPL for 1 hour. The BPWN signal was generated using custom Matlab software (The Mathworks), and delivered by an amplifier to a set of four Ultrasonic Vifa speakers (Avisoft Bioacoustics). The speakers were attached to the tops of four custom-made, cylindrical sound-isolation chambers (15 cm in radius) in which the mice were enclosed. The noise intensity delivered by the speakers was calibrated with a BK4812 probe (Bruel & Kjaer) placed centrally at the bottom surfaces of the isolation chambers. The sound field inside each chamber varied by less than 10 dB over its bottom surface.

Generation of an Anti-Pejvakin Monoclonal Antibody

The coding sequence of the Pjvk cDNA (accession no. NM_001080711.2) 3'-end was amplified and cloned into a pGST-parallel-2 vector (derived from pGEX-4T-1; Amersham). The resulting construct, encoding the C-terminal region of pejvakin (residues 290-352; accession no. NP_001074180.1) fused to a N-terminal glutathione S-transferase (GST) tag, was transformed into *E. coli* BL21-Gold (DE3) competent cells (Stratagene). The pejvakin protein fragment was purified using a glutathione Sepharose 4B column, followed by size-exclusion chromatography and used as the antigen for immunization. Young (4-6 weeks old) Pjvk$^{-/-}$ mice were immunized with 15-50 mg of antigen by subcutaneous injection. Mice were bled from eye vein after 3 injections, and presence of the antibody in the plasma was tested by ELISA and western blot. Once plateau of antibody production was detected, hybridoma fusion was performed. Antibody titre was determined by ELISA.

Treatment of Mouse Embryonic Fibroblasts with $H_2O_2$

Fibroblasts were isolated from mouse embryos at embryonic day 13.5 and cultured as described by Xu (2005). The cells were incubated in DMEM (Gibco) supplemented with 0.1 mM β-mercaptoethanol, and 0.5 mM $H_2O_2$ for 4 hours at 37° C., under normoxic conditions (95% air). The culture medium was then replaced with $H_2O_2$-free medium. Cell viability was checked 18 hours after $H_2O_2$ treatment, by measuring mitochondrial reductase activity with the MTT (3-(4,5-dimethylthiazol-2-yl)-2,5-diphenyl tetrazolium bromide) (Sigma M2128) assay. A polyclonal antibody against peroxisome membrane protein 70 (PMP70, Abcam ab3421) was used to label peroxisomes.

Plasmids and DNA Transfections

The full-length Pjvk cDNA was obtained by RT-PCR on a double-strand cDNA library prepared from organs of Corti of postnatal day 7 (P7) C57BL/6 mice, and then was cloned into the pIRES2-EGFP vector (Clontech). The mutant Pjvk clones (missense mutations) were prepared from the wild-type clone using QuikChange™ Site-Directed Mutagenesis kit (Stratagene). HeLa, COS-7, HEK293 cells were transiently transfected using lipofectamine™ 2000 (Invitrogen), according to the manufacturer's instructions.

Immunofluorescence Studies

For cryosections, inner ears were dissected in PBS and fixed by immersion in 4% paraformaldehyde (PFA) in PBS for 2 hours at 4° C. The samples were decalcified in 10% EDTA in PBS, pH 7.4 for 4 days at 4° C., fixed again in 4% PFA in PBS for 1 hour, rinsed twice in PBS for 10 min, and immersed in 20% sucrose in PBS for 12 hours. They were embedded in Tissue Freezing Medium (Triangle Biomedical Sciences, USA). Cryostat sections (12 μm thick) were used for immunohistochemistry. An antibody against 4-hydroxy-2-nonenal (HNE) (Calbiochem) was used to detect the lipid oxidation products.

For whole-mount immunolabelling analyses, the inner ears were fixed in 4% PFA in PBS, and the cochlear sensory areas (organ of Corti) were microdissected. The tissues were rinsed twice in PBS, then permeabilized and blocked by incubation in PBS containing 20% normal goat serum and 0.3% Triton X-100 for 1 hour at room temperature. For GFP detection, whole-mount cochleas were incubated with a mixture of rabbit anti-GFP antibody (Invitrogen) and chicken anti-GFP antibody (Abcam) in 1% bovine serum albumin (BSA) in PBS. A monoclonal antibody against parvalbumin (Sigma) was used to label auditory neurons. A polyclonal antibody against peroxisome membrane protein 70 (PMP70, Abcam) was used to label peroxisomes. Anti-myosin VI (Roux et al., 2009), anti-ribeye/CtBP2 (Santa Cruz), and anti-glutamate receptor 2 (GluR2, Invitrogen) antibodies were used to delimit the contours of IHCs, to label and count IHC ribbons, and to label post-synaptic glutamate receptors on the dendritic ends of cochlear ganglion neurons, respectively.

For immunocytochemistry, HeLa, COS-7, HEK293, and HepG2 cells were fixed in 4% PFA for 15 min, washed in PBS, and incubated in $NH_4Cl$ 50 mM—Triton X-100 0.2% solution for 15 min at room temperature (RT). After washing, cells were incubated in PBS—Normal Goat Serum 20% solution for 1 hour. Cells were incubated with the primary antibody in PBS-BSA 1% solution for 1 hour. Peroxisomes were labelled using a rabbit polyclonal antibody against peroxisome membrane protein 70 (PMP70, Abcam). Antibodies against mitochondrial import receptor subunit TOMM22 (Sigma) and lysosomal-associated membrane protein 1, LAMP1 (Abcam) were used to label mitochondria and lysosomes, respectively. The mouse monoclonal antibody against pejvakin (Pjvk-G21) was used to detect the subcellular location of pejvakin. Cells were then washed in PBS and incubated with the appropriate secondary antibody for 1 hour at RT. For immunofluorescence, the antibodies Atto-488- or Atto-647-conjugated goat anti-rabbit IgG, Atto-594-conjugated goat anti-mouse IgG (Sigma) and Alexa-Fluor-488-conjugated goat anti-chicken IgG (Invitrogen) were used. TRITC-conjugated phalloidin (Sigma) and DAPI (Sigma) were used to label actin and cell nuclei, respectively. Images were collected using a Zeiss LSM700 Meta confocal microscope (Carl Zeiss MicroImaging, Inc.). Automated quantification of peroxisomes was realised using the Particles Analysis plugin of ImageJ software (Collins, 2007). Data were expressed as a number of peroxisomes per 100 $\mu m^2$, and enlarged peroxisomes were measured in two perpendicular directions using ImageJ software.

Morphological Analyses and Peroxisome Staining

For scanning electron microscopy studies, inner ears from adult mice were fixed by perfusion of the perilymphatic compartment with 2.5% phosphate-buffered glutaraldehyde, and rinsed in PBS. Cochleae were then microdissected, dehydrated in graded ethanol solutions, and dried up to critical point. Processed specimens were then mounted on aluminium stubs with colloidal silver adhesive and sputter-coated with gold palladium before imaging in a JSM-6700 F Jeol scanning electron microscope. Inner ears from a total of 10 $Pjvk^{+/+}$ mice (three at P15, four at P30, three at P60), and 12 $Pjvk^{-/-}$ mice (three at P15, five at P30, four at P60) were analysed by scanning electron microscopy.

For transmission electron microscopy studies, the cochleas were prepared as previously described (Thelen et al., 2009). They were fixed in 2.5% glutaraldehyde in 0.1 M Sörensen's buffer pH 7.4 for 2 hours at 4° C. After several washes in 0.1 M Sorensen's buffer pH 7.4, the samples were postfixed at 4° C. with 2% osmium tetroxide in Sorensen's buffer for 60 min. The selective staining of peroxisomes is adapted from (Angermüller & Fahimi, 1981). Briefly, the cochleas were fixed at 4° C. in 1% glutaraldehyde in 0.1 M cacodylate buffer pH 7.2 for 1 hour. After several washes in the same buffer, the samples were immersed in 2 mg/ml 3,3'-Diaminobenzidine (DAB) and 0.15% $H_2O_2$ in 0.05 M Teorell-Stenhagen buffer (T/S: 57 mM boric acid, 50 mM phosphoric acid, 35 mM citric acid, 345 mM NaOH) pH 10.5 for 45 min at 30° C. After several washes in T/S, the samples were postfixed at 4° C. with 2% osmium tetroxide in $H_2O$ for 60 min. All the cochleas were then washed in deionized water, dehydrated in graded ethanol solutions, and embedded in Epon (Epon-812, Electron Microscopy Sciences) for 48 hours at 60° C.

Ultrathin sections (70 nm thick) were obtained using an ultramicrotome (Reichert Ultracut E) equipped with a diamond knife (Diatome), and mounted on copper grids coated with collodion. Sections for the morphological analysis were contrasted with uranyl acetate and lead citrate for 15 min each. Sections stained with DAB were contrasted with lead citrate for 15 min. The ultrathin sections were observed under a JEM-1400 transmission electron microscope (Jeol) at 80 kV and photographed with an 11 MegaPixel bottom-mounted TEM camera system (Quemesa, Olympus). The images were analysed via iTEM software (Olympus). The quantitative data were obtained using the same software.

Microarray Analysis and Real-Time Quantitative PCR

Total RNA was extracted from dissected organs of Corti of $Pjvk^{-/-}$ and wild-type P15 mice (an age at which no cellular defect could be detected in the organ of Corti of $Pjvk^{-/-}$ mice) using TRIzol reagent (Invitrogen), purified on Rneasy columns (Qiagen, Valencia, Calif.), and tested on an Agilent (Waldbronn, Germany) 2100 Bioanalyzer. Three biological replicates were run for each genotype. cRNAs obtained from 100 ng of RNA were amplified by using the GeneChip Expression Two-Cycle 3' amplification system (Affymetrix, High Wycombe, U.K.). Fragmented biotin-labeled cRNA samples were hybridized to Affymetrix Mouse Gene ST 1.0 arrays. Following hybridization, the array was washed and stained according to the Affymetrix protocol. The stained array was scanned at 532 nm using an Affymetrix GeneChip Scanner 3000, producing CEL files for each array. Gene-level expression values were derived from the CEL file probe-level hybridization intensities using the model-based Robust Multichip Average algorithm (RMA) (Bolstad et al. 2003). Arrays were compared using the Local Pool Error test (Jain et al., 2003), and the P values were adjusted by using the Benjamini-Hochberg algorithm (Benjamini & Hochberg, 1995). The fold differences reflect the relative expression levels of the genes in the organs of Corti of $Pjvk^{-/-}$ mice normalized to the expression levels of the same genes in the organs of Corti of $Pjvk^{+/+}$ mice.

The fold changes of Mpv17, Dct, Gpx2, CypA, c-Fos, and Hsp70 transcripts between sound-exposed and unexposed cochleas were analysed by quantitative PCR. Cochleas were collected from unexposed and sound-exposed mice at 1 hour, 3 hours, 6 hours, and 18 hours after sound exposure. RNA was extracted from dissected organs of Corti using NucleoSpin® RNA II (Macherey-Nagel). Real-time quantitative PCR was performed using the Universal Probe Library (UPL) system from Roche. UPL probes were labelled with FAM, and the fluorescence was read with the Applied Biosystems 7500 Real-Time PCR System. The thermocycling conditions were 50° C. for 2 min followed by 95° C. for 2 min, and then 40 cycles at 95° C. for 15 s and 60° C. for 30 s. Three independent experiments were performed for each exposed or unexposed cochlea. Each assay was conducted for target transcript probe-set in a multiplex reaction in which glyceraldehyde-3-phosphate dehydrogenase (Gapdh) probe-set was used as an internal control. Relative levels of target transcript dosage were determined using the comparative CT method. The relative transcript copy number for each target transcript was calculated as $2^{-\Delta\Delta C_T}$. UPL probes and primers were indicated in the table below. To compare the transcription level of each gene in the organ of Corti of exposed and unexposed mice, statistical significance was assessed using the unpaired, Student's t-test.

List of Primers and Probes Used for Quantitative PCR.

| Gene | UPL probe (Roche) | Forward primer (5'-3') | Reverse primer (5'-3') |
| --- | --- | --- | --- |
| Pjvk | #60 (cat. no. 04688589001) | CCAGTGCTCTCTGTCAGTGC (SEQ ID NO: 5) | TCTGTTCATCCATAAAATGAAACC (SEQ ID NO: 6) |
| Mpv17 | #75 (cat. no 04688988001) | CGCACTCTGACCATGGTATC (SEQ ID NO: 7) | CCCGGGATTAAGTGGTCTAAA (SEQ ID NO: 8) |
| Dct | #6 (cat. no. 04685032001) | GGCTACAATTACGCCGTTG (SEQ ID NO: 9) | CACTGAGAGAGTTGTGGACCAA (SEQ ID NO: 10) |
| Gpx2 | #2 (cat. no. 04684982001) | GTTCTCGGCTTCCCTTGC (SEQ ID NO: 11) | TTCAGGATCTCCTCGTTCTGA (SEQ ID NO: 12) |
| CypA | #46 (cat. no. 04688066001) | ACGCCACTGTCGCTTTTC (SEQ ID NO: 13) | GCAAACAGCTCGAAGGAGAC (SEQ ID NO: 14) |
| c-Fos | #26 (cat. no. 04687574001) | GGCTCTCCTGTCAACACACA (SEQ ID NO: 15) | GACCAGAGTGGGCTGCAC (SEQ ID NO: 16) |
| Hsp70 | #80 (cat. no. 04689038001) | GAAGACATATAGTCTAGCTGCCCAGT (SEQ ID NO: 17) | CCAAGACGTTTGTTTAAGACACTTT (SEQ ID NO: 18) |
| Gadph | (cat. no. 0504621) | ATGGTGAAGGTCGGTGTGA (SEQ ID NO: 19) | AATCTCCACTTTGCCACTGC (SEQ ID NO: 20) |

Measurement of Total GSH and GSSG

Total glutathione (GSH+GSSG) and oxidized glutathione (GSSG) levels were measured by the method of Rahman et al. (2006). Three independent experiments were performed. Cochleas and livers were collected from Pjvk$^{+/+}$ and Pjvk$^{-/-}$ mice at 3 weeks of age. The tissues were quickly removed and placed in ice-cold 0.1 M potassium phosphate buffer with 5 mM EDTA disodium salt, pH 7.5 (KPE), and homogenized on ice-cold extraction buffer (0.1% Triton-X, 0.6% sulfosalicylic acid and 5% metaphosphoric acid in KPE). The homogenate was centrifuged at 8,000×g for 10 min at 4° C. The supernatant was used as lysate for assay. To measure GSSG only, reduced GSH was derivatized with 2-vinylpyridine. Measurement of GSH/GSSG levels was done by adding 5,5'-dithio-bis (2-nitrobenzoic acid) (DTNB) to the lysate. Both GSH and GSSG react with DTNB and form a yellow derivate 5'-thio-2-nitrobenzoic acid (TNB). The rates of TNB formation were calculated by spectrometry at 405 nm. The total GSH and GSSG concentrations in the samples were measured by using linear regression to calculate the values obtained from the standard curve. The GSH concentration was calculated by subtracting the GSSG concentration from the total GSH concentration.

TBARS Assay for Quantification of Lipid Peroxidation

To test the level of MDA, a by-product of lipid peroxidation, the TBARS assay kit was used (Cayman Chemical Company, Ann Arbor, Mich., USA). Three independent experiments were performed. For each assay, cochlear sensory areas were microdissected from 30 Pjvk$^{+/+}$ and 30 Pjvk$^{-/-}$ mice. Cochlear tissue was homogenized on ice in RIPA buffer (50 mM Tris-HCl, pH 7.6, containing 150 mM NaCl, 1% NP-40 (Igepal), 0.5% sodium deoxycholate, and 0.1% SDS). Cochlear homogenate was used for the assay. The prescribed TBARS protocol was applied, in addition to the triplicate pipeting of MDA aliquots of known concentration to produce a standard curve. Fluorescence was read at excitation and emission wavelengths of 530 and 590 nm, respectively, using a Synergy 2 thermoregulated spectrophotometer plate reader (BioTek). The averaged values were used to determine MDA concentration from the MDA standard curve graph.

AAV-Pjvk Viral Constructs and Intracochlear Viral Transduction

To obtain AAV2/8-Pjvk-IRES-EGFP, the mouse Pjvk cDNA flanked by an IRES-EGFP reporter cDNA sequence was subcloned into the multiple cloning site of vector pENN.AAV.CB7.CI.RBG (PennVector P1044, Penn Medicine Vector Core—University of Pennsylvania School of Medicine). The virus production and titration were performed by Penn Medicine Vector Core. To product AAV8-Pjvk, mouse Pjvk cDNA was subcloned in a single promoter Ad.MAX™ shuttle vector (ITR-CAG-Dfnb59-WPRE-PolyA-ITR; SignaGen Laboratories). The virus packaging and titration were done by SignaGen Laboratories.

Intracochlear viral transduction was carried out as described by Akil et al. (2012). Three-day old Pjvk$^{-/-}$ pups were anesthetized by hypothermia, and the left ear was approached through a dorsal incision. A small hole was made in the bulla with an 18 G needle, and the round window membrane was gently punctured with a borosilicate capillary pipette. A fixed volume of AAV8-Pjvk or AAV2/8-Pjvk-IRES-EGFP (0.5 µl of a 1×10$^{13}$ vg/ml) was then gently injected (during 1-2 min) into the perilymphatic compartment of the cochlea. After pulling out the pipette, the round window niche was quickly sealed with fascia and adipose tissue, and the bulla was sealed with dental cement. Auditory function was tested at P21 in treated and untreated ears by recording of ABR, DPOAEs, and EEBR.

Antioxidant Treatment

N-acetyl-L-cysteine (L-NAC; Sigma) or taurine (Sigma) was administrated to pregnant $Pjvk^{-/-}$ mice in the drinking water. A daily dose of 1% L-NAC or 2% taurine was given to the mother during and after pregnancy, so that pups received them from birth on by feeding on the mother's milk. The treatment was continued until P21, and the auditory function of the treated $Pjvk^{-/-}$ pups was tested at P21.

Statistical Analyses

After checking for data normality and homoscedasticity, statistical differences were evaluated using the Student's t-test and one-way ANOVA. A p value <0.05 was set for statistical significance.

II. Results

1. Extreme Heterogeneity in Hearing Sensitivity in $Pjvk^{-/-}$ Mice

Figure 2:
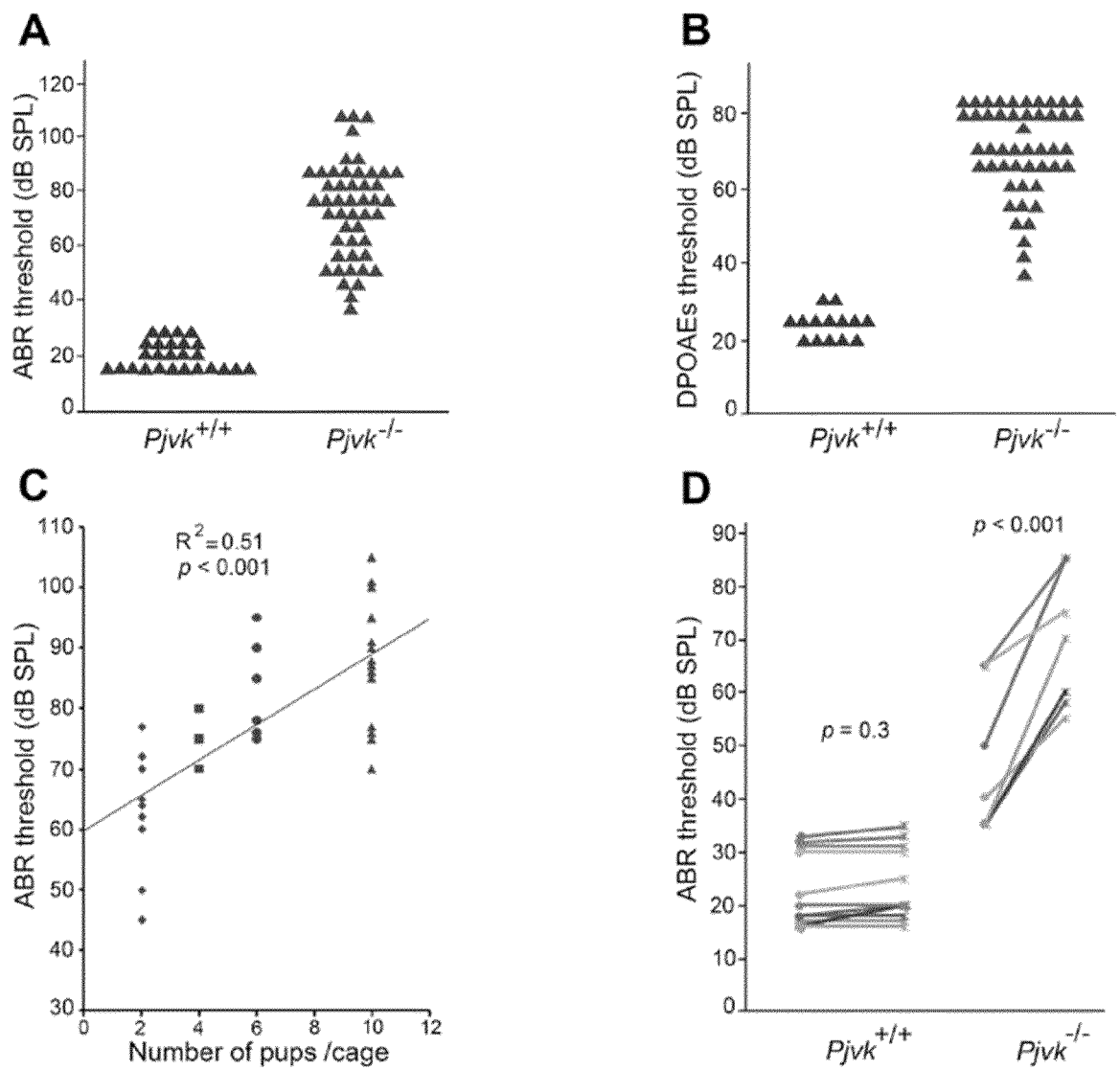
FIG. 2 describes the hearing loss variability and increased sensitivity to "controlled sound exposure" in $Pjvk^{-/-}$ mice. (A) ABR thresholds for 10 kHz pure tones in 1-month old $Pjvk^{-/-}$ and wild-type littermates. (B) DPOAE thresholds at $2f_1-f_2$ (in dB SPL) in $Pjvk^{-/-}$ and $Pjvk^{+/+}$ mice for identical levels of sound stimuli at $f_1$ (8 kHz) and $f_2$ (10 kHz). Stimulus level was kept below 80 SPL to avoid any contribution of instrumental distortion. In ears with no DPOAE even for 75 dB SPL stimulus levels, DPOAE thresholds were arbitrarily set at 80 dB SPL. (C) Natural acoustic environment effect on ABR thresholds for 10 kHz pure tones in P21 $Pjvk^{-/-}$ mice. ABR thresholds show a highly significant correlation with the number of pups (2 to 10) present in the cage ($R^2$=0.51; p<0.001). (D) Effect of a 1-min exposure to 10-kHz, 105 dB SPL tone-bursts (2-ms plateau) separated by 60-ms silent intervals on the ABR threshold of Pjvk$^{-/-}$ mice. Re-measured just after sound exposure, ABR threshold increased to 21.7±10.3 dB (p<0.001) in Pjvk$^{-/-}$ mice whilst producing no effect in Pjvk$^{+/+}$ mice (2.2±2.4 dB; p=0.3, NS).

Pejvakin-null mice, $Pjvk^{-/-}$, carrying a deletion of exon 2 resulting in a frameshift at codon position 71 (p.G71fsX9) (FIG. 1) were analysed at postnatal day 30 (P30), for hearing sensitivity by ABR thresholds. ABR thresholds at 10 kHz ranged from 35 to 110 dB SPL in $Pjvk^{-/-}$ mice (n=50), whilst they never exceeded 30 dB SPL in $Pjvk^{+/+}$ and $Pjvk^{+/-}$ littermates (n=50) (FIG. 2A). This broad range in hearing sensitivity, from near-normal to near-totally absent, extended across the whole frequency spectrum. OHC activity was tested by the thresholds of the distortion-product otoacoustic emissions (DPOAEs). The DPOAEs thresholds were affected, establishing OHC dysfunction, and differ widely, from 30 to 75 dB SPL in 30 $Pjvk^{-/-}$ mice up to undetectable DPOAEs regardless of stimulus intensity in 20 $Pjvk^{-/-}$ mice (FIG. 2B). A puzzling degree of variability of the hearing phenotype results from the absence of pejvakin.

2. Hypervulnerability to Natural Acoustic Environment in $Pjvk^{-/-}$ Mice

To gain insight into the origin of the considerable variations of $Pjvk^{-/-}$ auditory phenotypes, the ABR thresholds of the $Pjvk^{-/-}$ littermates were first examined from different crosses. Large variations were detected from one cross to another, which contrasted with only marginal differences between the $Pjvk^{-/-}$ littermates of individual crosses. This observation might be consistent with a phenotypic heterogeneity of genetic origin. However a careful observation pointed to an alternative explanation. ABR thresholds elevations tended to vary according to the number of pups in the litter (6 to 10); the larger this number, the more elevated ABR thresholds. This suggested that the natural acoustic environment resulting from pups' calls might have a deleterious effect on hearing of $Pjvk^{-/-}$ mice. Indeed pups are vocally very active from birth to about P20, when crowding around the mother, at the feeding time (Ehret & Riecke, 2002). To directly evaluate whether hearing of $Pjvk^{-/-}$ pups could be compromised by their vocalizations, large litters were randomly split in groups of 2, 4, 6 and 10 pups per cage kept with a foster mother, from P10 (i.e. before onset of hearing which occurs at P14). ABR thresholds at P21 showed a highly significant correlation (p<0.001) with the number of pups present in a given cage (FIG. 2C). The coefficient of determination, $R^2=0.51$, indicates that 51% of ABR threshold variations was described by the independent variable, number of pups per cage.

Acoustic measurements showed that the most energetic pup calls, in a 12-pup litter, are harmonics of about 5 kHz that reach 105±5 dB SPL from P0 to P21, at the entrance of the ear canals of the pups. A 1-hour exposure is energetically equivalent to a continuous exposure of 42-50 s to the sound of a call. To directly test the effect of sound stimulation and evaluate its possible deleterious consequences on hearing in a controlled manner, 10-kHz 105 dB SPL tone-bursts (2-ms plateau stimulation separated by 60-ms silent intervals) were used, such that one thousand presentations of this stimulus are energetically equivalent to a 3-min stay in the natural environment of a 12-pup litter, whilst allowing ABRs to be monitored during exposure. This is referred as "controlled sound exposure" henceforth. ABR tests performed before and after controlled sound exposure to assess its effects negligibly contributed to the exposure, as they were limited to 50 repetitions each. Indeed, alone, they had no effect on $Pjvk^{-/-}$ mice hearing threshold (data not shown).

In a sample of P30 old $Pjvk^{-/-}$ mice (n=8) with initial ABR thresholds inferior to 65 dB SPL, "controlled sound exposure" resulted in increased ABR thresholds in the 12-20 kHz frequency interval (corresponding to cochlear places where intense 10-kHz sound induces the largest hair-cell stimulations (Cody & Johnstone, 1981)). The ABR threshold increase was 21.7±10.3 dB (p<0.001) in $Pjvk^{-/-}$ mice whilst producing no effect in $Pjvk^{+/+}$ mice (n=12) (2.2±2.4 dB, p=0.3) (FIG. 2D). $Pjvk^{-/-}$ mice immediately transferred in a silent environment after "controlled sound exposure", displayed a further elevation of their ABR threshold, reaching 33.7±16.0 dB (n=8), 2 days after exposure. It decreased to 23.7±18.0 dB after 7 days and disappeared after 14 days. ABR threshold elevations of $Pjvk^{-/-}$ mice with initial ABR thresholds larger than 65 dB SPL (n=8) showed a similar yet smaller trend, due to the ceiling effect of their already large initial hearing loss. The lack of pejvakin thus results in an inordinate vulnerability to very low acoustic energy, slowly reversible.

3. Hair Cells, Afferent Auditory Neurons and Neurons of Auditory Brainstem Pathways are Targets of the Pejvakin Defect.

Which cells are the targets of the pejvakin defect, and are they all hypervulnerable to sound exposure? To address this issue, the outcomes of functional tests specific of various types of auditory cell were compared among $Pjvk^{-/-}$, hair-cell conditional knock-out for pjvk ($Pjvk^{fl/fl}Myo15\text{-}cre^{+/-}$) and $Pjvk^{+/+}$ 2-3 weeks old mice, at baseline and after "controlled sound exposure". Moreover, Electrically-Evoked Brainstem Responses (EEBR) to a direct electric stimulation of the auditory neurons, which test the response of the auditory pathway beyond the cochlea, was also analysed. A "controlled electric exposure" (as it will be named henceforth), an electric-impulse stimulation rate of 200/s for a 1-min duration was delivered, as compared to 16/s and 10-s duration of the stimulus used for the pre and post-exposure EEBRs.

Figure 3:
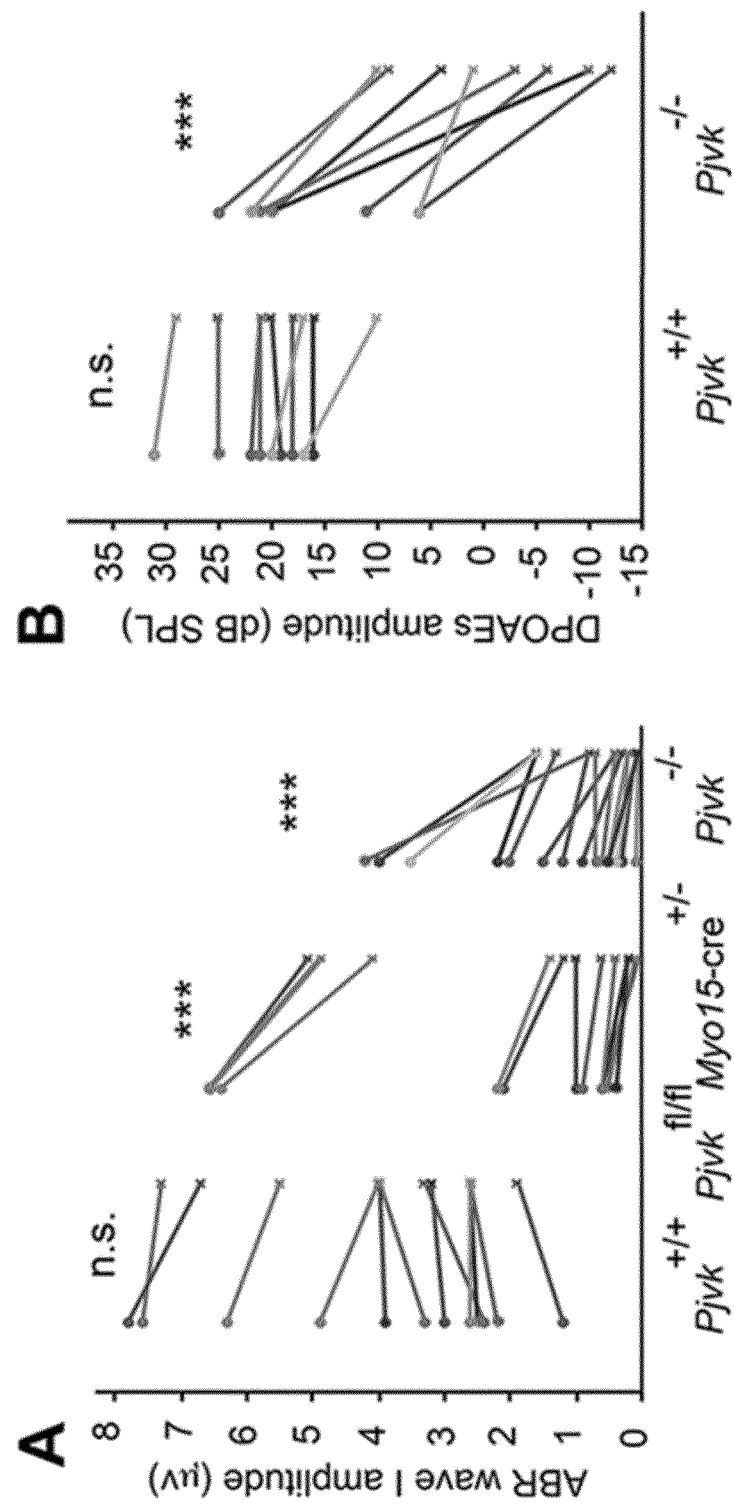
FIG. 3 represents effects of a brief exposure to moderately intense stimuli on the auditory function in Pjvk$^{-/-}$ and Pjvk$^{fl/fl}$Myo/5-cre$^{+/-}$ mice. (A-C) ABR wave I amplitude (A), DPOAE amplitude (B) and ABR interwave I-IV latency (C) in Pjvk$^{-/-}$ and Pjvk$^{fl/fl}$Myo15-cre$^{+/-}$ mice, before (left) and after (right) "controlled sound exposure", which reveals hypervulnerability to sound of IHCs, OHCs, and auditory pathway (the latter, only in Pjvk$^{-/-}$ mice, not in Pjvk$^{fl/fl}$Myo15-cre$^{+/-}$ mice with a pejvakin defect only in hair cells), respectively. (D) EEBR wave EIV amplitude before and after "controlled electrical exposure" in Pjvk$^{-/-}$ and Pjvk$^{fl/fl}$Myo15-cre$^{+/-}$ mice, showing that this amplitude is abnormal and hypervulnerable only when pejvakin is absent from auditory neurons. (E and F) Examples of ABRs before and after "controlled sound exposure" of Pjvk$^{-/-}$ and Pjvk$^{fl/fl}$Myo15-cre$^{+/-}$ mice; wave I is affected by exposure in both mice, and wave IV undergoes an additional latency increase only in Pjvk$^{-/-}$ mice. (G-I) Examples of EEBRs before and after "controlled electrical stimulation" in Pjvk$^{+/+}$, Pjvk$^{-/-}$ and Pjvk$^{fl/fl}$Myo15-cre$^{+/-}$ mice; EEBRs are affected by controlled electric exposure only in Pjvk$^{-/-}$ mice. (J-L) Effects of neuronal function rescuing in Pjvk$^{-/-}$ mice by injection of AAV8-Pjvk, on ABR interwave I-IV latency (J), EEBR wave EIV amplitude before and after "controlled electrical stimulation" (K) and EEBR interwave EII-EIV latency (one example in L), showing that transfected ears tend to normalize and lose their hypersensitivity to "controlled electric exposure". n.s., not statistically significant; ***p<0.001. Error bars indicate±SEM.
Figure 3:
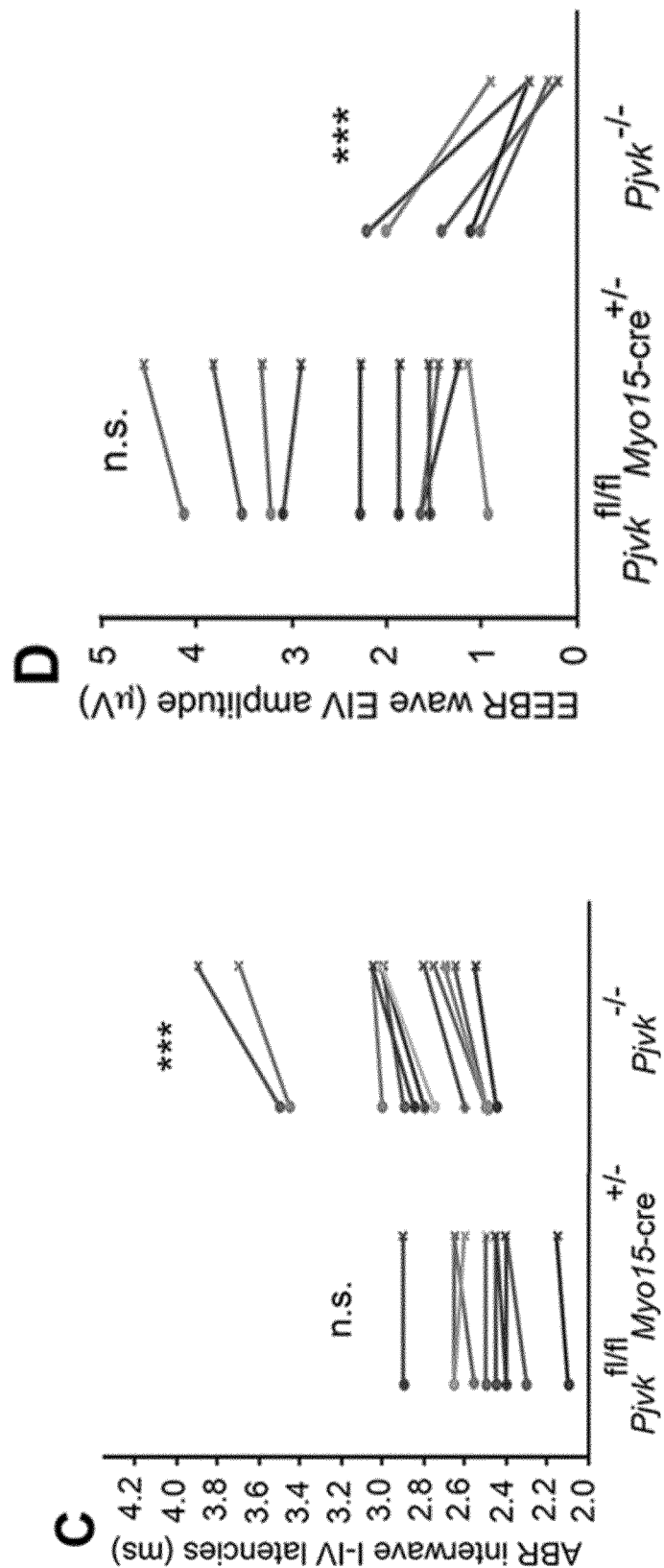
Figure 3:
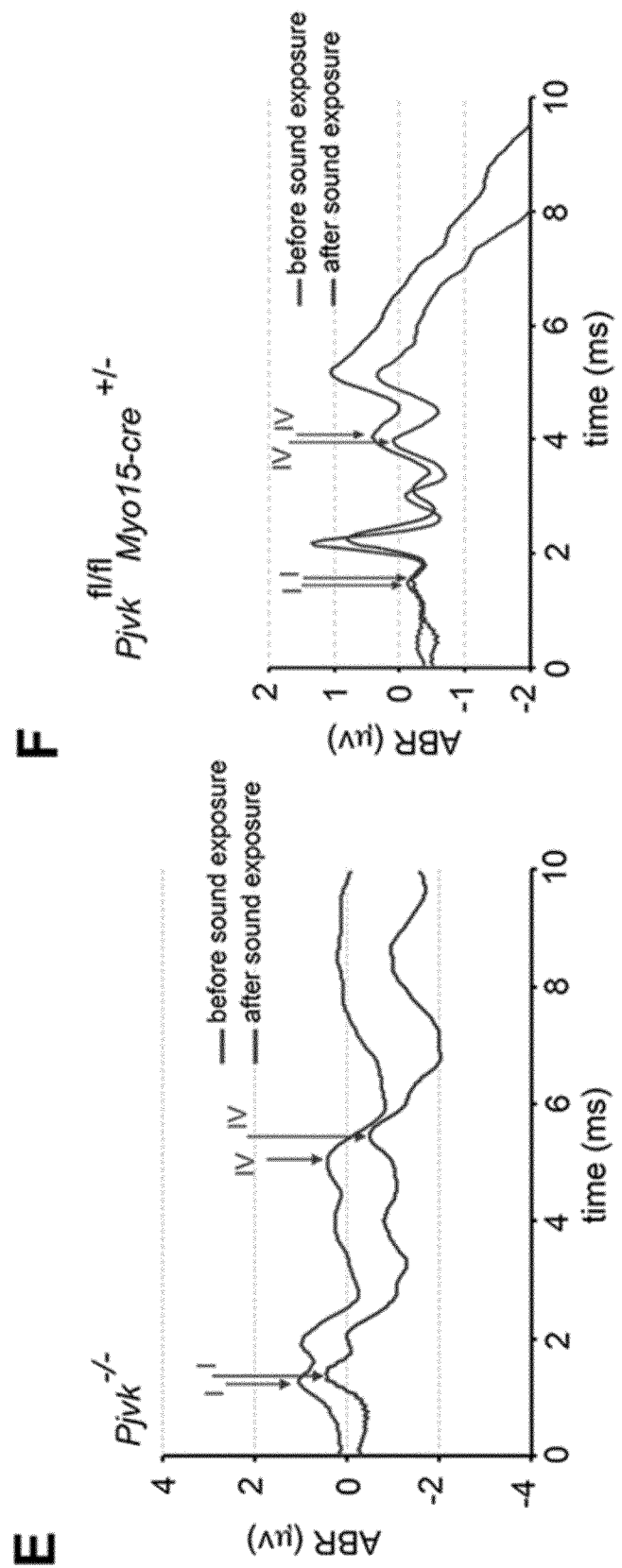
Figure 3:
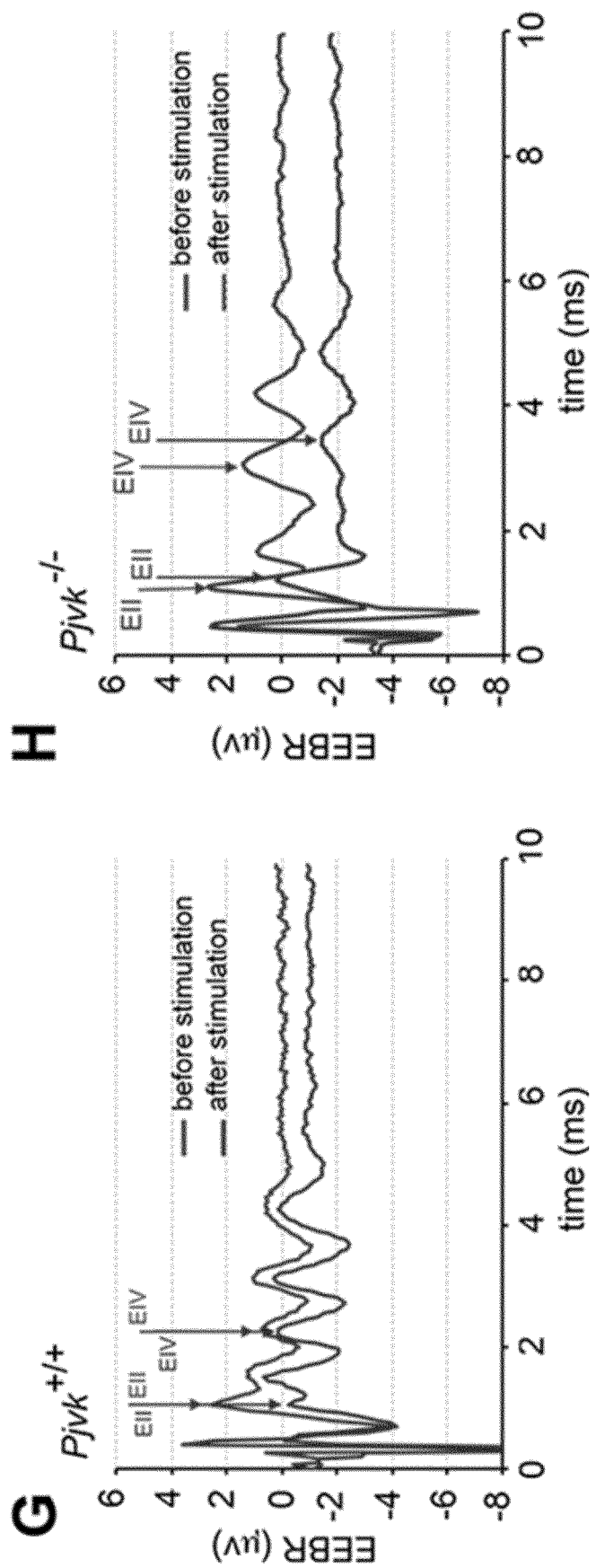
Figure 3:
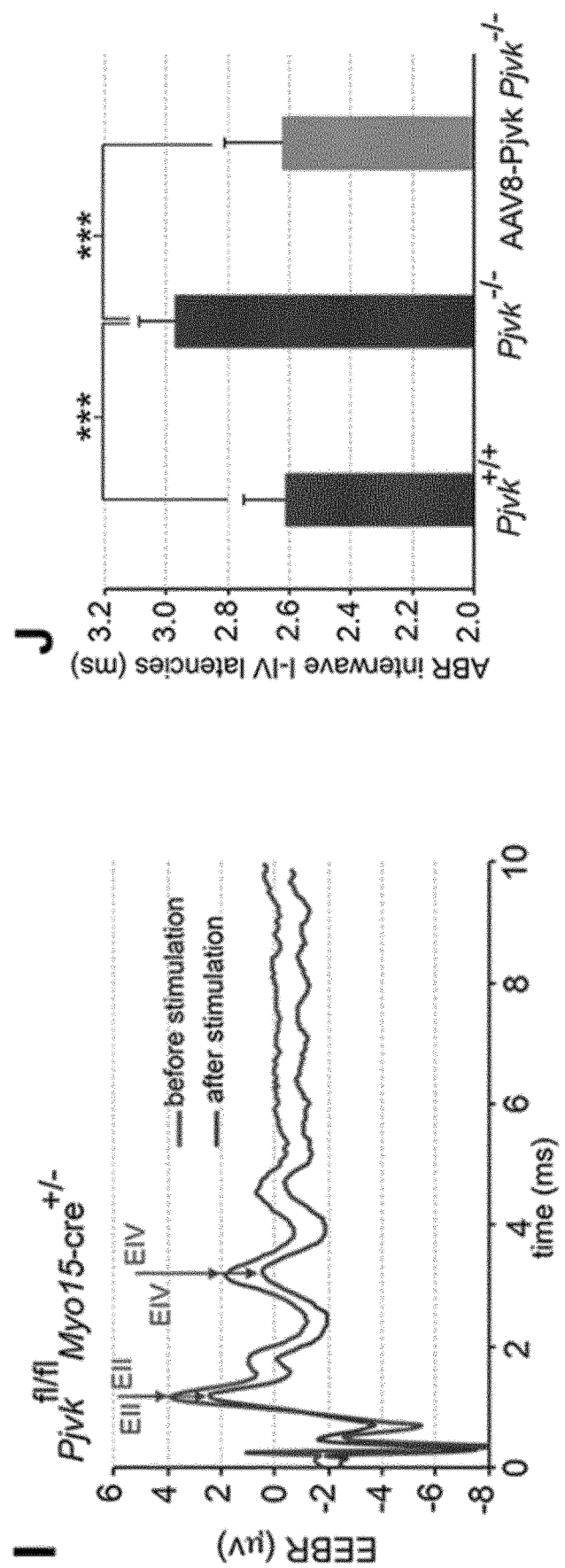
Figure 3:
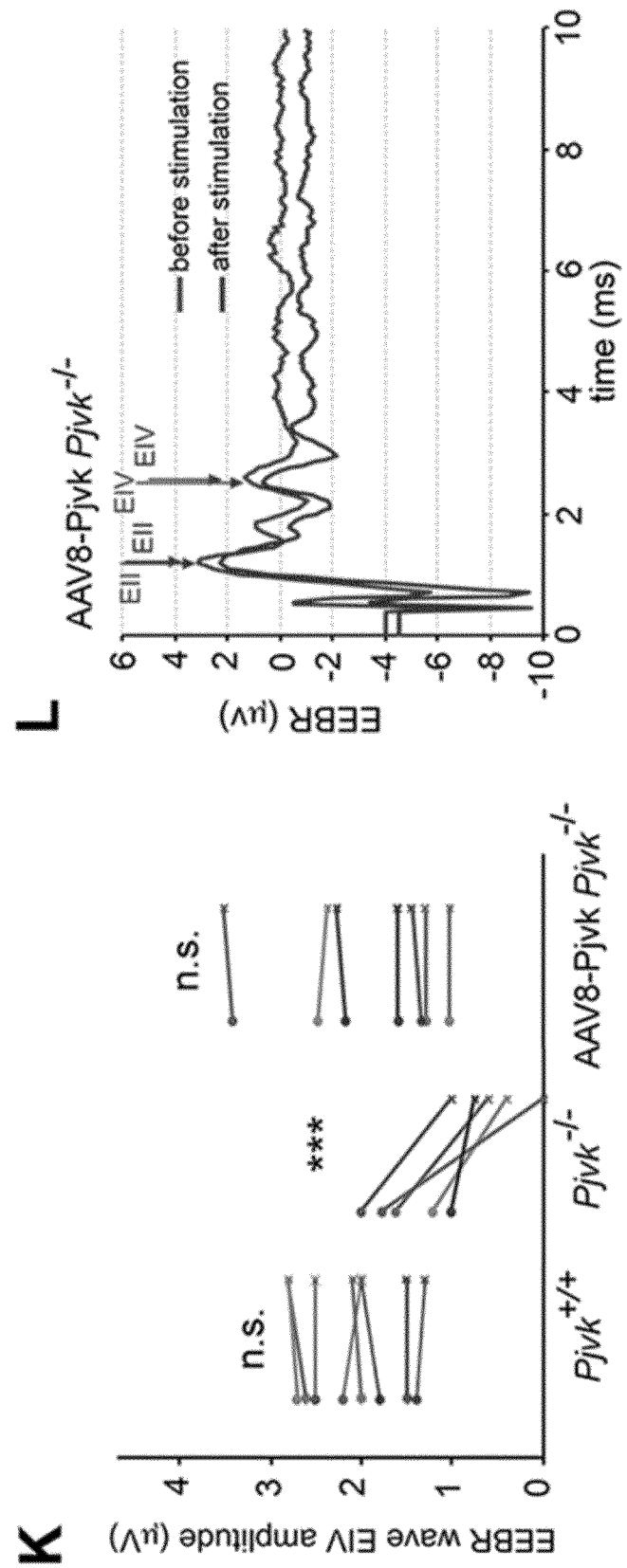

The inner hair cells (IHCs) are the genuine auditory sensory cells. Their responses to vibrations produced by tone bursts and amplified by the mechanical activity of OHCs trigger action potentials in the auditory neurons, which make up the auditory nerve. Synchronized action potentials in the peripheral part of this nerve generate ABR wave-I. In $Pjvk^{fl/fl}Myo15\text{-}cre^{+/-}$, as a result of pejvakin absence from the hair cells only, and stimulation condition in which the IHCs' response is made independent of the OHC activity by a sound stimulation intensity exceeding 90 dB SPL (Robles & Ruggero, 2001), ABR wave-I amplitude and latency specifically reflect IHC function. An increase of wave-I latency (1.58 ms in $Pjvk^{fl/fl}Myo15\text{-}cre^{+/-}$ (n=20), vs. 1.32 ms in $Pjvk^{+/+}$ littermates (n=30); p<0.001) and a decrease of wave-I amplitude (37% of the amplitude in control littermates; p<0.001), incriminate IHC dysfunction in the hearing impairment caused by pejvakin defect. "Controlled sound exposure" induced further decreases of ABR wave-I amplitude in $Pjvk^{-/-}$ and $Pjvk^{fl/fl}Myo15\text{-}cre^{+/-}$ (48% and 55% of pre-exposure amplitude respectively compared to 108% in Pjvk$^{+/+}$ mice, p<0.001; FIG. 3A). Pejvakin-lacking IHCs are thus defective and hypervulnerable to sound.

As shown above, OHCs, are also target cells of the pejvakin-defect. In Pjvk$^{-/-}$ mice with persisting DPOAEs (n=8), the "controlled sound exposure" produced an average increase in DPOAE threshold of 17.1±6.7 dB in the 12 to 20 kHz frequency interval (p<0.0001) whilst Pjvk$^{+/+}$ mice (n=9) were unaffected (p=0.5) (FIG. 3B). Pejvakin-lacking OHCs are thus also hypervulnerable to sound.

To investigate the influence of the absence of pejvakin on neural conduction whilst excluding any confounding effect of cochlear damage, we compared EEBR waves E II and E IV (easiest to reliably measure owing to their sharpness) between Pjvk$^{-/-}$ and Pjvk$^{fl/fl}$Myo15-cre$^{+/-}$ mice. The amplitudes of these waves did not differ (for wave E IV for example, average amplitudes were 2.6±1.8 μV in Pjvk$^{-/-}$ mice (n=18) as against 2.2±1.2 μV in Pjvk$^{fl/fl}$Myo15-cre$^{+/-}$ mice (n=11); t-test, p=0.13). However upon controlled electric exposure, EEBR waves E II and E IV were reduced in amplitude by 41% and 47% respectively for at least 3 min, in Pjvk$^{-/-}$ mice (n=10; p=0.02 and p=0.012 respectively) (FIG. 3D for E IV; E II not shown), in contrast with Pjvk$^{fl/fl}$Myo15-cre$^{+/-}$ mice (n=10), which were insensitive to controlled electric exposure even prolonged 10 min (FIG. 3D, 3G-3I). The interwave E II-E IV interval differed between Pjvk$^{-/-}$ mice and Pjvk$^{fl/fl}$Myo15-cre$^{+/-}$ (n=10 for each group), by 0.41 ms (unpaired t-test; p=0.003). Controlled electric exposure induced a further increase of interwave E II-E IV interval, of 0.15 ms, in Pjvk$^{-/-}$ mice (paired t-test, p=0.001), whilst being ineffective in Pjvk$^{fl/fl}$Myo15-cre$^{+/-}$ mice (FIG. 3G-3I). Neural activity evoked by sound can also be assessed independent of OHC and IHC function by measuring the neuronal conduction time between ABR wave I and wave IV (the counterpart of wave E IV), which was increased beyond the normative interval in about one third of tested Pjvk$^{-/-}$ mice (n=25) (FIG. 3C, 3E) and further increased in all Pjvk$^{-/-}$ mice in response to 'controlled sound exposure' (n=16 ears with an ABR threshold <95 dB SPL, average increase 0.16 ms relative to their pre-exposure value; p<0.001, paired t-test) whilst both Pjvk$^{+/+}$ and Pjvk$^{fl/fl}$Myo15-cre$^{+/-}$ mice maintained normal interwave I-IV intervals (p=0.5, paired t-test, for the two genotypes) (FIG. 3C, 3F). So as to clarify whether these anomalies are of neuronal or glial origin, a rescuing experiment was performed in Pjvk$^{-/-}$ mice using the murine pejvakin cDNA vectorised by the adenoviral associated vector 8, AAV8, which transduces exclusively neurons in the auditory pathway, from the auditory neurons to the brainstem, upon direct injection into the cochlea. All Pjvk$^{-/-}$ mice (n=7) injected on P3 by AAV8-PjvkcDNA tested at P21, displayed normal ABR interwave I-IV intervals (FIG. 3J), and EEBR wave-E IV amplitude insensitivity to controlled electric stimulation (FIG. 3K, 3L, 1.91±0.97 μV before and 1.87 μV±1.07 after; paired t-test, p=0.5).

4. Redox Metabolism Anomalies in the Absence of Pejvakin

Figure 4:
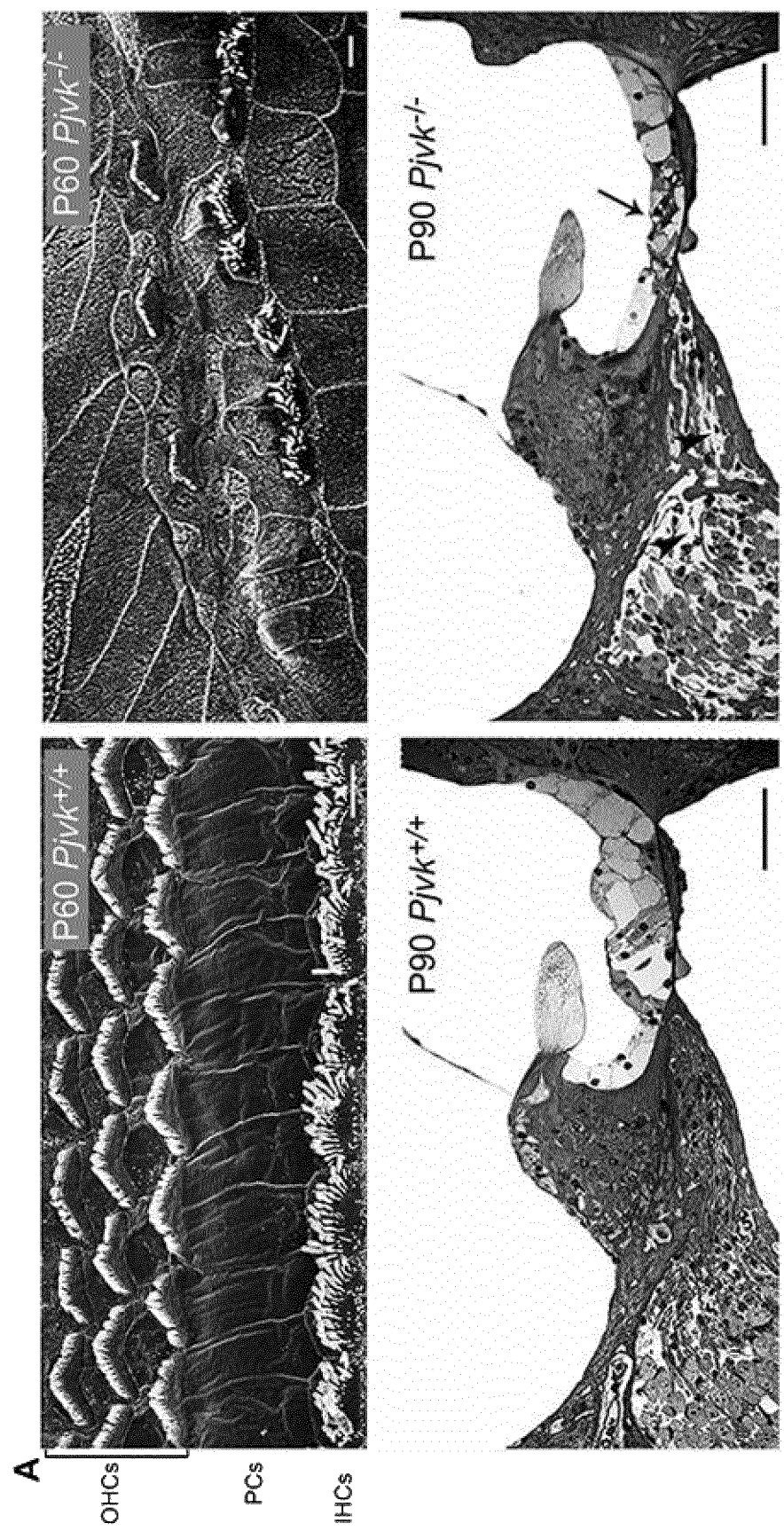
FIG. 4 shows progressive degeneration of the organ of Corti in Pjvk$^{-/-}$ mice (FIG. 4A) and increased lipid peroxidation in the cochlea of Pjvk$^{-/-}$ mice (FIG. 4B). (A) Upper panels: Scanning electron micrographs showing surface views of the organ of Corti in the basal turn of the cochlea from P60 Pjvk$^{+/+}$ and Pjvk$^{-/-}$ mice. In the Pjvk$^{-/-}$ mouse, many outer hair cells (OHCs), inner hair cells (IHCs), and pillar cells (PCs) are missing. Scale bars are 5 µm. Lower panels: Light micrographs of cross sections taken from the middle turn of the cochlea in Pjvk$^{+/+}$ and Pjvk$^{-/-}$ mice on P90. In the Pjvk$^{-/-}$ mouse, OHCs, IHCs, and supporting cells can't be identified anymore, and the organ of Corti has degenerated (arrow). In addition, the numbers of nerve fibres and cochlear ganglion neurons (arrowheads) are markedly decreased. Scale bars are 80 µm. (B) Cryosections of the organ of Corti (middle turn, upper panels) and of the cochlear ganglion (apical and basal turns, lower panels) from P60 Pjvk$^{+/+}$ and Pjvk$^{-/-}$ mice, immunolabelled for 4-HNE, a by-product of lipid peroxidation (green), and stained with DAPI (blue) to show cell nuclei. Asterisks indicate the nuclei of OHCs and IHCs. In the Pjvk$^{-/-}$ mouse, some OHCs and cochlear ganglion neurons are missing, but the OHCs present are highly immunoreactive for 4-HNE (arrows), as are the cochlear ganglion neurons, especially in the basal turn. Scale bars are 20 µm.
Figure 4:
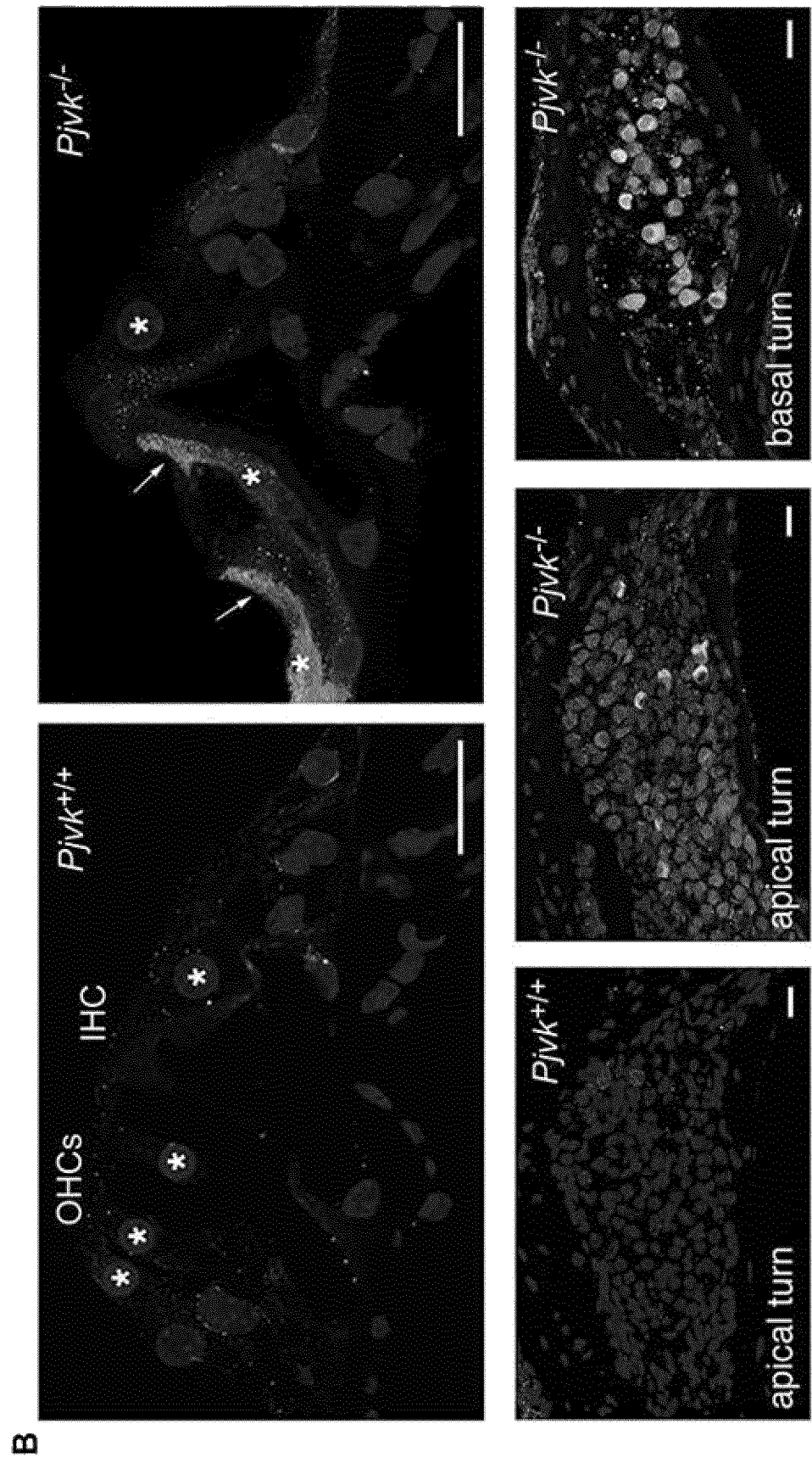

To address the pathogenesis of the hearing impairment of Pjvk$^{-/-}$ mice, it was first proceeded with the morphological analysis of their cochlea, by light microscopy on semithin sections and scanning (SEM) and transmission electron microscopy (TEM). On P15, hair cells and auditory neurons showed normal morphology and numbers. Notably, the OHC and IHC hair bundles, the mechanoreceptive structures to sound of the hair cells, analysed from P15 to P60 by SEM, and the ribbon synapses of the IHCs and their afferent auditory neurons studied by TEM, were unmodified (FIG. 4A and data not shown). On P30, a loss of a few OHCs (16%), restricted to the base of the cochlea, tuned to high frequency sounds, was observed. From P30 onwards, OHCs and cochlear ganglion neurons, then IHCs, disappeared, and the sensory epithelium (organ of Corti) progressively degenerated.

Since the above-described physiological anomalies were already present in a broad range of frequencies in Pjvk$^{-/-}$ mice at P15, i.e. well before any morphologically abnormal features could be detected, the hearing impairment of young Pjvk$^{-/-}$ mice can be attributed to functional defects.

Figure 5:
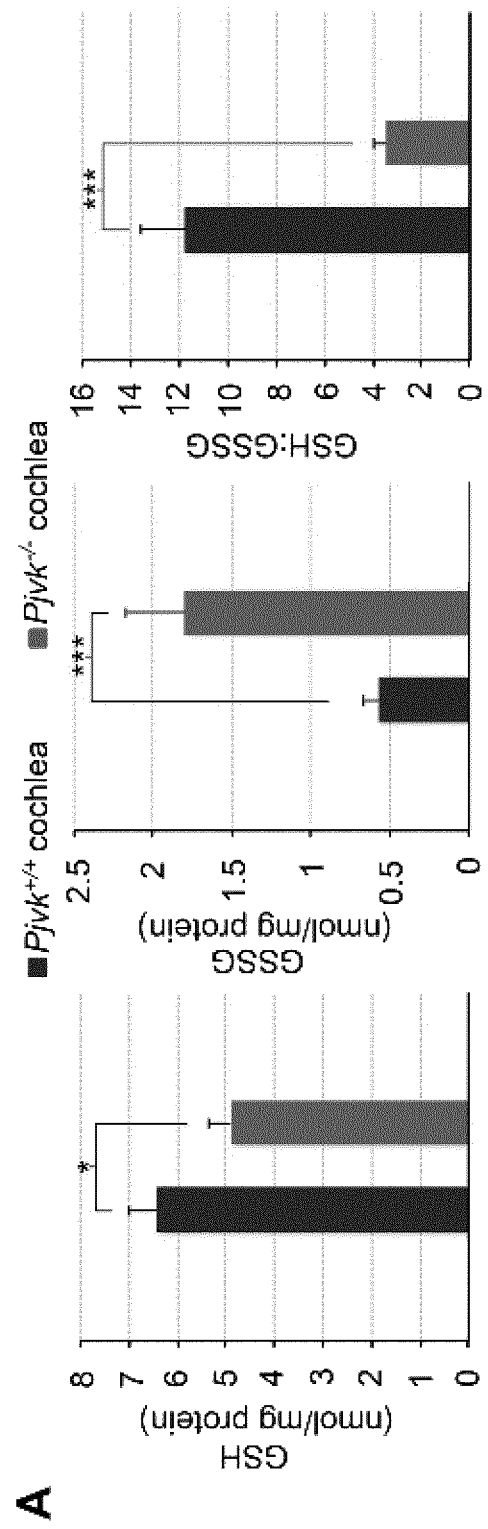
FIG. 5 represents increased oxidative stress and ROS-induced cell damage in the Pjvk$^{-/-}$ cochlea. (A) Reduced-glutathione (GSH) (left bar chart), oxidized-glutathione (GSSG) (middle bar chart) contents, and GSH:GSSG ratio (right bar chart), in P21 Pjvk$^{-/-}$ versus Pjvk$^{+/+}$ cochlea. Error bars represent the SEM of 3 independent experiments. (B) Marked decrease in the BK α-subunit immunolabelling in Pjvk$^{-/-}$ IHCs. Left: P20 Pjvk$^{+/+}$ and Pjvk$^{-/-}$ IHCs. Scale bar is 5 µm. Right: quantitative analysis of BK channel clusters. Error bars represent the SD. *p<0.05, ***p<0.001.
Figure 5:
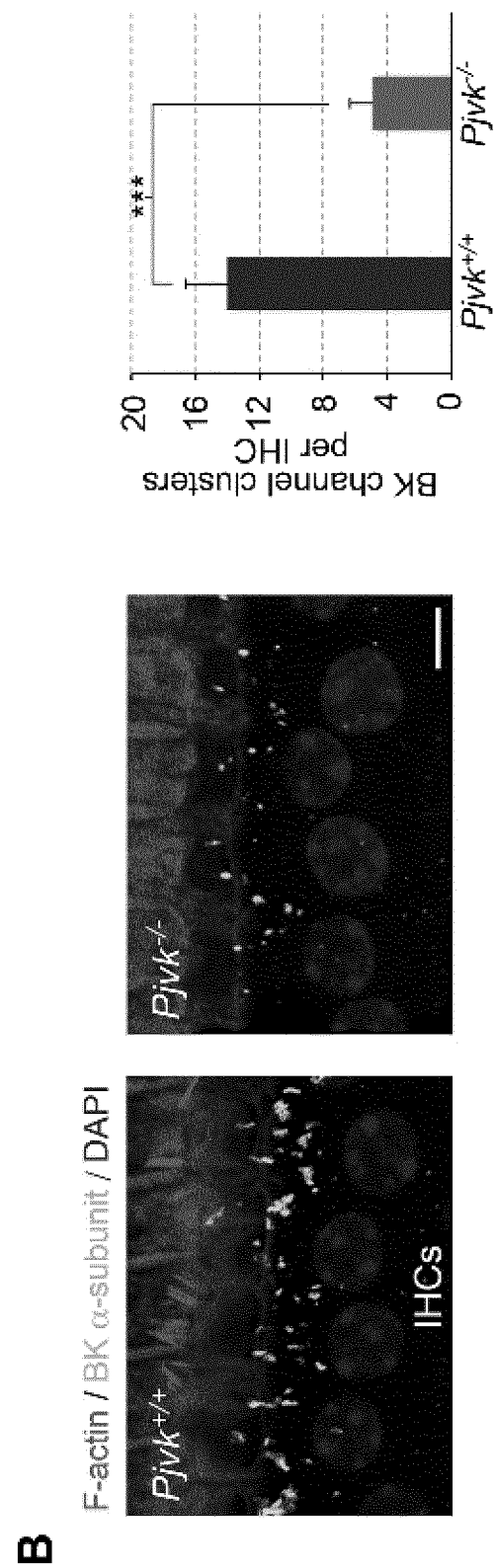

Possible changes in gene expression in Pjvk$^{-/-}$ organ of Corti, the cochlear sensorineural epithelium, were then investigated by microarrays in P15 old mice. Eighteen genes showed changes of their expression levels in Pjvk$^{-/-}$ mice above or below 1.5-fold relative to Pjvk$^{+/+}$ mice. Major changes were found in four genes involved in redox metabolism, specifically, CypA, Gpx2, c-Dct, and, Mpv17, which encode cyclophilin A, glutathione peroxidase 2, c-dopachrome tautomerase and Mpv17, respectively. All these genes displayed a down-regulated expression in Pjvk$^{-/-}$ mice, a result confirmed by quantitative RT-PCR (qRT-PCR), and all encode proteins with antioxidant function. Glutathione peroxidase 2 and cyclophilin A are involved in the reduction of hydrogen peroxide ($H_2O_2$) into $H_2O$, directly and indirectly via the activation of several peroxiredoxins, respectively (Lee et al., 2001; Evans & Halliwell, 1999). Although Mpv17 has a yet unknown activity, Mpv17-defect in both human and mouse results in a hepatocerebral mitochondrial DNA depletion syndrome with profound deafness (Binder et al., 1999) reported in the mutant mice and reactive oxygen species (ROS) accumulation (Meyer zum Gottesberge et al., 2001). Finally, c-dopachrome tautomerase decreases cell sensitivity to oxidative stress by increasing reduced glutathione (GSH) level, the major small antioxidant molecule of the cell (Michard Q et al, 2008a; 2008b). The antioxidant defence in the cochlea of 3 weeks old Pjvk$^{-/-}$ mice was then assessed by measuring the level of oxidized glutathione (GSSG) and the ratio between reduced and oxidized glutathione (GSH:GSSG). GSSG content was increased about 3 fold in Pjvk$^{-/-}$ cochlea compared to Pjvk$^{+/+}$ (1.80±0.57 nmole/mg protein and 0.57±0.12 nmole/mg protein, respectively; unpaired t-test, p=0.01), whilst GSH level was moderately decreased in Pjvk$^{-/-}$ cochlea compared to Pjvk$^{+/+}$ (4.91±0.80 nmole/mg protein and 6.42±0.92 nmole/mg protein, respectively; unpaired t-test, p=0.05). The ratio of GSH:GSSG decreased in Pjvk$^{-/-}$ cochlea compared to Pjvk$^{+/+}$ cochlea (3.45±1.77 and 11.74±1.90 in Pjvk$^{-/-}$ and Pjvk$^{+/+}$ cochlea, respectively; unpaired t-test, p<0.001) (FIG. 5A). Increase in GSSG and decrease of the GSH:GSSG are markers of oxidative stress; taken together these results show that lack of pejvakin results in oxidative stress in the Pjvk$^{-/-}$ cochlea. Since $Ca^{2+}$-activated potassium (BK) channels are well known as target of ROS (Tang et al., 2004), we investigated whether the number of these channels is altered in Pjvk$^{-/-}$ IHCs. The mean number of spots immunolabelled for the BK α-subunit per IHC was much lower in Pjvk$^{-/-}$ mice (5.0±1.4, n=283 IHCs from 7 mice) than in Pjvk$^{+/+}$ mice (13.9±2.6, n=204 IHCs from 9 mice; t-test, p<0.001) (FIG. 5B).

The presence of possible ROS damage in Pjvk$^{-/-}$ mice was thus tested. Lipids are natural targets of oxidation by ROS; 4-hydroxy-2-nonenal (4-HNE), a by-product of lipid peroxidation, was not immunodetected in P15 Pjvk$^{-/-}$ cochlea but both the hair cells and cochlear ganglion neurons were labelled in P30 Pjvk$^{-/-}$ mice with a marked increase at P60 (FIG. 4B). We quantified lipid peroxidation in cochlear lysates from P30 Pjvk$^{-/-}$ and Pjvk$^{+/+}$ mice using the thiobarbituric acid-reactive substances (TBARS) colorimetric assay, which detects malondialdehyde (MDA), another end product of lipid peroxidation (Janero D R et al., 1990). Cochlea tested independently, gave consistent results, specifically, a 16% average increases in MDA content in $Pjvk^{-/-}$ (2.15±0.14 µM) compared to $Pjvk^{+/+}$ (1.84±0.11 µM) mice (unpaired t-test, p=0.04). These results suggested that Pjvk defect results in an antioxidant metabolism failure progressively leading to ROS cellular damages.

5. Pejvakin is a Peroxisomal Protein

Figure 6:
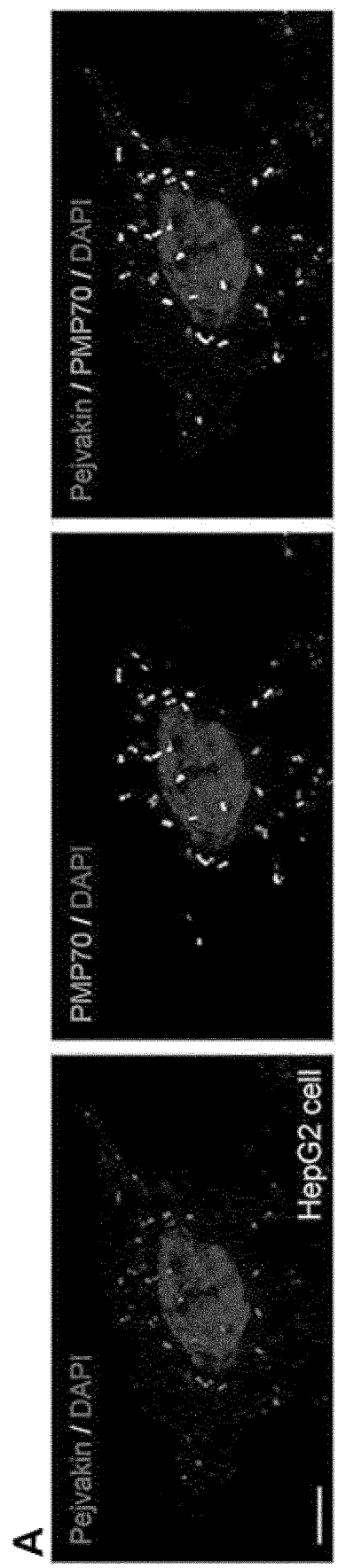
FIG. 6 shows that Pejvakin is a peroxisome-associated protein involved in the oxidative stress-induced peroxisomal proliferation. (A, B) Immunolabelling of PMP70 and endogenous pejvakin in a HepG2 cell (A) and in two P20 Pjvk$^{+/+}$ IHCs (B). (C) Number of peroxisomes in Pjvk$^{+/+}$ and Pjvk$^{-/-}$ mouse embryonic fibroblasts (MEFs) subjected to 0.5 mM $H_2O_2$, versus untreated MEFs (n=30 cells for each condition). (D) Untransfected HeLa cells (NT), and transfected cells producing either EGFP alone or EGFP together with the wild-type pejvakin (Pjvk) or a mutated Pjvk (p.T54I, p.R183W, p.C343S, or p.V330Lfs*7). Left panel: Bar chart showing the numbers of peroxisome per cell 48 hours after transfection. There were on average 33% more peroxisomes in cells producing both EGFP and Pjvk (n=200) than in cells producing EGFP alone (n=150). Right panel: for every range of enlarged peroxisome size, x (0.6-0.8 µm, 0.8-1.0 µm, and >1.0 µm), in two perpendicular directions, the proportion of cells containing at least one peroxisome. (E) Abnormalities in shape and distribution of peroxisomes in mature Pjvk$^{-/-}$ OHCs detected by TEM (transmission electron microscopy; P30 Pjvk$^{-/-}$ (middle and right panels) and Pjvk$^{+/+}$ (left panel) OHCs. Insets (middle panel) show enlarged views of individual peroxisomes. In Pjvk$^{+/+}$ OHCs, peroxisomes are grouped just under the cuticular plate (CP) (arrowheads), with none detected in the perinuclear region (n=33 sections, upper bar chart). In Pjvk$^{-/-}$ OHCs, some peroxisomes remain under the CP (arrowheads), but catalase-containing structures, misshapen peroxisomes (arrows), are detected in the perinuclear region (n=24 sections, upper bar chart). Peroxisomes located under the CP are larger in Pjvk$^{-/-}$ OHCs (n=92 peroxisomes) than in Pjvk$^{+/+}$ OHCs (n=89 peroxisomes) (lower bar chart). N: cell nucleus. p<0.01, *p<0.001. Error bars represent the SEM. Scale bars are 5 µm in (A) and (B), and 0.5 µm in (E).
Figure 6:
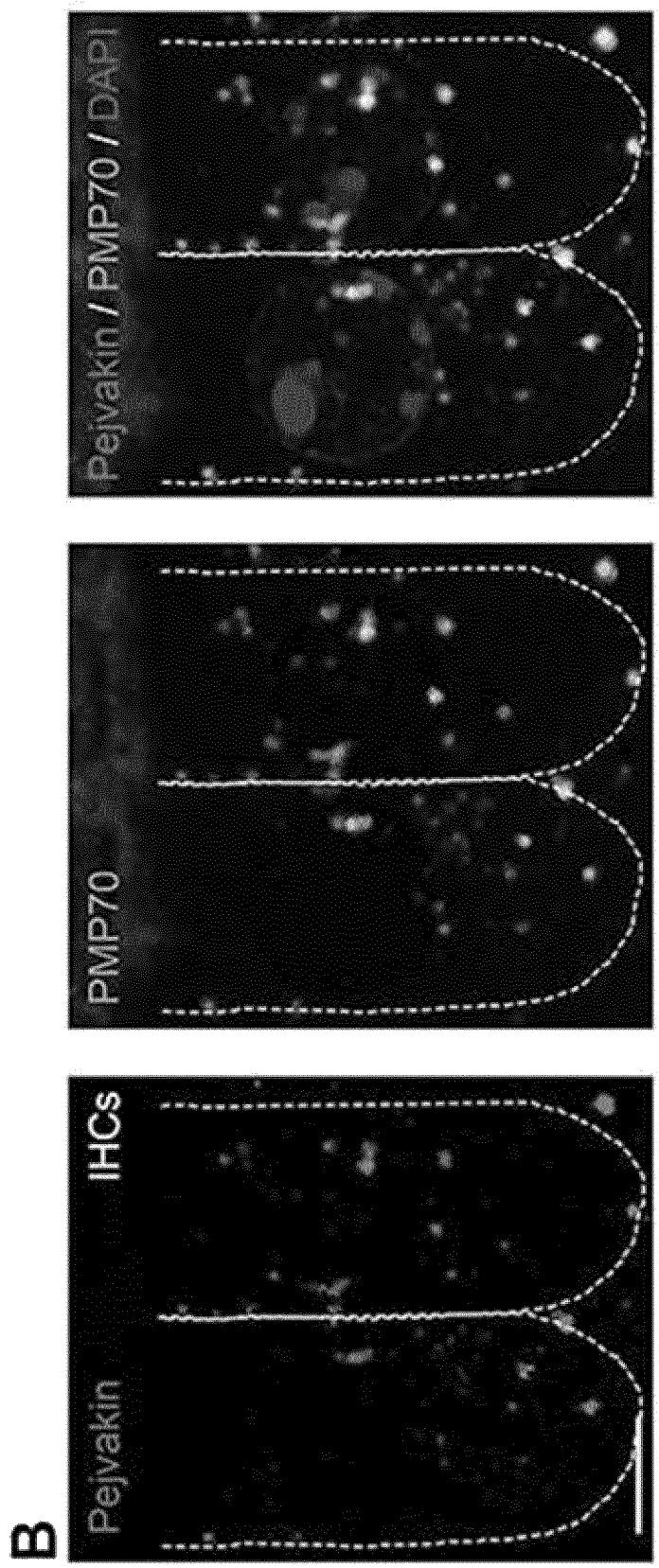
Figure 6:
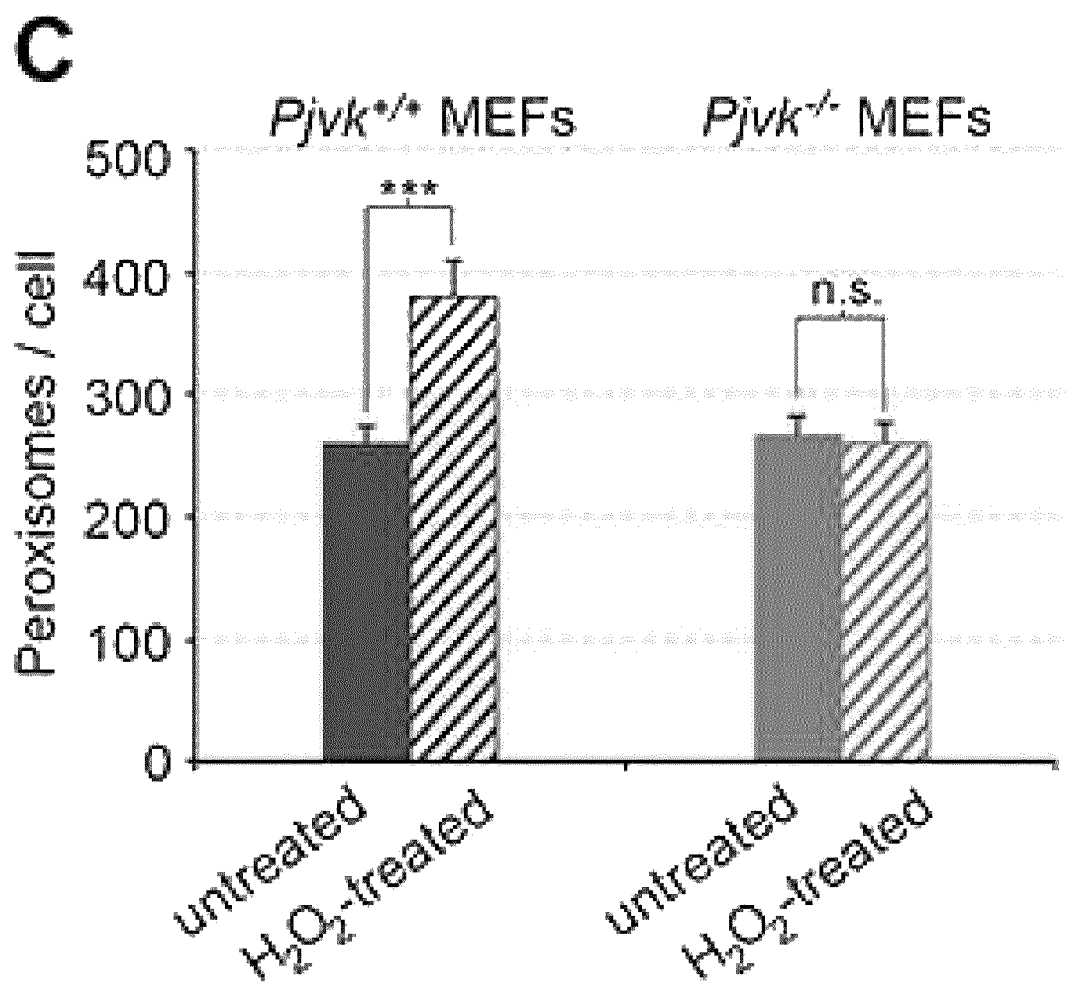
Figure 6:
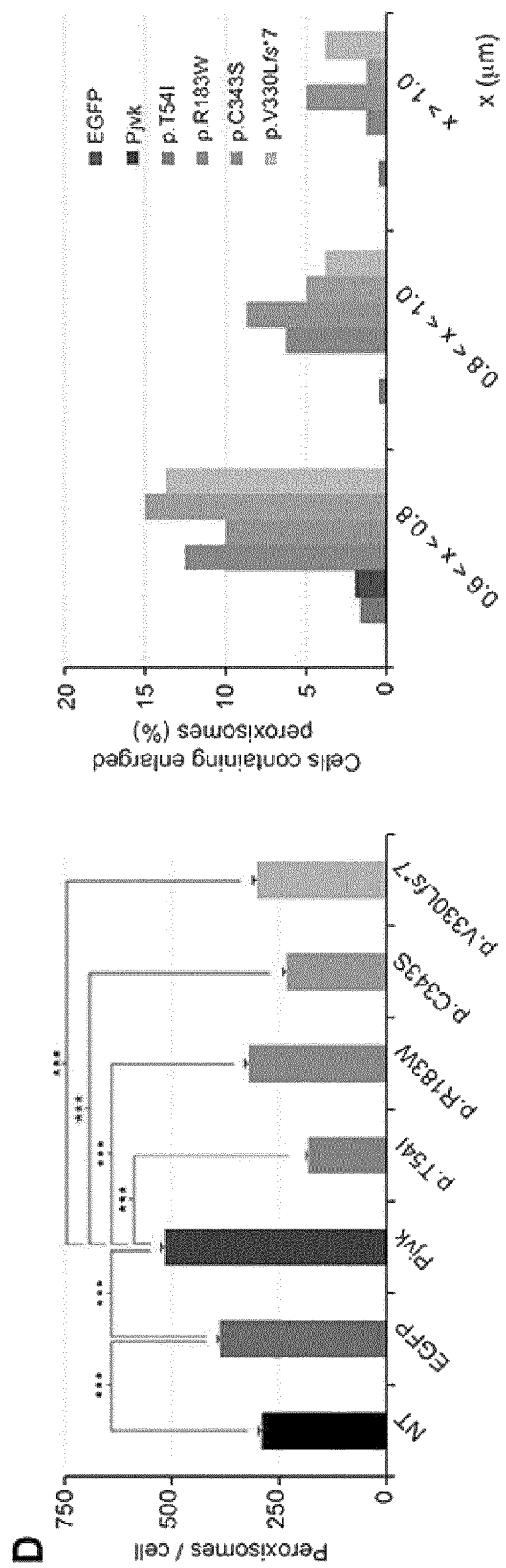
Figure 6:
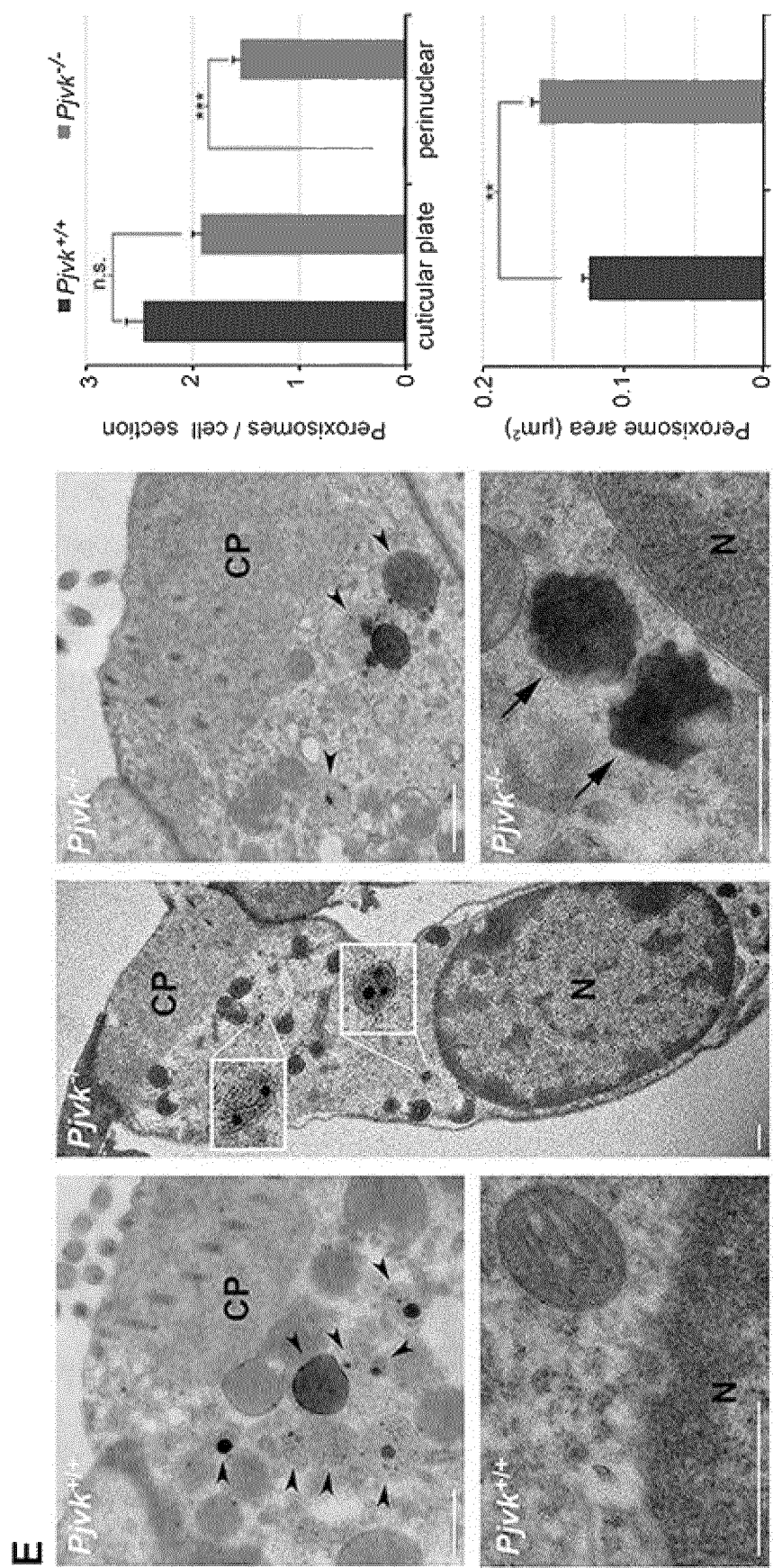
Figure 7:
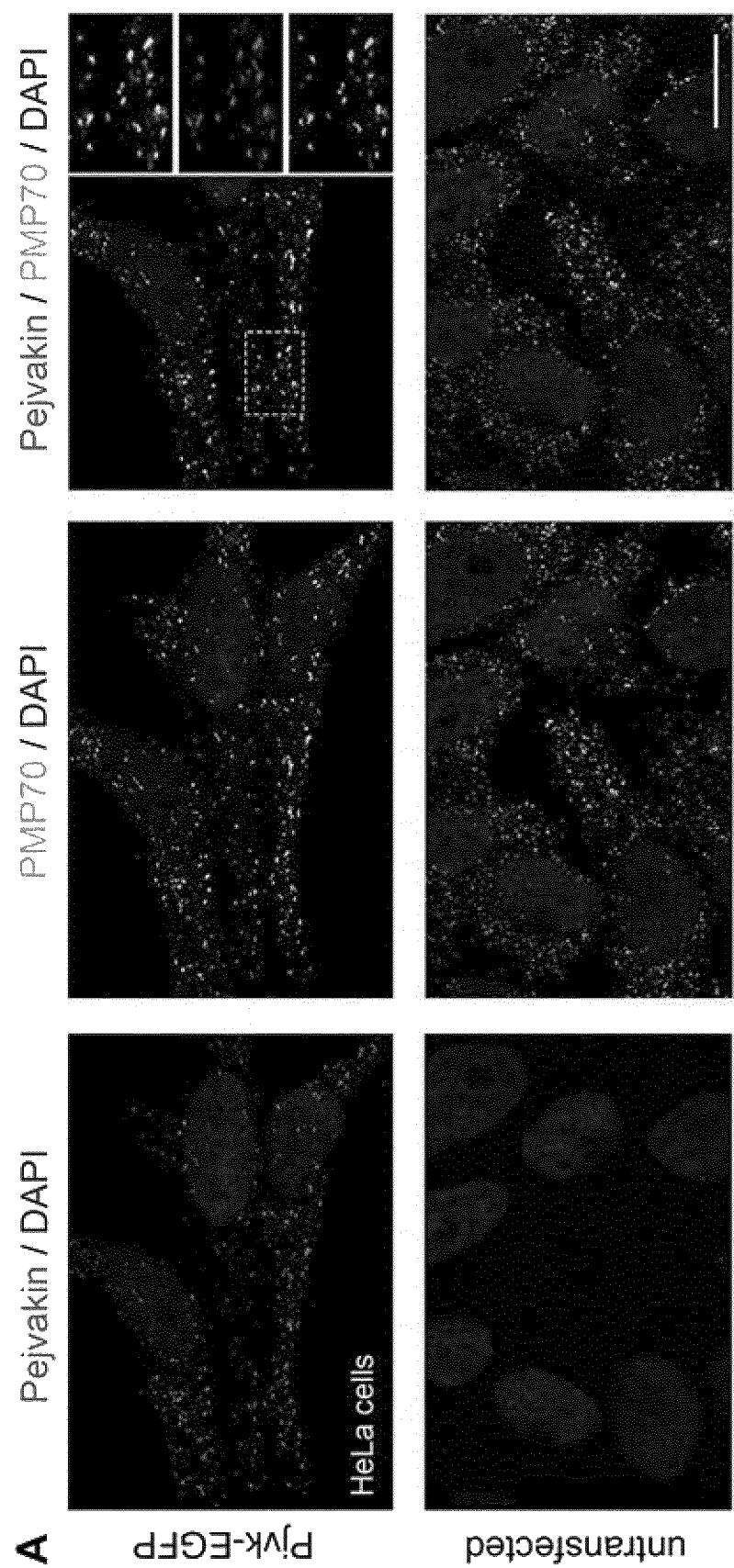
FIG. 7 shows that Pejvakin is associated with peroxisomes in transfected HeLa cells (A), the specificity of the antibody (B) and the immunostaining of dividing peroxisomes (C). (A) Transfected HeLa cells producing pejvakin (Pjvk-EGFP, upper panel) and untransfected cells (lower panel) were immunostained with both an anti-pejvakin antibody (Pjvk-G21) and an antibody against peroxisome membrane protein 70 (PMP70). Cell nuclei were stained with DAPI (dark grey). Colocalization of the immunostainings of pejvakin (light grey) and PMP70 (white) was observed in transfected cells (see inset for higher magnification of the boxed area). Pejvakin was not detected in untransfected cells. (B) Absence of immunolabelling in inner hair cells (IHCs) from P21 Pjvk$^{-/-}$ and Pjvk$^{fl/fl}$Myo15-cre$^{+/-}$ mice with the Pjvk-G21 antibody demonstrates the specificity of this antibody (see FIG. 6B for immunolabelling in Pjvk$^{+/+}$ IHCs). (C) Pejvakin immunostaining of dividing peroxisomes. Double immunolabelling of HepG2 cells for pejvakin (light grey) and PMP70 (white). Upper panel: arrowheads indicate pejvakin-immunoreactive protrusions from pre-existing peroxisomes. Lower panel: boxed areas show pejvakin-immunoreactive string-of-beads structures corresponding to elongated and constricted peroxisomes (preceding final fission). Scale bar is 10 µm in (A), 5 µm in (B), and 2 µm in (C).
Figure 7:
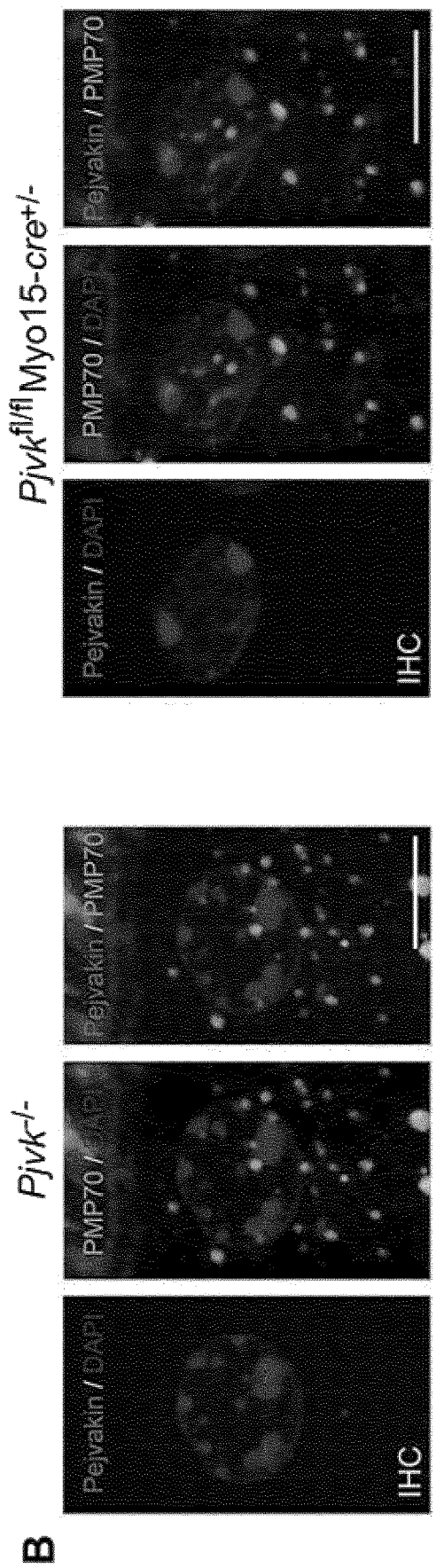
Figure 7:
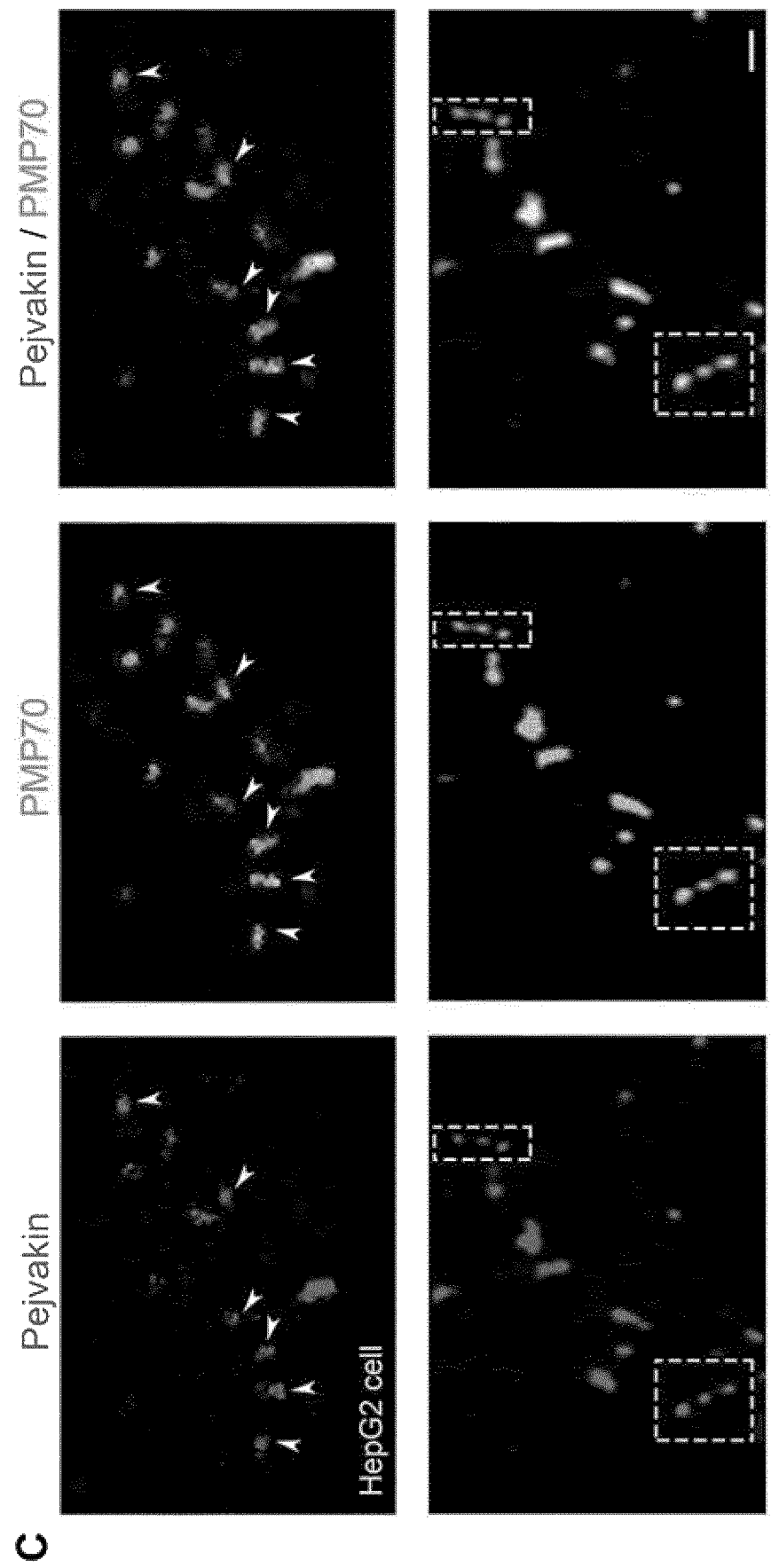

In order to assess the subcellular localization of pejvakin, HeLa cells were transfected with recombinant vectors expressing the GFP-tagged C-terminal or N-terminal regions of mouse pejvakin and obtained a diffuse labelling throughout the cytoplasm. Pejvakin detection by immuno-labeling also turned out to be unsuccessful, as none of the antibodies (commercially available or generated in the lab), specifically recognized this protein. Considering the very limited sequence divergence of pejvakin amino-acid sequence among vertebrates, it was attempted to elicit an antibody response in $Pjvk^{-/-}$ mice. A monoclonal antibody (Pjvk-G21) was obtained, that revealed a punctate immuno-staining throughout the cytoplasm of transfected HeLa cells expressing pejvakin, absent in non-transfected cells. Co-staining with a marker of peroxisomes (peroxisome membrane protein 70, PMP70) revealed a strict colocalisation between pejvakin and peroxisomes (FIG. 7A). Our observations were extended to transfected HEK cells and COS-7 cells (not shown). Finally, in the human hepatoblastoma cell line HepG2, particularly rich in peroxisomes, a strong endogenous pejvakin-immunolabelling was detected, strictly localised at the peroxisomes (FIGS. 6A and 6B). The specificity of the Pjvk-G21 antibody was demonstrated by the immunolabelling of peroxisomes in the hair cells of $Pjvk^{+/+}$, but not $Pjvk^{-/-}$ and $Pjvk^{fl/fl}Myo15\text{-}cre^{+/-}$ mice (FIG. 7B).

6. Pejvakin Role in Peroxisome Proliferation

Figure 8:
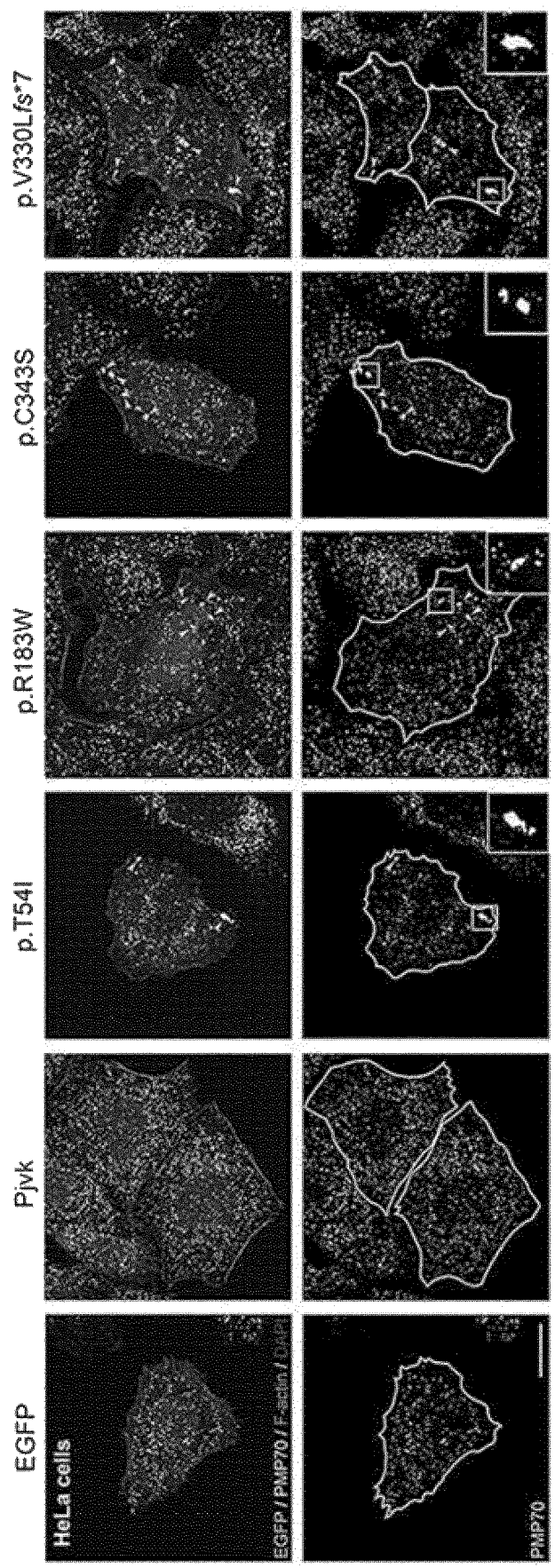
FIG. 8 shows the role of pejvakin in the proliferation and maintenance of peroxisomes. This figure shows larger numbers and enlargement of peroxisomes in transfected HeLa cells producing wild-type and mutant forms of pejvakin, respectively. In cells producing EGFP alone, EGFP and wild-type pejvakin (Pjvk), or EGFP and the p.T54I, p.R183W, p.C343S, or p.V330Lfs*7 mutated forms of pejvakin, peroxisomes were identified on the basis of their PMP70-immunoreactivity. The upper panel shows F-actin (medium grey), DAPI (dark grey), EGFP (light grey), and PMP70 (white) staining, whereas the lower panel shows only the PMP70 immunostaining of individual cells delimited by a white border. The number of peroxisomes is larger in cells producing wild-type pejvakin, and smaller in the cells producing any of the mutated forms of pejvakin, than in cells producing EGFP alone (see quantification in FIG. 6D). In addition, cells producing the mutated forms of pejvakin contain enlarged peroxisomes (arrowheads, and see insets for magnification; see also quantification in FIG. 6D). Scale bar is 10 µm.

In HepG2 cells, protrusions emerging from some peroxisomes, the first step of peroxisome biogenesis from pre-existing peroxisomes, were immunoreactive for pejvakin. String-of-beads structures corresponding to elongated and constricted peroxisomes, preceding final fission (Smith and Aitchison, 2013), were also pejvakin-immunoreactive, suggesting a role of this protein in peroxisome proliferation (FIG. 7C). HeLa cells were transfected with constructs encoding either GFP alone (GFP), or the normal form (Pjvk-GFP) or one of the six mutated forms (mutPjvk-GFP) of mouse pejvakin, carrying the causative mutations of DFNB59 reported so far, p.T54I, p.R183W, p.C343S, and p.V330LfsX7. Thirty hours later, the peroxisomes labelled by PMP70 were analysed in GFP expressing cells. A 27.2% increase of the peroxisome density was observed in Pjvk-GFP expressing cells as compared to GFP cells (p<0.001; FIGS. 6D and 8). In contrast, cells expressing the mutated forms of pejvakin, whatever the mutation, displayed a significant decrease in peroxisome density compared to cells expressing the normal form of pejvakin (p<0.001 for each mutation; FIGS. 6D and 8). No difference in the number of elongated peroxisomes (measuring less than 0.4 µm in one dimension and more than 0.4 µm in the perpendicular dimension (<0.4 µm×>0.4 µm)) per cell was observed, (p>0.05 for each mutation; FIG. 6D). In contrast, the percentage of transfected cells containing enlarged peroxisomes, that is with an area exceeding 0.4×0.4 µm in two perpendicular dimensions (>0.4 µm×>0.4 µm) was 3 to 4 fold higher among mutpjvk-GFP cells expressing any of the four mutations tested than in GFP or Pjvk-GFP expressing cells for every mutation (FIG. 6D); the number of these enlarged peroxisomes per cell displayed a modest (32%-40%) but significant increase in mutPjvk-GFP expressing cells compared to non-transfected cells or GFP or pjvk-GFP cells (p.R183W, p.C343S and: p<0.05, p.T54I and p.V330LfsX7; p<0.01), whatever the mutation (FIG. 6D).

Both the decrease of peroxisome density and the development of enlarged peroxisomes in cells expressing the mutated forms of pejvakin suggested that mutation in pjvk results in a defect of peroxisome proliferation.

Based on these results, peroxisome distribution and morphology in $Pjvk^{-/-}$ mice were investigated. Peroxisomes in $Pjvk^{-/-}$ and $Pjvk^{+/+}$ cochlea were labelled using catalase detection by 3,3'-diaminobenzidine (DAB) and analysed in transmission electron microscopy (TEM; FIG. 6E). It was focused on OHCs, the cells that display the earliest dysfunctioning. In P15 mice, no differences regarding the distribution and the shape of peroxisomes were detected in $Pjvk^{-/-}$ and $Pjvk^{+/+}$ mice. In contrast at P30, the peroxisome subcellular distribution and morphology were clearly distinct in $Pjvk^{-/-}$ and $Pjvk^{+/+}$ mice. The total number of peroxisomes per cell remained similar in $Pjvk^{-/-}$ and $Pjvk^{+/+}$ mice ($Pjvk^{+/+}$=2.45 vs. $Pjvk^{-/-}$=2.12; FIG. 6E). In $Pjvk^{+/+}$ mice, peroxisomes were strictly localized just beneath the cuticular plate, a rigid network of actin filaments immediately below the apical surface of the hair cells. Strikingly, in $Pjvk^{-/-}$ mice, peroxisomes were observed underneath the cuticular plate and irregular catalase labelled structures were observed with no visible membrane in the perinuclear region. The catalase positive (catalase$^+$) area of such perinuclear peroxisomes is significantly larger compared the one of peroxisomes present at the cuticular plate from either $Pjvk^{+/+}$ or $Pjvk^{-/-}$ mice (catalase$^+$ area of perinuclear peroxisomes from $Pjvk^{-/-}$ mice: 0.11 µm$^2$ vs catalase$^+$ area of peroxisomes present at the cuticular plate from $Pjvk^{+/+}$ mice: 0.04 µm$^2$, vs catalase$^+$ area of peroxisomes present at the cuticular plate from $Pjvk^{-/-}$ mice: 0.05 µm$^2$, p<0.001 in both cases). Such structures were never observed in $Pjvk^{+/+}$ mice (Perinuclear peroxisomes/cell: $Pjvk^{+/+}$0.00 vs. $Pjvk^{-/-}$1.54, p<0.001) (FIG. 6E). Moreover peroxisomes just below the cuticular plate were slightly but significantly larger and also less numerous in $Pjvk^{-/-}$ compared to $Pjvk^{+/+}$ mice (peroxisome area $Pjvk^{+/+}$0.125 vs. $Pjvk^{-/-}$0.16 µm$^2$, p<0.05, and peroxisomes at the cuticular plate/cell $Pjvk^{+/+}$=2.45 vs $Pjvk^{-/-}$=1.91) (FIG. 6E). No mitochondria ultrastructural anomaly was observed; their morphology and localisation were indistinguishable in P30 $Pjvk^{+/+}$ and $Pjvk^{-/-}$ mice.

Because $Pjvk^{-/-}$ mice displayed features of marked oxidative stress in the cochlea, we investigated the possible role of pejvakin in peroxisome proliferation in response to oxidative stress induced by $H_2O_2$ (Lopez-Huertas et al., 2000). Embryonic fibroblasts derived from $Pjvk^{+/+}$ and $Pjvk^{-/-}$ mice were exposed to $H_2O_2$ (see Extended Experimental Procedures). In unexposed cells, the number of peroxisomes was similar between the two genotypes (t-test, p=0.82). After $H_2O_2$ treatment, it increased by 46% in $Pjvk^{+/+}$ fibroblasts (p=0.004), but remained unchanged in $Pjvk^{-/-}$ fibroblasts (p=0.83), resulting in a statistically significant difference between the two genotypes (p<0.001; FIG. 6C).

The lack of pejvakin thus results in an in vivo peroxisomal morphological defect that occurs after hearing onset.

7. Pjvk Transcriptional Regulation Belong to the Adaptative Response to Sound

Figure 9:
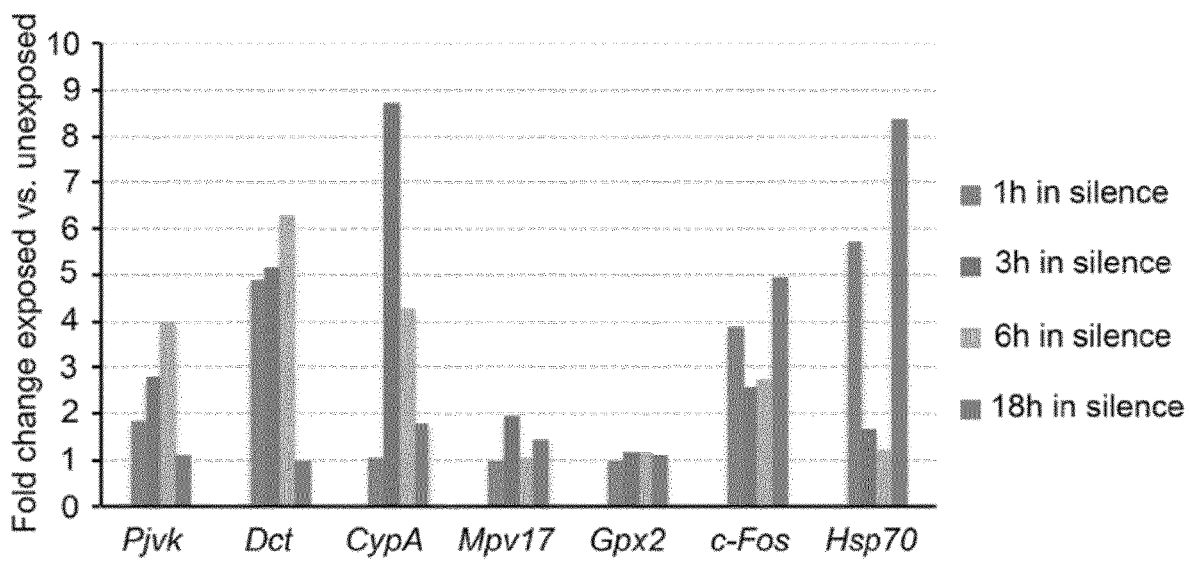
FIG. 9 shows the effect of loud sound exposure on the expression of Pjvk and other antioxidant genes in the organ of Corti. (A) The levels of Pjvk transcripts and of CypA, Gpx2, c-Dct, and Mpv17 transcripts (genes that are down-regulated in Pjvk$^{-/-}$ mice) were measured by qRT-PCR in the organ of Corti of sound-exposed (5-40 kHz, 105 dB during 1 hour) P21 wild-type mice at various times (1, 3, 6, and 18 hours in a silent environment) after the sound exposure. In the sound-exposed animals, the Pjvk transcript showed an almost 2-fold increase at 1 hour and a 4-fold increase at 6 hours, and had returned to pre-exposure level at 18 hours. The levels of CypA, c-Dct, and Mpv17 transcripts, and of Hsp70 and c-Fos transcripts (used as a positive control of the response to sound stimulation), but not that of the Gpx2 transcript, also increased in variable proportions after sound exposure. (B) Sound exposure at 5-40 kHz, 90 dB, during 1 hour, also leads to a marked increase of the levels of Pjvk and CypA transcripts, but only a moderate (less than 2-fold) increase in the levels of c-Dct and both Hsp70 and c-Fos transcripts 6 hours after the sound exposure. This indicates that Pjvk and CypA are involved in the early physiological response to noise. Error bars indicate±SEM.
Figure 9:
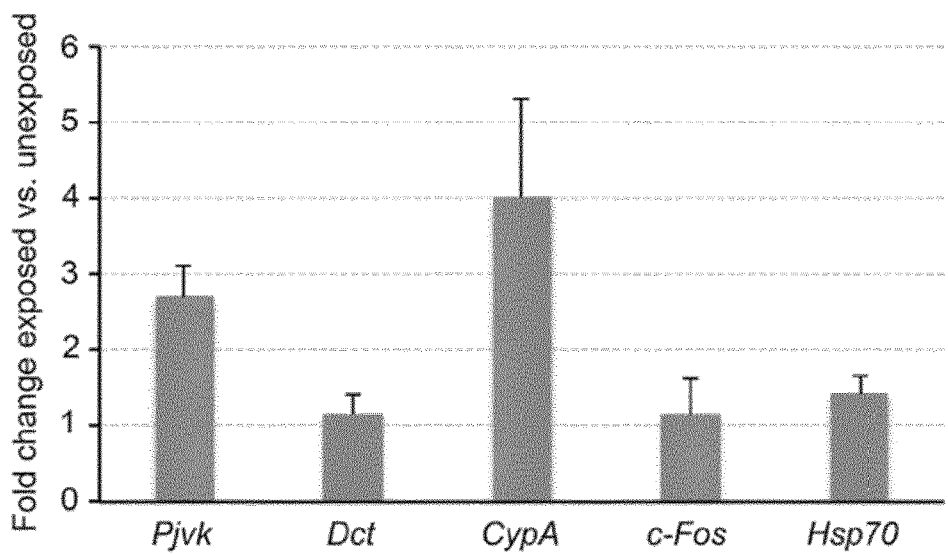

It was then asked whether this pathological condition was relevant to the cochlear physiological response to sound. Noise overexposure is known to induce oxidative stress due to the overproduction of oxygen species resulting from cellular hyperactivity that overwhelm the antioxidant defence of the cells. Could transcription of the pjvk gene be modulated by sound exposure? The level of Pjvk transcripts and of CypA, Gpx2, c-Dct, and Mpv17 transcripts, the down regulated genes observed in Pjvk$^{-/-}$ mice, were first measured in microdissected organs of Corti from non-stimulated and over-stimulated by sound (5-40 kHz, 105 dB SPL for 1 hour) P21 wild-type mice, at various times (1, 3, 6, and 18 hours) after the sound exposure, by qRT-PCR (FIG. 9A). Pjvk transcripts increased 2-fold after 1 hr, reaching 4-fold after 6 hours. CypA, c-Dct, and Mpv17 also showed an up regulation, as well as c-Fos and Hsp70 used as a positive control, but not Gpx2. This increase reached up to 6.26 and 8.71-folds for c-Dct and CypA, respectively, but was only 2 fold for Mpv17.

In contrast to sound overexposure that produces a permanent auditory thresholds shift (PTS), exposure to low acoustic energy can result in a temporary thresholds elevation (TTS), which indicates a reversible stress of the cochlea. A TTS is evoked by sound preconditioning, which refers to a low energy sound stimulation that exerts a protective effect against a subsequent sound overexposure (Roy et al., 2013). To test whether pejvakin transcriptional up-regulation could also be implicated in sound-preconditioning, P21 mice were exposed to standard preconditioning sound stimulation (5-40 kHz at 90 dB SPL for 2 hours) (Roy et al., 2013), and the expression level of Pjvk, c-Dct, CypA was measured after 6 hours by qRT-PCR. Sound preconditioning up regulated the expression of Pjvk and CypA (2.69±0.42 fold and 3.99±1.32 fold, respectively) but not of c-Dct (FIG. 9B). These results showed that Pjvk and CypA transcriptional regulation belongs to the physiological response to noise and are likely involved in the early antioxidant protective pathway.

8. Hypervulnerability to Sound of DFNB59 Affected Patients

Finally, it was asked whether hearing of DFNB59 patients was also hypervulnerable to sound exposure. Five patients carrying the p.T54I mutation who were living in Iran were tested (Delmaghani et al., 2006). Transient-evoked OAEs (TEOAEs) testing OHC function over a broad range of frequencies were analysed. All patients had bilateral broadband TEOAEs despite pure-tone audiograms showing severe hearing impairment (from 66 dB HL at 250 Hz to 84 dB at 8 kHz).

Figure 10:
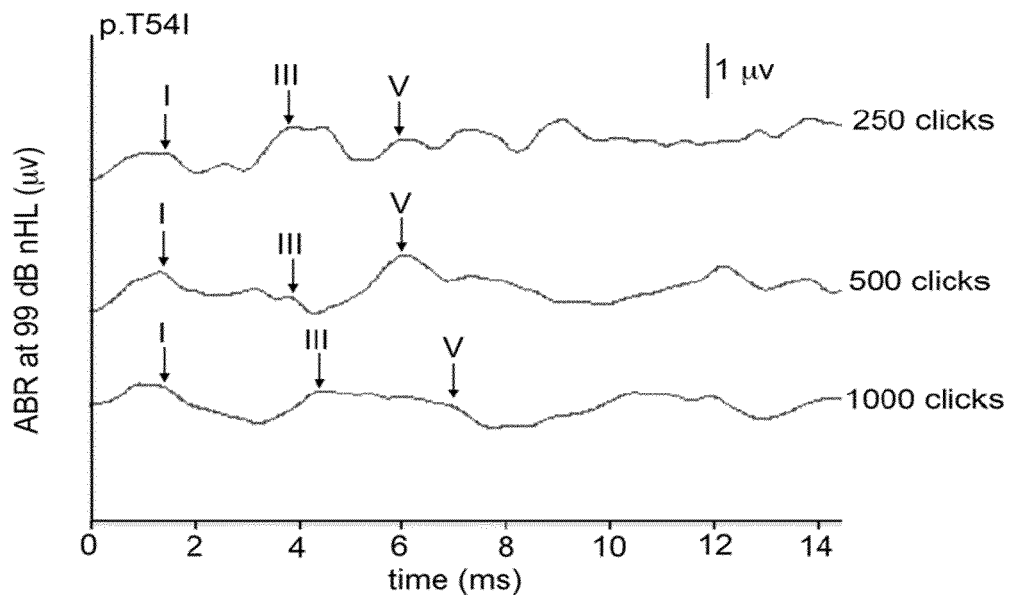
FIG. 10 highlights the hypervulnerability of DFNB59 patients to sound. (A) ABR waves in a patient carrying the PJVK p.T54I mutation, in response to 250, 500, and 1000 impulse stimuli (clicks) at 99 dB above normal detection threshold (dB nHL), delivered to one ear. After 250 clicks, waves were spotted at normal latencies. A dramatic decrease in amplitude of waves III and V (the equivalents of waves II and IV of mice) was observed after 500 clicks, with a shift in their latencies after 1000 clicks. (B) A second test was carried out on the same ear after 10 minutes spent in a silent environment. Initially, full recovery of amplitude and latency of ABR waves was observed, but prolonged exposure to clicks produced even more dramatic changes. (C, D) In the tested sample of p.T54I patients (n=8 ears), a significant decrease in the amplitude of wave V (C) and an increase in its latency were observed, whereas in a control group of patients with sensorineural hearing impairments of cochlear origin and matched ABR thresholds (n=13), the same sound exposure (even when prolonged beyond 4000 clicks) had no effect, either on the amplitude of ABR waves or on wave V latency.
Figure 10:
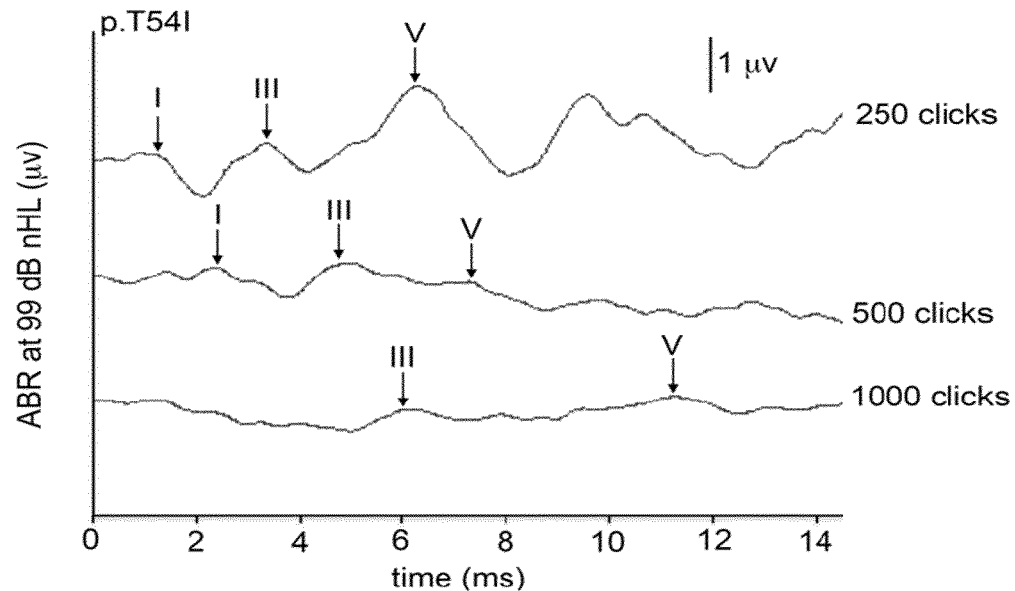
Figure 10:
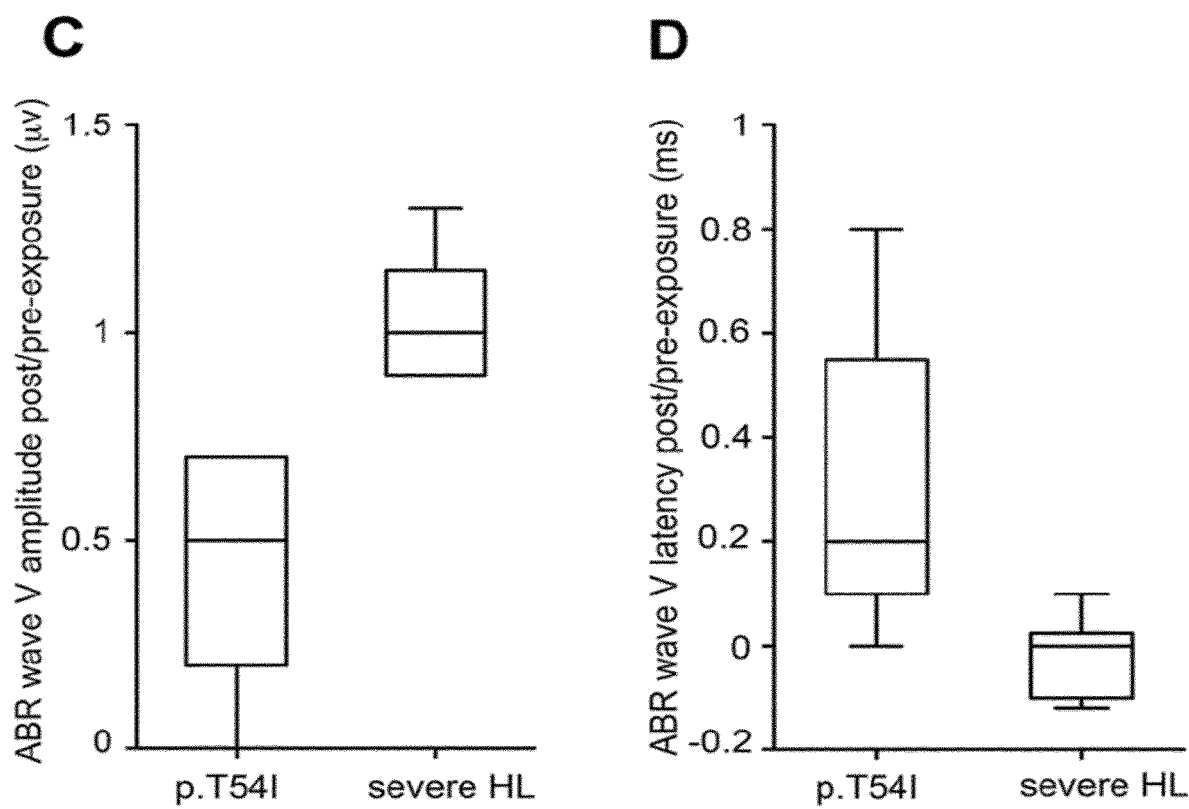

To test their possible hearing hypervulnerability to sound, a minimal sound exposure eliciting ABRs was used. ABR waves were clearly identified in response to 250 impulse stimuli—clicks—at 99 dB above normal detection threshold. Extending sound exposure to 1000 stimulus presentations (the standard clinical procedure for ABR recording), spectacularly affected ABR waves. The equivalent of mouse ABR-wave IV, wave V, the most reliably spotted wave after the shortest sound exposure, 250 clicks, exhibited after 500 then 1000 clicks, a progressive decrease in amplitude (to 39±30% of its initial amplitude, FIG. 10C, left boxplot, and FIG. 10A) and an increase in latency (of 0.30±0.15 ms, right panel of FIG. 10D, left boxplot, and FIG. 10A). The interwave latency I-V also increased by 0.30±0.15 ms. Full recovery of wave-V amplitude and latency was obtained after 10-min in silence (FIG. 10B). In a control group of patients with matched ABR thresholds and sensorineural hearing impairments of cochlear origin, the same sound stimulation, even extended to 4000 clicks, had no influence on ABR wave amplitude (105±14% of its initial amplitude after exposure; n=13) or latency (−0.02±0.07 ms post-exposure change; FIGS. 10C and 10D, right boxplots).

Therefore, in DFNB59 patients as in pejvakin-deficient mice, IHC, OHC, and neuronal responses are affected by abnormally low energy sound-exposure.

Figure 11:
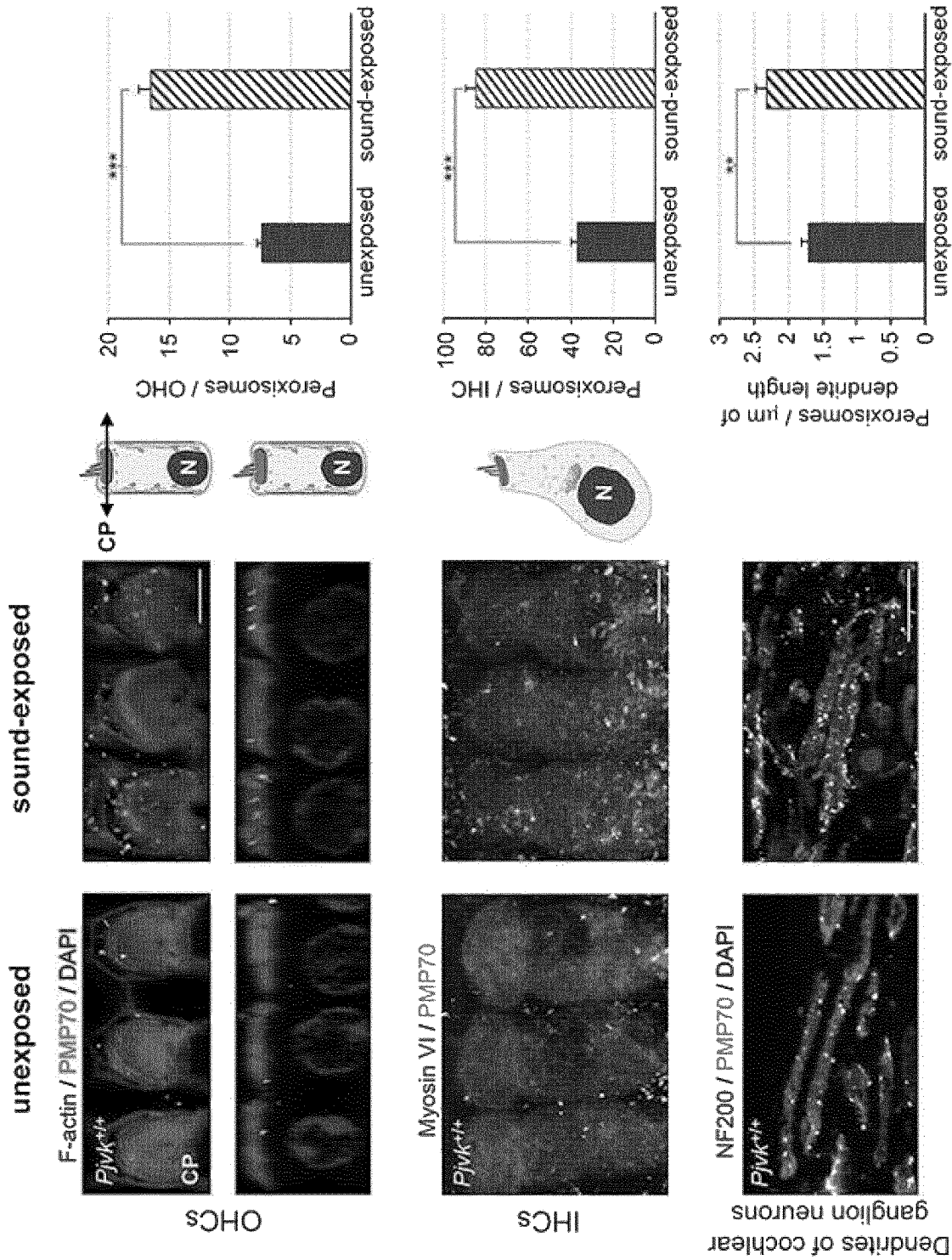
FIG. 11 shows the effect of exposure to loud sounds on the number of peroxisomes in cochlear hair cells and ganglion neurons. Peroxisome proliferation in P21 Pjvk$^{+/+}$ hair cells and cochlear ganglion neurons after sound-exposure (same conditions as in A). Peroxisomes were counted 48 hours after sound-exposure. OHCs, IHCs, and neuronal processes stained for F-actin, myosin VI, and neurofilament protein NF200, respectively. In OHCs and IHCs, the peroxisomes are located below the CP and throughout the cytoplasm, respectively. For OHCs, both a lateral view and a transverse optical section at the level of CP (scheme on the right) are shown. The number of peroxisomes was increased in OHCs, IHCs, and dendrites after sound-exposure. N: cell nucleus. ***p<0.001. Error bars represent the SEM. Scale bars are 5 µm.

These results predicted that sound-exposure would lead to peroxisome proliferation in the auditory system of wild-type mice. Six hours after exposure (5-40 kHz, 105 dB SPL for 1 hour), the numbers of peroxisomes were unchanged (34.5±0.8 and 35.9±1.0, mean±SEM, per IHC from unexposed and sound-exposed mice, respectively, n=75 cells from 6 mice; t-test, p=0.25). However, at 48 hours, they had markedly increased, by a factor of 2.3, in both IHCs and OHCs (84.7±5.0 per IHC and 16.5±1.0 per OHC, n=90 cells and n=150 cells from 6 mice, respectively) compared to unexposed mice (36.8±3.0 per IHC and 7.3±0.4 per OHC, n=90 cells and n=150 cells from 6 mice, respectively; t-test, p<0.0001 for both comparisons). The number of peroxisomes had also increased, by 35%, in the dendrites of primary auditory neurons (1.7±0.1 and 2.3±0.2 peroxisomes per μm of neurite length, n=40 neurites from 5 unexposed and 5 sound-exposed Pjvk$^{+/+}$ mice, respectively; t-test, p=0.003; FIG. 11).

9. Therapeutic Approaches of the DFNB9 Form of Deafness

Figure 12:
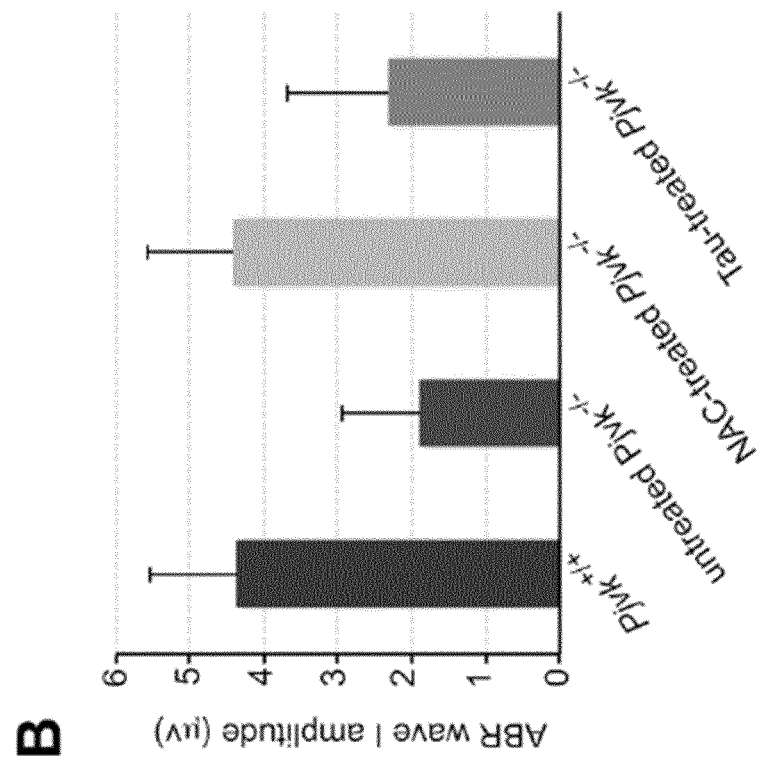
FIG. 12 discloses the therapeutic effect of N-acetyl cysteine on the auditory function of Pjvk$^{-/-}$ mice. The pregnant Pjvk$^{-/-}$ mice were treated with either N-acetyl cysteine (NAC) or taurine (TAU), two antioxidant drugs, in the drinking water. The treatment was continued until pups reached P21, the age that auditory tests were performed. (A) ABR thresholds at 10, 20, 32, and 40 kHz. A slight recovery of ABR thresholds is observed in Pjvk$^{-/-}$ mice treated with NAC compared to both TAU-treated and untreated mice. (B) ABR wave I amplitude fell within the normative range in NAC-treated Pjvk$^{-/-}$ compared to the untreated Pjvk$^{-/-}$ and TAU-treated Pjvk$^{-/-}$ mice, but no significant recovery of ABR wave I latency and ABR interwave I-IV was observed in treated Pjvk$^{-/-}$ mice (C, D). (E, F) EEBRs of NAC-treated Pjvk$^{-/-}$ mice, unlike those of untreated Pjvk$^{-/-}$ mice, resisted to high-rate (a rate of 200/s for 1 minute) electrical stimulation of the auditory nerve, as the amplitude of wave E IV remained unaffected. (E). Full recovery of neuronal function (unchanged amplitudes and latencies) was obtained 5 minutes after high-rate electrical stimulation in this NAC-treated Pjvk$^{-/-}$ ear (F).
Figure 12:
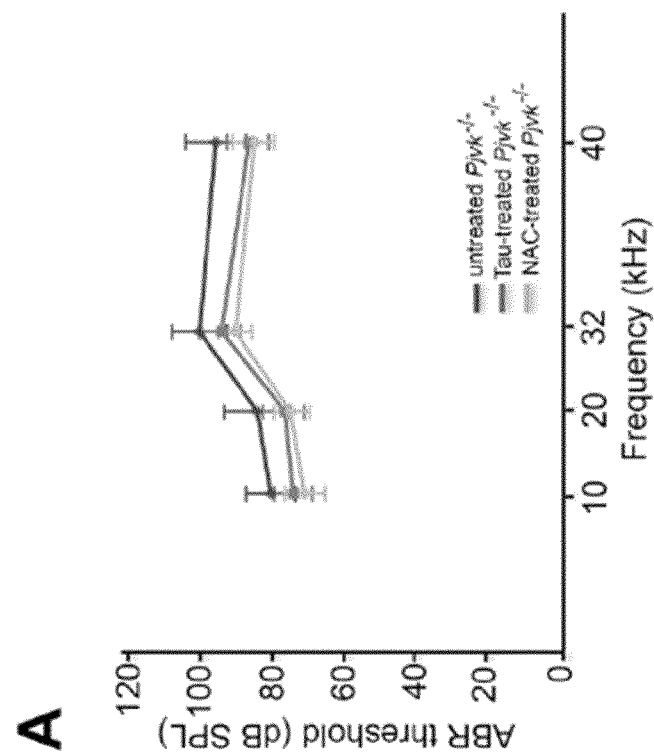
Figure 12:
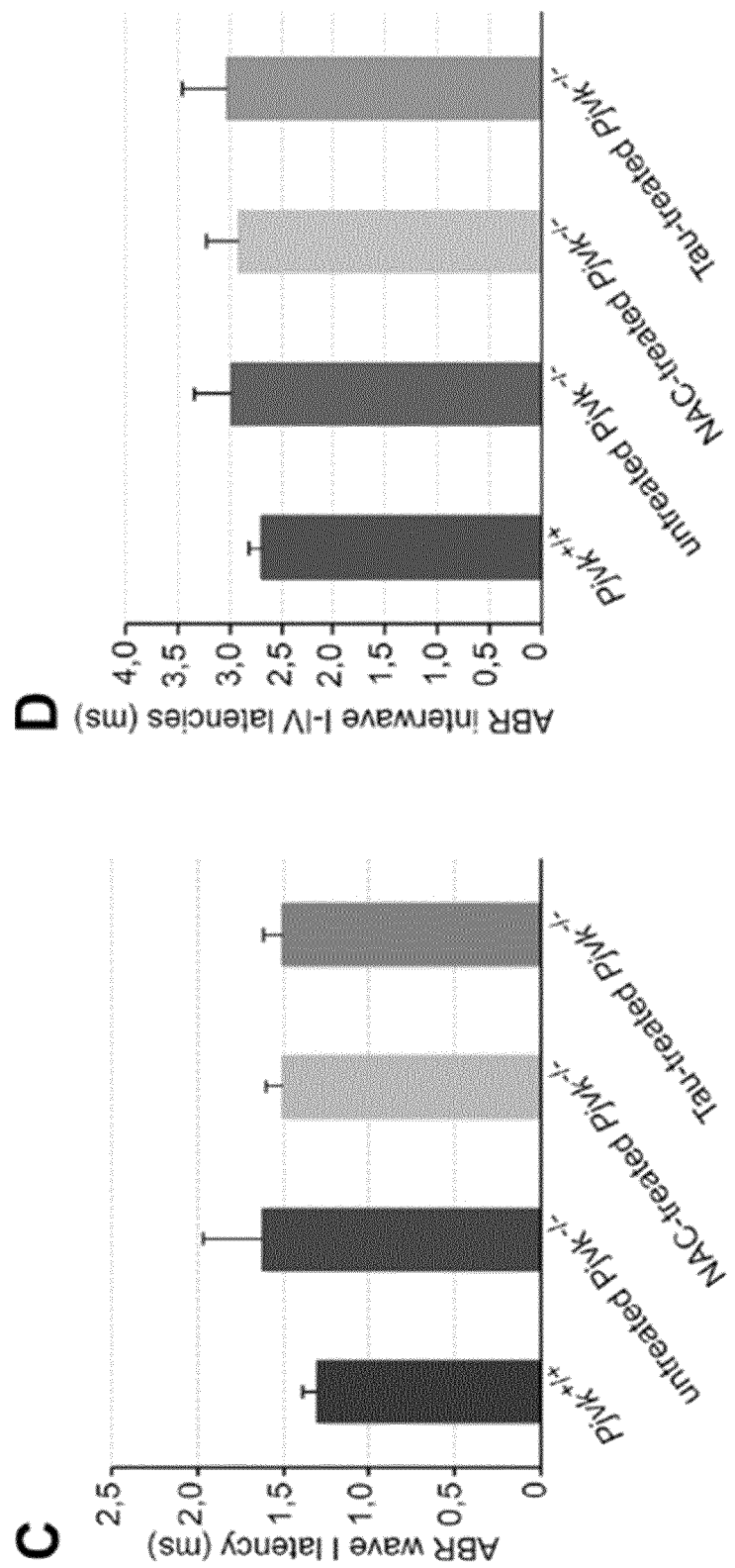
Figure 12:
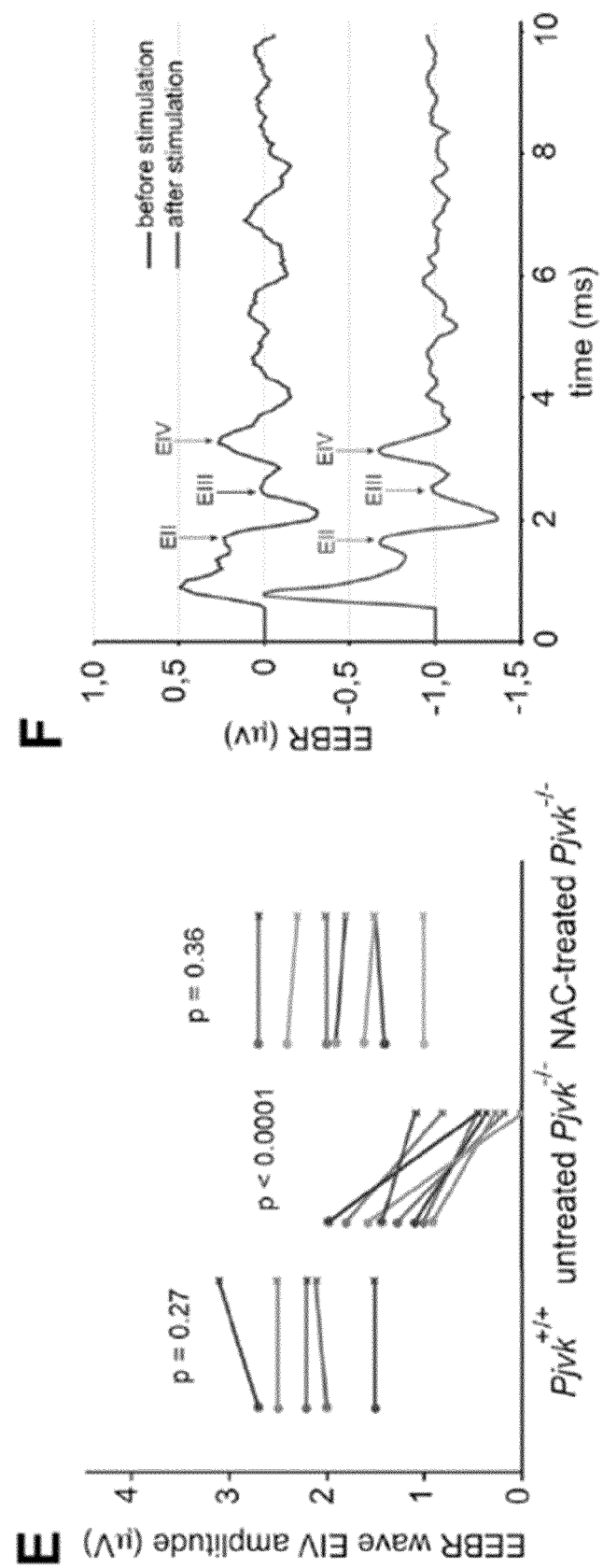

The above results validate Pjvk$^{-/-}$ mice as a model to investigate therapeutic approaches for human deafness. Based on these results, the effect of antioxidants was tested on the auditory function of Pjvk$^{-/-}$ mice. N-acetyl cysteine, the most common antioxidant, and taurine, were ingested by mothers during and after pregnancy so that pups received them from birth on by feeding on the mother's milk. When tested around P21, treated Pjvk$^{-/-}$ pups (n=21) raised in batches of about 10, i.e., maximally exposed to natural sound exposure, had for most of them, no DPOAE, thus N-acetyl cysteine and taurin had no beneficial effect on OHCs. The ABR thresholds were however slightly improved only in NAC-treated Pjvk$^{-/-}$ pups compared to those of untreated Pjvk$^{-/-}$ pups (n=24) (e.g. at 10 kHz, 72.2±9.3 dB SPL, as against 84.4±6.3 dB SPL, p<0.001) (FIG. 12A). The amplitude of ABR wave I in response to 105 dB SPL (which bypasses OHC activity) was similar to age-matched Pjvk$^{+/+}$ mice (n=18) in NAC-treated Pjvk$^{-/-}$ mice, in contrast with untreated mice (4.35±1.16 μV, as against 4.36±1.15 μV in Pjvk$^{+/+}$ mice, but only 1.88±1.07 μV in untreated Pjvk$^{-/-}$ mutants, ANOVA, p<0.001; FIG. 12B). ABR wave I latencies did not significantly shorten under treatment (1.55±0.18 ms as against 1.62±0.34 ms in untreated mutants, both being similarly longer than controls, 1.30±0.08 ms; ANOVA, p<0.001 between controls and mutants; FIG. 12C). Likewise, ABR interwave I-IV latencies hardly responded to treatment (2.91±0.32 ms in treated pups, 2.68±0.13 ms in controls, as against 2.98±0.35 ms in untreated mutants; FIG. 12D). The EEBRs of N-acetyl cysteine treated animals resisted to high-rate electric stimulation of auditory pathways better than untreated Pjvk$^{-/-}$ mice (FIG. 12E). Full recovery of neuronal function was obtained 5 min after high-rate exposure in treated mice. (FIG. 12F), as opposed to an absence of recovery at that time in untreated mice. This suggests a moderate protective effect of IHCs and neurons by N-acetyl cysteine.

Figure 13:
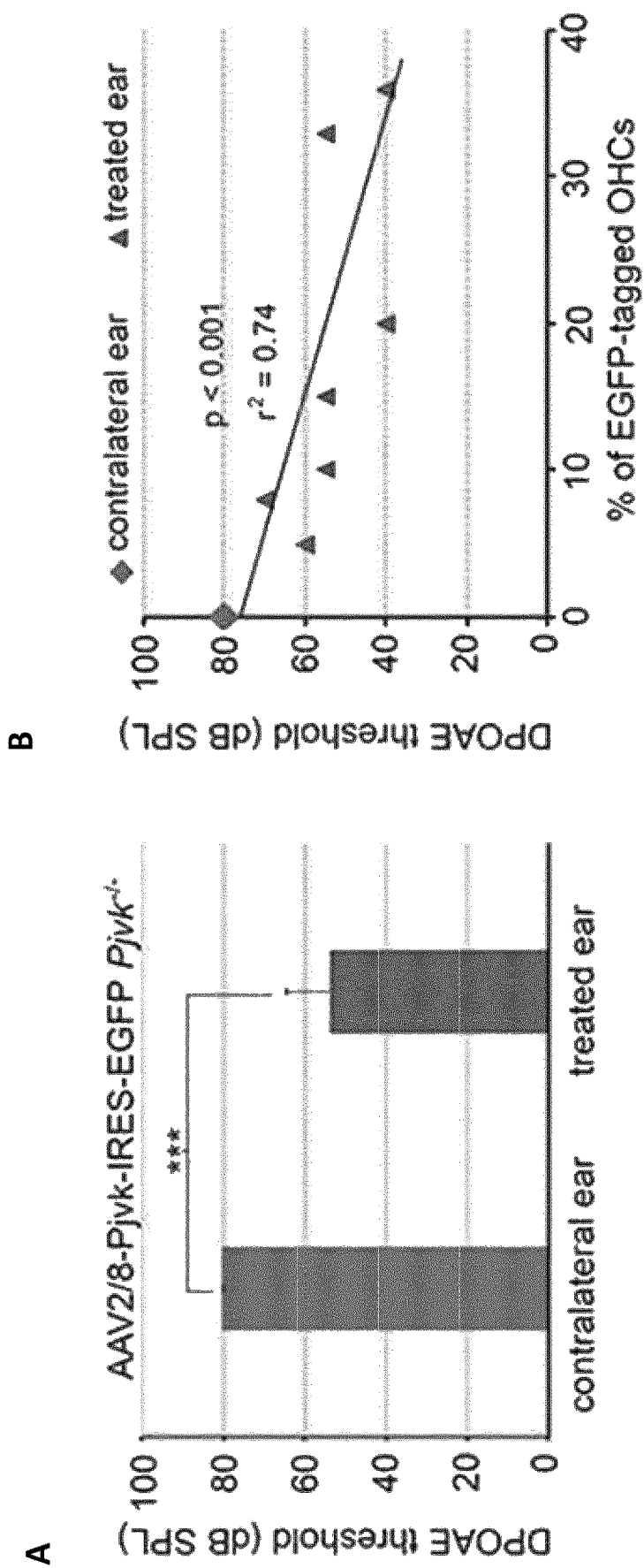
FIG. 13 shows the preventing hair cell dysfunction by adenovirus-mediated gene transfer in Pjvk$^{-/-}$ mice. Pjvk$^{-/-}$ P3 mice were injected with AAV2/8-Pjvk-IRES-EGFP, which specifically transduces in IHCs and OHCs, in one cochlea through round window. (A, B) Effect of the transfection on DPOAE thresholds at 10 kHz in treated ears compared to contralateral (untreated) ears. The improved DPOAE thresholds in treated ears correlate with the number of GFP-tagged OHCs (B), in relation to the partial recovery of OHC function. (C, D) The amplitudes of ABR wave I in response to 10 kHz, 105 dB SPL sound stimulations become normal in the treated ears compared to contralateral ears, and this reversion is highly correlated with the number of GFP-tagged IHCs (D). Error bars represent the SD. ***p<0.001
Figure 13:
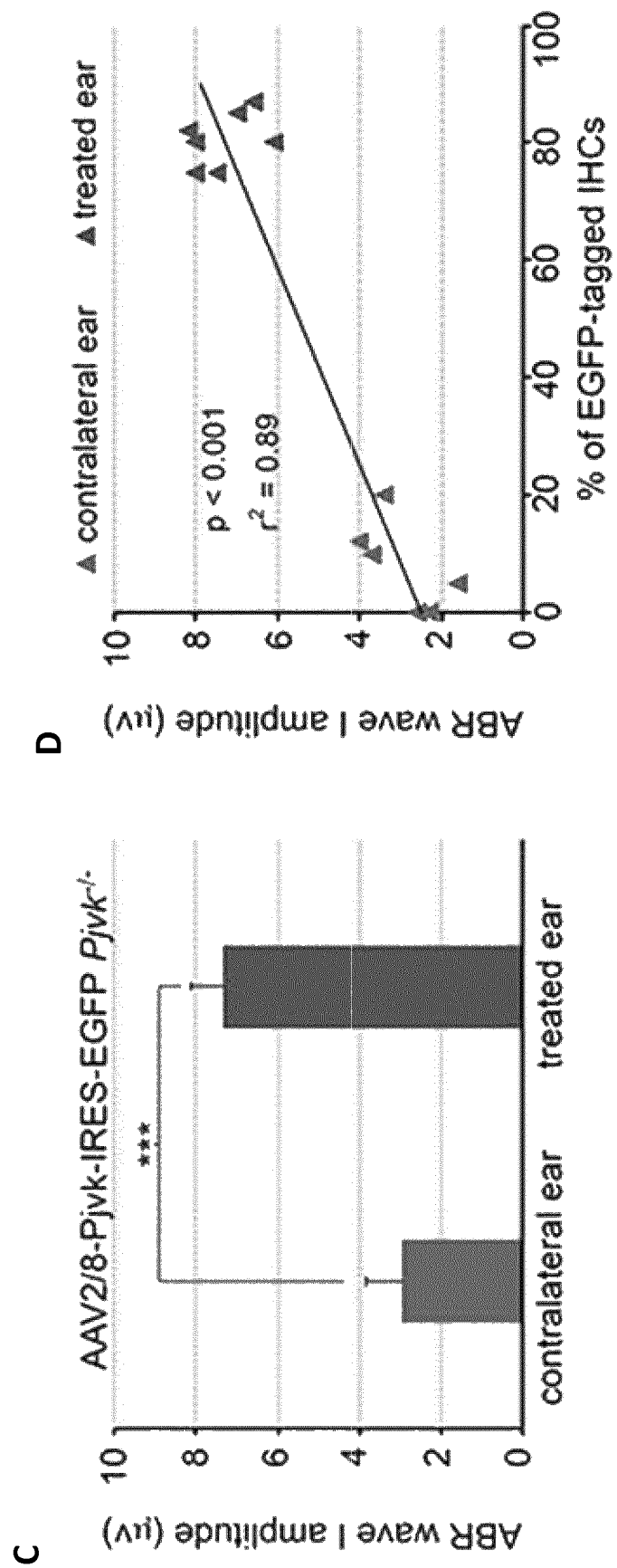

Because a full recovery of the neural phenotype was obtained by intracochlear injection of AAV8 expressing the murine Pjvk cDNA, the potential of AAV2/8, which transduces hair cells exclusively, to rescue the hair-cell phenotype was tested in Pjvk$^{-/-}$ mice (n=7). Auditory function of Pjvk$^{-/-}$ mice injected on P3 by this vector expressing the pejvakin cDNA (mPjvk-IRES-GFP) were examined at P21 and the percentage of transduced by IHC and OHC in every cochlea was evaluated by the fluorescence of GFP. A partial reversion of OHC function with detectable DPOAEs was obtained, with a decrease in DPOAE thresholds (from 80 dB in untreated ears, to 57.1±14.7 dB in treated ears), with a highly significant linear correlation ($R^2=0.72$, $p<0.001$) with the number of GFP-tagged OHCs in the treated ear (FIGS. 13A and 13B). Its linear extrapolation suggests that the DPOAE threshold might be normalized if more OHCs could be treated. As a result of improved OHC function, ABR thresholds improved, e.g. at 10 kHz, from 85.7±9.3 dB SPL in the contralateral ears, to 51.1±15.3 dB SPL in the treated ears. The amplitude of ABR wave I in response to 105 dB SPL stimulations fell within the normative range in treated ears (7.0±2.3 µV (n=6) compared to the contralateral ears (2.3±1.1 µV)) (FIG. 13C), and a highly significant correlation was observed ($R^2=0.89$, $p<0.001$) with the number of GFP-tagged IHCs in the treated ears (FIG. 13D), which indicates reversion to a normal phenotype in transduced IHC.

Figure 14:
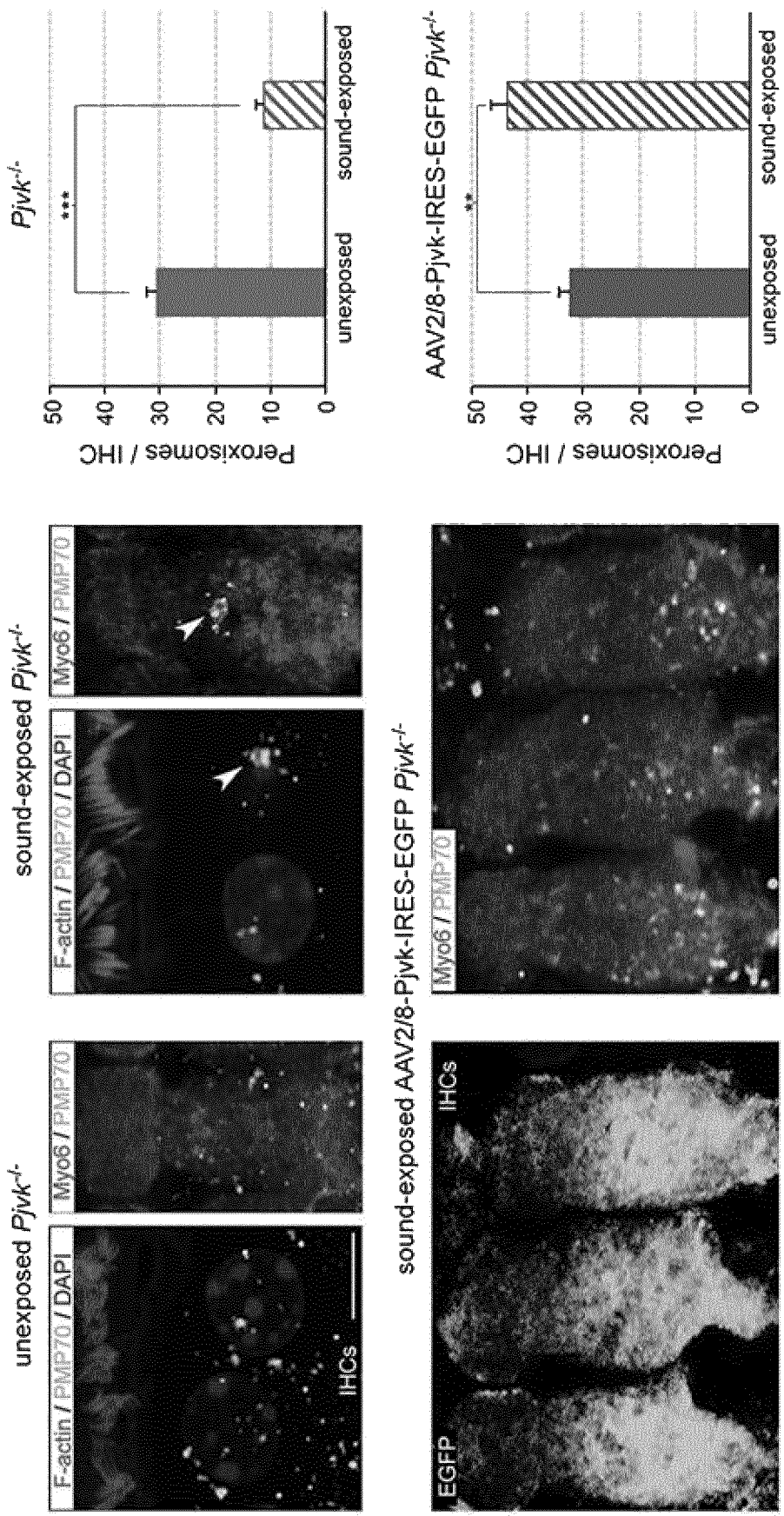
FIG. 14 represents the effect of AAV2/8-Pjvk-IRES-EGFP on the peroxisomes in Pjvk$^{-/-}$ IHCs. Upper and lower panels show and quantify (bar charts) the peroxisomes in untreated mice 48 hours after sound-exposure (5-40 kHz, 105 dB SPL for 1 hour) (peroxisome abnormalities are indicated by arrowheads). Error bars represent the SEM. p<0.01, *p<0.001.

Finally, the effect of the transduction of $Pjvk^{-/-}$ IHCs by AAV2/8-Pjvk-IRES-EGFP on their peroxisomes was investigated. Before sound-exposure, the numbers of peroxisomes in IHCs of P21 $Pjvk^{-/-}$ and AAV2/8-Pjvk-IRES-EGFP injected $Pjvk^{-/-}$ mice did not differ from that of $Pjvk^{+/+}$ mice (30.5±1.9, 32.3±2.1, and 36.8±3.0 peroxisomes, mean±SEM per IHC, n=60 cells from 4 $Pjvk^{-/-}$ and 4 AAV2/8-Pjvk $Pjvk^{-/-}$ mice, and n=90 cells from 6 $Pjvk^{+/+}$ mice, respectively; t-test, p=0.11 and p=0.30, respectively). By contrast, 48 hours after sound-exposure (5-40 kHz) at 105 dB SPL for 1 hour, the number of peroxisomes had decreased by 63% in $Pjvk^{-/-}$ IHCs (30.5±1.9 and 11.2±1.3 peroxisomes per IHC, n=75 cells from 5 unexposed and 5 sound-exposed $Pjvk^{-/-}$ mice, respectively; t-test, $p<0.0001$), and enlarged PMP70-labeled structures were present close to the nucleus (FIG. 14). In response to the same sound but of a lower intensity, i.e. 97 dB SPL for 1 hour, the number of peroxisomes was unchanged in $Pjvk^{-/-}$ IHCs (30.5±1.9 and 34.6±2.3 peroxisomes per IHC, n=60 cells from 4 unexposed and 4 sound-exposed $Pjvk^{-/-}$ mice, respectively; t-test, p=0.17), and no enlarged PMP70-stained structures were detected (data not shown). The absence of pejvakin thus resulted in defective sound-induced peroxisomal proliferation (both at 105 dB SPL and 97 dB SPL), and even, in peroxisome degeneration (at 105 dB SPL) in IHCs. In $Pjvk^{-/-}$ mice injected with AAV2/8-Pjvk-IRES-EGFP on P3 and exposed to 105 dB SPL for 1 hour on P21, enlarged PMP70-labeled structures were no longer detected in transduced IHCs, and the number of peroxisomes increased by 35% (32.3±2.1 and 43.7±3.0 peroxisomes per IHC, n=60 cells from unexposed and exposed transduced $Pjvk^{-/-}$ IHCs, respectively; t-test, p=0.002) (FIG. 14). We conclude that pejvakin re-expression fully protects $Pjvk^{-/-}$ IHCs from the degeneration of peroxisomes, and partially restores their impaired adaptive proliferation.

These results show that gene therapy approaches could provide protective or therapeutic opportunities in DFNB59 affected patients.

Discussion

Noise overexposure is a major and increasingly prevalent cause of hearing loss accounted for by the overcrowding of the towns and the overuse of portable music players by younger children, worldwide. Noise-induced hearing loss (NIHL), considered as the most preventable and treatable/remediable hearing impairment, currently does not benefit of efficient therapeutic intervention. This situation echoes the still limited information regarding its underlying pathogenic processes as well as its genetic susceptibility. The above-disclosed results uncovered a new origin of NIHL by showing that pejvakin defect in mouse and human (DFNB59 patients) leads to a hypervulnerability to sound due to a peroxisomal deficiency. No such a hypersensitivity to sound has ever been reported. This study introduces the peroxisome as a key regulatory organelle of the redox homeostasis of the auditory system, pivotal to cope with ROS overproduction induced by high acoustic energy. It shows that pejvakin is involved in peroxisome proliferation. This understanding pinpoints hearing impairment in DFNB59 patients as calling for a specific management and suggests that pejvakin and the proteins of its associated networks may be useful for preventing and curing NIHL.

Acoustic energy is the main factor that determines the damaging effects of exposure to loud sounds. The so-called Lex index for workplace noise exposure has been introduced to calculate the energies delivered by sounds of different levels and time courses in order to evaluate and compare their detrimental potential (see material and methods). The legal limit in western countries varies from 80 to 90 dBA Lex, an acoustic energy not leading to a permanent threshold shift (PTS). In $Pjvk^{-/-}$ mice a single exposure to a 63 dBA Lex produces an about 30 dB hearing threshold elevation. As the dB scale is a logarithmic one, a 3-dB increase translates in a two-fold increase in energy, and a 10-dB increase in a ten-fold increase in energy. Up until now, the lowest dBA Lex reported as producing an elevation of the hearing threshold in wild type mice of the same background strain as $Pjvk^{-/-}$ mutants was 73 dB (10 times fold more energetic) (Housley G, 2013). Moreover it was a temporary threshold shift (TTS) of only 18 dB with a recovery time constant of twelve hours compared to the threshold shift of 30 dB with a recovery time constant of about one week in $Pjvk^{-/-}$ mice. The second observation herein made, is that the natural acoustic environment of a mouse litter, due to pup cries in relation to feeding and crowding, is about 83 dBA Lex in a cage of 10 pups (100 times fold more energetic than the sound exposure affecting hearing threshold of $Pjvk^{-/-}$ mice) during the few days from the onset of hearing to weaning. This possible effect of this natural exposure to high acoustic energy has been overlooked so far in the studies carried out on NIHL. Based on the present results, it should be systematically taken into account in future works addressing the origin of the variability of the hearing threshold in the mouse. Because transduction in hair cells begins to operate more and more efficiently with the progressive increase of the endocochlear potential from P5 to P17 (Sadanaga and Morimitsu, 1995), this raises the possibility that hearing loss in $Pjvk^{-/-}$ mice might be due entirely to naturally occurring sound exposure. Consistently when mouse pups are kept in small numbers (pups n=2) with foster mothers and in quiet rooms, their hearing thresholds is 30 dB lower, on average (and 60 dB lower, in some individuals) than their littermates maintained in their regular sound environment. DFNB59 patients, who carry deleterious mutations in PJVK, also display an astonishing sound sensitivity, since it is evidenced under the standard conditions used in clinics to record ABRs in response to impulse sounds. At a 57 dBA Lex, these sounds, routinely used for audiological diagnosis at much higher levels induced in all tested DFNB59 patients large changes in their evoked responses, with an increase in latency of all identifiable waves, which often exceeded 0.5 ms for wave V, and a two- to three-fold decrease in amplitude of these waves. Such changes are never observed in a sample of 13 patients with matched hearing thresholds and auditory profile could be exposed to at least four times as much acoustic energy without suffering any change in latency or amplitude of their auditory evoked potentials.

These hearing features unique to DFNB59 patients, and akin to auditory fatigue, were reversible after 10 min in silence.

The effects of loud sound of excessive energy are two-pronged,—mechanical alterations affecting the stereocilia bundles including inter-stereociliary links and the cell-cell junctions of the auditory hair cells and—cellular hyperactivity related disturbances leading to an excessive release of glutamate by the IHC synapses that results in excitotoxicity, characterized by a swelling of the post-synaptic dendrites of their afferent neurons. A strong emphasis is increasingly placed/put on the contribution of oxidative stress to NIHL, a condition in which the production of ROS, including oxygen-based free radicals and hydrogen peroxide, $H_2O_2$, exceeds the capacity of the antioxidant defence systems, and subsequently creates oxidative cellular damages of DNA, proteins and lipids becoming progressively irreversible (Henderson et al., 2006). Superoxide radical ($O_2^{•-}$) and the hydroxyl radical ($OH^•$), have indeed been observed in the cochlea after noise exposure (Yamane et al., 1995; Ohlemiller et al., 1999b; Ohinata et al., 2000; Yamashita et al., 2004). Also supporting the key role of the oxidative stress in NIHL, defect in Cu/Zn superoxide dismutase, SOD1 that converts $O_2^{•-}$ in $H_2O_2$ (Ohlemiller et al., 1999a), and in glutathione peroxidase 1 (Gpx1) that reduces $H_2O_2$ in $H_2O$ (Ohlemiller et al., 2000), both proposed to lead to $H_2O_2$ accumulation, and an increase of susceptibility to NIHL. The present work establishes that the defect in pejvakin impacts the cellular redox status of the auditory system followed by ROS induced cellular damages: (i) in $Pjvk^{-/-}$ mice already at P15, whilst no morphological anomalies can be detected, the down regulated expression of Mpv17, CypA, Gpx2 and c-Dct indicate that the organ of Corti is submitted to an oxidative stress: an increase of ROS production (Mpv17) and a decrease in the reduction of $H_2O_2$ (CypA, Gpx2, c-Dct) then converted in OH by the Haber-Weiss and the Fenton reactions, are indeed predicted (ii) at around P21, markers the oxidative stress, the increase in GSSG as well the decrease in GSH:GSSG ratio, are observed (iii) at P30, lipid peroxidation by OH in hair cells and auditory neurons reveals ROS induced cellular damage (iv) hair cell and auditory neuron loss present throughout the cochlea but the apical region from P60 onwards (data not shown). OHCs, display an especially high vulnerability to noise, whilst IHCs are also susceptible but to a lesser degree (Wang et al., 2002). Sound vulnerability is well known to extend to the primary auditory neurons (that compose the spiral ganglion nerve) (Kujawa and Liberman, 2009), as well as the central auditory pathways including the cochlear nucleus, the inferior colliculus and even the auditory cortex (Imig and Durhan, 2005; Basta et al., 2005; Pienkowski and Eggermont, 2009). Of note $Pjvk^{-/-}$ mice, $Pjvk^{fl/fl}Myo15$-$cre^{+/-}$ mice and rescuing targeted to auditory neurons or hair cells, unambiguously show that all the cells here explored, the sensory hair cells (with a more pronounced effect on the OHCs), the primary auditory neurons and neurons of the brainstem, are indeed hypervulnerable to sound in the absence of pejvakin.

Noise exposure highly solicits the mitochondrial activity to generate large amount of ATP through aerobic respiration which in parallel produces ROS (Ohlemiller et al., 1999b) and its intermediate of formation, $H_2O_2$. In particular, $O_2^{•-}$, a by-product of the mitochondrial oxidative phosphorylation, is generated through the capture of an electron (derived from the activity of complex I and complex III) by molecular oxygen, $O_2$. Recent results further documented this ROS production by showing that the decrease of mitochondrial $NAD^+$ induced by noise exposure, reduces the activity of sirtuin 3, a mitochondrial $NAD^+$-dependent deacetylating/deacylating enzyme which is essential to the functioning of numerous mitochondrial enzymes (He et al., 2012; Han and Someya, 2013).

The association of pejvakin with peroxisomes and the structural alterations of peroxisomes in $Pjvk^{-/-}$ mice, including the presence peroxisome-derived matrix in the perinuclear region, reminiscent of the translocation of damaged mitochondria at the same emplacement (Okatsu et al., 2010), unveiled the first peroxisomal origin of an isolated form of inherited deafness. This peroxisomal deficiency in addition underlies an auditory phenotypic variability that has no equivalent so far, and that can be attributed to a hypersensitivity to natural environmental noise. No attention has been payed to this organelle in the auditory system so far, with the exception of a recent report indicating that cultured organ of Corti in the presence of a proteasome inhibitor leads to hair cell degeneration associated with peroxisome dysfunction (Lee et al., 2015). In the various forms of Zellweger syndrome, the most severe peroxisome biogenesis disorders (peroxisomes can be undetectable), sensory hearing impairment has been reported. Probably due to the focus on the associated impaired vital functions which includes a ubiquitous failure of neuronal conduction, auditory tests have not been extended beyond ABRs threshold measurements. The defective neuronal conduction has been attributed to the faulty synthesis of two essential components of the myelin sheaths, plasmalogens and DHA (docosahexaenoic acid), which is critically dependent on peroxisomes, and this conclusion extended to the pathogenesis of the hearing defect. Our results suggest that this hypothesis should be revisited. Contrary to peroxins defective in Zellweger syndrome, our results point to an essential role of pejvakin, restricted to cells of the auditory pathway. This is in line with the well-known extreme diversity of the peroxisomes in shape, density and protein/enzyme equipment and concentration, from one cell type to another, which may explain that, although expressed in a large variety of cells, pejvakin may be essential only in a few. Also contrary to peroxins, pejvakin is dispensable for the constitutive biogenesis of peroxisomes, and the structural failures of this organelle become apparent only in the context of the redox stress elicited by sound. In principle, sound hypervulnerability of $Pjvk^{-/-}$ mice may be the manifestation of an exacerbation by sound of pre-existing redox homeostasis failure, with at ultimate stage, perinuclear inclusions containing catalase and probably other factors too, contributing to cell degeneration. However Pjvk transcriptional up-regulation in wild type mice, immediately upon a sound exposure, whether being traumatic (leading to PTS) or protective (leading to PTS) that is likely involving in the immediate adaptive antioxidant response to noise, pinpoints the existence of a peroxisomal response as part of the physiological response to high acoustic energy. The ability of the peroxisomes to rapidly adapt to the demand created by changes in environmental and physiological conditions, thanks to a panel of possible adjustments (dynamic shape and size changes, proliferation, degradation, and modification of their molecular content), grants them with an amazing functional plasticity. These organelles, actively contribute to cellular redox homeostasis by producing (by its rich content in oxidases, SOD1, and SOD2) and degrading $H_2O_2$ ($O2^{•-}$ being possibly also involved in this transduction) by per-oxidases (Schrader and Fahimi, 2006; Bonekamp and Schrader, 2009; Fransen et al., 2012).

Transfection experiments indicate that pejvakin is involved in peroxisome proliferation. Although its exact role in this process cannot be directly inferred from the changes of peroxisome shapes observed upon expression of mutated forms of pejvakin, the observed enlarged and spherical-like PMP70 positive structures, indicates the involvement of pejvakin in the pathway leading to the formation of new peroxisomes from pre-existing peroxisomes. This pathway, referred to as growth and fission cycle, is faster than the other one, the de novo formation in which peroxisomes form from endoplasmic reticulum derived vesicles (for a review see Smith and Aitchison, 2013). The growth and fission cycle involves the emergence of an elongation from pre-existing spherical peroxisomes. This elongation process is mediated by Pex11β and Pex11α (Delille et al., 2010; Koch et al., 2010; Li et al., 2002; Schrader et al., 1998), which consistently were associated with 70% and 55% of the pejvakin stained peroxisomes in HepG2 cells. Moreover, stress-induced peroxisome formation pathway, involves the recruitment of COP1, which promotes membrane protrusion at the elongation initiation site (Lay et al., 2006; Passreiter et al., 1998), where pejvakin colocalises. Altogether the present results provide evidence that sound-stress evokes a pejvakin-dependent peroxisomal response that leads to the generation of new peroxisomes from pre-existing ones. They also involve the peroxisome in redox signalling pathway elicited by sound, that likely uses $H_2O_2$, as signal molecule. In coherence, $H_2O_2$ has been shown to up-regulate the expression of peroxisome biogenesis genes (Lopez-Huertas et al., 2000) and induced elongation of the peroxisomes has been blocked by antioxidants (Schrader et al., 1999). Other roles could be ensured by this pejvakin-dependent stress-induced proliferation of peroxisomes, such as a matrix import of ROS degrading or scavenging molecules within peroxisomes (Motley, 2007) or a regulation of the activity of their redox enzymes by their changes in shape (Lizana, 2008). Of note, whilst peroxisome proliferation has been reported either to induce oxidative stress (Reddy et al., 1980) or to reduce ROS production (Santos et al., 2005; Diano et al., 2011), the rapid transcriptional up regulation response already set up one hour after sound exposure and in addition observed under PTS generating conditions, as well as the early massive oxidative stress detected in $Pjvk^{-/-}$ mice, argue for an antioxidant role of pejvakin-dependent peroxisomal proliferation in the context of noise-induced oxidative stress. Finally, the transcriptional down-regulation of CypA encoding cyclophilin A and c-Dct encoding the dopachrome tautomerase, in $Pjvk^{-/-}$ mice and conversely, their transcriptional up-regulation (limited to the highest energy sound tested for c-Dct) associated with the transcriptional up-regulation of Pjvk in response to sound exposure in wild type mice, indicates that these proteins may belong to the same redox homeostasis pathway.

The conclusion is that as a result of peroxisomal deficiency, ROS metabolism is perturbed enough, so that sound of normally harmless energy can become harmful, has never been brought forward or tested, as done here in DFNB59 patients and $Pjvk^{-/-}$ mice. In patients, conventional intervention in case of sensorineural hearing impairment includes sound amplification by hearing aids and cochlear implant fitting, depending on the degree of impairment. However, conventional hearing aids, routinely used in severely hearing-impaired patients, might have harmful results in DFNB59 patients, as exposure to amplified sound is expected to lead to long-lasting damage to cochlear sensory cells and auditory neurons. Cochlear implant, an acoustico-electronic device that bypasses the cochlea and delivers a direct electrical stimulation to the primary auditory neurons, which is particularly beneficial for patients affected by profound deafness of cochlear origin, should similarly increase ROS in these neurons, thereby threatening their long-term survival. In both cases, specific protection against the production or the effects of the ROS is anticipated to be mandatory. However, used alone in the absence of pejvakin, N-acetyl cysteine, the most effective antioxidant drug here observed, had only a limited impact on the sensory hair cells although it reduces some adverse effects of controlled sound exposures in $Pjvk^{-/-}$ mice, restoring in particular the number of auditory neurons able to respond in synchrony to a loud tone-burst. Molecules targeting ROS metabolism might thus provide some benefice to DFNB59 patients. Moreover, our results on AAV-mediated Pjvk-cDNA transfer in $Pjvk^{-/-}$ mice clearly show that gene therapy has the potential to fully protect all these cells. Finally, after an acoustic trauma, subjects often experience protracted worsening of their hearing lesions in relation to disrupted ROS cellular homeostasis, which Pjvk gene therapy could improve.

Gene Therapy for Treating Usher Syndrome

BACKGROUND OF THE INVENTION

As yet described above, hearing impairment—herein defined as referring to any hearing defect that can either be congenital or not—is a major concern and a serious burden for Public health.

The early-onset forms of severe deafness are mostly genetic in origin and are frequently due to sensory hair cells defect.

In particular, Usher syndrome (USH) is an autosomal recessive disease that affects both the inner ear and the retina. It is the most frequent cause of hereditary deaf-blindness, affecting 1 child in 25,000.

The following three USH clinical subtypes have been defined:

USH type I (USH1), the most severe, involves severe to profound congenital sensorineural deafness, constant vestibular dysfunction and retinitis pigmentosa with prepubertal onset;

USH2 differing from USH1 mainly in the deafness being less severe, the absence of vestibular dysfunction and the onset of retinitis pigmentosa after puberty; and USH3 differing from USH1 and USH2 in the progressiveness of hearing loss and the occasional presence of vestibular dysfunction.

USH1 is genetically heterogeneous. Seven loci responsible for this disease have been defined and called USH1A-G, with four of the corresponding genes having been identified: USH1B, C, D and F. USH1B encodes the actin-based motor protein myosin Vila. USH1C encodes harmonin which is a PDZ domain-containing protein. Mutations in the genes encoding two cadherin-related proteins, cadherin 23 and procadherin 15, have been shown to cause USH1D and USH1F, respectively.

Studies of USH1G-affected families allowed to identify SANS, the human orthologue of the gene defective in Jackson shaker (js) mutant mice, as the causative gene (Mustapha et al., 2002; Weil et al., 2003).

Current clinical approaches to remedy hearing impairment, in particular USH, include hearing aids for mild to moderate impairments and cochlear implants for severe to profound impairments. These existing solutions are however not curative treatments and are not adapted to noisy environments.

There is thus a need in the art for therapeutic approaches to cure genetic forms of human deafness with or without balance defects, in particular USH, yet in particular USH1G.

In this aim, the present inventors studied Ush1g knockout mice (Ush1g$^{-/-}$ model as described in Caberlotto et al., 2011). This study allowed them to provide a virally-mediated gene therapy for restoring genetically-impaired auditory and vestibular functions. More precisely, their results show that it is possible to efficiently target hair cells and to restore the normal morphology of both cochlear and vestibular hair bundles, which is shown to be critical for auditory and balance functions.

These findings have major therapeutic implications, as described below.

DETAILED DESCRIPTION OF THE INVENTION

In Vivo Administration of a USH1 Gene Product: Vectors

According to the present invention, an USH1 gene product, preferably the SANS protein, is administered to a subject in need thereof by in vivo gene therapy wherein the gene product/protein of interest is produced in situ in the appropriate auditory cells.

Two alternative strategies for gene therapy can be contemplated for treating subjects in need thereof. One strategy is to administer a vector encoding the gene of interest directly to the subject. The second is to use cells that have been i) removed from the subject and ii) treated ex vivo with a vector expressing the gene of interest; these cells are then re-administered to the same subject.

As used herein, the term "subjects" is intended to mean humans or non-human mammals such as primates, cats, dogs, swine, cattle, sheep, goats, horses, rabbits, rats, mice and the like. In a preferred embodiment, said subjects are human subjects. This definition applies to all aspects and embodiments of the present invention.

Thus, in an aspect, the present invention relates to vectors expressing at least one USH1 gene product, in particular AAV2/8 vectors expressing at least one USH1 gene product, preferably expressing at least the SANS gene product.

In one embodiment, the AAV2/8 vector of the invention comprises a nucleic acid sequence encoding at least one USH1 gene product, preferably encoding at least the SANS gene product.

In another embodiment, the AAV2/8 vector of the invention comprises at least one nucleic acid sequence of an USH1 gene, preferably at least the SANS gene.

According to the present invention, the vector is of interest as it is capable of expressing a functional protein.

As indicated, the vector of the invention is a viral vector that is able to transfect the cells of the auditory pathway and, more specifically, to target hair cells.

Among well-known viral vectors, adeno-associated viruses (AAV) vectors display several advantages such as i) a long lasting expression of synthesized genes (Cooper et al, 2006), ii) a low risk for pathogenic reactions (because they are artificially manufactured and not ototoxic), iii) they trigger low immunogenic response, and iv) they do not integrate the human genome (Kaplitt et al., 1994). AAV is therefore preferred to produce in situ a functional USH1 gene product in order to efficiently cure USH1 syndrome.

The Inventors could show that AAV serotypes have different cell tropism in the cochlea. Accordingly, they could select an AAV2/8 configuration (i.e., vectors having the nucleotide sequence of an AAV2 genome that is modified so as to encode AAV8 capsid proteins) as being the most efficient to target hair cells (FIG. 1).

Thus, in the context of the present invention, the vector expressing an USH1 gene product, preferably expressing the SANS protein, yet preferably expressing the SANS protein of amino acid sequence SEQ ID NO:49, is an AAV2/8 vector, preferably comprising a viral nucleic acid sequence SEQ ID NO:47 and/or SEQ ID NO:48.

In one embodiment, the AAV2/8 vector of the invention comprises a viral nucleic acid sequence of SEQ ID NO:47 and/or SEQ ID NO:48.

Advantageously, the AAV2/8 vector of the invention comprises both viral nucleic acid sequences SEQ ID NO:47 and SEQ ID NO:48, both of them forming an empty AAV2/8 vector, wherein a USH1 gene is in turn incorporated.

In one embodiment, said USH1 gene is the SANS gene product having the amino acid sequence SEQ ID NO:49.

In another aspect, the present invention also relates to a vector as described above, for use as a medicament.

In Vivo Administration of a USH1 Gene Product: Viral Particles

In another aspect, the present invention relates to viral particles comprising at least one vector as described above.

Advantageously, the viral particles of the invention are infectious viral particles.

In yet another aspect, the present invention relates to such viral particles, for use as a medicament.

Pharmaceutical Compositions

Vectors and/or viral particles of the invention as described above can be incorporated into pharmaceutical compositions suitable for an administration to a subject.

Accordingly, another aspect of the present invention concerns a pharmaceutical composition comprising at least one vector of the invention and/or at least one viral particle of the invention, and a pharmaceutically acceptable carrier.

As used herein, the term "pharmaceutically acceptable carrier" refers to any and all solvents, dispersion media, coatings, antibacterial and antifungal agents, isotonic and absorption delaying agents, and the like that are physiologically compatible. Examples of pharmaceutically acceptable carriers include one or more of water, saline, phosphate buffered saline, dextrose, glycerol, ethanol and the like, as well as combinations thereof. In many cases, it can be preferable to include isotonic agents, for example, sugars, polyalcohols such as mannitol, sorbitol, or sodium chloride in the composition. Pharmaceutically acceptable carriers can further comprise minor amounts of auxiliary substances such as wetting or emulsifying agents, preservatives or buffers, which enhance the shelf life or effectiveness of the vector(s) and/or viral particle(s) or of the pharmaceutical compositions containing same. This definition applies to all aspects and embodiments of the present invention.

The pharmaceutical compositions of the invention may be in a variety of forms. These include, for example, liquid, semi-solid and solid dosage forms, such as liquid solutions (e.g., injectable and infusible solutions), dispersions or suspensions, tablets, pills, powders, liposomes and suppositories. The form used depends on the intended mode of administration and therapeutic application. Typical compositions are in the form of injectable or infusible solutions.

Pharmaceutical compositions typically must be sterile and stable under the conditions of manufacture and storage. The pharmaceutical composition of the invention is preferably formulated as a solution, microemulsion, dispersion, liposome, or other ordered structure suitable to high drug concentration. Sterile injectable solutions can be prepared by incorporating the vector(s) and/or the viral particle(s) of the invention in the required amount in an appropriate solvent optionally with one or a combination of ingredients enumerated above, as required, followed by filtered sterilization. Generally, dispersions are prepared by incorporating the vector(s) and/or the viral particle(s) of the invention into a sterile vehicle that contains a basic dispersion medium and optionally other ingredients from those enumerated above, as required. In the case of sterile lyophilized powders for the preparation of sterile injectable solutions, the preferred methods of preparation are vacuum drying and spray-drying that yields a powder of the active ingredient plus any additional desired ingredient from a previously sterile-filtered solution thereof. The proper fluidity of a solution can be maintained, for example, by the use of a coating such as lecithin, by the maintenance of the required particle size in the case of dispersion and by the use of surfactants. Prolonged absorption of injectable compositions can be achieved by including an agent in the compositions that delays absorption, for example, monostearate salts and/or gelatine.

In the context of the invention, the typical mode of administration of the composition of the invention is a local administration, or intratympanic (in the middle ear) or intracochlear, or parenteral (e.g., intravenous, subcutaneous, intraperitoneal, intramuscular, intrathecal). In one example, the pharmaceutical composition of the invention is delivered to a specific location using stereostatic delivery, particularly through the tympanic membrane or mastoid into the middle ear of a subject. In one example, the pharmaceutical composition of the invention is injected in the cochlea of a subject. In another example, the pharmaceutical composition of the invention is administered by intravenous infusion or injection. In another example, the pharmaceutical composition of the invention is administered by intramuscular or subcutaneous injection. In another example, the composition of the invention is administered perorally.

Preferably, the pharmaceutical composition of the invention is injectable, yet preferably it is injectable in the cochlea of a subject.

The pharmaceutical compositions of the invention include a "therapeutically effective amount" of the vectors and/or the viral particles of the invention. A "therapeutically effective amount" refers to the amount of the vectors and/or the viral particles of the invention that is effective, at dosages and for periods of time necessary, to achieve the desired therapeutic result in a subject in need thereof, in this case to efficiently treat hearing impairment, preferably USH1 syndrome, yet preferably USH1G syndrome, without unacceptable toxicity or undesirable side effects.

A therapeutically effective amount of the vectors and/or the viral particles of the invention can vary according to factors such as the disease state, age, sex, and weight of the subject, and the ability of said vectors and/or said viral particles to elicit a desired response in same. A therapeutically effective amount can also be one in which any toxic or detrimental effects of the vectors and/or the viral particles are outweighed by the therapeutically beneficial effects.

Dosage regimens can be adjusted to provide the optimum desired response (e.g., to cure USH1G syndrome). For example, a single bolus can be administered, several divided doses can be administered over time or the dose can be proportionally reduced or increased as indicated by the exigencies of the therapeutic situation. It can be especially advantageous to formulate injectable compositions in dosage unit form for ease of administration and uniformity of dosage. Dosage unit form as used herein refers to physically discrete units suited as unitary dosages for the subjects to be treated; each unit containing a predetermined quantity of the vector(s) or the viral particle(s) of the invention calculated to produce the desired therapeutic effect in association with the required pharmaceutical carrier. The specification for the dosage unit forms can be dictated by and directly dependent on (a) the unique characteristics of the vector(s) and/or the viral particle(s) and the particular therapeutic effect to be achieved, and (b) the limitations inherent in the art of formulating such vector(s) and/or the viral particle(s) for treating Usher syndrome, in particular USH1 syndrome, preferably USH1G syndrome, in a subject in need thereof.

Use for Treating USH1 Hearing Impairment

A further aspect of the present invention relates to vectors and/or viral particles and/or pharmaceutical compositions as described above, for use in a method for treating Usher syndrome in a subject in need thereof.

In other words, the present invention relates to the use of a vector and/or a viral particle and/or a pharmaceutical composition, in a method for treating Usher syndrome in a subject in need thereof.

These methods preferably comprise an injection, preferably a cochlear injection, of said vector.

Yet in other words, the present invention relates to a method for treating Usher syndrome in a subject in need thereof, comprising administering to said subject, preferably by injection, a vector and/or a viral particle and/or a pharmaceutical composition. In a particular embodiment, said injection is a cochlear injection.

In another aspect, the present invention relates to the use of the vectors and/or the viral particles of the invention for manufacturing pharmaceutical compositions intended to treat subjects suffering from Usher syndrome, in particular from USH1 syndrome, preferably from USH1G syndrome.

Preferably, said pharmaceutical compositions are as described above.

Kit

In another aspect, the present invention relates to a kit comprising, in one or more containers in a single package, at least one vector and/or at least one viral particle and/or at least one pharmaceutical composition as described above, and means for injecting said vector(s) and/or viral particle(s) and/or pharmaceutical composition(s).

Accordingly, the vector(s) and/or the viral particle(s) and or the pharmaceutical composition(s) in the kit are capable of expressing at least one USH1 gene product, preferably of expressing the SANS gene product, advantageously for use in a method for treating Usher syndrome, in particular USH1 syndrome, preferably USH1G syndrome in a subject in need thereof.

In one embodiment, the means for injecting said vector(s) and/or viral particle(s) and/or pharmaceutical composition(s) as provided in the kit of the invention include or are means for a cochlear injection of said vector(s) and/or viral particle(s) and/or pharmaceutical composition(s).

Particular kits according to the present invention further comprise a means for communicating information and/or instructions and/or recommendations to allow a proper use of the kits' elements.

BRIEF DESCRIPTION OF THE DRAWINGS

Figure 15:
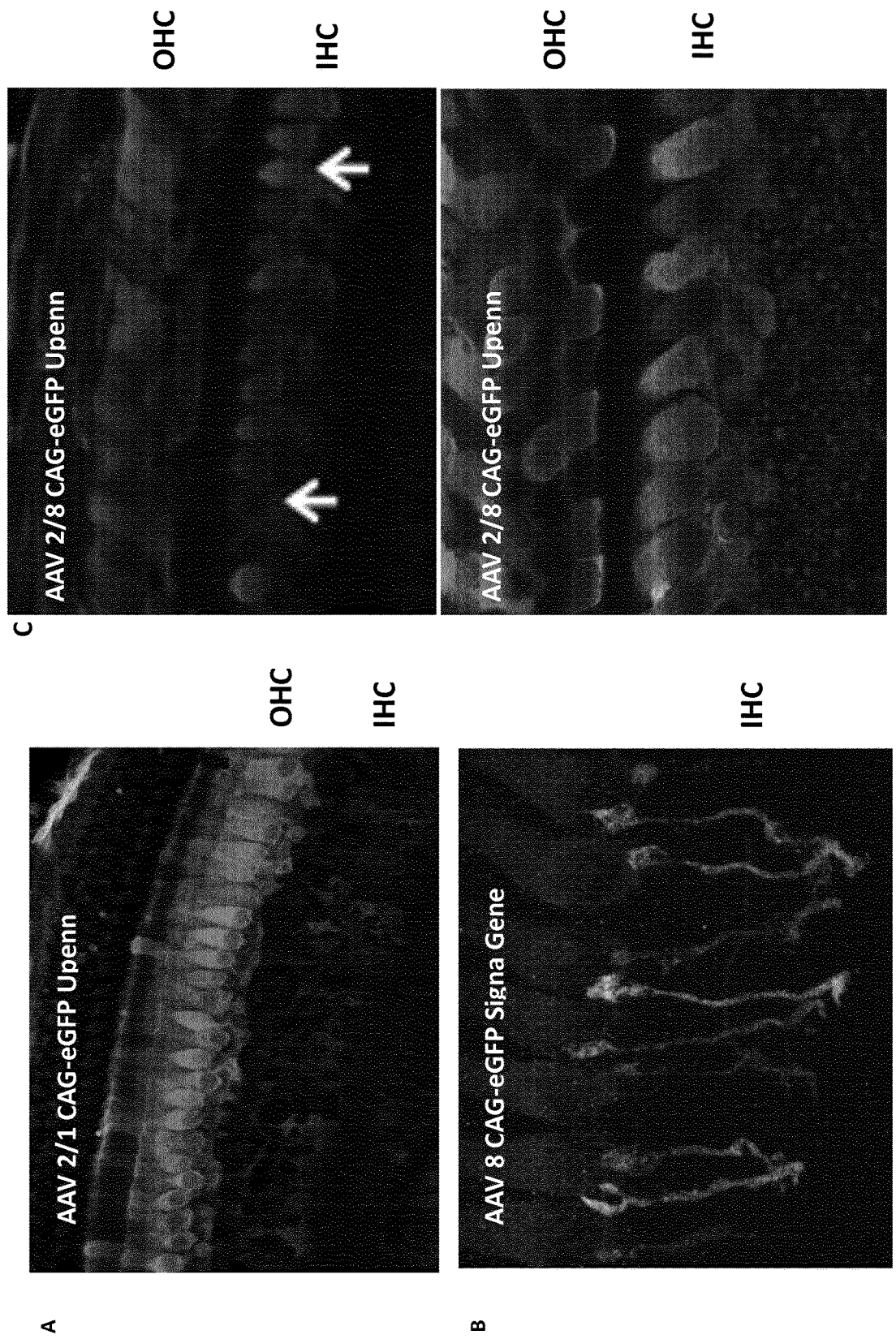
Figure 15:
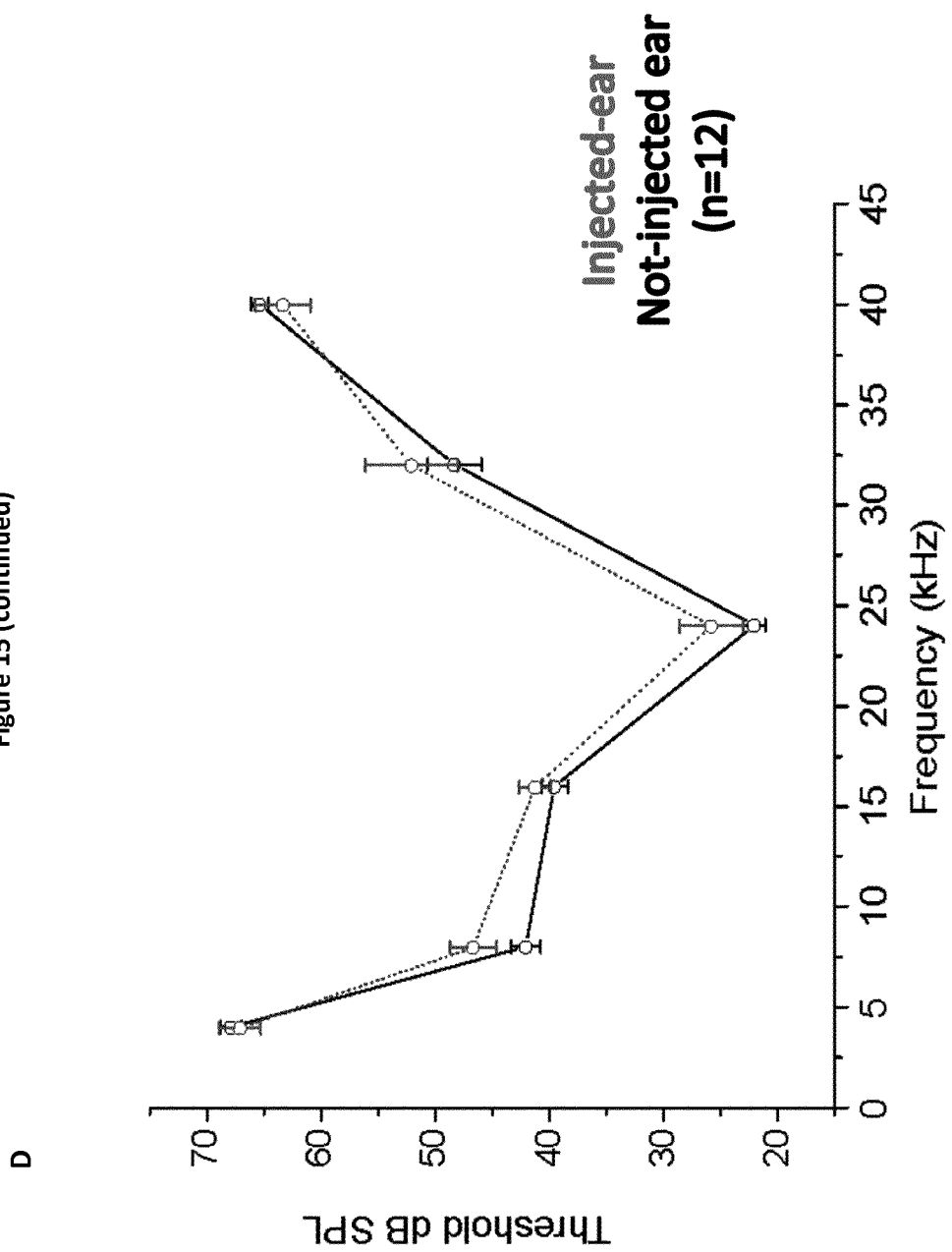

FIG. 15 describes different expression and efficiency, in cochlear hair cell, of AAV based on their serotype and promoter efficiency. Wild type mice were injected at P2 with AAV containing GFP as a gene reporter. Organs of Corti were harvested at P8, and immunolabelled for GFP (in light grey) and otoferlin (in dark grey) (A) AAV2/1-CAG mainly transduced supporting cell, and some neurons. (B) AAV2/8-CAG (SignaGen Laboratories) transduced neurons and afferent fibers. (C) AAV2/8-CAG (Penn Vector Core) transduced 85% of auditory hair cells. (D) ABR thresholds measured in a left injected cochlea did not differ from ABR thresholds of right non-injected cochlea.

Figure 16:
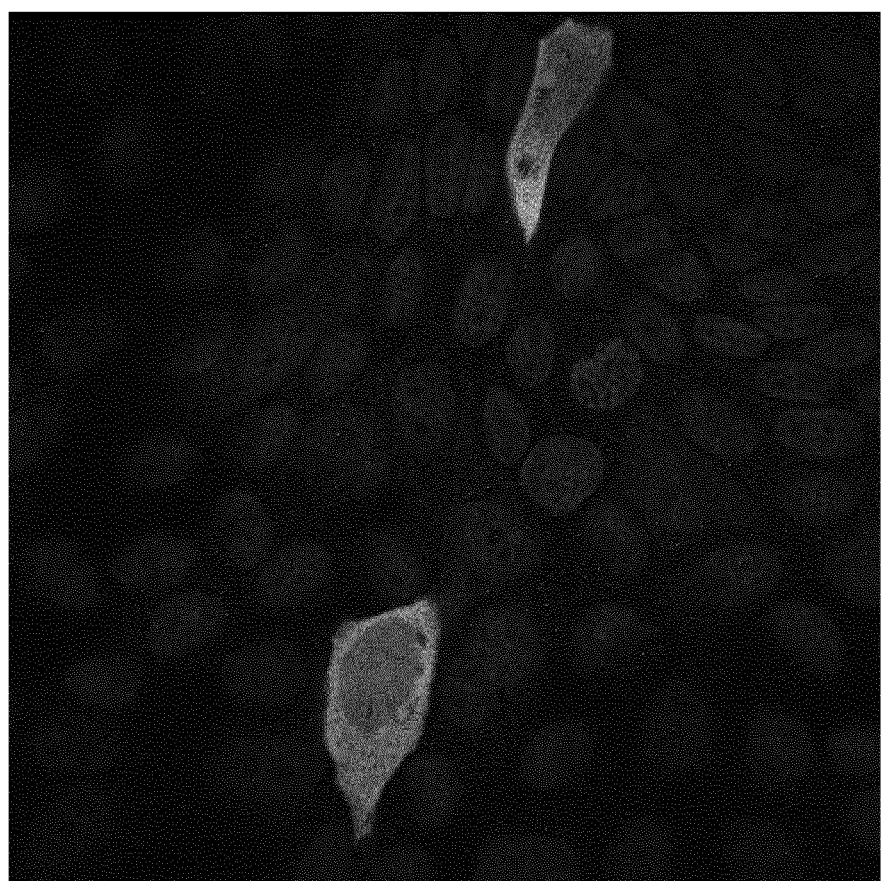
Figure 17:
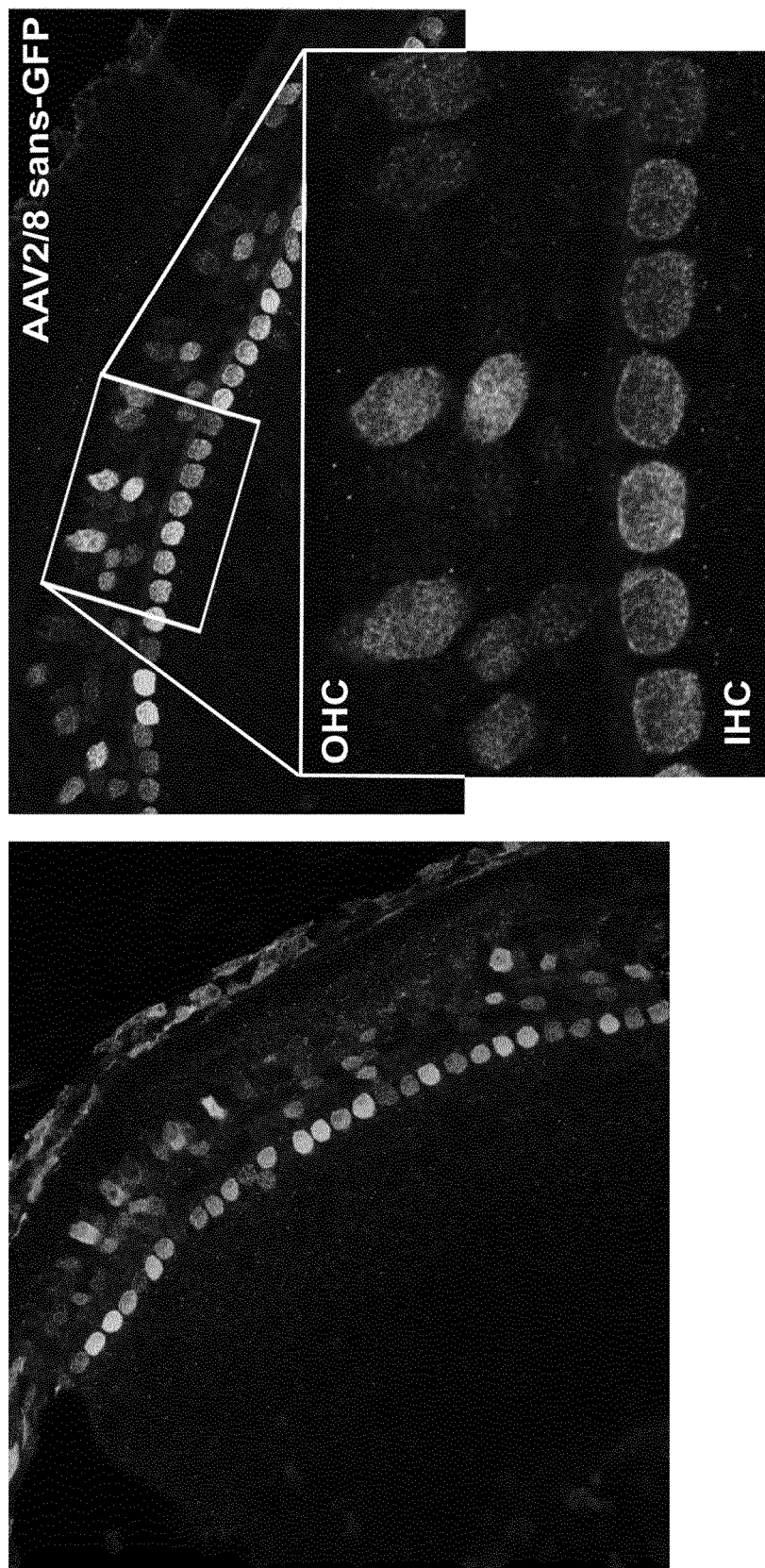

FIG. 16 describes MDCK cells transduced by AAV2/8-SANS-IRES-GFP. MDCK cells were plated on coverslips and infected with AAV2/8-sans-IRES-GFP. 24 h after cells were immunolabelled for GFP (in light grey). 90% of MDCK cells were e-GFP positive FIG. 17 represents AAV2/8-Sans transduced cochlear hair cells, and restored sans expression. Wild type mice were injected by AAV2/8-sans at P2. Organs of Corti were harvested at P8, and immunolabelled for GFP (in light grey), and sans (dark grey). A) Tonotopic gradient was observed for viral transduction of AAV2/8-sans, with more eGFP-positive cells in IHCs than OHCs, and at the apex than at the base. B) Sans expression and distribution was restored.

Figure 18:
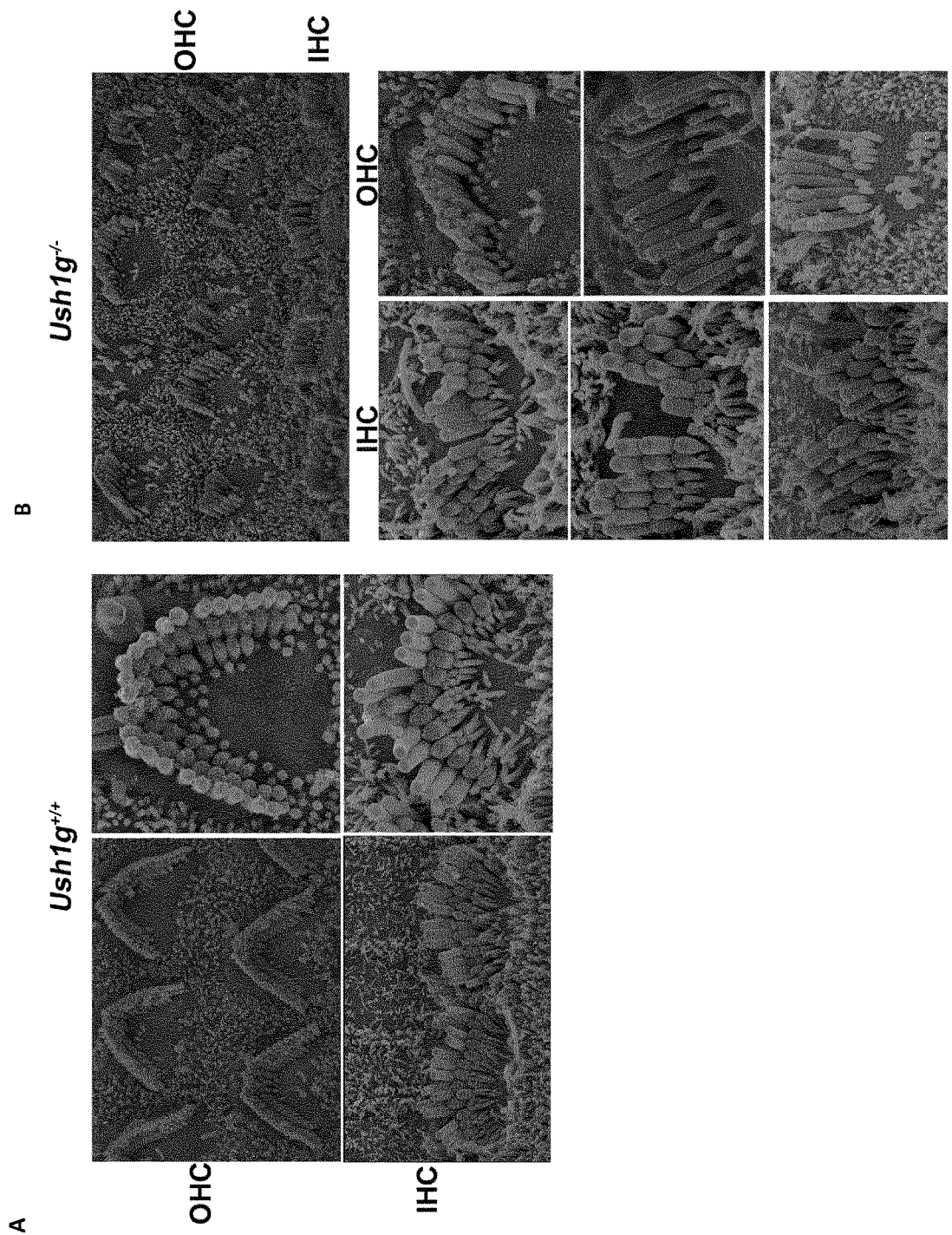
Figure 18:
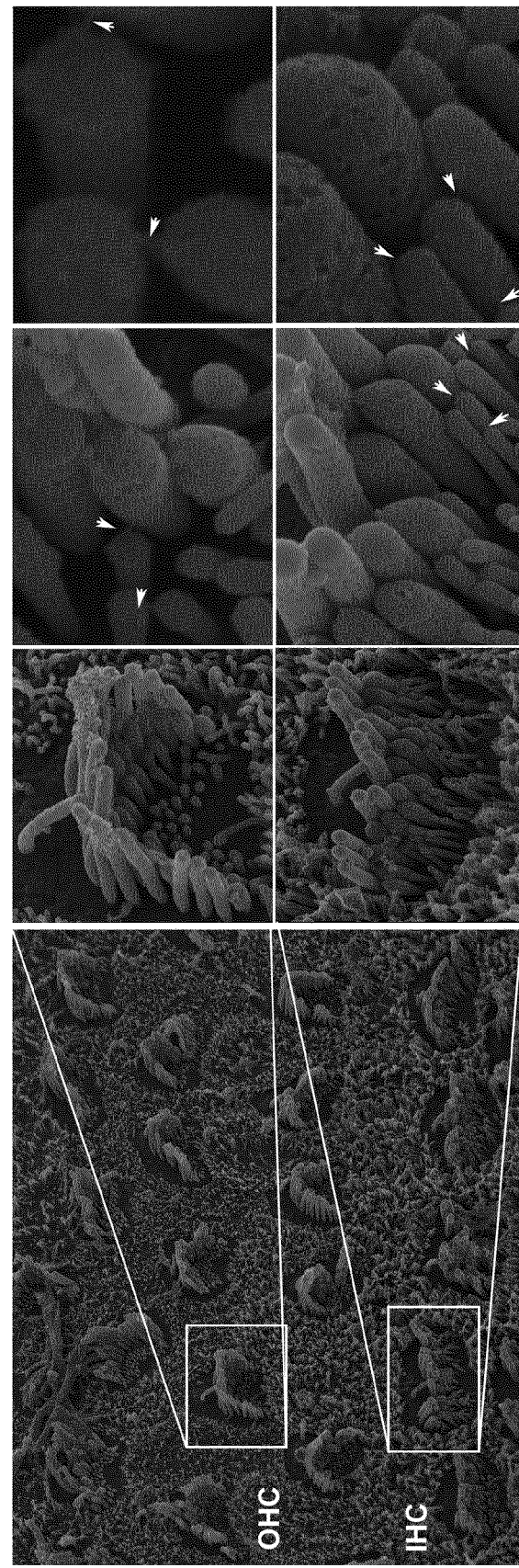

FIG. 18 shows that AAV2/8-Sans restored the morphology of cochlear hair cells. Scanning electron microscopy of cochlear hair cells shows degeneration of the hair bundle, abnormal staircase pattern and no prolate shape in $Ush1g^{-/-}$ mice (A) compared to and $Ush1g^{+/+}$ mice (B). Restore of the staircase pattern and the prolate shape is observed in $Ush1g^{-/-}$ mice treated with AAV2/8-Sans (C).

Figure 19:
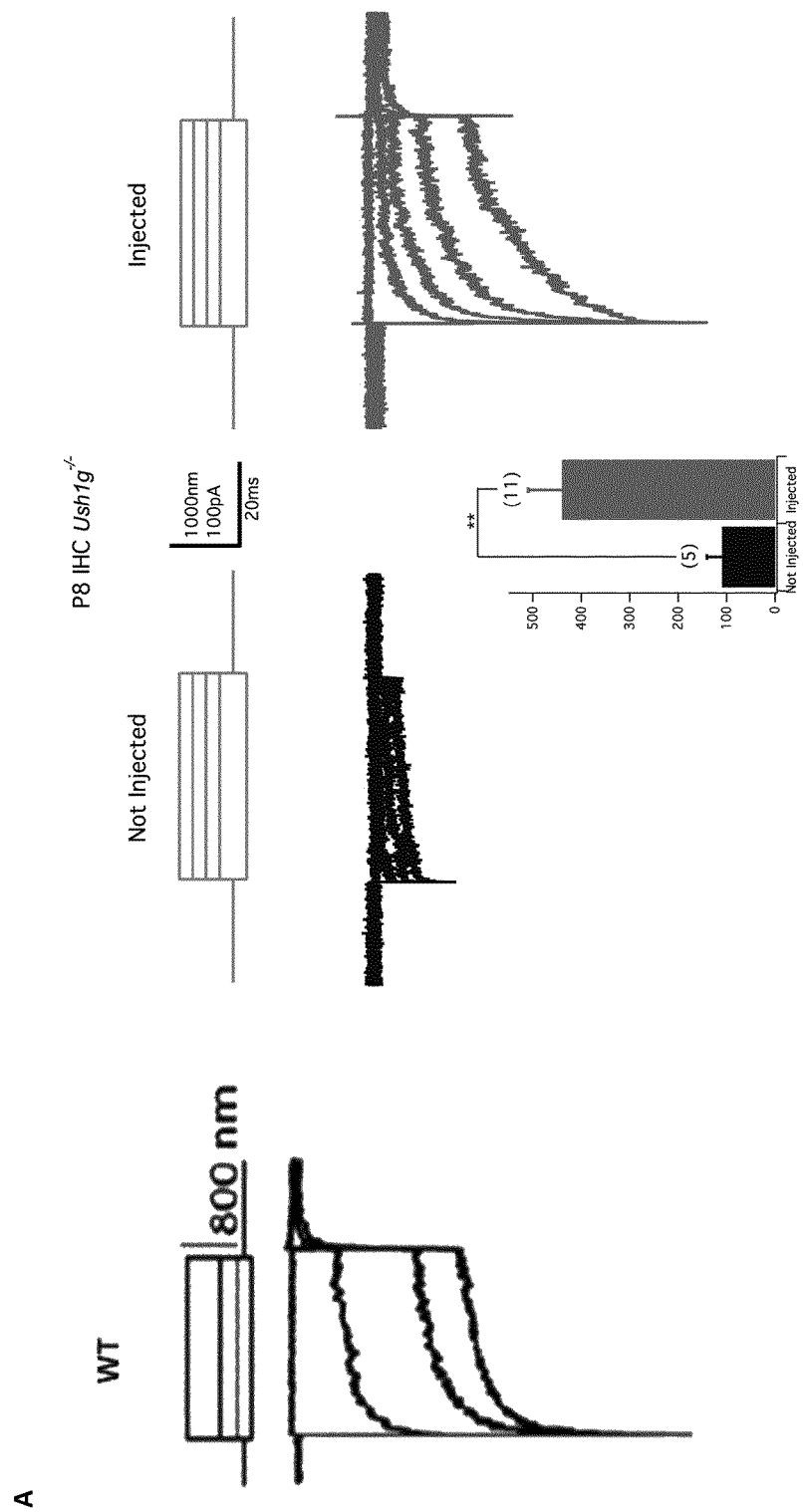
Figure 19:
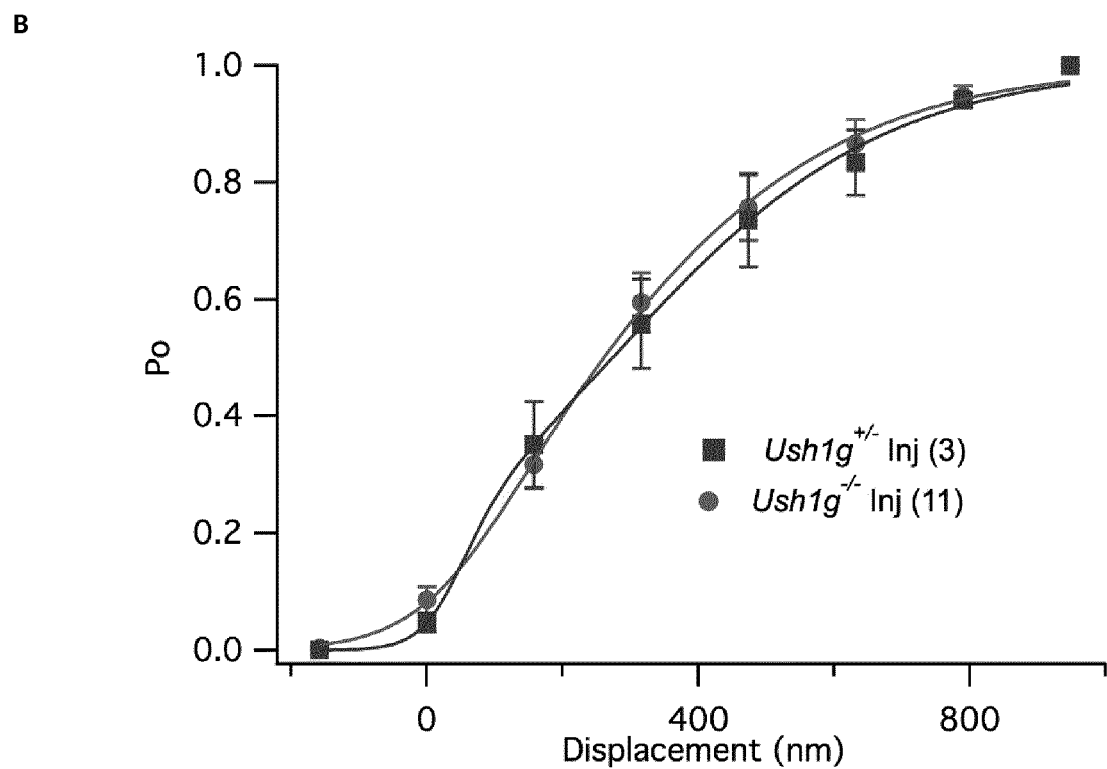
Figure 19:
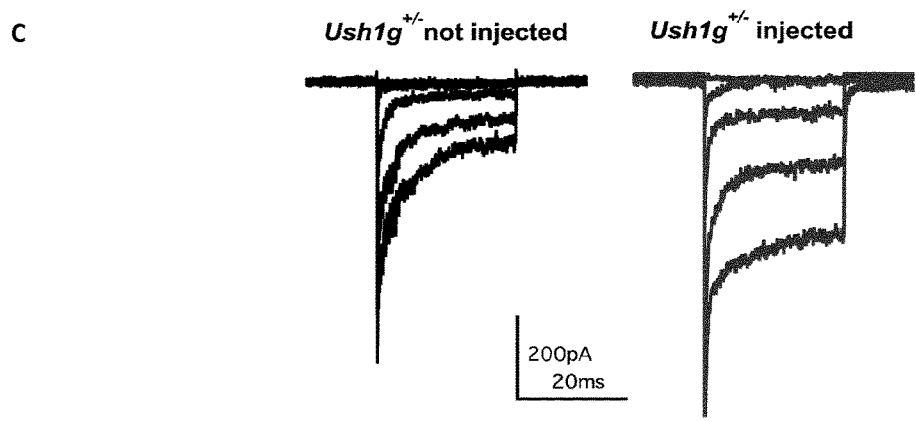
Figure 19:
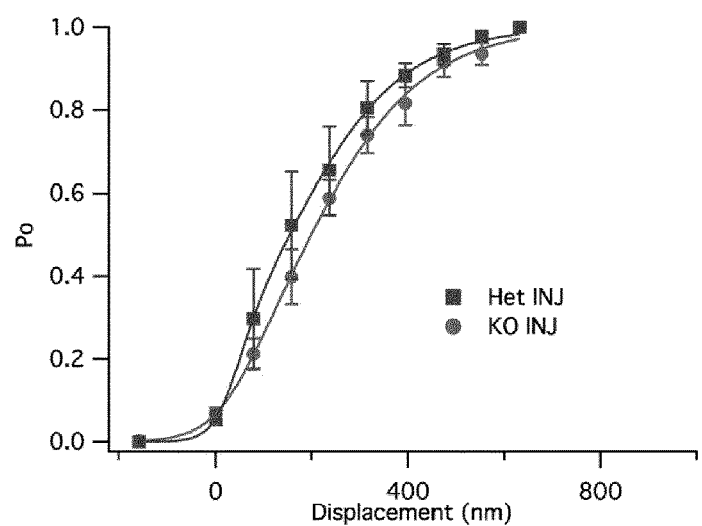
Figure 19:
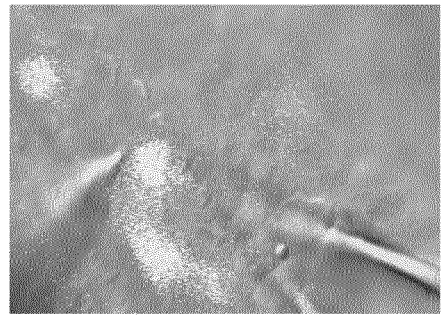
Figure 19:
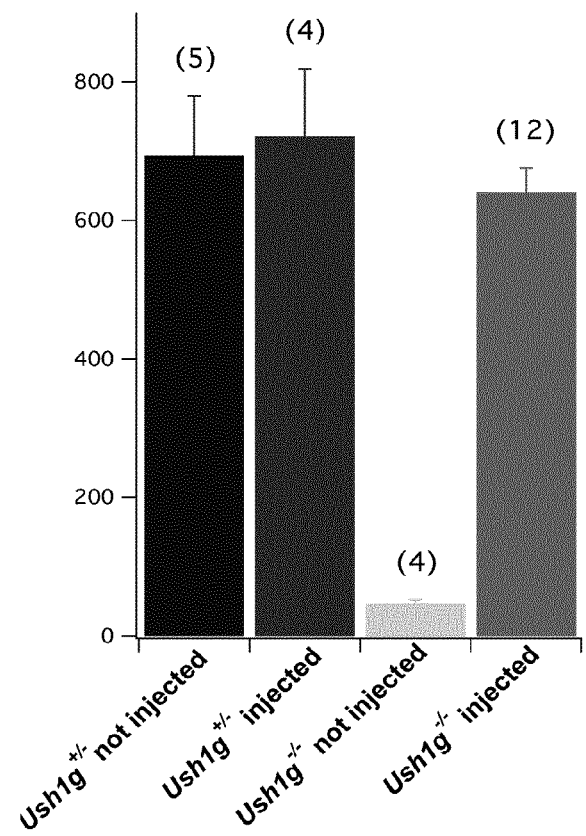

FIG. 19 shows that AAV2/8-Sans rescued the mechano-electrical transduction currents in cochlear hair cells. $Ush1g^{-/-}$ mice were injected at P2 with AAV2/8-Sans. Measurements of MET currents were realized at P8.

Figure 20:
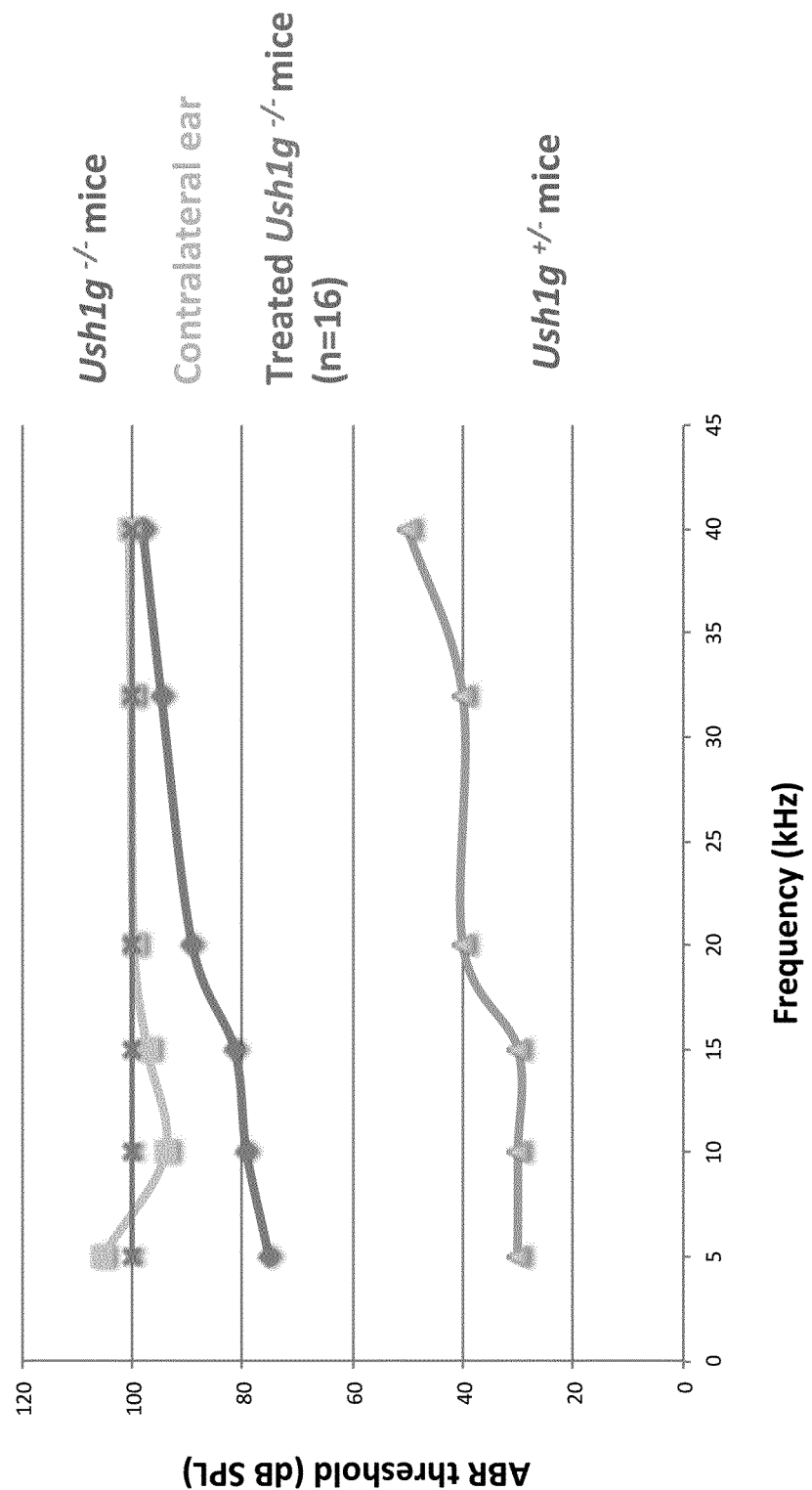

FIG. 20 shows that AAV2/8-Sans delivery restored the auditory function. $Ush1g^{-/-}$ and $Ush1g^{f/f}$ $Myo15\text{-}Cre^{+/-}$ mice were injected at P2 with AAV2/8-sans, and ABR measurements were recorded between P17 and P37, in response to 5 to 40 kHz tone bursts, and for sounds level between 10 and 115 dB. ABR thresholds measured in $Ush1g^{-/-}$ mice. ABR thresholds of $Ush1g^{-/-}$ mice were elevated at 100 dB. ABR thresholds of $Ush1g^{-/-}$ treated mice showed a partial restore of 20-25 dB for low-frequencies, and 5-10 dB for high-frequencies. Variability of restore in $Ush1g^{-/-}$ injected mice. ABR thresholds measured in $Ush1g^{f/f}$ $Myo15\text{-}Cre^{+/-}$ mice. ABR thresholds of $Ush1g^{f/f}$ $Myo15\text{-}Cre^{+/-}$ mice were elevated at 100 dB. ABR thresholds of $Ush1g^{f/f}$ $Myo15\text{-}Cre^{+/-}$ treated mice showed a partial restore of 30-40 dB for low-frequencies.

Figure 21:
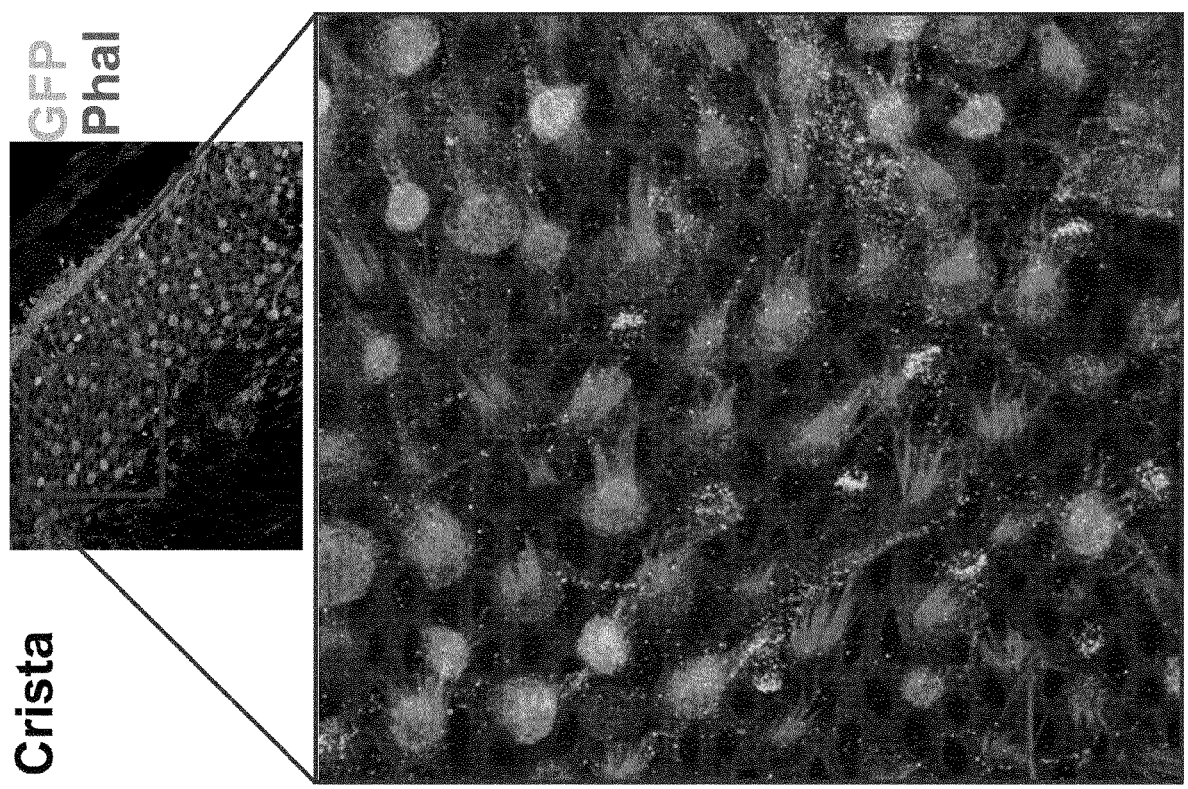

FIG. 21 represents AAV2/8-sans transduced vestibular hair cells, and restored Sans expression. Wild type mice were injected by AAV2/8-sans at P2. Vestibules were harvested at P8, and immunolabeled for GFP (in light grey), and sans (dark grey). A) A high rate of transduction (90%) was observed for viral delivery of AAV2/8-sans in vestibular hair cells. Sans expression and distribution was also restored.

Figure 22:
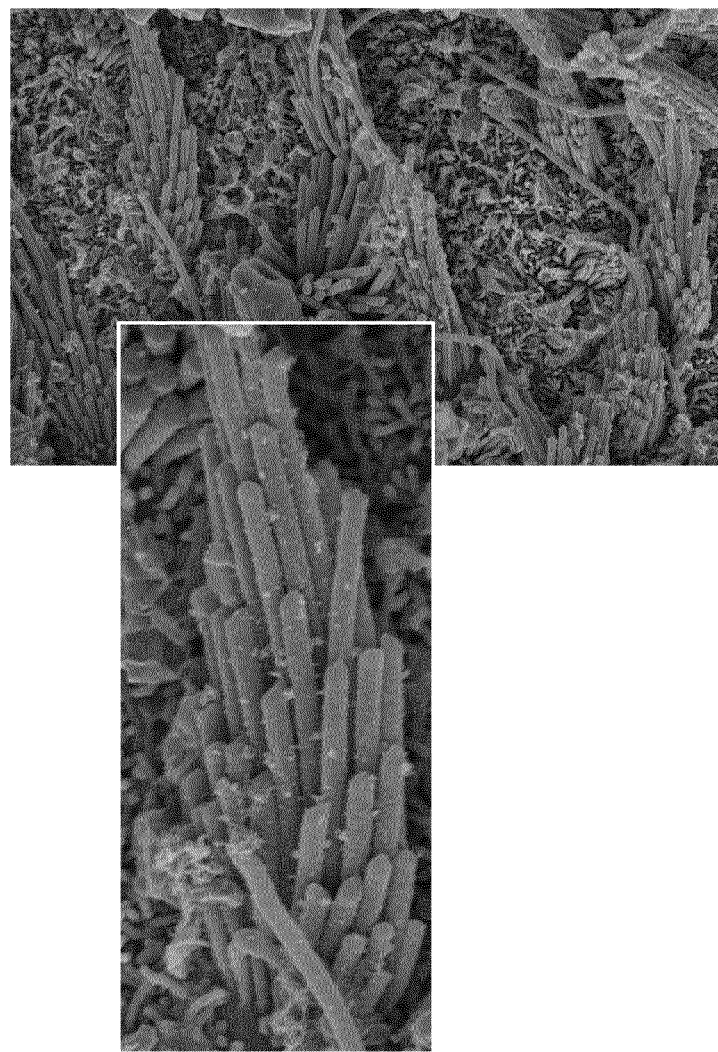
Figure 22:
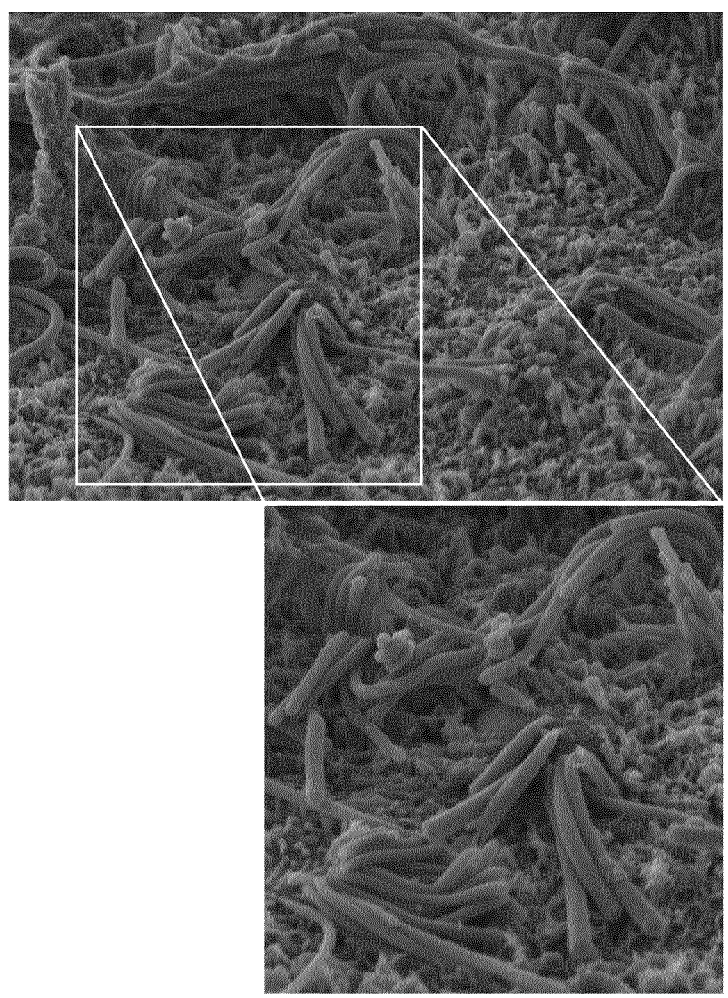
Figure 22:
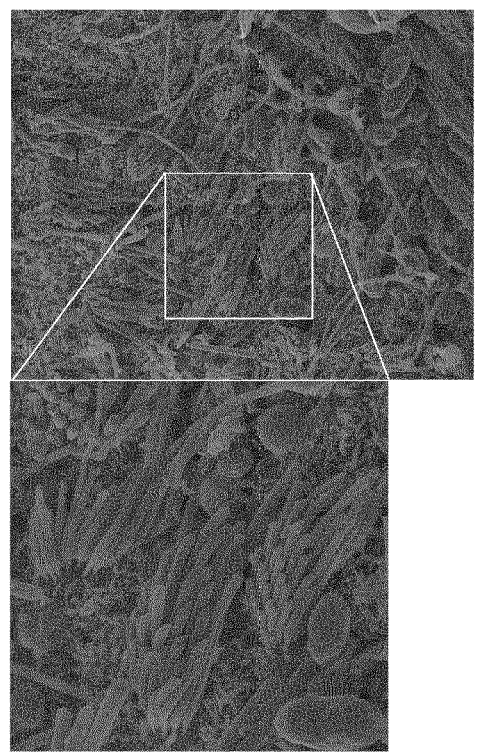
Figure 22:
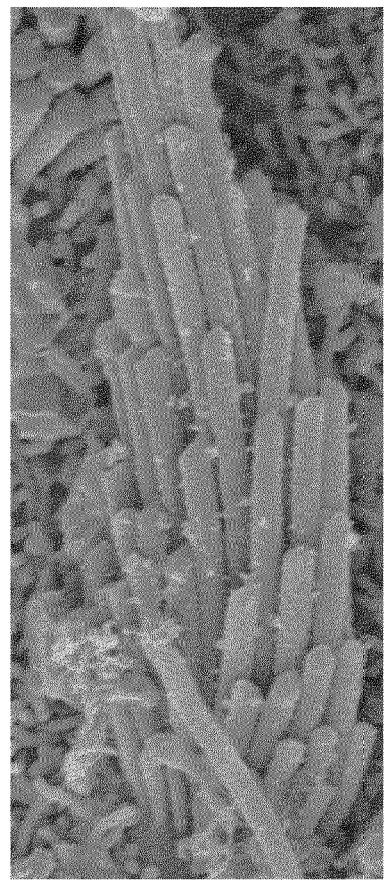

FIG. 22 shows that AAV2/8-Sans restored the morphology of vestibular hair bundles—$Ush1g^{-/-}$ mice were injected at P2 with AAV2/8-sans, and structure of hair bundles were assessed by scanning electron microscopy at P8. (A) Characteristic staircase pattern of vestibular hair bundles observed in not treated heterozygous mice. (B) No difference of morphology in treated heterozygous mice, showing that injection did not alter the bundle structure. (C) Vestibular hair bundles of not treated $Ush1g^{-/-}$ mice showed not organized hair bundles with fused stereocilia, with irregular diameters and heights. Treated $Ush1g^{-/-}$ mice presented heterogeneous organized vestibular hair bundles, with normal shape and the characteristic staircase pattern. Some stereocilia observed had a prolate shape. Smaller hair bundles with a kinocilium, were also frequently observed, showing that these young cells were transduced since the beginning of their development. In contralateal vestibule less hair cells were restored.

Figure 23:
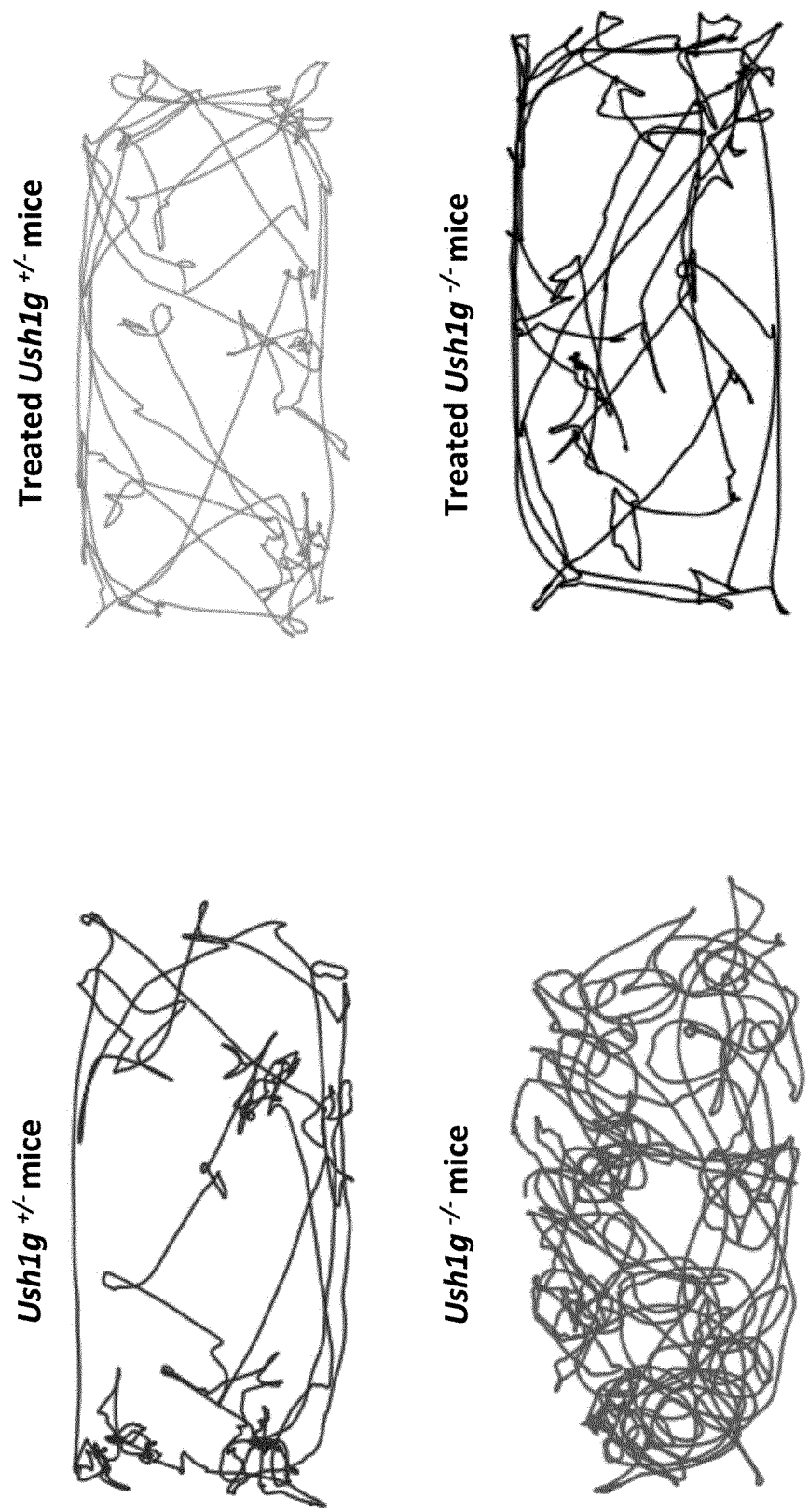

FIG. 23 shows AAV2/8-Sans restored the vestibular function. The circling behavior in an open-field chamber was evaluated at P40 in treated or untreated $Ush1g^{-/-}$ mice $Ush1g^{-/-}$ mice using a tracking software system. Turns in clockwise and counter clockwise were counted: treated $Ush1g^{-/-}$ mice did not show any circling behavior, like heterozygous mice (3 turns during 2 min for treated $Ush1g^{-/-}$ mice vs. 23 turns for uninjected $Ush1g^{-/-}$ mice).

EXAMPLES

I. Material and Methods

Animals

Experiments on mice were carried out according to Institut National de la Santé et de la Recherche Médicale and Institut Pasteur welfare guidelines.

Animals were housed in the Institut Pasteur animal facilities accredited by the French Ministry of Agriculture to perform experiments on live mice.

Knockout sans mice ($Ush1g^{-/-}$) were generated, as described in Caberlotto et al., 2011, in C57BL/6-129/Sv strain mice. Intracochlear injections were achieved on P2-P3 aged-mice.

Viral Construction

Recombinant AAV vectors were obtained from Penn Vector Core (Perelman, Philadelphia, Pa., USA) and SignaGen Laboratories (Bethesda, Md., USA) containing a CMV or CAG promoter driving expression of eGFP. AAV2/1-CAG-GFP and AAV2/1-CMV-GFP were produced at a titer of $1.2 \times 10^{12}$ genome copies (gc)/mL by SignaGen Laboratories. AAV2/1-CAG-GFP-rhodopsine at a titer of $1.4 \times 10^{13}$ gc/mL by Penn Vector Core. The AAV2/2-CAG-GFP was produced at a titer of $6.4 \times 10^{13}$ gc/mL, by Penn Vector Core. The AAV2/5-CMV=-GFP was produced at a titer of $1.13 \times 10^{13}$ gc/mL, by Penn Vector Core. The AAV2/8-CAG produced by SignaGen Laboratories at a titer of $1.6 \times 10^{12}$ gc/mL. And the AAV2/8-CAG from Penn Vector Core had a titer of $1.4 \times 10^{13}$ gc/mL.

Murine Sans cDNA flanked by an IRES eGFP reporter cDNA sequence was subcloned into the multiple cloning site of the pENN.AAV.CB6.PI.rBG vector (Penn Vector p1045, Penn Medicine Vector Core).

Vectors were generated by transient transfection of HEK293 cells using three plasmids: the cis ITR-containing plasmid, the trans plasmid encoding AAV replicase and capsid genes and the adenoviral helper plasmid. The recombinant vectors were purified by tangential flow filtration followed by iodixanol gradient purification and buffer exchange (Upenn website).

Concentrated AAV2/8-mSANS-IRES-eGFP titer was $1.47 \times 10^{13}$ genomes copies per mL. Virus aliquots were stored at 80° C. and thawed prior to surgery.

Transfection in MDCK Cells (p1045 SANS IRES GFP, AAV2/8 SANS IRES GFP)

MDCK cell lines were cultured in Dulbecco's modified Eagle medium (DMEM, Gibco) supplemented with 10% foetal bovine serum, 1% penicillin-streptomycin antibiotics and 1% fungizone antimycotic.

Both plasmid and virus forms containing mSANS.IRES.eGFP in MDCK cells were tested. For the plasmid, cells were transfected with Lipofectamine 2000 (Invitrogen). For the vector form cells were directly transfected without reagent. Cells were fixed 24 h after transfection with 4% paraformaldehyde (PFA) in phosphate buffered saline (PBS) for 20 minutes. Cells were rinsed three times for 10 minutes in PBS, permeabilized in PBS containing 0.3 TritonX-100 supplemented with $NH_4Cl$, and blocked with PBS containing 20% normal goat serum (NGS). Then cells were processed for immunochemistry with chicken anti-GFP (Abcam, 1:250) in PBS containing 1% of bovine serum albumin (BSA) overnight. After washing three times for 10 minutes in PBS, cells were incubated 1 hour in ATTO-488 conjugated goat anti-chicken IgG antibody (Sigma-Aldrich, 1:500 dilution). Actin was labelled with ATTO-647N-conjugated phalloidin (Sigma-Aldrich, 1:200 dilution). Samples were then mounted in Fluorsave (Calbiochem, USA).

Intracochlear Injection

Animal protocols were approved by animal care and use of committee of Pasteur Institute.

Intracochlear viral transduction was carried out as described by Akil et al. (2012). After anesthesia on ice, a left postauricular incision was made, and using two landmarks including the cochlear basal turn and the stapedia artery, the otic bulla was exposed and then opened. Next, a glass micropipette of 10 µm outer tip diameter containing 2 µl of the viral vector was inserted into the round window membrane (RWM). The viral preparation was then gently injected through the round window. After pulling out the pipette, the hole in the RWM was plugged with connective tissue and the incision sealed with biological glue (3M Vetbond).

Immunofluorescence

After dissection, mice cochleae were perfused with 4% PFA in PBS for 45 minutes at 4° C. Cochleae were further microdissected, rinsed three times for 10 minutes, incubated 1 hour at room temperature in PBS containing 20% NGS and 0.3% Triton X-100, and incubated overnight with the primary rabbit antibody anti-Sans (Caberlotto et al., 2011), and/or chicken anti-GFP (Abcam, 1:250) in PBS containing 1% of NGS. Cochleae were rinsed three times for 10 minutes in PBS, and then incubated for 1 hour in ATTO-550 conjugated goat anti-rabbit IgG antibody (Sigma-Aldrich, 1:500 dilution) and ATTO-488 conjugated goat anti-chicken IgG antibody (Sigma-Aldrich, 1:500 dilution). Actin was labelled with ATTO-647N-conjugated phalloidin (Sigma-Aldrich, 1:200 dilution). Samples were then mounted in Fluorsave (Calbiochem, USA). The z-stack images were captured with a ×63 Plan Apochromat oil immersion lens (NA 1.4) using a Zeiss LSM-700 confocal microscope and processed using Zeiss LSM image browser.

Hair Cell Counting

To evaluate the rate of transduction, the expression of eGFP used as a gene reporter was analysed in mice injected with the viral construction. For counting, the total number of inner or outer hair cells positive for eGFP was divided by the total number of inner or outer hair cells existing in the tissue, detectable by rhodamine phalloidin staining. For mature stages, rate of transduction was calculated in middle turn and apex of each cochlea.

Electrophysiological Recordings

Electrophysiological cell recordings were performed on cochlear and utricular explants from mice at P8 as previously described (Michalski, 2009). Cochlea and utricule were finely dissected, placed under nylon meshes and observed under a ×40 water-immersion Olympus objective mounted on an Axioscope Zeiss microscope.

Extracellular and dissecting solutions were identical and composed of 146 mM NaCl, 5.8 mM KCl, 1.5 mM CaCl2, 0.7 mM NaH2PO4, 2 mM Na-pyruvate, 10 mM glucose and 10 mM N-2-hydroxyethylpiperazine-N-2-ethanesulfonic acid (HEPES; pH=7.4, 305 mosmol/kg). Intracellular solution contained 130 mM KCl, 10 mM NaCl, 3.5 mM MgCl2, 1 mM ethyleneglycoltetraacetic acid (EGTA), 5 mM K2ATP, 0.5 mM GTP and 5 mM HEPES (pH=7.3, 290 mosmol/kg). Borosilicate patch pipettes (2-3 MO) were approached parallel to the hair cell rows through a hole in the reticular lamina. During this step, extracellular solution was abundantly perfused to avoid contact between EGTA and the transduction apparatus, which is sensitive to calcium chelators. Hair cells were whole-cell voltage clamped at room temperature (20-25° C.) at −80 mV using an EPC-9 patch clamp amplifier and the Patchmaster software (HEKA, Lambrecht, Germany). No correction was made for liquid junction potential. Series resistance was always below 10 M$\Omega$ and was compensated to 70%. Data were sampled at 100 kHz and filtered at 10 kHz (8-pole Bessel). Each hair bundle was mechanically stimulated by applying axial step displacements with a rigid glass rod that had been fire-polished prior to the experiment to yield a tip diameter of 2-3 µm. The probe was systematically positioned against the top of the hair bundle in the bundle's plane of bilateral symmetry towards the tallest row of stereocilia at an angle of ~30° relative to the cell apical surface. The probe used for mechanical stimulation of the hair bundles was secured to a stacktype piezo-electric actuator (PA8/12; Piezosystem Jenas) driven by a low-voltage power supply (30V300, Piezosystem Jena). As measured offline with a displacement monitor containing photodiodes, the first two milliseconds of the time course of probe motion were well described by an exponential rise with a time constant of 100 ms. Data were analyzed in Matlab, version 7.0 (MathWorks). Po(X) curves were fitted with a three-state Boltzmann relation. For sensitivity measurements, the mean value of the three-state Boltzmann relation derivative was calculated for displacements corresponding to P0 values between 0.2 and 0.8.

Audiological Tests

Auditory Brainstem Responses (ABR) were recorded and analysed as described previously (Le Calvez et al., 1998). Mice were anesthetized with xylazine and ketamine, and places in a sound-attenuated room. Three electrodes were placed at the vertex and ipsilateral mastoid, with the lower back as the earth. Pure tone stimuli at 5, 10, 15, 20, 32 and 40 KHz were used. Sounds level between 10 dB and 100 dB in 10 dB steps were tested. ABR thresholds were determined about 20 days after injection. Thresholds were determined as the lowest stimulus level resulting in recognizable waves.

Distortion product otoacoustic emissions (DPOAEs) were collected in the ear canal using a microphone. Two simultaneous pure tone stimuli, at frequencies f1 and f2, were used with the same levels, from 30 to 75 dB SPL in 5 dB steps. The f2 frequency was swept from 5 to 20 kHz in $\frac{1}{8}^{th}$ octave steps, with f1 chosen such that the frequency ratio f2/f1 was 1.20. Only the cubic difference tone at 2f1-f2, the most prominent one from the ear, was measured (Le Calvez et al., 1998). Statistical significance was tested by the two-tailed unpaired t test with Welch's correction.

Cochlear microphonic (CM) responses to a 5 kHz pure tone stimulus at 105 dB SPL were collected between an electrode inserted in the round window and the vertex. The response from the electrodes was amplified (gain 10000), filtered, digitally converted and averaged using a comprised-data acquisition system.

Behavioral Analysis

Firstly, mice were observed in cage to evaluate signs like circling or head bobbing. Then various tests were performed on mice, to assess the vestibular function before and after intracochlear injection, as described in Hardisty-Hughes et al., 2010. The trunk curl test was performed by holding the mouse by the tail and observing whether the mouse reached a horizontal surface or curls its trunk toward its tail. Mice's equilibrium was also evaluated with the platform test, were mice are positioned upon a platform (height: 29 cm, platform: 7 cm×7 cm) and the number of fells of the mouse was counted over a period of 1 min.

The contact righting test was realized by placing the mouse into a closed clear tube and observing if the mouse re-orientates when the tube was rotated through 180°. The swimming ability of each mouse in a container filled of 24-26° C. water was also scored. Finally, the circling behavior was evaluated with a tracking software system (Ethovision de Noldus Information Technology, Wageningen, The Netherlands+Lentz et al., 2013). Turns in clockwise and counter clockwise were counted.

Scanning Electron Microscopy

Scanning electron microscopy (SEM) analyzes were realized to assess the morphology of cochlear and vestibular hair bundles after intracochlear injections. Organs of Corti were finely dissected and fixed in 2.5% glutaraldehyde in 0.1M aqueous sodium cacodylate solution at room temperature. Then samples were rinsed in cacodylate 0.1M three times for 1-2 minutes, and incubated alternatively in 1% osmium tetroxide and 0.1M thiocarbohydrazide (OTOTO), with water washing between each incubation. Cochleae were then dehydrated in graded series of ethanol and critical point dried. Observations were done by field emission scanning electron microscopy with Jeol JSM6700F operating at 3 kV.

II. Results

Evaluation of AAV Mediated Transgene Expression, Tropism and Promoters Efficiency in Cochlear Hair Cell The AAV are on the top of a list of promising gene delivery carrier for gene therapy for human diseases. The main advantages of the AAV virus are their capacity to infect non-dividing cells, the absence of immune response and long-term transgene expression. The AAV serotypes identified up to date display variable cell tropism. The ability of several AAV to transduce sensory hair cell in odor was evaluated to determine which AAV would best transduce the inner ear sensory cells.

To this end, transgene expression and cellular distribution of several AAV pseudotypes were investigated after intra-cochlear injection. Wild type mice were subjected to the viral cochlear delivery, through the round window membrane (RWM), at postnatal day 2-3 (P2-3). Left cochleae were injected with either AAV1, AAV2/1, AAV2/2, AAV2/5 or with AAV2/8, encoding the green fluorescent protein (GFP) as a gene reporter, at titers ranged from $1.2 \times 10^{12}$ to $6.4 \times 10^{13}$ genome copies (gc)/mL. Six days after the injection, organs of Corti were microdissected and immunolabelled for otoferlin, a protein highly expressed in IHCs, and for GFP. All the tested AAVs were able to transduce cells within the cochlea, but with different cochlear cell tropism and transduction rates. Interestingly, two AAV with the same serotype and promoter (CAG or CMV) but from different suppliers did not transduce the same cell within the cochlea. In fact, while the AAV2/1 from SignaGen Laboratories mainly transduced supporting cells, (FIG. 15A) the one from Penn Vector Core, transduced primarily IHCs (40%) but only in 1 out of 5 mice (FIG. 15A). The AAV2/2 serotype with CAG promoter (Penn Vector Core) transduced only supporting cells. The AAV2/5 with the CMV as promoter did not transduced any cochlear cell types. The AAV2/8-CAG serotype (SignaGen Laboratories) transduced predominantly primary neurons (FIG. 15B). On the contrary, in the present experimental tests, the AAV2/8 with CAG as promoter (Penn Vector Core) transduced mainly the hair cells (FIG. 15C). A tonotopic gradient viral transduction for AAV2/8-GFP establishes, with more eGFP-positive hair cells at the apex (70%), than at the base (40%). Thus, the AAV2/8-CAG from Penn Vector Core was chosen for this study, as it was the most efficient to transduce sensory auditory hair cells.

Next, the effects of surgery and of the cochlear injection of the viral preparation through the round window membrane on the development of auditory function were assessed. The auditory brainstem responses (ABRs) were examined at different frequencies (from 4 kHz to 40 kHz), fourteen days after the injection. In the twelve treated mice, ABR hearing thresholds of the injected ear recorded at the frequencies tested did not differ significantly from those of the control ear (FIG. 15D), suggesting that surgery and viral injection did not interfere with the normal development and maturation of the auditory system.

AAV2/8-SANS-IRES-GFP Transduced MDCK Cells

The coding sequence for the murine sans cDNA was subcloned into AAV2 genome downstream of internal ribosome entry sites (IRES) eGFP cDNA sequence. The expression cassette was flanked with AAV2 inverted terminal repeats (ITRsp) and pseudotyping strategy was used to produce AAV2 vectors packaged with AAV8. To evaluate the relative expression efficiencies of this viral particle and to assess specificity of sans protein expressed, MDCK cells were plated on coverslips and infected with AAV2/8-sans-IRES-GFP using MOI (Multiplicity Of Infection) of 10,000. Sans expression was then probed by immunohistochemistry using a specific anti sans antibody, and the transduced cell were quantified. The results show that all cells expressing GFP also expressed sans, and that AAV2/8-sans-IRES-GFP transduced an average of 90% of MDCK cells (FIG. 16).

Gene Therapy Restored Sans Expression and Targeting in Inner Ear Hair Cells of Ush1g$^{-/-}$ Mice Having established the efficiency of the AAV2/8-sans in vitro, the expression of AAV2/8-sans was investigated in the cochlea in vivo. To this end, 2 µL of AAV2/8-sans were injected through the round window membrane into one ear of wild type mice. Eight days after inoculation, organs of Corti, from the injected and the contralateral cochlea, were microdissected, immunolabelled for GFP. Positive eGFP-hair cells were then counted. The transduction rate of both IHCs and OHCs upon cochlear injection of the AAV2/8-sans was comparable to that observed for AAV2/8-GFP. Indeed, the hair cell transduction efficacy of AVV2/8-sans displayed a basoapical gradient higher at the apex than at the base. In addition the number of the transduced IHCs was much greater than OHC regardless of the cochlear region. The viral transduction efficiency tended to be higher in the apical turn. The rate of the transduced IHC was about 87% at the apex and gradually declined to 45% at the base. The rate of the transduced OHCs was about 33% at the apex and gradually declined to 25% at the base (FIG. 17). Transduced hair cells were also observed in the contralateral ear although at a lower rate (IHCs: 66% at the apex, 30% in the mid turn, 32% at the base; OHCs: around 10% all along the cochlea). Interestingly the vestibular sensory hair cells of the treated and untreated ear were also transduced at a rate of 90% and 80% respectively (FIG. 21). These data show that the efficiency of inner ear hair cell transduction with AAV2/8-sans vectors qualifies this AAV pseudotype to carry out sans gene therapy in Ush1g$^{-/-}$ mice.

The ability of AAV2/8-sans to restore the normal expression and targeting of the protein in cochlear and vestibular hair cell of the Ush1g-/- mice was tested. To this end, several Ush1g-/- mice were subjected to cochlear injection of the AAV2/8-sans viral particle as described above. To monitor vector-mediated sans expression, the mice were sacrificed 5 days after injection and the organ of Corti and the vestibule were subjected to double immunostaining for GFP and sans, using previously characterized antibodies (Caberlotto, 2011). A widespread expression of GFP was observed in both IHC and OHCs of the injected cochleas. Remarkably, in all GFP positive cells, sans immunolabelling was evident in both IHC and OHC where it was readily localized at the tip of the hair cell stereocilia. These observations are consistent with what has been reported for the native protein. These observations demonstrate that GFP and sans protein are transduced independently, enabling the normal targeting the later to the stereocilia.

Sans Gene Therapy Prevents Cochlear and Vestibular Hair Cell Stereocilia Degeneration in Ush1g$^{-/-}$ Mice The Ush1g–/– mice are characterized by profound congenital sensorineural deafness and severe balance defect. In these mice, the sensory hair cell of both the vestibule and the cochlea displayed abnormal hair bundle, including fused and decreased numbers of stereocilia, dissociation of hair bundles fragmented or flat stereocilia, and the kinocilia misposition. The most striking feature is the loss of the staircase pattern due to the loss the middle and the short rows of inner and outer hair cell. Therefore, it was verified whether the normal expression and targeting of the protein sans in the inner ear hair cell of the Ush1g–/– mice prevents the abnormal morphological features of their stereocilia and kinocilia to take place. On P8, organs of Corti and utricules of the Ush1g$^{-/-}$ mice treated ear were microdissected and processed for scanning electron microscopy to closely scrutinized stereocilia morphology at high resolution. The bundle architecture of hair cells was preserved in all transduced hair cell at a degree reminiscent of the transduction rate observed using GFP expression as proxy (FIG. 18C). The hair bundles of the transduced cochlear hair cells retained their typical staircase pattern with the three rows. The stereocilia of all transduced hair cells of both vestibule and cochlea retained their typical staircase pattern including the short, middle and tall row of cochlear (FIGS. 18C and 22C). Remarkably the tallest row displayed a characteristic oblate tip and the stereocilia of the lower and the middle rows typically displayed a prolate tip that points toward its taller neighbors (FIG. 18C). These prolate shapes are believed to be a hallmark of the presence of functional tip links. The vestibular hair bundles of utricle hair cells appear nearly normal and displayed staircase tenting at stereocilia tips suggesting that tip links were also present. Finally, using a custom MATLAB (MathWorks) interface, stereocilium numbers, projected heights, and distances between stereocilia were estimated. No differences were found that there were in the number, the form or the height of the vestibular hair bundles in the Ush1g–/– treated mice relative to those observed and measured in the Ush1g+/– mice. Of note the morphology of cochlear and vestibular hair bundles of treated wild type mice did not differ from the untreated ones, suggesting that the injection through the round window membrane did not impaired the development of the morphology of hair bundles. These data show that sans gene therapy restored nearly to normal the stereocilia structure in transduced inner ear hair cell, including thickness, length and number in sans deficient mice.

Sans Gene Therapy Rescue the Mechanosensory Transduction of Ush1g–/– Mice Hair Cells In Vivo.

To evaluate if the restored hair bundle by sans gene therapy are functional, mechanoelectrical transduction (MET) currents were recorded from both IHCs and OHCs of Ush1g$^{-/-}$ mice, five days after treatment. In untreated Ush1g$^{-/-}$ mice, MET currents were nearly absent in both cochlear hair cells (Caberlotto, 2011) (111±31 pA for IHCs (n=5), and 47±6 pA for OHCs (n=4)). However, maximal amplitudes of MET currents of treated Ush1g$^{-/-}$ mice were comparable to currents observed in wild type mice (763±128 pA for IHCs (n=3), and 721±97 pA for OHCs (n=4)). The average (±SEM) peak sensory transduction current for rescued IHCs was 424±70 pA (n=11), and 641±35 pA for OHCs (n=12) (FIG. 19). Given the high rate of transduction in IHCs, MET currents were measured in cells randomly. Although for OHCs, in which less transduced cells were observed, currents were observed and measured in GFP-transduced cells. No difference of sensitivity to the hair bundle displacement between treated Ush1g$^{-/-}$ and heterozygous mice were observed (FIG. 19). Moreover, MET currents measured in treated wild type mice showed no significant difference, suggesting that the injection did not damage the mechanoelectrical machinery. These results demonstrated that single intracochlear injection of sans in Ush1g$^{-/-}$ mice, completely restored the auditory hair cell-MET.

Sans Gene Therapy Rescued the Auditory Function

To evaluate if sans-transduced cells can rescue auditory function, AAV2/8-sans was injected in Ush1g$^{-/-}$ mice, and hearing was probed by in vivo audiometric tests: auditory brainstem responses (ABR), which explore activities of IHCs and OHCs, distortion-product otoacoustic emissions (DPOAEs), which involve OHC MET channel function (Avan et al, 2013), and cochlear microphonics (CM), which record phasic extracellular potentials reflecting MET currents in the OHCs of the basal region of the cochlea. These auditory tests were recorded between 15 to 35 days after treatment.

According to early studies, uninjected Ush1g$^{-/-}$ mice showed a lack of identifiable ABR waves for all sound frequencies, indicating profound deafness (Caberlotto, 2011). Moreover, DPOAEs and CM were not detected in these mice. However, injection of AAV2/8-sans in Ush1g$^{-/-}$ mice led to a significant hearing recovery. Indeed, a partial restore of hearing was observed mainly for low-frequencies of 20-25 dB (5-15 kHz), and a lower restore 5-10 dB for high-frequencies (20-32 KHz) (FIG. 20), in the injected ear. These results were obtained in all treated mice, with variability between each animal.

Thus, a single intracochlear injection of AAV2/8-sans is sufficient to restore a hearing function in Ush1g$^{-/-}$ mice.

To circumvent the early morphogenetic defect present in the hair bundles of Ush1g$^{-/-}$ mice, ABR of Ush1g$^{f/f}$Myo15-Cre$^{+/-}$ mice was also probed (Caberlotto, 2011). In these mice, Ush1g is deleted postnatally, under the control of the Myo15 promoter, specific for auditory hair cells. Thus, the viral particle is injected before the deletion of sans. Caberlotto et al., showed that these mice are profoundly deaf from P13, for all sound frequencies. Nonetheless, the delivery of AAV2/8-sans through the RWM at P2, resulted in higher ABR thresholds, of about 30-40 dB for low-frequencies (5-15 kHz), than in Ush1g$^{-/-}$ rescued mice.

Sans Gene Therapy Completely Corrected the Vestibular Defect

After having evaluated the morphological restore of vestibular hair bundles, the vestibular function, i.e. the behavior of treated Ush1g$^{-/-}$ mice was studied. In fact, Ush1g$^{-/-}$ mice are characterized by vestibular defects, which result in circling and head tossing (Caberlotto et al., 2011). This phenotype was no longer observed in all treated Ush1g$^{-/-}$ mice at mature stages. To deepen these observations, various behavioral tests were performed. During the platform test, the heterozygous mice never fall over a period of 1 min, as the treated Ush1g$^{-/-}$ mice. Uninjected mice deficient for sans did not hold on platform more than few seconds. The trunk-curl test showed that treated mutant mice, as heterozygous mice, reached the surface without curling its trunk toward its tail. On the contrary, untreated Ush1g$^{-/-}$ mice cur the trunk and did not reach the surface. The contact righting test strengthened that treated Ush1g$^{-/-}$ mice, as heterozygous mice, had no vestibular dysfunction because they could re-orientates perfectly after a rotation of the tube, unlike the untreated mice deficient for sans. Finally, by scoring swim test (0=swim; 1=irregular swim; 2=immobile floating; 3=underwater tumbling, Hardisty-Hughes et al., 2010) it was noted that treated Ush1g$^{-/-}$ mice swum with no difficulty (score 0=swim), like heterozygous mice, while untreated Ush1g$^{-/-}$ mice drowned very rapidly (score 3=underwater tumbling). Treated Ush1g$^{-/-}$ mice did not show any circling behavior, like heterozygous mice, as shown by videotracking mice in an open-field chamber (3 turns during 2 min for treated Ush1g$^{-/-}$ mice vs. 23 turns for uninjected Ush1g$^{-/-}$ mice, FIG. 23).

It is important to consider that these tests were also achieved for injected heterozygous mice, and that they behaved as non-injected heterozygous mice, showing that the injection through the RWM did not impair the vestibular function.

These behavioral analyses show that sans gene therapy completely restores the vestibular function.

REFERENCES

Akil, O., Seal, R. P., Burke, K., Wang, C., Alemi, A., During, M., Edwards, R. H., Lustig, L. R. (2012). Restoration of hearing in the VGLUT3 knockout mouse using virally mediated gene therapy. *Neuron* 75(2), 283-93.

Akino K, Toyota M, Suzuki H, Imai T, Maruyama R, Kusano M, Nishikawa N, Watanabe Y, Sasaki Y, Abe T, Yamamoto E, Tarasawa I, Sonoda T, Mori M, Imai K, Shinomura Y, Tokino T (2007). Identification of DFNA5 as a target of epigenetic inactivation in gastric cancer. Cancer Sci. 98(1):88-95.

Angermüller, S., and Fahimi, H. D. (1981). Selective cytochemical localization of peroxidase, cytochrome oxidase and catalase in rat liver with 3,3'-diaminobenzidine. *Histochemistry* 71(1), 33-44.

Basta, D., Tzschentke, B., and Ernst, A. (2005). Noise-induced cell death in the mouse medial geniculate body and primary auditory cortex. *Neuroscience letters* 381, 199-204.

Benjamini, Y., and Hochberg, Y. (1995). Controlling the false discovery rate: a practical and powerful approach to multiple testing. *J. Roy. Statist. Soc. Ser.* B. 57, 289-300.

Binder, C. J., Weiher, H., Exner, M., Kerjaschki, D. (1999). Glomerular overproduction of oxygen radicals in Mpv17 gene-inactivated mice causes podocyte foot process flattening and proteinuria: A model of steroid-resistant nephrosis sensitive to radical scavenger therapy. *Am. J. Pathol.* 154(4), 1067-75.

Bischoff A M, Luijendijk M W, Huygen P L, van Duijnhoven G, De Leenheer E M, Oudesluijs G G, Van Laer L, Cremers F P, Cremers C W, Kremer H (2004). A novel mutation identified in the DFNA5 gene in a Dutch family: a clinical and genetic evaluation. Audiol Neurootol. 9(1): 34-46.

Bolstad, B. M., Irizarry, R. A., Astrand, M., Speed, T. P. (2003). A comparison of normalization methods for high density oligonucleotide array data based on variance and bias. *Bioinformatics* 19(2), 185-93.

Bonekamp, N. A., Volkl, A., Fahimi, H. D., and Schrader, M. (2009). Reactive oxygen species and peroxisomes: struggling for balance. *BioFactors* 35, 346-355.

Borck, G., Rainshtein, L., Hellman-Aharony, S., Volk, A. E., Friedrich, K., Taub, E., Magal, N., Kanaan, M., Kubisch, C., Shohat, M., Basel-Vanagaite, L. (2012). High frequency of autosomal-recessive DFNB59 hearing loss in an isolated Arab population in Israel. *Clin Genet.* 82(3), 271-6.

Caberlotto, E., Michel, V., Foucher, I., Bahloul, A., Goodyear, R. J., Pepermans, E., Michalski, N., Perfettini, I., Alegria-Prévot, O., Chardenoux, S., Do Cruzeiro, M., et al. (2011). Usher type 1G protein sans is a critical component of the tip-link complex, a structure controlling actin polymerization in stereocilia. *Proc. Natl. Acad. Sci. USA* 108(14), 5825-30.

Chai Y, Chen D, Wang X, Wu H, Yang T (2014). A novel splice site mutation in DFNA5 causes late-onset progressive non-syndromic hearing loss in a Chinese family. Int J Pediatr Otorhinolaryngol. 78(8):1265-8.

Cheng J, Han D Y, Dai P, Sun H J, Tao R, Sun Q, Yan D, Qin W, Wang H Y, Ouyang X M, Yang S Z, Cao J Y, Feng G Y, Du L L, Zhang Y Z, Zhai S Q, Yang W Y, Liu X Z, He L, Yuan H J (2007). A novel DFNA5 mutation, IVS8+4 A>G, in the splice donor site of intron 8 causes late-onset non-syndromic hearing loss in a Chinese family. Clin Genet. 72(5):471-7.

Cody, A. R., and Johnstone, B. M. (1981). Acoustic trauma: Single neuron basis for the "half-octave shift". *J. Acoust. Soc. Am.* 70, 707-711.

Collin, R. W., Kalay, E., Oostrik, J., Caylan, R., Wollnik, B., Arslan, S., den Hollander, A. I., Birinci, Y., Lichtner, P., Strom, T. M. (2007). Involvement of DFNB59 mutations in autosomal recessive nonsyndromic hearing impairment. *Hum. Mutat.* 28(7), 718-23.

Collins, T. J. (2007). Image) for microscopy. *Biotechniques* 43, 25-30.

Cooper, L. B., Chan D K, Roediger F C, Shaffer B R, Fraser J F, Musatov S, Selesnick S H, Kaplitt M G. AAV-mediated delivery of the caspase inhibitor XIAP protects against cisplatin ototoxicity. Otol Neurotol. 2006 June; 27(4):484-90

Delille, H. K., Agricola, B., Guimaraes, S. C., Borta, H., Luers, G. H., Fransen, M., and Schrader, M. (2010). Pex11pbeta-mediated growth and division of mammalian peroxisomes follows a maturation pathway. *Journal of cell science* 123, 2750-2762.

Delmaghani, S., del Castillo, F. J., Michel, V., Leibovici, M., Aghaie, A., Ron, U., Van Laer, L., Ben-Tal, N., Van Camp, G., Weil, D., et al. (2006). Mutations in the gene encoding pejvakin, a newly identified protein of the afferent auditory pathway, cause DFNB59 auditory neuropathy. *Nat. Genet.* 38, 770-8.

Diano, S., Liu, Z. W., Jeong, J. K., Dietrich, M. O., Ruan, H. B., Kim, E., Suyama, S., Kelly, K., Gyengesi, E., Arbiser, J. L., et al. (2011). Peroxisome proliferation-associated control of reactive oxygen species sets melanocortin tone and feeding in diet-induced obesity. *Nat Med* 17, 1121-1127.

Dobie, R. A. (2005) Audiometric Threshold Shift Definitions: Simulations and Suggestions, *Ear and Hearing* 26(1) 62-77

Ebermann, I., Walger, M., Scholl, H. P., Charbel Issa, P., Lüke, C., Nürnberg, G., Lang-Roth, R., Becker, C., Nürnberg, P., Bolz, H. J. (2007). Truncating mutation of the DFNB59 gene causes cochlear hearing impairment and central vestibular dysfunction. *Hum. Mutat.* 28(6), 571-7.

Ehret, G., and Riecke, S. (2002). Mice and humans perceive multiharmonic communication sounds in the same way. *Proc. Natl. Acad. Sci. USA* 99(1), 479-482.

Evans, P., and Halliwell, B. (1999). Free radicals and hearing. Cause, consequence, and criteria. *Ann. N Y Acad. Sci.* 884, 19-40.

Fransen, M., Nordgren, M., Wang, B., and Apanasets, O. (2012). Role of peroxisomes in ROS/RNS-metabolism: implications for human disease. *Biochim Biophys Acta* 1822, 1363-1373.

Han, C., and Someya, S. (2013). Mouse models of age-related mitochondrial neurosensory hearing loss. *Molecular and cellular neurosciences* 55, 95-100.

Hashemzadeh Chaleshtori, M., Simpson, M. A., Farrokhi, E., Dolati, M., Hoghooghi Rad, L., Amani Geshnigani, S., Crosby, A. H. (2007). Novel mutations in the pejvakin gene are associated with autosomal recessive non-syndromic hearing loss in Iranian families. *Clin. Genet.* 72(3), 261-3.

He, W., Newman, J. C., Wang, M. Z., Ho, L., and Verdin, E. (2012). Mitochondrial sirtuins: regulators of protein acylation and metabolism. *Trends in endocrinology and metabolism: TEM* 23, 467-476.

Henderson, D., Bielefeld, E. C., Harris, K. C., and Hu, B. H. (2006). The role of oxidative stress in noise-induced hearing loss. *Ear and hearing* 27, 1-19.

Housley, G. D., Morton-Jones, R., Vlajkovic, S. M., Telang, R. S., Paramananthasivam, V., Tadros, S. F., Wong, A. C., Froud, K. E., Cederholm, J. M., Sivakumaran, Y., et al. (2013). ATP-gated ion channels mediate adaptation to elevated sound levels. *Proc Natl Acad Sci USA*. 110(18), 7494-9.

Imig, T. J., and Durham, D. (2005). Effect of unilateral noise exposure on the tonotopic distribution of spontaneous activity in the cochlear nucleus and inferior colliculus in the cortically intact and decorticate rat. *The Journal of comparative neurology* 490, 391-413.

Jain, N., Thatte, J., Braciale, T., Ley K., O'Connell, M., Lee, J. K. (2003). Local-pooled-error test for identifying differentially expressed genes with a small number of replicated microarrays. *Bioinformatics* 19(15), 1945-51.

Janero, D. R. (1990). Malondialdehyde and thiobarbituric acid-reactivity as diagnostic indices of lipid peroxidation and peroxidative tissue injury. *Free Radic. Biol. Med.* 9(6), 515-40.

Kaplitt, M. G., Leone P, Samulski R J, Xiao X, Pfaff D W, O'Malley K L, During M J. Long-term gene expression and phenotypic correction using adeno-associated virus vectors in the mammalian brain. *Nat Genet*. 1994 October; 8(2):148-54.

Kayagaki N, Stowe I B, Lee B L, O'Rourke K, Anderson K, Warming S, Cuellar T, Haley B, Roose-Girma M, Phung Q T, Liu P S, Lill J R, Li H, Wu J, Kummerfeld S, Zhang J, Lee W P, Snipas S J, Salvesen G S, Morris L X, Fitzgerald L, Zhang Y, Bertram E M, Goodnow C C, Dixit V M (2015). Caspase-11 cleaves gasdermin D for non-canonical inflammasome signaling. Nature. September 16. doi: 10.1038/nature15541.

Kim M S, Lebron C, Nagpal J K, Chae Y K, Chang X, Huang Y, Chuang T, Yamashita K, Trink B, Ratovitski E A, Califano J A, Sidransky D (2008). Methylation of the DFNA5 increases risk of lymph node metastasis in human breast cancer. Biochem Biophys Res Commun. 370(1): 38-43.

Kim M S, Chang X, Yamashita K, Nagpal J K, Baek J H, Wu G, Trink B, Ratovitski E A, Mori M, Sidransky D (2008). Aberrant promoter methylation and tumor suppressive activity of the DFNA5 gene in colorectal carcinoma. Oncogene. 27(25):3624-34.

Kemp, D. T. (2002). Otoacoustic emissions, their origin in cochlear function, and use. *Br. Med. Bull.* 63, 223-241.

Koch, J., Pranjic, K., Huber, A., Ellinger, A., Hartig, A., Kragler, F., and Brocard, C. (2010). PEX11 family members are membrane elongation factors that coordinate peroxisome proliferation and maintenance. *Journal of cell science* 123, 3389-3400.

Kress, C., Vandormael-Pournin, S., Baldacci, P., Cohen-Tannoudji, M., Babinet, C. (1998). Nonpermissiveness for mouse embryonic stem (ES) cell derivation circumvented by a single backcross to 129/Sv strain: establishment of ES cell lines bearing the Omd conditional lethal mutation. *Mamm. Genome* 9, 998-1001.

Kujawa, S. G., and Liberman, M. C. (2009). Adding insult to injury: cochlear nerve degeneration after "temporary" noise-induced hearing loss. *The Journal of neuroscience: the official journal of the Society for Neuroscience* 29, 14077-14085.

Lallemand, Y., Luria, V., Haffner-Krausz, R., Lonai, P. (1998). Maternally expressed PGK-cre transgene as a tool for early and uniform activation of the Cre site-specific recombinase. *Transgenic Res.* 7, 105-112.

Lay, D., Gorgas, K., and Just, W. W. (2006). Peroxisome biogenesis: where Arf and coatomer might be involved. *Biochim Biophys Acta* 1763, 1678-1687.

Lee, S P., Hwang, Y. S., Kim, Y. J., Kwon, K. S., Kim, H. J., Kim, K., Chae, H. Z. (2001). Cyclophilin A binds to peroxiredoxins and activates its peroxidase activity. *J. Biol. Chem.* 276(32), 29826-32.

Lee, J. N., Kim, S. G., Lim, J. Y., Kim, S. J., Choe, S. K., and Park, R. (2015). Proteasome inhibitors induce auditory hair cell death through peroxisome dysfunction. *Biochemical and biophysical research communications* 456, 269-274.

Li, X., Baumgart, E., Dong, G. X., Morrell, J. C., Jimenez-Sanchez, G., Valle, D., Smith, K. D., and Gould, S. J. (2002). PEX11alpha is required for peroxisome proliferation in response to 4-phenylbutyrate but is dispensable for peroxisome proliferator-activated receptor alpha-mediated peroxisome proliferation. *Molecular and cellular biology* 22, 8226-8240.

Li-Yang M N, Shen X F, Wei Q J, Yao J, Lu Y J, Cao X, Xing G Q (2015). IVS8+1 DelG, a Novel Splice Site Mutation Causing DFNA5 Deafness in a Chinese Family. Chin Med J (Engl). 128(18):2510-2515.

Lizana, L., Bauer, B., and Orwar, O. (2008). Controlling the rates of biochemical reactions and signaling networks by shape and volume changes. *Proceedings of the National Academy of Sciences of the United States of America* 105, 4099-4104.

Lopez-Huertas, E., Charlton, W. L., Johnson, B., Graham, I. A., and Baker, A. (2000). Stress induces peroxisome biogenesis genes. *The EMBO journal* 19, 6770-6777.

Matise, M. P., Auerbach, W., Joyner, A. (1999). Production of targeted embryonic stem cell clones. In: Joyner A, ed. *Gene targeting. A practical approach*. Oxford: Oxford University Press; p. 101-132.

Menuet, C., Cazals, Y., Gestreau, C., Borghgraef, P., Gielis, L., Dutschmann, M., Van Leuven, F., Hilaire, G. (2011). Age-Related Impairment of Ultrasonic Vocalization in Tau.P301L Mice: Possible Implication for Progressive Language Disorders. *PLoS One* 6(10), e25770.

Meyer zum Gottesberge, A. M., Felix, H., Reuter, A., Weiher, H. (2001). Ultrastructural and physiological defects in the cochlea of the Mpv17 mouse strain. A comparison between young and old adult animals. *Hear. Res.* 156(1-2), 69-80.

Michard, Q., Commo, S., Belaidi, J. P., Alleaume, A. M., Michelet, J. F., Daronnat, E., Eilstein, J., Duche, D., Marrot, L., Bernard, B. A. (2008b). TRP-2 specifically decreases WM35 cell sensitivity to oxidative stress. *Free Radic. Biol. Med.* 44(6), 1023-31.

Michard, Q., Commo, S., Rocchetti, J., El Houari, F., Alleaume, A. M., Wakamatsu, K., Ito, S., Bernard, B. A. (2008a). TRP-2 expression protects HEK cells from dopamine- and hydroquinone-induced toxicity. *Free Radic. Biol. Med.* 45(7), 1002-10.

Motley, A. M., and Hettema, E. H. (2007). Yeast peroxisomes multiply by growth and division. *J Cell Biol* 178, 399-410.

Mujtaba, G., Bukhari, I., Fatima, A., Naz, S. (2012). A p.C343S missense mutation in PJVK causes progressive hearing loss. *Gene* 504(1), 98-101.

Needleman, S. B., and Wunsch, C. D. (1970). A general method applicable to the search for similarities in the amino acid sequence of two proteins. *J. Mol. Biol.* 48(3), 443-453.

Nishio A, Noguchi Y, Sato T, Naruse T K, Kimura A, Takagi A, Kitamura K (2014). A DFNA5 mutation identified in Japanese families with autosomal dominant hereditary hearing loss. Ann Hum Genet. 78(2):83-91.

Ohinata, Y., Miller, J. M., Altschuler, R. A., and Schacht, J. (2000). Intense noise induces formation of vasoactive lipid peroxidation products in the cochlea. *Brain research* 878, 163-173.

Ohlemiller, K. K., McFadden, S. L., Ding, D. L., Flood, D. G., Reaume, A. G., Hoffman, E. K., Scott, R. W., Wright, J. S., Putcha, G. V., and Salvi, R. J. (1999a). Targeted deletion of the cytosolic Cu/Zn-superoxide dismutase gene (Sod1) increases susceptibility to noise-induced hearing loss. *Audiology & neuro-otology* 4, 237-246.

Ohlemiller, K. K., Wright, J. S., and Dugan, L. L. (1999b). Early elevation of cochlear reactive oxygen species following noise exposure. Audiol Neurootol 4, 229-236.

Ohlemiller, K. K., McFadden, S. L., Ding, D. L., Lear, P. M., and Ho, Y. S. (2000). Targeted mutation of the gene for cellular glutathione peroxidase (Gpx1) increases noise-induced hearing loss in mice. *Journal of the Association for Research in Otolaryngology: JARO* 1, 243-254.

Okatsu, K., Saisho, K., Shimanuki, M., Nakada, K., shiara, H., Sou, Y. S., Kimura, M., Sato, S., Hattori, N., Komatsu, M., et al. (2010). p62/SQSTM1 cooperates with Parkin for perinuclear clustering of depolarized mitochondria. *Genes to cells: devoted to molecular & cellular mechanisms* 15, 887-900.

Op de Beeck K, Van Camp G, Thys S, Cools N, Callebaut I, Vrijens K, Van Nassauw L, Van Tendeloo V F, Timmermans J P, Van Laer L (2011). The DFNA5 gene, responsible for hearing loss and involved in cancer, encodes a novel apoptosis-inducing protein. Eur J Hum Genet. 19(9):965-73.

Park H J, Cho H J, Baek J I, Ben-Yosef T, Kwon T J, Griffith A J, Kim U K (2010). Evidence for a founder mutation causing DFNA5 hearing loss in East Asians. J Hum Genet. 55(1):59-62.

Passreiter, M., Anton, M., Lay, D., Frank, R., Harter, C., Wieland, F. T., Gorgas, K., and Just, W. W. (1998). Peroxisome biogenesis: involvement of ARF and coatomer. J Cell Biol 141, 373-383.

Pienkowski, M., and Eggermont, J. J. (2009). Long-term, partially-reversible reorganization of frequency tuning in mature cat primary auditory cortex can be induced by passive exposure to moderate-level sounds. *Hearing research* 257, 24-40.

Rahman, I., Kode, A., and Biswas, S. K. (2006). Assay for quantitative determination of glutathione and glutathione disulfide levels using enzymatic recycling method. *Nat. Protoc.* 1, 3159-3165.

Reddy, J. K., Azarnoff, D. L., and Hignite, C. E. (1980). Hypolipidaemic hepatic peroxisome proliferators form a novel class of chemical carcinogens. *Nature* 283, 397-398.

Robles, L., and Ruggero M. A. (2001). Mechanics of the mammalian cochlea. *Physiol Rev.* 81(3), 1305-52.

Roux, I., Safieddine, S., Nouvian, R., Grati, M., Simmler, M. C., Bahloul, A., Perfettini, I., Le Gall, M., Rostaing, P., Hamard, G., et al. (2006). Otoferlin, defective in a human deafness form, is essential for exocytosis at the auditory ribbon synapse. *Cell* 127(2), 277-89.

Roux, I., Hosie, S., Johnson, S. L., Bahloul, A., Cayet, N., Nouaille, S., Kros, C. J., Petit, C., and Safieddine, S. (2009). Myosin VI is required for the proper maturation and function of inner hair cell ribbon synapses. Hum. Mol. Genet. 18, 4615-4628.

Roy, S., Ryals, M. M., Van den Bruele, A. B., Fitzgerald, T. S., Cunningham, L. L. (2013). Sound preconditioning therapy inhibits ototoxic hearing loss in mice. *J. Clin. Invest.* 123(11), 4945-9.

Sadanaga, M., and Morimitsu, T. (1995). Development of endocochlear potential and its negative component in mouse cochlea. *Hearing research* 89, 155-161.

Saeki and Sasaki (2011) «Endothelium and epithelium» ISBN 978-1-61470-874-2, Ed. J. Carrasco and M. Mota, pp 193-211, © 2012 Nova Science Publishers.

Santos, M. J., Quintanilla, R. A., Toro, A., Grandy, R., Dinamarca, M. C., Godoy, J. A., and Inestrosa, N. C. (2005). Peroxisomal proliferation protects from beta-amyloid neurodegeneration. *The Journal of biological chemistry* 280, 41057-41068.

Schrader, M., and Fahimi, H. D. (2006). Peroxisomes and oxidative stress. *Biochim Biophys Acta* 1763, 1755-1766.

Schrader, M., Reuber, B. E., Morrell, J. C., Jimenez-Sanchez, G., Obie, C., Stroh, T. A., Valle, D., Schroer, T. A., and Gould, S. J. (1998). Expression of PEX11beta mediates peroxisome proliferation in the absence of extracellular stimuli. *The Journal of biological chemistry* 273, 29607-29614.

Schrader, M., Wodopia, R., and Fahimi, H. D. (1999). Induction of tubular peroxisomes by U V irradiation and reactive oxygen species in HepG2 cells. *J Histochem Cytochem* 47, 1141-1148.

Schwander, M., Sczaniecka, A., Grillet, N., Bailey, J. S., Avenarius, M., Najmabadi, H., Steffy, B. M., Federe, G. C., Lagler, E. A., Banan, R. (2007). A forward genetics screen in mice identifies recessive deafness traits and reveals that pejvakin is essential for outer hair cell function. *J. Neurosci.* 27(9), 2163-75.

Shi J, Zhao Y, Wang K, Shi X, Wang Y, Huang H, Zhuang Y, Cai T, Wang F, Shao F (2015). Cleavage of GSDMD by inflammatory caspases determines pyroptotic cell death. September 16. doi: 10.1038/nature15514. [Epub ahead of print]

Shi P, Tang A, Xian L, Hou S, Zou D, Lv Y, Huang Z, Wang Q, Song A, Lin Z, Gao X (2015). Loss of conserved Gsdma3 self-regulation causes autophagy and cell death. Biochem J. 468(2):325-36.

Smith, J. J., and Aitchison, J. D. (2013). Peroxisomes take shape. *Nat Rev Mol Cell Biol* 14, 803-817.

Tang, X. D., Garcia, M. L., Heinemann, S. H., and Hoshi, T. (2004). Reactive oxygen species impair Slo1 B K channel function by altering cysteine-mediated calcium sensing. Nat. Struct. Mol. Biol. 11, 171-178.

Thelen, N., Breuskin, I., Malgrange, B., Thiry, M. (2009). Early identification of inner pillar cells during rat cochlear development. Cell Tissue Res. 337, 1-14.

Tran, C., Hewson, S., Steinberg, S. J., Mercimek-Mahmutoglu, S. (2014). Late-onset Zellweger spectrum disorder caused by PEX6 mutations mimicking X-linked adrenoleukodystrophy. Pediatr Neurol. 51(2), 262-5.

Van Laer L, Huizing E H, Verstreken M, van Zuijlen D, Wauters J G, Bossuyt P J, Van de Heyning P, McGuirt W T, Smith R J, Willems P J, Legan P K, Richardson G P, Van Camp G (1998). Nonsyndromic hearing impairment is associated with a mutation in DFNA5. Nat Genet. 20(2):194-7.

Wang, Y., Hirose, K., and Liberman, M. C. (2002). Dynamics of noise-induced cellular injury and repair in the mouse cochlea. Journal of the Association for Research in Otolaryngology: JARO 3, 248-268.

Wang C J, Tang L, Shen D W, Wang C, Yuan Q Y, Gao W, Wang Y K, Xu R H, Zhang H (2013). The expression and regulation of DFNA5 in human hepatocellular carcinoma DFNA5 in hepatocellular carcinoma. Mol Biol Rep. 40(12):6525-31.

Yamane, H., Nakai, Y., Takayama, M., Iguchi, H., Nakagawa, T., and Kojima, A. (1995). Appearance of free radicals in the guinea pig inner ear after noise-induced acoustic trauma. Eur Arch Otorhinolaryngol 252, 504-508.

Yamashita, D., Jiang, H. Y., Schacht, J., and Miller, J. M. (2004). Delayed production of free radicals following noise exposure. Brain research 1019, 201-209.

Yu C, Meng X, Zhang S, Zhao G, Hu L, Kong X (2003). A 3-nucleotide deletion in the polypyrimidine tract of intron 7 of the DFNA5 gene causes nonsyndromic hearing impairment in a Chinese family. Genomics. 82(5):575-9.

Zhang, Q. J., Lan, L., Li, N., Qi, Y., Zong, L., Shi, W., Yu, L., Wang, H., Yang, J., Xie, L. Y., et al. (2015). Identification of a novel mutation of PJVK in the Chinese non-syndromic hearing loss population with low prevalence of the PJVK mutations. Acta oto-laryngologica 135, 211-216.

Avan P, Büki B, Petit C. (2013). Auditory distortions: origins and functions. Physiol Rev. October; 93(4):1563-619.

Hardisty-Hughes R E, Parker A, Brown S D (2010). A hearing and vestibular phenotyping pipeline to identify mouse mutants with hearing impairment. Nat Protoc., January; 5(1):177-90.

Le Calvez S, Avan P, Gilain L, Romand R., (1998) Hear Res. June; 120(1-2):37-50.

Michalski N, Michel V, Caberlotto E, Lefèvre G M, van Aken A F, Tinevez J Y, Bizard E, Houbron C, Weil D, Hardelin J P, Richardson G P, Kros O, Martin P, Petit C. 2009, Harmonin-b, an actin-binding scaffold protein, is involved in the adaptation of mechanoelectrical transduction by sensory hair cells. Pflugers Arch November; 459(1):115-30.

Mustapha et al., 2002. Hum. Genet. Vol. 110, 348-350.

Weil et al., 2003. Human Molecular Genetics vol. 12, no. 5, 463-471.

---

The invention claimed is:

1. A method for modulating cellular redox homeostasis, comprising administering a Pejvakin of SEQ ID NO:1 or a homologous sequence having an amino acid sequence at least 70% identical to SEQ ID NO:1 to a patient suffering from an age-related disease selected from Parkinson's disease (PD), Alzheimer's disease (AD), Familial Amyotrophic Lateral Sclerosis (FALS), age-related macular degeneration (ARMD), type 2 diabetes, atherosclerosis, arthritis, cataracts, osteoporosis, hypertension, skin aging, skin pigmentation, and cardiovascular diseases; a patient suffering from a peroxisomal disorder leading to ROS production, or a patient suffering from a mitochondrial disorder leading to ROS production;
    wherein administering the Pejvakin of SEQ ID NO:1 or the homologous sequence having an amino acid sequence at least 70% identical to SEQ ID NO:1 to the patient thereby treats the age-related disease selected from Parkinson's disease (PD), Alzheimer's disease (AD), Familial Amyotrophic Lateral Sclerosis (FALS), age-related macular degeneration (ARMD), type 2 diabetes, atherosclerosis, arthritis, cataracts, osteoporosis, hypertension, skin aging, skin pigmentation, and cardiovascular diseases, treats the peroxisomal disorder leading to ROS production, or treats the mitochondrial disorder leading to ROS production.

2. The method of claim 1, wherein administering the Pejvakin of SEQ ID NO:1 or the homologous sequence having an amino acid sequence at least 70% identical to SEQ ID NO:1 to the patient alleviates ROS-induced cellular damage in the patient.

3. The method of claim 1, wherein the patient normally expresses Pejvakin.

4. The method of claim 1, wherein the Pejvakin of SEQ ID NO:1 or the homologous sequence having an amino acid sequence at least 70% identical to SEQ ID NO:1 is administered to the patient by a method comprising administering a vector encoding the Pejvakin polypeptide to the patient.

5. The method of claim 1, wherein the patient suffers from an age-related disease selected from Parkinson's disease (PD), Alzheimer's disease (AD), Familial Amyotrophic Lateral Sclerosis (FALS), age-related macular degeneration (ARMD), type 2 diabetes, atherosclerosis, arthritis, cataracts, osteoporosis, hypertension, skin aging, skin pigmentation, and cardiovascular diseases.

6. The method of claim 1, wherein the patient suffers from a peroxisomal disorder leading to ROS production.

7. The method of claim 1, wherein the patient suffers from a mitochondrial disorder leading to ROS production.

* * * * *

SEQUENCE LISTING

```
<160> NUMBER OF SEQ ID NOS: 49

<210> SEQ ID NO 1
<211> LENGTH: 352
<212> TYPE: PRT
<213> ORGANISM: homo sapiens
<220> FEATURE:
<221> NAME/KEY: MISC_FEATURE
<223> OTHER INFORMATION: pejvakin (Homo sapiens) NP_001036167.1

<400> SEQUENCE: 1

Met Phe Ala Ala Ala Thr Lys Ser Phe Val Lys Gln Val Gly Asp Gly
1               5                   10                  15

Gly Arg Leu Val Pro Val Pro Ser Leu Ser Glu Ala Asp Lys Tyr Gln
            20                  25                  30

Pro Leu Ser Leu Val Val Lys Lys Lys Arg Cys Phe Leu Phe Pro Arg
        35                  40                  45

Tyr Lys Phe Thr Ser Thr Pro Phe Thr Leu Lys Asp Ile Leu Leu Gly
    50                  55                  60

Asp Arg Glu Ile Ser Ala Gly Ile Ser Ser Tyr Gln Leu Leu Asn Tyr
65                  70                  75                  80

Glu Asp Glu Ser Asp Val Ser Leu Tyr Gly Arg Arg Gly Asn His Ile
                85                  90                  95

Val Asn Asp Val Gly Ile Asn Val Ala Gly Ser Asp Ser Ile Ala Val
            100                 105                 110

Lys Ala Ser Phe Gly Ile Val Thr Lys His Glu Val Glu Val Ser Thr
        115                 120                 125

Leu Leu Lys Glu Ile Thr Thr Arg Lys Ile Asn Phe Asp His Ser Leu
    130                 135                 140
```

Ile Arg Gln Ser Arg Ser Ser Arg Lys Ala Val Leu Cys Val Val Met
145                 150                 155                 160

Glu Ser Ile Arg Thr Thr Arg Gln Cys Ser Leu Ser Val His Ala Gly
                165                 170                 175

Ile Arg Gly Glu Ala Met Arg Phe His Phe Met Asp Glu Gln Asn Pro
            180                 185                 190

Lys Gly Arg Asp Lys Ala Ile Val Phe Pro Ala His Thr Thr Ile Ala
        195                 200                 205

Phe Ser Val Phe Glu Leu Phe Ile Tyr Leu Asp Gly Ala Phe Asp Leu
    210                 215                 220

Cys Val Thr Ser Val Ser Lys Gly Gly Phe Glu Arg Glu Glu Thr Ala
225                 230                 235                 240

Thr Phe Ala Leu Leu Tyr Arg Leu Arg Asn Ile Leu Phe Glu Arg Asn
                245                 250                 255

Arg Arg Val Met Asp Val Ile Ser Arg Ser Gln Leu Tyr Leu Asp Asp
                260                 265                 270

Leu Phe Ser Asp Tyr Tyr Asp Lys Pro Leu Ser Met Thr Asp Ile Ser
            275                 280                 285

Leu Lys Glu Gly Thr His Ile Arg Val Asn Leu Leu Asn His Asn Ile
        290                 295                 300

Pro Lys Gly Pro Cys Ile Leu Cys Gly Met Gly Asn Phe Lys Arg Glu
305                 310                 315                 320

Thr Val Tyr Gly Cys Phe Gln Cys Ser Val Asp Gly Gln Lys Tyr Val
                325                 330                 335

Arg Leu His Ala Val Pro Cys Phe Asp Ile Trp His Lys Arg Met Lys
                340                 345                 350

<210> SEQ ID NO 2
<211> LENGTH: 352
<212> TYPE: PRT
<213> ORGANISM: mus musculus
<220> FEATURE:
<221> NAME/KEY: MISC_FEATURE
<223> OTHER INFORMATION: pejvakin (Mus musculus) NP_001074180.1

<400> SEQUENCE: 2

Met Phe Ala Ala Ala Thr Lys Ser Phe Val Lys Gln Val Gly Asp Gly
1               5                   10                  15

Gly Arg Leu Val Pro Val Pro Ser Leu Ser Glu Ala Asp Lys Tyr Gln
            20                  25                  30

Pro Leu Ser Leu Val Val Lys Lys Arg Cys Phe Leu Phe Pro Arg
        35                  40                  45

Cys Lys Phe Thr Ser Thr Pro Phe Thr Leu Lys Asp Ile Leu Leu Gly
50                  55                  60

Asp Arg Glu Ile Ser Ala Gly Ile Ser Ser Tyr Gln Leu Leu Asn Tyr
65                  70                  75                  80

Glu Asp Glu Ser Asp Val Ser Leu Tyr Gly Arg Arg Ser Asn His Ile
                85                  90                  95

Val Asn Asp Val Gly Ile Asn Val Thr Gly Ser Asp Ser Ile Ala Val
            100                 105                 110

Lys Ala Ser Phe Gly Val Val Thr Lys His Glu Val Glu Val Ser Thr
        115                 120                 125

Leu Leu Lys Glu Ile Thr Ala Arg Lys Ile Asn Phe Asp His Ser Leu
    130                 135                 140

Ile Arg Gln Ser Arg Ser Ser Arg Lys Ala Val Leu Cys Val Val Met
145                 150                 155                 160

```
Glu Ser Ile Arg Thr Thr Arg Gln Cys Ser Leu Ser Val His Ala Gly
            165                 170                 175
Ile Arg Gly Glu Ala Met Arg Phe His Phe Met Asp Glu Gln Asn Pro
        180                 185                 190
Lys Gly Arg Glu Lys Ala Ile Val Phe Pro Ala His Thr Thr Ile Ala
    195                 200                 205
Phe Ser Val Phe Glu Leu Phe Ile Tyr Leu Asp Gly Ala Phe Asp Ile
210                 215                 220
Cys Val Thr Ser Val Ser Lys Gly Gly Phe Glu Arg Glu Thr Thr
225                 230                 235                 240
Thr Phe Ala Met Phe Tyr Arg Leu Arg Asn Ile Leu Phe Glu Arg Asn
            245                 250                 255
Arg Arg Val Met Asp Ala Ile Ser Arg Ser Gln Leu Tyr Leu Asp Asp
        260                 265                 270
Leu Phe Ser Asp Phe Tyr Asp Lys Pro Leu Ser Met Thr Asp Ile Ser
    275                 280                 285
Leu Lys Glu Gly Thr His Ile Arg Val Asn Leu Asn His Asn Ile
290                 295                 300
Pro Lys Gly Pro Cys Ile Leu Cys Gly Met Gly Asn Leu Lys Arg Glu
305                 310                 315                 320
Thr Val Tyr Gly Cys Phe Gln Cys Ser Val Asp Gly Val Lys Tyr Val
            325                 330                 335
Arg Leu His Ala Val Pro Cys Phe Asp Ile Trp His Lys Arg Met Lys
        340                 345                 350

<210> SEQ ID NO 3
<211> LENGTH: 1534
<212> TYPE: DNA
<213> ORGANISM: homo sapiens
<220> FEATURE:
<221> NAME/KEY: misc_feature
<223> OTHER INFORMATION: Homo sapiens deafness, autosomal recessive 59
      (DFNB59), mRNA NM_001042702.3

<400> SEQUENCE: 3
tttcttgccg ggagagaggg attagaggga ttgtccggcg tgggtctagg gtcgttgagg      60
cctaaagtta agcctttgtg gggaggacgg attgggggct gggtcacttt aagaaaaaga    120
ttctaaaatt acgaaggcag aattccaggg agtctcccgg gcctggtcct gaagcttgag    180
accccggata tatacgctcc aggggggctgc ggtgcgctct tcgggtcccc gagccctgtg   240
tttaggaaca cgcggggacg tccaaacacc cgctcctctc ccgccgggcg ggctcctttg    300
tcttctgggc tttcgtcgcg agatggaacg ctggttgatg acgttttgat tttaatatgt    360
ttgctgctgc taccaagagc tttgtcaagc aagttggaga tggagggaga ttagttcctg    420
ttccaagcct cagtgaagct gacaaatatc aacctctaag tctggtggta aaaaagaagc    480
gatgctttct gtttcctaga tataaattta cttcaacacc ttttacactg aaagatattc    540
tcctaggaga cagagaaatt tcagctggta tttcatctta tcaattactg aattatgaag    600
atgaatcaga tgtttcactc tatggaaggc gaggtaacca tattgtaaat gacgttggga    660
ttaacgttgc tggatcagat tccattgcag tgaaagcttc atttggtata gtaaccaaac    720
atgaagtgga agtatcaaca ttactcaaag aaattactac acgaaaaatt aactttgacc    780
acagcttgat acgtcagtca aggagcagca gaaaggcagt attgtgtgtg gtcatggaga    840
gcatccgaac cacacgacag tgctcactgt ctgtgcatgc tggaattcga ggggaagcaa    900
tgcggtttca ctttatggat gaacagaatc ccaagggaag ggacaaagct attgttttcc    960
```

| | | |
|---|---|---|
| cagcacatac aaccatagct ttcagtgttt ttgaactctt catatacctg gatggtgcct | 1020 | |
| ttgacctttg tgtcacttca gtgtcaaaag gaggatttga aagggaagaa acggcaacat | 1080 | |
| ttgcactgct gtacaggttg agaaatatcc tatttgaaag aaatagaaga gtgatggatg | 1140 | |
| tcatttctcg ttcacagctt tacttggatg atcttttttc tgactactat gacaaacctc | 1200 | |
| tcagcatgac tgatatttca ctcaaagaag ggacccatat ccgagttaac ttacttaatc | 1260 | |
| acaacattcc caagggcct tgcatactct gtggaatggg gaacttcaaa agggagacag | 1320 | |
| tttatgggtg ctttcagtgt tctgttgatg gtcagaagta tgtgagactt catgcagttc | 1380 | |
| cttgttttga tatttggcac aagaggatga aataaaatga aaatgaata caccgtgttg | 1440 | |
| gtgttttagg tgcagttgtg ccacaaacct tccctaaatt atctaggttt gctttgatga | 1500 | |
| attaaattaa aatgagaaaa gcaaaaaaaa aaaa | 1534 | |

<210> SEQ ID NO 4
<211> LENGTH: 1217
<212> TYPE: DNA
<213> ORGANISM: mus musculus
<220> FEATURE:
<221> NAME/KEY: misc_feature
<223> OTHER INFORMATION: Mus musculus deafness, autosomal recessive 59
      (Dfnb59), mRNA NM_001080711.2

<400> SEQUENCE: 4

| | | |
|---|---|---|
| agcaaactac ttggtgagcg tgggctttat agttctaacc tgcgtaactg tatttaacat | 60 | |
| caaggaaggc ttagtttggt gtctgattct cttcttcaaa aatgggttcg ttgcctgagg | 120 | |
| gtcgcagttg atgacatctt gatattaata tgtttgctgc tgctaccaag agcttcgtta | 180 | |
| agcaagttgg agatggaggg agattagtcc ctgtcccaag cctcagcgaa gctgacaagt | 240 | |
| accaacccct gagtctggtg gtgaaaaaga agcggtgttt tctgttttcct agatgcaaat | 300 | |
| tcacatccac tccttcaca cttaaagata ttctcctggg agatcgagaa atttcagctg | 360 | |
| gaatttcatc ttatcagtta ctgaattatg aagatgagtc agatgttcc ctctatggaa | 420 | |
| ggcgaagcaa ccatattgtg aatgacgtgg ggattaatgt cactggatct gattccatcg | 480 | |
| cagtcaaagc ttcatttggt gtcgtgacca acatgaggt ggaagtttcg acattactca | 540 | |
| aggagattac tgcacgaaaa attaactttg accacagttt gatccgccaa tcaaggagca | 600 | |
| gcaggaaggc ggtgctgtgc gtggtcatgg agagcatccg aaccacacgc cagtgctctc | 660 | |
| tgtcagtgca cgctgggatt cgtggggaag ccatgcggtt tcattttatg gatgaacaga | 720 | |
| atcccaaggg aagggaaaag gctattgttt cccagcaca cacaactata gctttcagtg | 780 | |
| ttttttgagct cttcatctac ctggacggtg ccttcgacat ttgtgtcaca tctgtgtcaa | 840 | |
| aaggaggatt tgaaagggaa gaaacgacaa ccttttgccat gttctacaga ctgagaaata | 900 | |
| tactcttcga agaaacagg agagtgatgg acgccatctc tcgttcccag ctttacctgg | 960 | |
| acgacctctt ttctgacttc tacgacaaac ccctcagcat gactgacatt tccctcaagg | 1020 | |
| agggggactca catccgagtg aacttactaa accacaacat tcctaaaggg ccctgcatcc | 1080 | |
| tctgcggaat ggggaacttg aaagggaga cggtctacgg ctgcttccag tgttctgtgg | 1140 | |
| acggcgtgaa gtacgtgcgt cttcacgcag tcccttgctt tgatatctgg cacaagagaa | 1200 | |
| tgaaataaaa ggaagaa | 1217 | |

<210> SEQ ID NO 5
<211> LENGTH: 20
<212> TYPE: DNA
<213> ORGANISM: artificial

```
<220> FEATURE:
<223> OTHER INFORMATION: forward primer pjvk

<400> SEQUENCE: 5
ccagtgctct ctgtcagtgc                                              20

<210> SEQ ID NO 6
<211> LENGTH: 24
<212> TYPE: DNA
<213> ORGANISM: artificial
<220> FEATURE:
<223> OTHER INFORMATION: reverse primer pjvk

<400> SEQUENCE: 6
tctgttcatc cataaaatga aacc                                         24

<210> SEQ ID NO 7
<211> LENGTH: 20
<212> TYPE: DNA
<213> ORGANISM: artificial
<220> FEATURE:
<223> OTHER INFORMATION: forward primer Mpv17

<400> SEQUENCE: 7
cgcactctga ccatggtatc                                              20

<210> SEQ ID NO 8
<211> LENGTH: 21
<212> TYPE: DNA
<213> ORGANISM: artificial
<220> FEATURE:
<223> OTHER INFORMATION: reverse primer Mpv17

<400> SEQUENCE: 8
cccgggatta agtggtctaa a                                            21

<210> SEQ ID NO 9
<211> LENGTH: 19
<212> TYPE: DNA
<213> ORGANISM: artificial
<220> FEATURE:
<223> OTHER INFORMATION: forward primer Dct

<400> SEQUENCE: 9
ggctacaatt acgccgttg                                               19

<210> SEQ ID NO 10
<211> LENGTH: 22
<212> TYPE: DNA
<213> ORGANISM: artificial
<220> FEATURE:
<223> OTHER INFORMATION: reverse primer Dct

<400> SEQUENCE: 10
cactgagaga gttgtggacc aa                                           22

<210> SEQ ID NO 11
<211> LENGTH: 18
<212> TYPE: DNA
<213> ORGANISM: artificial
<220> FEATURE:
<223> OTHER INFORMATION: forward primer Gpx2

<400> SEQUENCE: 11
gttctcggct tcccttgc                                                18
```

```
<210> SEQ ID NO 12
<211> LENGTH: 21
<212> TYPE: DNA
<213> ORGANISM: artificial
<220> FEATURE:
<223> OTHER INFORMATION: reverse primer Gpx2

<400> SEQUENCE: 12
ttcaggatct cctcgttctg a                                           21

<210> SEQ ID NO 13
<211> LENGTH: 18
<212> TYPE: DNA
<213> ORGANISM: artificial
<220> FEATURE:
<223> OTHER INFORMATION: forward primer CypA

<400> SEQUENCE: 13
acgccactgt cgcttttc                                               18

<210> SEQ ID NO 14
<211> LENGTH: 20
<212> TYPE: DNA
<213> ORGANISM: artificial
<220> FEATURE:
<223> OTHER INFORMATION: reverse primer CypA

<400> SEQUENCE: 14
gcaaacagct cgaaggagac                                             20

<210> SEQ ID NO 15
<211> LENGTH: 20
<212> TYPE: DNA
<213> ORGANISM: artificial
<220> FEATURE:
<223> OTHER INFORMATION: forward primer c-Fos

<400> SEQUENCE: 15
ggctctcctg tcaacacaca                                             20

<210> SEQ ID NO 16
<211> LENGTH: 18
<212> TYPE: DNA
<213> ORGANISM: artificial
<220> FEATURE:
<223> OTHER INFORMATION: reverse primer c-Fos

<400> SEQUENCE: 16
gaccagagtg ggctgcac                                               18

<210> SEQ ID NO 17
<211> LENGTH: 26
<212> TYPE: DNA
<213> ORGANISM: artificial
<220> FEATURE:
<223> OTHER INFORMATION: forward primer Hsp70

<400> SEQUENCE: 17
gaagacatat agtctagctg cccagt                                      26

<210> SEQ ID NO 18
<211> LENGTH: 25
<212> TYPE: DNA
<213> ORGANISM: artificial
<220> FEATURE:
<223> OTHER INFORMATION: reverse primer Hsp70
```

<400> SEQUENCE: 18
ccaagacgtt tgtttaagac acttt                                          25

<210> SEQ ID NO 19
<211> LENGTH: 19
<212> TYPE: DNA
<213> ORGANISM: artificial
<220> FEATURE:
<223> OTHER INFORMATION: forward Gadph

<400> SEQUENCE: 19
atggtgaagg tcggtgtga                                                 19

<210> SEQ ID NO 20
<211> LENGTH: 20
<212> TYPE: DNA
<213> ORGANISM: artificial
<220> FEATURE:
<223> OTHER INFORMATION: reverse primer Gadph

<400> SEQUENCE: 20
aatctccact ttgccactgc                                                20

<210> SEQ ID NO 21
<211> LENGTH: 445
<212> TYPE: PRT
<213> ORGANISM: Homo sapiens
<220> FEATURE:
<221> NAME/KEY: SITE
<222> LOCATION: (1)..(445)
<223> OTHER INFORMATION: gasdermin-A [Homo sapiens], NP_835465.2

<400> SEQUENCE: 21

```
Met Thr Met Phe Glu Asn Val Thr Arg Ala Leu Ala Arg Gln Leu Asn
1               5                   10                  15

Pro Arg Gly Asp Leu Thr Pro Leu Asp Ser Leu Ile Asp Phe Lys Arg
            20                  25                  30

Phe His Pro Phe Cys Leu Val Leu Arg Lys Arg Lys Ser Thr Leu Phe
        35                  40                  45

Trp Gly Ala Arg Tyr Val Arg Thr Asp Tyr Thr Leu Leu Asp Val Leu
    50                  55                  60

Glu Pro Gly Ser Ser Pro Ser Asp Pro Thr Thr Gly Asn Phe Gly
65                  70                  75                  80

Phe Lys Asn Met Leu Asp Thr Arg Val Glu Gly Asp Val Asp Val Pro
                85                  90                  95

Lys Thr Val Lys Val Lys Gly Thr Ala Gly Leu Ser Gln Asn Ser Thr
            100                 105                 110

Leu Glu Val Gln Thr Leu Ser Val Ala Pro Lys Ala Leu Glu Thr Val
        115                 120                 125

Gln Glu Arg Lys Leu Ala Ala Asp His Pro Phe Leu Lys Glu Met Gln
    130                 135                 140

Asp Gln Gly Glu Asn Leu Tyr Val Val Met Glu Val Val Glu Thr Val
145                 150                 155                 160

Gln Glu Val Thr Leu Glu Arg Ala Gly Lys Ala Glu Ala Cys Phe Ser
                165                 170                 175

Leu Pro Phe Phe Ala Pro Leu Gly Leu Gln Gly Ser Ile Asn His Lys
            180                 185                 190

Glu Ala Val Thr Ile Pro Lys Gly Cys Val Leu Ala Phe Arg Val Arg
        195                 200                 205
```

```
Gln Leu Met Val Lys Gly Lys Asp Glu Trp Asp Ile Pro His Ile Cys
    210                 215                 220

Asn Asp Asn Met Gln Thr Phe Pro Pro Gly Glu Lys Ser Gly Glu Glu
225                 230                 235                 240

Lys Val Ile Leu Ile Gln Ala Ser Asp Val Gly Asp Val His Glu Gly
                245                 250                 255

Phe Arg Thr Leu Lys Glu Glu Val Gln Arg Glu Thr Gln Gln Val Glu
            260                 265                 270

Lys Leu Ser Arg Val Gly Gln Ser Leu Leu Ser Ser Leu Ser Lys
        275                 280                 285

Leu Leu Gly Lys Lys Lys Glu Leu Gln Asp Leu Glu Leu Ala Leu Glu
290                 295                 300

Gly Ala Leu Asp Lys Gly His Glu Val Thr Leu Glu Ala Leu Pro Lys
305                 310                 315                 320

Asp Val Leu Leu Ser Lys Glu Ala Val Gly Ala Ile Leu Tyr Phe Val
                325                 330                 335

Gly Ala Leu Thr Glu Leu Ser Glu Ala Gln Gln Lys Leu Leu Val Lys
            340                 345                 350

Ser Met Glu Lys Lys Ile Leu Pro Val Gln Leu Lys Leu Val Glu Ser
        355                 360                 365

Thr Met Glu Gln Asn Phe Leu Leu Asp Lys Glu Gly Val Phe Pro Leu
370                 375                 380

Gln Pro Glu Leu Leu Ser Ser Leu Gly Asp Glu Glu Leu Thr Leu Thr
385                 390                 395                 400

Glu Ala Leu Val Gly Leu Ser Gly Leu Glu Val Gln Arg Ser Gly Pro
                405                 410                 415

Gln Tyr Met Trp Asp Pro Asp Thr Leu Pro Arg Leu Cys Ala Leu Tyr
            420                 425                 430

Ala Gly Leu Ser Leu Leu Gln Gln Leu Thr Lys Ala Ser
        435                 440                 445

<210> SEQ ID NO 22
<211> LENGTH: 446
<212> TYPE: PRT
<213> ORGANISM: Mus musculus
<220> FEATURE:
<221> NAME/KEY: SITE
<222> LOCATION: (1)..(446)
<223> OTHER INFORMATION: gasdermin-A [Mus musculus], NP_067322.1

<400> SEQUENCE: 22

Met Thr Met Phe Glu Asn Val Thr Arg Ala Leu Ala Arg Gln Leu Asn
1               5                   10                  15

Pro Arg Gly Asp Leu Thr Pro Leu Asp Ser Leu Ile Asp Phe Lys Arg
            20                  25                  30

Phe His Pro Phe Cys Leu Val Leu Arg Lys Arg Lys Ser Thr Leu Phe
        35                  40                  45

Trp Gly Ala Arg Tyr Val His Thr Asp Tyr Thr Leu Leu Asp Val Leu
    50                  55                  60

Glu Pro Gly Ser Ser Pro Ser Asp Pro Thr Asp Ser Gly Asn Phe Ser
65                  70                  75                  80

Phe Lys Asn Met Leu Asp Ala Arg Val Glu Gly Asp Val Asp Val Pro
                85                  90                  95

Lys Thr Val Lys Val Lys Gly Thr Ala Gly Leu Ser Arg Ser Ser Thr
            100                 105                 110
```

```
Leu Glu Val Gln Thr Leu Ser Val Ala Pro Thr Ala Leu Glu Asn Leu
            115                 120                 125

His Lys Glu Arg Lys Leu Ser Ala Asp His Pro Phe Leu Lys Glu Met
        130                 135                 140

Arg Glu Arg Gly Glu Asn Leu Tyr Val Val Met Glu Val Val Glu Thr
145                 150                 155                 160

Leu Gln Glu Val Thr Leu Glu Arg Ala Gly Lys Ala Glu Gly Cys Phe
                    165                 170                 175

Ser Leu Pro Phe Phe Ala Pro Leu Gly Leu Gln Gly Ser Val Asn His
            180                 185                 190

Lys Glu Ala Val Thr Ile Pro Lys Gly Cys Val Leu Ala Tyr Arg Val
        195                 200                 205

Arg Gln Leu Met Val Asn Gly Lys Asp Glu Trp Gly Ile Pro His Ile
210                 215                 220

Cys Asn Asp Ser Met Gln Thr Phe Pro Pro Gly Glu Lys Pro Gly Glu
225                 230                 235                 240

Gly Lys Phe Ile Leu Ile Gln Ala Ser Asp Val Gly Glu Met His Glu
                    245                 250                 255

Asp Phe Lys Thr Leu Lys Glu Val Gln Arg Glu Thr Gln Glu Val
            260                 265                 270

Glu Lys Leu Ser Pro Val Gly Arg Ser Ser Leu Leu Thr Ser Leu Ser
        275                 280                 285

His Leu Leu Gly Lys Lys Glu Leu Gln Asp Leu Glu Gln Thr Leu
290                 295                 300

Glu Gly Ala Leu Asp Lys Gly His Glu Val Thr Leu Glu Ala Leu Pro
305                 310                 315                 320

Lys Asp Val Leu Leu Ser Lys Asp Ala Met Asp Ala Ile Leu Tyr Phe
                    325                 330                 335

Leu Gly Ala Leu Thr Val Leu Ser Glu Ala Gln Gln Lys Leu Leu Val
            340                 345                 350

Lys Ser Leu Glu Lys Lys Ile Leu Pro Val Gln Leu Lys Leu Val Glu
        355                 360                 365

Ser Thr Met Glu Lys Asn Phe Leu Gln Asp Lys Glu Gly Val Phe Pro
370                 375                 380

Leu Gln Pro Asp Leu Leu Ser Ser Leu Gly Glu Glu Leu Ile Leu
385                 390                 395                 400

Thr Glu Ala Leu Val Gly Leu Ser Gly Leu Glu Val Gln Arg Ser Gly
                    405                 410                 415

Pro Gln Tyr Thr Trp Asp Pro Asp Thr Leu Pro His Leu Cys Ala Leu
            420                 425                 430

Tyr Ala Gly Leu Ser Leu Leu Gln Leu Leu Ser Lys Asn Ser
        435                 440                 445

<210> SEQ ID NO 23
<211> LENGTH: 443
<212> TYPE: PRT
<213> ORGANISM: Mus musculus
<220> FEATURE:
<221> NAME/KEY: SITE
<222> LOCATION: (1)..(443)
<223> OTHER INFORMATION: gasdermin-A2 [Mus musculus], NP_084003.2
```

```
<400> SEQUENCE: 23

Met Ser Met Phe Glu Asp Val Thr Arg Ala Leu Ala Arg Gln Leu Asn
1               5                   10                  15

Pro Arg Gly Asp Leu Thr Pro Leu Asp Ser Leu Ile Asp Phe Lys Arg
            20                  25                  30

Phe His Pro Phe Cys Leu Val Leu Arg Lys Arg Lys Ser Thr Leu Phe
        35                  40                  45

Trp Gly Ala Arg Tyr Val Arg Thr Asp Tyr Thr Leu Leu Asp Val Leu
    50                  55                  60

Glu Pro Gly Ser Ser Pro Ser Asp Pro Thr Leu Leu Gly Asn Phe Ser
65                  70                  75                  80

Phe Lys Asn Met Leu Asp Val Arg Val Glu Gly Asp Val Glu Val Pro
                85                  90                  95

Thr Met Met Lys Val Lys Gly Thr Val Gly Leu Ser Gln Ser Ser Thr
            100                 105                 110

Leu Glu Val Gln Met Leu Ser Val Ala Pro Thr Ala Leu Glu Asn Leu
        115                 120                 125

His Met Glu Arg Lys Leu Ser Ala Asp His Pro Phe Leu Lys Glu Met
    130                 135                 140

Arg Glu Tyr Lys Gln Asn Leu Tyr Val Val Met Glu Val Val Lys Ala
145                 150                 155                 160

Lys Gln Glu Val Thr Leu Lys Arg Ala Ser Asn Ala Ile Ser Lys Phe
                165                 170                 175

Ser Leu Asn Leu Pro Ser Leu Gly Leu Gln Gly Ser Val Asn His Lys
            180                 185                 190

Glu Ala Val Thr Ile Pro Lys Gly Cys Val Leu Ala Tyr Arg Val Arg
        195                 200                 205

Gln Leu Ile Ile Tyr Gly Lys Asp Glu Trp Gly Ile Pro Tyr Ile Cys
    210                 215                 220

Thr Asp Asn Met Pro Thr Phe Asn Pro Leu Cys Val Leu Gln Arg Gln
225                 230                 235                 240

Gly Ser Thr Val Gln Met Ile Ser Gly Glu Met His Glu Asp Phe Lys
                245                 250                 255

Thr Leu Lys Lys Glu Val Gln Gln Glu Thr Gln Glu Val Glu Lys Leu
            260                 265                 270

Ser Pro Val Gly Arg Ser Ser Leu Leu Thr Ser Leu Ser His Leu Leu
        275                 280                 285

Gly Lys Lys Lys Glu Leu Gln Asp Leu Glu Gln Met Leu Glu Gly Ala
    290                 295                 300

Leu Asp Lys Gly His Glu Val Thr Leu Glu Ala Leu Pro Lys Asp Val
305                 310                 315                 320

Leu Leu Leu Lys Asp Ala Met Asp Ala Ile Leu Tyr Phe Leu Gly Ala
                325                 330                 335

Leu Thr Glu Leu Ser Glu Glu Gln Leu Lys Ile Leu Val Lys Ser Leu
            340                 345                 350

Glu Asn Lys Val Leu Pro Val Gln Leu Lys Leu Val Glu Ser Ile Leu
        355                 360                 365

Glu Gln Asn Phe Leu Gln Asp Lys Glu Asp Val Phe Pro Leu Arg Pro
    370                 375                 380

Asp Leu Leu Ser Ser Leu Gly Glu Asp Gln Ile Leu Thr Glu Ala
385                 390                 395                 400

Leu Val Gly Leu Ser Gly Leu Glu Val Gln Arg Ser Gly Pro Gln Tyr
                405                 410                 415
```

Thr Trp Asn Pro Asp Thr Cys His Asn Leu Cys Ala Leu Tyr Ala Gly
            420                 425                 430

Leu Ser Leu Leu His Leu Leu Ser Arg Asp Ser
        435                 440

<210> SEQ ID NO 24
<211> LENGTH: 464
<212> TYPE: PRT
<213> ORGANISM: Mus musculus
<220> FEATURE:
<221> NAME/KEY: SITE
<222> LOCATION: (1)..(464)
<223> OTHER INFORMATION: gasdermin-A3 [Mus musculus], NP_001007462.1

<400> SEQUENCE: 24

Met Pro Val Phe Glu Asp Val Thr Arg Ala Leu Val Arg Glu Leu Asn
1               5                   10                  15

Pro Arg Gly Asp Leu Thr Pro Leu Asp Ser Leu Ile Asp Phe Lys His
            20                  25                  30

Phe Arg Pro Phe Cys Leu Val Leu Arg Lys Arg Lys Ser Thr Leu Phe
        35                  40                  45

Trp Gly Ala Arg Tyr Val Arg Thr Asp Tyr Thr Leu Leu Asp Leu Leu
50                  55                  60

Glu Pro Gly Ser Ser Pro Ser Asp Leu Thr Asp Ser Gly Asn Phe Ser
65                  70                  75                  80

Phe Lys Asn Met Leu Asp Val Gln Val Gln Gly Leu Val Glu Val Pro
                85                  90                  95

Lys Thr Val Lys Val Lys Gly Thr Ala Gly Leu Ser Gln Ser Ser Thr
            100                 105                 110

Leu Glu Val Gln Thr Leu Ser Val Ala Pro Ser Ala Leu Glu Asn Leu
        115                 120                 125

Lys Lys Glu Arg Lys Leu Ser Ala Asp His Ser Phe Leu Asn Glu Met
130                 135                 140

Arg Tyr His Glu Lys Asn Leu Tyr Val Val Met Glu Ala Val Glu Ala
145                 150                 155                 160

Lys Gln Glu Val Thr Val Glu Gln Thr Gly Asn Ala Asn Ala Ile Phe
                165                 170                 175

Ser Leu Pro Ser Leu Ala Leu Leu Gly Leu Gln Gly Ser Leu Asn Asn
            180                 185                 190

Asn Lys Ala Val Thr Ile Pro Lys Gly Cys Val Leu Ala Tyr Arg Val
        195                 200                 205

Arg Leu Leu Arg Val Phe Leu Phe Asn Leu Trp Asp Ile Pro Tyr Ile
210                 215                 220

Cys Asn Asp Ser Met Gln Thr Phe Pro Lys Ile Arg Arg Val Pro Cys
225                 230                 235                 240

Ser Ala Phe Ile Ser Pro Thr Gln Met Ile Ser Glu Glu Pro Glu Glu
                245                 250                 255

Glu Lys Leu Ile Gly Glu Met His Gly Asp Phe Lys Thr Leu Lys Glu
            260                 265                 270

Glu Val Gln Arg Glu Thr Gln Glu Val Glu Lys Leu Ser Pro Val Gly
        275                 280                 285

Arg Ser Ser Leu Leu Thr Ser Leu Ser His Leu Leu Gly Lys Lys Lys
290                 295                 300

Glu Leu Gln Asp Leu Glu Gln Lys Leu Glu Gly Ala Leu Asp Lys Gly
305                 310                 315                 320

```
Gln Lys Val Thr Leu Glu Ala Leu Pro Lys Asp Val Leu Leu Ser Lys
            325                 330                 335

Asp Ala Met Asp Ala Ile Leu Tyr Phe Leu Gly Ala Leu Thr Glu Leu
        340                 345                 350

Thr Glu Glu Gln Leu Lys Ile Leu Val Lys Ser Leu Glu Lys Lys Ile
    355                 360                 365

Leu Pro Val Gln Leu Lys Leu Val Glu Ser Thr Leu Glu Gln Asn Phe
370                 375                 380

Leu Gln Asp Lys Glu Gly Val Phe Pro Leu Gln Pro Asp Leu Leu Ser
385                 390                 395                 400

Ser Leu Gly Glu Glu Glu Leu Thr Leu Thr Glu Ala Leu Val Gly Leu
            405                 410                 415

Ser Gly Leu Glu Val Gln Arg Ser Gly Pro Gln Tyr Ala Trp Asp Pro
            420                 425                 430

Asp Thr Arg His Asn Leu Cys Ala Leu Tyr Ala Gly Leu Ser Leu Leu
        435                 440                 445

His Leu Leu Ser Arg Lys Ser Asn Ala Leu Thr Tyr Cys Ala Leu Ser
    450                 455                 460
```

<210> SEQ ID NO 25
<211> LENGTH: 2164
<212> TYPE: DNA
<213> ORGANISM: Homo sapiens
<220> FEATURE:
<221> NAME/KEY: misc_feature
<223> OTHER INFORMATION: Homo sapiens gasdermin A (GSDMA), mRNA, NM_178171.4

<400> SEQUENCE: 25

```
ataaagcagc ctgtcctggc aagggatggt catcctctca acctacagac ccagtgagcc    60
ctaggccctc accccagacc cagctgctgg ataggaccca gccccgctcc cagagacaat   120
gaccatgttt gaaaatgtca cccgggcccct ggccagacag ctaaaccctc gaggggacct   180
gacaccactt gacagcctca tcgacttcaa gcgcttccat cccttctgcc tggtgctgag   240
gaagaggaag agcacgctct tctgggggc ccggtacgtc cgcaccgact acacgctgct   300
ggatgtgctt gagcccggca gctcaccttc agacccaaca gacactggga attttggctt   360
taagaatatg ctggacaccc gagtggaggg agatgtggat gtaccaaaga cggtgaaggt   420
gaagggaacg gcagggctct cgcagaacag cactctggag gtccagacac tcagtgtggc   480
tcccaaggcc ctggagaccg tgcaggagag gaagctggca gcagaccacc cattcctgaa   540
ggagatgcaa gatcaagggg agaacctgta tgtggtgatg gaggtggtgg agacggtgca   600
ggaggtcaca ctggagcgag ccggcaaggc agaggcctgc ttctccctcc ccttcttcgc   660
cccattgggg ctacagggat ccataaatca aaggaggct gtaaccatcc ccaagggctg   720
cgtcctggcc tttcgagtga cagctgat ggtcaaaggc aaagatgagt gggatattcc   780
acatatctgc aatgataaca tgcaaaacctt ccctcctgga gaaaagtcag agagggaaa   840
ggtcatcctt atccaggcat ctgatgttgg ggacgtacac gaaggcttca ggacactaaa   900
agaagaagtt cagagagaga cccaacaagt ggagaagctg agccgagtag gcaaagctc   960
cctgctcagc tccctcagca aacttctagg gaagaaaaag gagctacaag accttgagct  1020
cgcacttgaa ggggctctag acaagggaca tgaagtgacc ctggaggcac tccaaaaga  1080
tgtcctgcta tcaaggagg ccgtgggcgc catcctctat ttcgttggag ccctaacaga  1140
gctaagtgaa gcccaacaga agctgctggt gaaatccatg gagaaaaga tcctacccgt  1200
```

-continued

```
gcagctaaag ctggtggaga gcacgatgga acagaacttc ctgctggata agagggtgt    1260 tttccccctg caacctgagc tgctctcctc ccttggggac gaggagctga ccctcacgga    1320
ggctctagtc gggctgagtg gcctggaagt gcagagatcg ggcccccaat atatgtggga    1380
cccagacacc ctccctcgcc tctgtgctct ttatgcaggc ctctctctcc ttcagcagct    1440
taccaaggcc tcctaatttg cctttttacgt ctgcttcatg actccctaat gccttcccaa    1500
cctcgtggtg ctgtgtcctt accacctaag ggcatttcag agccatcagc tgaagacatc    1560
tgaaatctca gctggtcacc catgataacc aacttccacc tgcccaacca tatatcaccc    1620
cctacccctc cagctccgca acccactaag cccatctgct gatgcttaaa ttttctttac    1680
ttttcttttc tttttttttt ttttttgag atggaggctc actctgtcac ccaggctgga    1740
gtgcagtggc ttgatcttgg ctcactgcaa cctccgcctc caggttcaa gcaattctcc    1800 tgcctcagcc tctcgagcag ctggaattac aggcacgtgc cacgacaccc agctaatttt    1860 tgtatttta gtagacggg gtttcacca tgttgcccag gttggtctcg aactcctggc    1920
ctcaagtgat ctgcccgcct cggcctccca aagtgctggg attacaggcg tgagccaccg    1980
tgcccggcct gtgcttaaat attctaggag tagaagcact cagactttta aaactatgag    2040
ccgtttcagc aaaactgaga aaaaagaag attaattaat ttcctatcct aatccctcct    2100
acttatactt ccccaaaaaa caagctttac tggaattaat ggaaatatt atgtcaatct    2160 tagg                                                                  2164
```

<210> SEQ ID NO 26
<211> LENGTH: 2726
<212> TYPE: DNA
<213> ORGANISM: Mus musculus
<220> FEATURE:
<221> NAME/KEY: misc_feature
<223> OTHER INFORMATION: Mus musculus gasdermin A (Gsdma), mRNA, NM_021347.4

<400> SEQUENCE: 26

```
agtcattccc tcaccctata gacagaacga gctctggttc ctcaccacac accagctgcc     60
agacaggatc cagcatcacc cttccctgag acaatgacta tgtttgagaa tgtcacccgg    120
gccctggcta gacagctgaa ccctcgaggg gatctgacac ccctagacag cctcatcgac    180
ttcaaacgct tccatccctt ctgcctggtg ctgaggaaga ggaagagcac actgttctgg    240
ggagcccgct atgtgcacac cgactacact ctcctggatg tgctggagcc gggcagctcc    300
ccctcagatc cgacagacag tggcaacttt agctttaaga atatgctgga tgctcgagta    360
gagggagatg tggatgtgcc aaagacagtg aaggtaaagg ggactgcggg tctgtcacgg    420
agcagcacac tggaggtgca gacgctcagc gtggctccca cggctctgga gaacttgcac    480
aaggagagga aactgtcagc agaccaccca ttcctgaagg agatgcggga acgcggggag    540
aacctctatg tggtgatgga ggtggtggaa accctacagg aagtcactct ggagcgagcc    600
ggcaaggcag agggctgctt ctctctcccc ttctttgccc cactgggact acagggatcc    660
gtgaaccaca aggaggctgt aaccatcccc aagggctgtg ttctggccta tcgagtgaga    720
caactgatgg tcaacggcaa agatgagtgg ggcattccac acatttgcaa tgacagcatg    780
caaaccttcc ctcctggaga aaagccagga gaagggaagt tcatattgat ccaggcatct    840
gatgttgggg agatgcacga agacttcaag acattaaagg aagaggttca gcgagagact    900
caggaagtgg agaagttaag tccagtgggg cgaagctcac tactcacttc cctcagccat    960
ctcctaggaa agaagaaaga gctccaggac cttgagcaga cgcttgaagg ggctctagac   1020
```

```
aagggacacg aagtgaccct ggaagcactc cccaagatg tcctgctgtc aaaggacgct    1080
atggacgcca tcctttactt cctcggggct ctgacagtgc taagtgaagc ccaacagaag   1140
cttctagtaa aatccttgga gaaaaagatc ctaccggtgc aactgaagct ggttgaaagc   1200
accatggaga agaacttcct gcaagataaa gagggtgttt tccccctgca acctgatctg   1260
ctctcctccc tcggggagga ggaactgatc ctaacagaag cactggtggg actaagcggc   1320
ctggaagtcc agagatcagg cccccagtac acgtgggatc cggacacgct cccccacctt   1380
tgtgccctct atgctggcct ctccctcctt caactgctaa gcaagaattc ctaatgcacc   1440
ttctttgcct gctgccctaa agccttccca gccttactgt gctccatctg taacactgca   1500
agacactaca gagcctccag gctgaggaca actgaaatgc cagctcaaaa atcagtctcc   1560
aagttccttc tgcctcacca tctatctctc tccttctgtc ctccagctca gcacccacta   1620
agcccatctc ctgatgctta aatcctgaag atacagaatc attcaaaccc ttactacttt   1680
gagtcacttc attaagaggg gttggggggga ggcttgggggt ggtgatggtg gtggttatgg  1740
tgtgaggcag aggcaggtga atctcttaag ttcgaggcca gcctggtctg cagagtgaac   1800
tccaggacag ccagggcaac acagagaaac cttgtcttga aaacaacaaa accacattta   1860
tttcctagtc tgatccttcc catgtgtgcc tcaaaaaaaa aaaaaaaaa aaaaactgg     1920
tcttacaaga atgaatggag aatactatgt caatcctaga agaagctgtc ttctggtttt   1980
tctgtttaag ggaattgtcc caggtaaaga aacagccatg atccatacat acacgttact   2040
gcccacactg ttcctcaggc ctgctggaaa atgctcccag tgctcagagg gttagaatcc   2100
agaacatctg ctgtacactg gaaagatcat ccaagctgcc tgacctcacc aaagcgccca   2160
tgttctccag ccctggctga gggcttggga gaggaaagga aggtctaggg gactaagata   2220
caagcagaaa acaagacaat agatttcatg ttgattaagt agaaaatgaa ggtgaggttc   2280
tttctcaaaa taaataaata aataaataaa taaattagag gaagagggag ggggcaccca   2340
agaataagac ctaaaccttt aaatcagtgg tttgacctgt gagtcgcgac cccggtggga   2400
ggtcagatga ctcacaggag ttgcatatca gatatccttc atatcaaata tttacattat   2460
gacttctaac aggagcaaaa ttggagctat gaatttacaa tgaaaataat tctatggttg   2520
ggggtcacca cagcatgagg aactggatca aagggtcgca gtgttaggaa ggctgagagc   2580
cgctgcttca gttttgtttt caaccctcaa ctcaggatga gtgtggatga gcttggcttg   2640
tatattataa tctcattaaa catctgtata ttataatctc attaaacgtc tgggatctca   2700
tcaccctctg cccaacgctg gctttg                                        2726
```

<210> SEQ ID NO 27
<211> LENGTH: 1666
<212> TYPE: DNA
<213> ORGANISM: Mus musculus
<220> FEATURE:
<221> NAME/KEY: misc_feature
<223> OTHER INFORMATION: Mus musculus gasdermin A2 (Gsdma2), mRNA,
       NM_029727.2

<400> SEQUENCE: 27

```
ggacagtcag tcattctctc accctataga cagaacgagc tctggttcct taccacacat     60
ctgctgccag acaggaccca gcatcaccct tccctggaaa atctggatgt gtctcctgga   120
tgctcagaga caatgtctat gtttgaggat gtcacccggg ccctggctag acagctgaac   180
cctcgagggg atctgacacc cctagacagc ctcatcgact caaacgcttc catcccttc    240
tgcctggtgc tgaggaagag gaagagcaca ctgttctggg gagcccgcta tgtgcgcacc   300
```

```
gactacactc tcctggatgt gctggagccg ggcagctccc cctcagatcc aacactcctt    360
ggcaatttta gctttaagaa tatgctggat gtcagagtag agggagatgt ggaggtgcca    420
acaatgatga aggtaaaggg gactgtgggc ctgtcacaaa gcagcacgct ggaggtacag    480
atgctcagtg tggctcccac ggctctggag aacttgcaca tggagaggaa actgtcagca    540
gaccacccgt tcctgaagga gatgcgggaa tacaagcaaa acctgtatgt ggtgatggag    600
gtggtgaaag ccaagcagga agtcactctg aagcgagcta gcaacgcaat ttccaaattc    660
tctctcaacc ttccctcact gggactacag ggatccgtga accacaagga ggctgtaacc    720
atccccaagg gctgtgttct ggcctatcga gtgagacaac tgatcatcta tgggaaagat    780
gagtggggca ttccatacat ttgtactgac aacatgccaa cctttaaccc cctgtgtgtg    840
cttcagagac aaggcagtac tgtccagatg atatctgggg agatgcacga agacttcaag    900
acattaaaga aagaggttca gcaagagact caagaagtgg agaagttgag tccagtgggg    960
cgaagctccc tactcacttc cctcagccat ctcctaggaa agaagaaaga gctccaggac   1020
cttgagcaga tgcttgaagg ggctctagac aagggacacg aagtgaccct tgaagcactc   1080
cccaaagatg tcctgctgtt aaaggacgct atggacgcca tcctctactt cctcggggct   1140
ctgacagagc taagtgaaga acaactgaag attctagtaa aatccttgga gaacaaggtc   1200
ctaccggtgc aactgaagct ggttgagagc atcttggaac agaacttcct gcaagataaa   1260
gaggatgttt tccccctgcg acctgatctg ctctcctccc tcggggagga ggaccagatt   1320
ctaacagaag cactggtggg actaagcggc ctggaagtcc agagatcagg gccccagtac   1380
acgtggaatc cagacacttg tcacaacctc tgtgccctct atgctggcct ctccctcctt   1440
cacctgctaa gcagggattc ctaatgcaac ttctctgcct gctgccctaa agccttcccg   1500
gccttactgt gctctgtctg aaacactcca agatggtggc attcaccttt aatcccagca   1560
gtcaggaggc agaggcagtg agttcaagac cagccttgtc tacaggctgg ttccaggata   1620
acaagggcta tgttgtctca aaataaata aataaaaata tcaaat                   1666
```

<210> SEQ ID NO 28
<211> LENGTH: 1477
<212> TYPE: DNA
<213> ORGANISM: Mus musculus
<220> FEATURE:
<221> NAME/KEY: misc_feature
<223> OTHER INFORMATION: Mus musculus gasdermin A3 (Gsdma3), mRNA, NM_001007461.1

<400> SEQUENCE: 28

```
caacctatag accgaaagag ctctgatttc tcaccaaaca cctgctgctg aacaggacct     60
agcatcaccc ttccctgaga caatgcctgt gtttgaggat gtcacccggg ccctggttag    120
agagctgaac cctcgagggg atctgacacc cctagacagc ctcatcgact caaacactt    180
tcgtcccttc tgcctggtgc tgaggaagag gaagagcaca ttgttctggg gagcccgcta    240
tgtgcgcacc gactacactc tcctggattt gctggagccg ggcagctccc cctcagatct    300
gacagacagt ggcaacttta gctttaagaa tatgctggat gtccaagtac agggacttgt    360
ggaagtgcca agacagtga aggtaaaggg gactgcgggt ctgtcacaaa gcagcacact    420
ggaggtgcag acactcagcg tggctccctc ggctctggag aacttgaaga aggagaggaa    480
actgtcagca gaccactcgt tcctgaacga gatgaggtat catgagaaga acctgtatgt    540
ggtgatggag gcagtagaag ccaagcagga agttactgtg gagcaaactg gcaacgcaaa    600
tgccatcttc tctctcccca gcttggctct actgggacta caggagatcct tgaacaacaa    660
```

```
caaggctgta accatcccca agggctgtgt cctggcctat cgagtgagac tactgagagt    720 cttttttgttc aatctttggg atattccgta catttgcaat gacagcatgc aaaccttccc    780
taagatcagg cgtgtacctt gcagtgcctt catatctcct acccagatga tatctgaaga    840
gccagaagaa gagaagctca ttggggagat gcacgaagac ttcaagacat taaaggaaga    900
ggttcagcga gagactcaag aagtggagaa gttgagtcca gtgggtcgaa gctccctact    960
cacttccctc agccatctcc taggaaagaa gaaagagctc caggaccttg agcagaagct   1020
tgaaggggct ttagacaagg gtcagaaagt gaccctggaa gcactcccca agatgtcct   1080 gctgtcaaag gacgctatgg atgccatcct ctacttcctc ggggctctga cagagctaac   1140
tgaagaacaa ctgaagattc tagtaaaatc cttggagaaa aagatcttac cagtgcaact   1200
gaagctggtt gaaagcacct tggagcagaa cttcctgcaa gataaagagg gtgttttccc   1260
cctgcaacct gatctgctct cctccctcgg ggaggaggaa ctgaccctaa cggaagcact   1320
ggtgggacta agcggcctgg aagtccagag atcaggcccc cagtacgcgt gggatccaga   1380
cactcgccac aacctttgtg ccctctatgc tggcctctcc ctccttcacc tgctaagcag   1440
gaaatctaat gcacttactt attgtgctct atcttaa                            1477
```

<210> SEQ ID NO 29
<211> LENGTH: 416
<212> TYPE: PRT
<213> ORGANISM: Homo sapiens
<220> FEATURE:
<221> NAME/KEY: SITE
<222> LOCATION: (1)..(416)
<223> OTHER INFORMATION: gasdermin-B isoform 3 [Homo sapiens],
      NP_001159430.1

<400> SEQUENCE: 29

Met Phe Ser Val Phe Glu Glu Ile Thr Arg Ile Val Val Lys Glu Met
1               5                   10                  15

Asp Ala Gly Gly Asp Met Ile Ala Val Arg Ser Leu Val Asp Ala Asp
                20                  25                  30

Arg Phe Arg Cys Phe His Leu Val Gly Glu Lys Arg Thr Phe Phe Gly
            35                  40                  45

Cys Arg His Tyr Thr Thr Gly Leu Thr Leu Met Asp Ile Leu Asp Thr
        50                  55                  60

Asp Gly Asp Lys Trp Leu Asp Glu Leu Asp Ser Gly Leu Gln Gly Gln
65                  70                  75                  80

Lys Ala Glu Phe Gln Ile Leu Asp Asn Val Asp Ser Thr Gly Glu Leu
                85                  90                  95

Ile Val Arg Leu Pro Lys Glu Ile Thr Ile Ser Gly Ser Phe Gln Gly
            100                 105                 110

Phe His His Gln Lys Ile Lys Ile Ser Glu Asn Arg Ile Ser Gln Gln
        115                 120                 125

Tyr Leu Ala Thr Leu Glu Asn Arg Lys Leu Lys Arg Glu Leu Pro Phe
    130                 135                 140

Ser Phe Arg Ser Ile Asn Thr Arg Glu Asn Leu Tyr Leu Val Thr Glu
145                 150                 155                 160

Thr Leu Glu Thr Val Lys Glu Thr Leu Lys Ser Asp Arg Gln Tyr
                165                 170                 175

Lys Phe Trp Ser Gln Ile Ser Gln Gly His Leu Ser Tyr Lys His Lys
            180                 185                 190

Gly Gln Arg Glu Val Thr Ile Pro Pro Asn Arg Val Leu Ser Tyr Arg
        195                 200                 205

| | | | | | | | | | | | |
|---|---|---|---|---|---|---|---|---|---|---|---|
|Val|Lys|Gln|Leu|Val|Phe|Pro|Asn|Lys|Glu|Thr|Met|Asn|Ile|His|Phe|
| |210| | | |215| | | |220| | |

Arg Gly Lys Thr Lys Ser Phe Pro Glu Glu Lys Asp Gly Ala Ser Ser
225 230 235 240

Cys Leu Gly Lys Ser Leu Gly Ser Glu Asp Ser Arg Asn Met Lys Glu
245 250 255

Lys Leu Glu Asp Met Glu Ser Val Leu Lys Asp Leu Thr Glu Glu Lys
260 265 270

Arg Lys Asp Val Leu Asn Ser Leu Ala Lys Cys Leu Gly Lys Glu Asp
275 280 285

Ile Arg Gln Asp Leu Glu Gln Arg Val Ser Glu Val Leu Ile Ser Gly
290 295 300

Glu Leu His Met Glu Asp Pro Asp Lys Pro Leu Leu Ser Ser Leu Phe
305 310 315 320

Asn Ala Ala Gly Val Leu Val Glu Ala Arg Ala Lys Ala Ile Leu Asp
325 330 335

Phe Leu Asp Ala Leu Leu Glu Leu Ser Glu Glu Gln Gln Phe Val Ala
340 345 350

Glu Ala Leu Glu Lys Gly Thr Leu Pro Leu Leu Lys Asp Gln Val Lys
355 360 365

Ser Val Met Glu Gln Asn Trp Asp Glu Leu Ala Ser Ser Pro Pro Asp
370 375 380

Met Asp Tyr Asp Pro Glu Ala Arg Ile Leu Cys Ala Leu Tyr Val Val
385 390 395 400

Val Ser Ile Leu Leu Glu Leu Ala Glu Gly Pro Thr Ser Val Ser Ser
405 410 415

<210> SEQ ID NO 30
<211> LENGTH: 1616
<212> TYPE: DNA
<213> ORGANISM: Homo sapiens
<220> FEATURE:
<221> NAME/KEY: misc_feature
<223> OTHER INFORMATION: Homo sapiens gasdermin B (GSDMB), transcript
      variant 3, mRNA, NM_001165958.1

<400> SEQUENCE: 30
acaactttca gtttcattat tttagcttcc tgagattcag aggccaggaa ctgtgcagag    60
atctgtgggg attctcacaa cttccatttc tggtgaacag ctgaggtcag agaggagttg   120
gtccaggcgc aatgttcagc gtatttgagg aaatcacaag aattgtagtt aaggagatgg   180
atgctggagg ggatatgatt gccgttagaa gccttgttga tgctgataga ttccgctgct   240
tccatctggt gggggagaag agaactttct ttggatgccg gcactacaca acaggcctca   300
ccctgatgga cattctggac acagatgggg acaagtggtt agatgaactg gattctgggc   360
tccaaggtca aaaggctgag tttcaaattc tggataatgt agactcaacg ggagagttga   420
tagtgagatt acccaaagaa ataacaattt caggcagttt ccagggcttc caccatcaga   480
aaatcaagat atcggagaac cggatatccc agcagtatct ggctacccct gaaaacagga   540
agctgaagag ggaactaccc ttttcattcc gatcaattaa tacgagagaa aacctgtatc   600
tggtgacaga aactctggag acggtaaagg aggaacccct gaaaagcgac cggcaatata   660
aattttggag ccagatctct cagggccatc tcagctataa acacaagggc caaagggaag   720
tgaccatccc cccaaatcgg gtcctgagct atcgagtaaa gcagcttgtc ttccccaaca   780
aggagacgat gaatattcat ttcaggggca aaacaaaatc ctttccagaa gagaaggatg   840

```
gtgcttcatc ctgtttagga aagtctttgg gttcggagga ttccagaaac atgaaggaga    900
agttggagga catggagagt gtcctcaagg acctgacaga ggagaagaga aaagatgtgc    960
taaactccct cgctaagtgc ctcggcaagg aggatattcg gcaggatcta gagcaaagag   1020
tatctgaggt cctgatttcc ggggagctac acatggagga cccagacaag cctctcctaa   1080
gcagccttttt aatgctgct ggggtcttgg tagaagcgcg tgcaaaagcc attctggact   1140
tcctggatgc cctgctagag ctgtctgaag agcagcagtt tgtggctgag gccctggaga   1200
aggggaccct tcctctgttg aaggaccagg tgaaatctgt catggagcag aactgggatg   1260
agctggccag cagtcctcct gacatggact atgaccctga ggcacgaatt ctctgtgcgc   1320
tgtatgttgt tgtctctatc ctgctggagc tggctgaggg gcctacctct gtctcttcct   1380
aactacaaaa gccctttctc cccacaagcc tctgggtttt cccttttacca gtctgtcctc   1440
actgccatcg ccactaccat cctgtcacca gtgggacctc tttaaaacaa gcagccaacc   1500
attctttgat gtatcccatt cgctccatgt taacatccaa aaccagcctg gatttcatac   1560
atggacttct gattaaaagt ggcaggttgt gcatgttaaa aaaaaaaaa aaaaaa        1616
```

<210> SEQ ID NO 31
<211> LENGTH: 508
<212> TYPE: PRT
<213> ORGANISM: Homo sapiens
<220> FEATURE:
<221> NAME/KEY: SITE
<222> LOCATION: (1)..(508)
<223> OTHER INFORMATION: gasdermin-C [Homo sapiens], NP_113603.1

<400> SEQUENCE: 31

```
Met Pro Ser Met Leu Glu Arg Ile Ser Lys Asn Leu Val Lys Glu Ile
1               5                   10                  15

Gly Ser Lys Asp Leu Thr Pro Val Lys Tyr Leu Leu Ser Ala Thr Lys
            20                  25                  30

Leu Arg Gln Phe Val Ile Leu Arg Lys Lys Asp Ser Arg Ser Ser
        35                  40                  45

Phe Trp Glu Gln Ser Asp Tyr Val Pro Val Glu Phe Ser Leu Asn Asp
    50                  55                  60

Ile Leu Glu Pro Ser Ser Ser Val Leu Glu Thr Val Val Thr Gly Pro
65                  70                  75                  80

Phe His Phe Ser Asp Ile Met Ile Gln Lys His Lys Ala Asp Met Gly
                85                  90                  95

Val Asn Val Gly Ile Glu Val Ser Val Ser Gly Glu Ala Ser Val Asp
            100                 105                 110

His Gly Cys Ser Leu Glu Phe Gln Ile Val Thr Ile Pro Ser Pro Asn
        115                 120                 125

Leu Glu Asp Phe Gln Lys Arg Lys Leu Leu Asp Pro Glu Pro Ser Phe
    130                 135                 140

Leu Lys Glu Cys Arg Arg Arg Gly Asp Asn Leu Tyr Val Val Thr Glu
145                 150                 155                 160

Ala Val Glu Leu Ile Asn Asn Thr Val Leu Tyr Asp Ser Ser Val
                165                 170                 175

Asn Ile Leu Gly Lys Ile Ala Leu Trp Ile Thr Tyr Gly Lys Gly Gln
            180                 185                 190

Gly Gln Gly Glu Ser Leu Arg Val Lys Lys Ala Leu Thr Leu Gln
        195                 200                 205

Lys Gly Met Val Met Ala Tyr Lys Arg Lys Gln Leu Val Ile Lys Glu
    210                 215                 220
```

```
Lys Ala Ile Leu Ile Ser Asp Asp Glu Gln Arg Thr Phe Gln Asp
225                 230                 235                 240

Glu Tyr Glu Ile Ser Glu Met Val Gly Tyr Cys Ala Ala Arg Ser Glu
            245                 250                 255

Gly Leu Leu Pro Ser Phe His Thr Ile Ser Pro Thr Leu Phe Asn Ala
                260                 265                 270

Ser Ser Asn Asp Met Lys Leu Lys Pro Glu Leu Phe Leu Thr Gln Gln
        275                 280                 285

Phe Leu Ser Gly His Leu Pro Lys Tyr Glu Gln Val His Ile Leu Pro
290                 295                 300

Val Gly Arg Ile Glu Glu Pro Phe Trp Gln Asn Phe Lys His Leu Gln
305                 310                 315                 320

Glu Glu Val Phe Gln Lys Ile Lys Thr Leu Ala Gln Leu Ser Lys Asp
                325                 330                 335

Val Gln Asp Val Met Phe Tyr Ser Ile Leu Ala Met Leu Arg Asp Arg
                340                 345                 350

Gly Ala Leu Gln Asp Leu Met Asn Met Leu Glu Leu Asp Ser Ser Gly
            355                 360                 365

His Leu Asp Gly Pro Gly Gly Ala Ile Leu Lys Lys Leu Gln Gln Asp
370                 375                 380

Ser Asn His Ala Trp Phe Asn Pro Lys Asp Pro Ile Leu Tyr Leu Leu
385                 390                 395                 400

Glu Ala Ile Met Val Leu Ser Asp Phe Gln His Asp Leu Leu Ala Cys
                405                 410                 415

Ser Met Glu Lys Arg Ile Leu Gln Gln Gln Glu Leu Val Arg Ser
            420                 425                 430

Ile Leu Glu Pro Asn Phe Arg Tyr Pro Trp Ser Ile Pro Phe Thr Leu
                435                 440                 445

Lys Pro Glu Leu Leu Ala Pro Leu Gln Ser Glu Gly Leu Ala Ile Thr
450                 455                 460

Tyr Gly Leu Leu Glu Glu Cys Gly Leu Arg Met Glu Leu Asp Asn Pro
465                 470                 475                 480

Arg Ser Thr Trp Asp Val Glu Ala Lys Met Pro Leu Ser Ala Leu Tyr
                485                 490                 495

Gly Thr Leu Ser Leu Leu Gln Gln Leu Ala Glu Ala
            500                 505

<210> SEQ ID NO 32
<211> LENGTH: 468
<212> TYPE: PRT
<213> ORGANISM: Mus musculus
<220> FEATURE:
<221> NAME/KEY: SITE
<222> LOCATION: (1)..(468)
<223> OTHER INFORMATION: gasdermin-C [Mus musculus], NP_113555.1

<400> SEQUENCE: 32

Met Ser Tyr Thr Phe Asp Trp Leu Ser Lys Asp Val Val Lys Lys Leu
1               5                   10                  15

Gln Gly Arg Asp Leu Arg Pro Val Lys Cys Leu Ser Asp Ala Thr Lys
            20                  25                  30

Phe Cys Leu Phe Asn Ile Leu Gln Glu Thr Ser Ser Arg Leu Ala Leu
        35                  40                  45

Lys Thr Glu Tyr Ile Pro Val Gly Phe Thr Leu Leu His Leu Leu Glu
50                  55                  60
```

```
Pro Asn Ile Pro Val Pro Glu Pro Glu Val Ser Ala Pro Ile Pro Leu
 65                  70                  75                  80

Lys His Thr Ile Ser Gln Lys Leu Lys Ala Asp Leu Asp Val Glu Thr
                 85                  90                  95

Ile Ala Gly Gly Glu Ala Gly Phe Val Lys Ser Cys Gly Tyr Asp Ile
            100                 105                 110

Glu Val Gln Ser Lys Ser Ile Pro Asn Pro Lys Leu Glu Ser Leu Gln
        115                 120                 125

Asn Arg Lys Leu Leu Asp Gln Leu Pro Thr Phe Met Lys Thr Cys Trp
130                 135                 140

Lys Asp Gly Lys Asn Leu Tyr Val Val Thr Glu Ala Tyr Glu Val Thr
145                 150                 155                 160

Lys Asp Thr Val Leu Glu Gly Thr Ser Asn Ser Lys Phe Ala Ile Lys
                165                 170                 175

Gly Ile Ile Asn Gln Leu Val Lys Val Gly Ser Gly Gln Trp Gln
            180                 185                 190

Thr Glu Lys Thr Asp Ser Ile Pro Ile Gln Lys Gly Ser Val Leu Ala
        195                 200                 205

Tyr Lys Lys Gln Gln Leu Val Ile Glu Asp Asn Thr Cys Val Ile Leu
210                 215                 220

Thr Ser Ala Asn Thr Lys Lys Met Thr Phe Pro Met Arg Phe Val
225                 230                 235                 240

Gly Met Ser Gly His Leu Arg Tyr Gln Asp Leu Val Ile Glu Thr Gly
                245                 250                 255

Ser Trp Ile Asn Asp Ile Asp Pro Ile Gly Thr Ile Lys Glu Pro Thr
                260                 265                 270

His Leu Asp Phe Met Cys Leu Gln Asn Glu Val Ser Glu Gln Thr Arg
            275                 280                 285

Leu Leu Ala Glu Leu Ser Lys Asp Val Gln Glu Val Val Phe Ser Ser
        290                 295                 300

Phe Leu His Met Leu Cys Asp Arg Asp Val Leu Tyr Asp Leu Met Lys
305                 310                 315                 320

Met Leu Glu Leu Asn Gln Leu Gly His Met Asp Gly Pro Gly Gly Lys
                325                 330                 335

Ile Leu Asp Glu Leu Arg Lys Asp Ser Ser Leu Ser Trp Ile Asn Leu
            340                 345                 350

Lys Asp Leu Ile Leu Tyr Leu Leu Gln Ala Leu Met Val Leu Ser Asp
        355                 360                 365

Thr Gln Leu Cys Leu Leu Ala Leu Ser Val Glu Met Arg Leu Leu Pro
370                 375                 380

His Gln Val Glu Leu Val Lys Ser Ile Leu Gln Pro Asn Phe Lys Tyr
385                 390                 395                 400

Pro Trp Asn Ile Pro Phe Thr Leu Gln Pro Gln Leu Leu Ala Pro Leu
                405                 410                 415

Gln Gly Glu Gly Leu Ala Ile Thr Tyr Glu Leu Leu Glu Glu Cys Gly
            420                 425                 430

Leu Lys Met Glu Leu Asn Asn Pro Arg Ser Thr Trp Asp Leu Glu Ala
        435                 440                 445

Lys Met Pro Leu Ser Ala Leu Tyr Gly Ser Leu Ser Phe Leu Gln Gln
        450                 455                 460

Leu Ser Glu Ala
465
```

<210> SEQ ID NO 33
<211> LENGTH: 480
<212> TYPE: PRT
<213> ORGANISM: Mus musculus
<220> FEATURE:
<221> NAME/KEY: SITE
<222> LOCATION: (1)..(480)
<223> OTHER INFORMATION: gasdermin-C2 [Mus musculus], NP_001161746.1

<400> SEQUENCE: 33

```
Met Gly Tyr Ser Phe Asp Arg Ala Ser Lys Asp Val Val Lys Lys Leu
1               5                   10                  15

Gln Gly Arg Asp Leu Arg Pro Val Glu Cys Leu Ser Asp Ala Thr Lys
            20                  25                  30

Phe Arg Leu Phe His Ile Leu Gln Glu Thr Pro Arg Ser Gly Trp Glu
        35                  40                  45

Thr Glu Asp Ile Pro Val Gly Phe Thr Leu Leu Asp Leu Leu Glu Pro
    50                  55                  60

Asn Phe Pro Val Pro Glu Pro Glu Val Ser Ala Pro Lys Pro Phe Ile
65                  70                  75                  80

His Val Gln Ser Thr Asp Leu Glu Ala Asn Leu Asn Val Ala Asp Ile
                85                  90                  95

Ala Arg Gly Gly Val Gly Tyr Val Gly Tyr Gly Gly Tyr Asn Ile Glu
            100                 105                 110

Val Gln Ser Thr Ser Ile Pro Asn Pro Lys Leu Glu Ile Leu Gln Asn
        115                 120                 125

Arg Lys Leu Leu Asp Asn Leu Pro Thr Phe Met Lys Phe Cys Arg Met
130                 135                 140

Glu Arg Lys Asn Leu Tyr Val Val Thr Glu Ala Tyr Glu Val Ser Lys
145                 150                 155                 160

Asp Thr Met Leu Thr Gly Leu Ser Ser Val Asn Leu Ser Val Lys Gly
                165                 170                 175

Phe Phe Lys Gln Leu Phe Lys Val Arg Gly Lys Ala Gly Arg Ser Glu
            180                 185                 190

Lys Tyr Ser Ile Pro Ile Pro Lys Gly Ser Val Leu Ala Tyr Lys Lys
        195                 200                 205

Gln Gln Leu Val Ile Glu Asn Asn Thr Cys Val Ile Leu Pro Ser Ala
    210                 215                 220

Thr Lys Lys Lys Met Thr Phe Pro Gly Thr Pro Lys Tyr Ala Ser Ala
225                 230                 235                 240

Ser Glu Pro Thr Glu Ile Tyr Arg Thr Glu Leu Gln Gly Leu Trp Ile
                245                 250                 255

Asn Asp Ile Val Pro Ile Gly Arg Ile Gln Glu Pro Ala His Leu Asp
            260                 265                 270

Phe Met Cys Leu Gln Asn Glu Val Tyr Lys Gln Thr Glu Gln Leu Ala
        275                 280                 285

Glu Leu Ser Lys Gly Val Gln Glu Val Leu Ser Ser Ile Leu Ser
    290                 295                 300

Met Leu Tyr Glu Gly Asp Arg Lys Val Leu Tyr Asp Leu Met Asn Met
305                 310                 315                 320

Leu Glu Leu Asn Gln Leu Gly His Met Asp Gly Pro Gly Gly Lys Ile
                325                 330                 335

Leu Asp Glu Leu Arg Lys Asp Ser Ser Asn Pro Cys Val Asp Leu Lys
            340                 345                 350
```

-continued

```
Asp Leu Ile Leu Tyr Leu Leu Gln Ala Leu Met Val Leu Ser Asp Ser
            355                 360                 365

Gln Leu Asn Leu Leu Ala Gln Ser Val Glu Met Gly Ile Leu Pro His
        370                 375                 380

Gln Val Glu Leu Val Lys Ser Ile Leu Gln Pro Asn Phe Lys Tyr Pro
385                 390                 395                 400

Trp Asn Ile Pro Phe Thr Leu Gln Pro Gln Leu Leu Ala Pro Leu Gln
                405                 410                 415

Gly Glu Gly Leu Ala Ile Thr Tyr Glu Leu Leu Glu Glu Cys Gly Leu
                420                 425                 430

Lys Met Glu Leu Asn Asn Pro Arg Ser Thr Trp Asp Leu Glu Ala Lys
            435                 440                 445

Met Pro Leu Ser Ala Leu Tyr Gly Ser Leu Ser Phe Leu Gln Gln Leu
        450                 455                 460

Arg Lys Ala Asn Ser Ser Ser Lys Pro Ser Leu Arg Pro Gly Tyr Ile
465                 470                 475                 480

<210> SEQ ID NO 34
<211> LENGTH: 480
<212> TYPE: PRT
<213> ORGANISM: Mus musculus
<220> FEATURE:
<221> NAME/KEY: SITE
<222> LOCATION: (1)..(480)
<223> OTHER INFORMATION: gasdermin-C3 [Mus musculus], NP_899017.2

<400> SEQUENCE: 34

Met Gly Tyr Ser Phe Asp Arg Ala Ser Lys Asp Val Val Lys Lys Leu
1               5                   10                  15

Gln Gly Arg Asp Leu Arg Pro Val Glu Cys Leu Ser Asp Ala Thr Lys
            20                  25                  30

Phe Arg Leu Phe His Ile Leu Gln Glu Thr Pro Arg Ser Gly Trp Glu
        35                  40                  45

Thr Glu Asp Ile Pro Val Gly Phe Thr Leu Leu Asp Leu Leu Glu Pro
    50                  55                  60

Asn Phe Pro Val Pro Glu Pro Glu Val Ser Ala Pro Lys Pro Phe Ile
65                  70                  75                  80

His Val Gln Ser Thr Asp Leu Glu Ala Asn Leu Asn Val Ala Asp Ile
                85                  90                  95

Ala Arg Gly Gly Val Gly Tyr Val Gly Tyr Gly Gly Tyr Asn Ile Glu
            100                 105                 110

Val Gln Ser Thr Ser Ile Pro Asn Pro Lys Leu Glu Ile Leu Gln Asn
        115                 120                 125

Arg Lys Leu Leu Asp Lys Leu Pro Thr Phe Met Lys Phe Cys Arg Met
    130                 135                 140

Glu Arg Lys Asn Leu Tyr Val Val Thr Glu Ala Tyr Glu Val Ser Lys
145                 150                 155                 160

Asp Thr Met Leu Thr Gly Leu Ser Ser Val Asn Leu Val Lys Gly
                165                 170                 175

Phe Phe Lys Gln Leu Phe Lys Val Arg Gly Lys Ala Gly Arg Ser Glu
            180                 185                 190

Lys Tyr Ser Ile Pro Ile Pro Lys Gly Ser Val Leu Ala Tyr Lys Lys
        195                 200                 205

Gln Gln Leu Val Ile Glu Asn Asn Thr Cys Val Ile Leu Pro Ser Ala
    210                 215                 220
```

Thr Lys Lys Lys Met Thr Phe Pro Gly Thr Pro Lys Tyr Ala Ser Ala
225                 230                 235                 240

Ser Glu Pro Thr Glu Ile Tyr Arg Thr Glu Leu Gln Gly Leu Trp Ile
            245                 250                 255

Asn Asp Ile Glu Pro Ile Gly Arg Ile Gln Glu Pro Ala His Leu Asp
            260                 265                 270

Phe Lys Cys Leu Gln Tyr Glu Val Ser Glu Gln Thr Arg Leu Leu Pro
        275                 280                 285

Glu Leu Ser Lys Asp Val Gln Glu Val Val Leu Ser Ser Phe Leu Ser
        290                 295                 300

Met Leu Tyr Glu Gly Asp Arg Asn Val Leu His Asp Leu Met Lys Met
305                 310                 315                 320

Leu Glu Leu Ser Gln Leu Gly His Met Asp Gly Pro Gly Lys Ile
            325                 330                 335

Leu Asp Glu Leu Arg Lys Asp Ser Ser Asn Pro Cys Val Asp Leu Lys
            340                 345                 350

Asp Leu Ile Leu Tyr Leu Leu Gln Ala Leu Met Val Leu Ser Asp Ser
            355                 360                 365

Gln Leu Asn Leu Leu Ala Arg Ser Val Glu Met Arg Leu Leu Pro His
370                 375                 380

Gln Val Glu Leu Val Thr Ser Ile Leu Gln Pro Asn Phe Lys Tyr Pro
385                 390                 395                 400

Trp Asn Ile Pro Phe Thr Val Gln Pro Gln Leu Leu Ala Pro Leu Gln
                405                 410                 415

Gly Glu Gly Leu Ala Ile Thr Tyr Glu Leu Leu Glu Glu Cys Gly Leu
            420                 425                 430

Lys Met Glu Leu Asn Asn Pro Arg Ser Thr Trp Asp Leu Glu Ala Lys
            435                 440                 445

Met Pro Leu Ser Ala Leu Tyr Gly Ser Leu Ser Phe Leu Gln Gln Leu
450                 455                 460

Gln Lys Ala Asn Ser Ser Phe Lys Pro Ser Leu Arg Pro Gly Tyr Ile
465                 470                 475                 480

<210> SEQ ID NO 35
<211> LENGTH: 2731
<212> TYPE: DNA
<213> ORGANISM: Homo sapiens
<220> FEATURE:
<221> NAME/KEY: misc_feature
<223> OTHER INFORMATION: Homo sapiens gasdermin C (GSDMC), mRNA,
      NM_031415.2

<400> SEQUENCE: 35
ccacatgtag gcagttcaga ggtgcttccc agggccctgg cgctagtgcc tgtccctcct      60
gctgaagttg cctttcctgg tgtccagtga ttgaattcta aattcagcac atataccaga    120
ggaatacgag ccaaagaagt tgttccagct agagttgctg gaatccatg aatcaaagac    180 ttgctcagct agttctgtat gtgaaaggaa atgggtgtga ctctgaggaa gccttttaa    240 ttctgattca ggagatacat aattagatgc cacttgattt tgttccacag acttttgct    300 gaggacttga gagctaaggt tctgtgatcc agaactagtt ccagacttac tcttctggaa    360
atgaacaggg ccctcctgtg cttattttc caggatactg cattggaaat tgagtcaggg    420
acccattggt gagaagagaa cagtgaacag aatcacattg atctggtcct ggagtttgtc    480
tgacaatttc tacttgaccg caggaggtct gaagattgga aggggcccta ctcaattgtg    540
ctatttttct ctcttttttt ttttttgag acggagttgc ccaggctgga gtgcagcggc    600

```
atggtctcag ctcactgcaa cctctgcctc ccgggttcaa gcagttctct gcctcagcct    660
cccaagtagc tgggattaca ggtgcctgcc accattcctg ctaattttt gtattttcag    720 tagagacagg gtttcaccat cttggcctgg ctgatcttga actcctgacc tcgtgatcca    780
ccggcctcag cctcccaaag tgctgggatt acagacgtga gccaccgtgc ccggccaatc    840
ctgctatttc tctacaggac aaagggatat ataatctgca acatgccctc catgttggaa    900
cgcattagca aaaatttggt caaagagatt ggaagcaaag acctgacacc tgtcaaatac    960
ctattgagtg ccaccaaatt acgtcagttt gttatattac gaaagaagaa ggattctcgt   1020
tcatcatttt gggaacaatc tgactatgtt ccagttgaat ctccctcaa tgacatcctg    1080 gagccaagtt cttcagtcct agaaactgtt gtgacaggac cgttccactt cagtgacatt   1140
atgatccaga agcataaggc tgacatgggt gtgaatgttg gtatagaagt gagtgtgtca   1200
ggggaggcct ctgtggacca tggatgctcc ctcgagtttc aaattgttac catcccatca   1260
ccaaacctgg aagactttca aaaaggaaa ctgttggatc cagagccatc atttctgaag   1320
gagtgccgga ggagagggga caacctgtac gtggtgacag aggctgttga actgatcaac   1380
aatactgtgc tgtacgatag cagtagtgtg aatattttag ggaaaattgc tctttggatt   1440
acctatggca agggtcaagg ccaaggagag agtctcagag tgaagaagaa ggcgctgact   1500
cttcagaaag gcatggtgat ggcttataag agaaagcagc tggttatcaa ggagaaagcc   1560
attctcatct cagatgatga tgaacagaga acctttcaag atgagtacga aatttccgaa   1620
atggtaggct actgtgctgc gaggagtgag gggttgctac catcatttca taccatctct   1680
ccaaccctct tcaatgcctc atccaatgat atgaagttaa accagagct atttctgaca   1740 cagcaatttt tgagcgggca tttgccaaaa tacgaacaag ttcacatcct cccagtagga   1800
agaatagagg aaccctctg gcaaaatttc aagcatctac aagaggaggt tttccagaaa   1860
ataaagacac tggctcagct ctcaaaggat gttcaggatg tcatgttcta cagtatcctg   1920
gccatgctca gagacagagg ggctctacag gacctgatga acatgctgga attggacagc   1980
tcaggtcatt tggatggccc tggtggtgcc atcctaaaga aacttcaaca ggattcaaac   2040
catgcatggt ttaacccaaa ggaccccatt ctttatctcc ttgaagccat aatggtgctg   2100
agtgacttcc aacacgattt gctggcctgt tccatggaga agaggatcct gcttcagcaa   2160
caggagctgg taaggagcat cctggagcca aacttcagat accctggag cattcccttc   2220 accctcaaac ctgagctcct cgccccactc cagagtgagg gtttggccat cacctatggc   2280
ctgctggagg agtgtggcct taggatggag ctggataacc ccaggtcaac ctgggatgta   2340
gaagcaaaga tgcccctgtc tgccctctat gggactctct cgttgctgca gcagctggct   2400
gaggcctaag ccctccctga tgggcagtca gtccagagat gctggccctc gcccagtcta   2460
tgctgtgagt gtccttatgg gtgcaagaga tagggctgtg cctctctgcg tttccaggtg   2520
gagtagagac agtaatgggt agagacttta ggaaatgttt tggggtggtg gaatactcta   2580
tatattgaca agagtttata tattgacaag agtttatata tttgtcaaaa ctcctcaaat   2640
agtatgttaa agacgtaagc gtttcactat gtataaattt tacttcaaaa taataaaaac   2700
aaatactgac tctaaaaaaa aaaaaaaaaa a                                  2731
```

<210> SEQ ID NO 36
<211> LENGTH: 2382
<212> TYPE: DNA
<213> ORGANISM: Mus musculus

```
<220> FEATURE:
<221> NAME/KEY: misc_feature
<223> OTHER INFORMATION: Mus musculus gasdermin C (Gsdmc), mRNA,
      NM_031378.3

<400> SEQUENCE: 36
acagtctttt gaatggtggc tttgagcact ggttctgagc tcagagctta gttcctggag      60
aacagagttc atccccgagc ttacctggcc agaatactgc attgaaaatt gactcggacc     120
tgctaaaagg aaggagacag taaagagaat cacgttgatt tggtcctgga tttcgtacaa     180
gttatacttg gattagaagg tccaaggact aaggagccac attcaattgc actttctcta     240
gaggagataa cgcagcttct gcctggaaca tgtcctacac atttgactgg cttagcaagg     300
atgtggttaa aaagcttcaa ggaagagatc tgaggcctgt caaatgcctg tcagatgcaa     360
ccaaattctg cctgttttaac atacttcagg aaacttcttc ccggttggct ttgaaaactg     420
aatatattcc agttggattt acccttctgc atctcttgga gcccaatatt cctgttccag     480
agcctgaagt gtcagctccc atccccctta aacacaccat atcccagaaa ctgaaggctg     540
acctggatgt cgaaaccatt gcaggaggag aagcagggtt tgttaagtcc tgtggatatg     600
acatcgaggt tcagagtaag agcatcccaa atccaaaact ggaaagtctt caaaacagaa     660
aactgttgga tcagttgccc acatttatga agacttgctg gaaggatgga agaacctgt      720 atgtggtgac agaggcctat gaagtgacca aggatactgt gctggaaggc acaagcaata     780
gcaaatttgc aatcaaaggg atcatcaacc agcttgtcaa ggttggaggc agtggacagt     840
ggcaaacaga gaaacagat tcaataccta tccaaaaggg ttcagtgttg gcctacaaga      900
agcagcaatt ggtcattgag gataacactt tgttattct cacttctgct aacactaaga      960
agaagatgac ctttccaatg agatttgtgg gaatgtctgg acatctaaga tatcaggatc    1020
tagtcattga gacaggctcg tggataaatg acatcgatcc aattggaaca attaaggagc    1080
ccacccatct agatttcatg tgcctacaaa atgaagtttc tgaacaaaca cggctactgg    1140
ctgaactctc aaaggatgtt caagaagttg tgttctccag tttcctgcac atgctctgtg    1200
acagggatgt tctgtatgac ctgatgaaaa tgctggagtt gaatcagttg gggcatatgg    1260
atggcccagg tggcaaaatc ctggatgagc ttcgaaagga ctcgagcctt tcatggatta    1320
acctaaagga cctcattctt tatctccttc aagccctgat ggtgctgagt gatacccaac    1380
tctgtctgct ggccctgtct gtggagatgc ggctcctccc gcaccaagtg gagctggtaa    1440
agagcatctt acagccaaac ttcaagtatc cctggaacat tcccttcaca ctccagcctc    1500
agcttcttgc cccactccag ggtgagggct tggccattac ttatgaattg ctggaggagt    1560
gtggtctgaa gatggagctg aataatccca ggtcaacttg ggatttggaa gccaagatgc    1620
ccctgtctgc tctctatgga agcctgtcat ttttacagca actttcagaa gcctaactct    1680
tcttccaagc ccagcctcag tcctggatac atttgagata ttgcaccata gcatacacaa    1740
gagttgtgat tgagtgcat gctttaggct ggtgggaata aagatgctac ggctccttt       1800 tttttttttt aaagtattat tgattcacaa ttatacaaat aatatacttg gatcagattc    1860
tacctacccc cattgcttct tttaatccac cccttccaag ttccttttc ctcaacaact      1920 tctcattcat catttgtctg tttgtttgat gctatgctac gtttaattag ggttgtttgc    1980
ataagtgtgt gattattcat ttgagcaaga gtagccttcc agaggctacc tcctgccagc    2040
agcattgaga gcctataggt gttttaggga gggtgagttt cttttccatt catgtggaat    2100
gttggttggc ttgggtttgc ttggtcttgt gcgggtaccc attgccactt tgagtttatg    2160
```

| | | | | |
|---|---|---|---|---|
| ggtttagcta | ttccatatcc | ttaccacgtc | taggaaacag | gatgttgtta tctatcaaaa | 2220 |
| ctagtcaaat | ggtatgctaa | ataaagattt | agatgttttc | tctatataaa aggatatata | 2280 |
| ttttactttt | actcaattgt | gtgcattttg | agttgttctg | ggtgaaaggt actggtgcca | 2340 |
| gtaactttga | aatgcatcag | caataaattg | ggatgtttta | tg | 2382 |

<210> SEQ ID NO 37
<211> LENGTH: 2312
<212> TYPE: DNA
<213> ORGANISM: Mus musculus
<220> FEATURE:
<221> NAME/KEY: misc_feature
<223> OTHER INFORMATION: Mus musculus gasdermin C2 (Gsdmc2), transcript
      variant 1, mRNA, NM_001168274.1

<400> SEQUENCE: 37

| | | | | |
|---|---|---|---|---|
| gcttgtttgc | ctgcttgcac | ttccttgctg | gcacttcggt | tgttacctac ttcttctgga | 60 |
| ttctagttta | tacagaagac | cagctgaaac | acctagaggt | atgcatacat gagggcctga | 120 |
| ggaggctgga | agatagcatt | caattccttg | gagctgagt | tacaggttct tccatgagtc | 180 |
| cctgactgac | ttccctcaaa | gacagttatg | acctgggagt | gtaagatgaa ctaaatcctt | 240 |
| ccctcgacat | gcttgtagcc | atggtggtta | tcccagcaac | agaaagcaaa ctaggaaacg | 300 |
| acattcacct | tcaatatctg | aaagccagca | acgcaacatg | ggctacagtt ttgaccgggc | 360 |
| tagcaaggat | gtggttaaaa | agcttcaagg | aagagatctg | aggcctgtgg aatgcttgtc | 420 |
| cgatgcaacc | aaattccgcc | tatttcacat | actccaggag | actcctcgat caggttggga | 480 |
| aactgaagat | attccagttg | gatttaccct | tctggatctc | ttggagccca actttcctgt | 540 |
| tccagagcct | gaagtgtctg | ctcccaagcc | cttcatacat | gtccaatcaa cggacctgga | 600 |
| ggctaacttg | aatgtcgcag | acattgcaag | aggaggtgta | gggtatgttg ggtacggtgg | 660 |
| atacaacatc | gaggttcaga | gtacaagcat | cccaaatcca | aaactggaaa ttcttcaaaa | 720 |
| caggaaactg | ttggataatt | tgcccacatt | tatgaagttt | tgccggatgg aaaggaagaa | 780 |
| cctgtatgtg | gtgacagagg | cctatgaagt | gtccaaggat | actatgctga caggcttaag | 840 |
| cagtgtcaat | ctttcagtta | aagggttctt | caaacagctt | ttcaaggttc gaggcaaggc | 900 |
| gggaaggtcg | gaaaagtatt | caataccgat | cccaaagggt | tcggtgttgg cctataagaa | 960 |
| gcagcaactt | gtcattgaga | ataacacttg | tgtcattctc | ccttctgcta ctaagaagaa | 1020 |
| gatgactttt | ccaggcacac | ctaagtacgc | ttctgcttcc | gaacccactg agatttatag | 1080 |
| aacagaattg | caaggcttgt | ggataaatga | catcgttcca | attggaagaa tacaggagcc | 1140 |
| cgcccatcta | gatttcatgt | gcctacaaaa | tgaagtttac | aaacaaacag agcaactggc | 1200 |
| tgaactctca | aagggtgttc | aagaagttgt | gttgtccagt | atcctgtcca tgctctatga | 1260 |
| aggtgacagg | aaagttctgt | atgacctgat | gaacatgctg | gagttgaatc agttggggca | 1320 |
| tatggatggc | ccaggtggca | aaatcctgga | tgagctgcga | aaggattcta gcaacccatg | 1380 |
| tgttgaccta | aaggacctca | ttctttatct | ccttcaagct | ctgatggtgc tgagcgatag | 1440 |
| ccaactcaat | ctgctggccc | agtctgtgga | gatggggatc | ctcccgcacc aagtagagct | 1500 |
| ggtaaagagc | atcttacagc | caaacttcaa | gtatccctgg | aacattccct tcacactcca | 1560 |
| gcctcagctt | cttgccccac | tccagggtga | gggcttggcc | attacttatg aattgctgga | 1620 |
| ggagtgtggt | ctgaagatgg | agctgaataa | tcccaggtca | acttgggatt tggaagccaa | 1680 |
| aatgccctg | tctgctctct | atggaagcct | gtcatttta | cagcaacttc ggaaggctaa | 1740 |
| ctcttcctcc | aagcccagcc | tacgtcctgg | atacatttga | tatattgcac catgcatgtt | 1800 |

```
ttaggccagt gggaataaag atgctatggc tcctttttt ttcttttta cgtattattg    1860 attcacaatt atacaaataa tatacttgga tcagattcta cctaccctcc attgtttctt   1920
ttaatccacc ccttccaagt tccttttcc tcaacaactt ctcattcatc atttgtctgt    1980
ttgtttgatg ctatgctacg tttaattagg gttgtttgca taagtgtgtg attattcatt   2040
tgagcaaggg tagccttcca gaggctacct cctgccagca gcattgagag cctgtaggtg   2100
ttttagggag ggtgaggttc tcctccattc ttgtggaatg ttggtgggct cgggcttgct   2160
tggtcttgtg cgggtaccca ttgccacttt gagtttatgg gtttagctat tccatatcct   2220
taccacgtct aggaaacagg atgttgttat ctgtcaaaaa tacttaaatg gtatgttaaa   2280
taaagattta cacattttct ctatataaaa gg                                 2312
```

<210> SEQ ID NO 38
<211> LENGTH: 2142
<212> TYPE: DNA
<213> ORGANISM: Mus musculus
<220> FEATURE:
<221> NAME/KEY: misc_feature
<223> OTHER INFORMATION: Mus musculus gasdermin C3 (Gsdmc3), mRNA, NM_183194.3

<400> SEQUENCE: 38

```
gcttgtttgc ctgcttgcac ttccttgctg gcacttcggt tgttacctac ttcttctgga     60
ttctagttta tacagaagac cagctgaaac cctagagat atttagattg tttctacatt    120
ttggcctttg tgaatagtct gccatgaacc aacatgggct acagttttga ccgggctagc    180
aaggatgtgg ttaaaaagct tcaaggaaga gatctgaggc tgtggaatg cttgtcagat    240 gcaaccaaat tccgcctatt tcacatactc caggagactc ctcgatcagg ttgggaaact    300
gaagatattc cagttggatt tacccttctg gatctcttgg agcccaactt tcctgttcca    360
gagcctgaag tgtctgctcc caagcccttc atacatgtcc aatcaacgga cctggaggct    420
aacttgaatg tcgcagacat tgcaagagga ggtgtagggt atgttgggta cggtggatac    480
aacatcgagg ttcagagtac aagcatccca atccaaaac tggaaattct tcaaaacagg    540
aaactgttgg ataagttgcc cacatttatg aagttttgcc ggatggaaag gaagaacctg    600
tatgtggtga cagaggctta tgaagtgtcc aaggatacta tgctgacagg cttaagcagt    660
gtcaatcttt tagttaaagg gttcttcaaa cagcttttca aggttcgagg caaggcggga    720
aggtcggaaa agtattcaat acctatccca aagggttcgg tgttggccta agaagcag     780 caacttgtca ttgagaataa cacttgtgtc attctcccctt ctgctactaa gaagaagatg    840
acctttccag gcacacctaa gtacgcttct gcttccgaac ccactgagat ttatagaaca    900
gaattacaag gtttgtggat aaatgacatc gaaccaattg gaagaatcca ggagcccgcc    960
catctagatt tcaagtgcct acaatatgaa gtttctgaac aaacacgact actgcctgaa   1020
ctctcaaagg atgttcaaga gttgtgttg tccagtttcc tgtccatgct ctatgaaggt   1080
gacaggaacg ttctgcatga cctgatgaaa atgctggagt tgagtcagtt ggggcatatg   1140
gatggcccag gtggcaaaat cctggatgag cttcgaaagg attctagcaa cccatgtgtt   1200
gacctaaagg acctcattct ttatctcctt caagcgctga tggtgctcag tgatagccaa   1260
ctcaatctgc tggcccggtc tgtggagatg cggctcctcc cgcaccaagt agagctggta   1320
acgagcatcc tacagccaaa cttcaagtat ccctggaaca ttcccttcac agtccagcct   1380
cagcttcttg ccccactcca gggtgagggc ttggccatta cttatgaatt gctgaggag    1440 tgtggtctga agatggagct gaataatccc aggtcaactt gggatttgga agccaagatg   1500
```

-continued

```
ccccttgtctg ctctctatgg aagcctgtca tttttacagc aacttcagaa ggctaactct    1560
tccttcaagc ccagcctccg acctggatac atttgatata ttgcaccatg catacacaa    1620 gagtcgtgat ttgagtgcat gttttaggcc agtgggaata aagatgctat ggctcctttt    1680
tttaaaaaag tattattgat tcacaattat acaaataata tacttggatc agattgtacc    1740 taccccatt gtttctttta atccaccact tccaagtccc ccttttcctc aacaacttct    1800
cattcaacat ttgtctgttt gtttgatgct atgctacgtt taattagggt tgtttgcata    1860
agtgtgtgat tattcatttg agcaagggta gccttccaga ggctacctcc tgccagcagc    1920
attgagagtc tgtaggtgtt ttagggaggg tgaggttctc ctccattctt gtggaatgtt    1980
ggtgggctcg ggtttgcttg gtcttgtgag ggtacccatt gccactttga gtttatgggt    2040
ttagctattc catatcctta ccacgtctag gaaacaggat gttgttatct gtcaaaaata    2100
cttaaatggt atgttaaata aagatttaca cattttctct at                      2142
```

<210> SEQ ID NO 39
<211> LENGTH: 484
<212> TYPE: PRT
<213> ORGANISM: Homo sapiens
<220> FEATURE:
<221> NAME/KEY: SITE
<222> LOCATION: (1)..(484)
<223> OTHER INFORMATION: gasdermin-D [Homo sapiens], NP_001159709.1

<400> SEQUENCE: 39

```
Met Gly Ser Ala Phe Glu Arg Val Val Arg Arg Val Gln Glu Leu
1               5                  10                  15

Asp His Gly Gly Glu Phe Ile Pro Val Thr Ser Leu Gln Ser Ser Thr
            20                  25                  30

Gly Phe Gln Pro Tyr Cys Leu Val Val Arg Lys Pro Ser Ser Ser Trp
        35                  40                  45

Phe Trp Lys Pro Arg Tyr Lys Cys Val Asn Leu Ser Ile Lys Asp Ile
    50                  55                  60

Leu Glu Pro Asp Ala Ala Glu Pro Asp Val Gln Arg Gly Arg Ser Phe
65                  70                  75                  80

His Phe Tyr Asp Ala Met Asp Gly Gln Ile Gln Gly Ser Val Glu Leu
                85                  90                  95

Ala Ala Pro Gly Gln Ala Lys Ile Ala Gly Gly Ala Ala Val Ser Asp
            100                 105                 110

Ser Ser Ser Thr Ser Met Asn Val Tyr Ser Leu Ser Val Asp Pro Asn
        115                 120                 125

Thr Trp Gln Thr Leu Leu His Glu Arg His Leu Arg Gln Pro Glu His
    130                 135                 140

Lys Val Leu Gln Gln Leu Arg Ser Arg Gly Asp Asn Val Tyr Val Val
145                 150                 155                 160

Thr Glu Val Leu Gln Thr Gln Lys Glu Val Glu Val Thr Arg Thr His
                165                 170                 175

Lys Arg Glu Gly Ser Gly Arg Phe Ser Leu Pro Gly Ala Thr Cys Leu
            180                 185                 190

Gln Gly Glu Gly Gln Gly His Leu Ser Gln Lys Lys Thr Val Thr Ile
        195                 200                 205

Pro Ser Gly Ser Thr Leu Ala Phe Arg Val Ala Gln Leu Val Ile Asp
    210                 215                 220

Ser Asp Leu Asp Val Leu Leu Phe Pro Asp Lys Lys Gln Arg Thr Phe
225                 230                 235                 240
```

-continued

Gln Pro Pro Ala Thr Gly His Lys Arg Ser Thr Ser Glu Gly Ala Trp
                245                 250                 255

Pro Gln Leu Pro Ser Gly Leu Ser Met Met Arg Cys Leu His Asn Phe
        260                 265                 270

Leu Thr Asp Gly Val Pro Ala Glu Gly Ala Phe Thr Glu Asp Phe Gln
            275                 280                 285

Gly Leu Arg Ala Glu Val Glu Thr Ile Ser Lys Glu Leu Glu Leu Leu
        290                 295                 300

Asp Arg Glu Leu Cys Gln Leu Leu Glu Leu Gly Leu Gly Val Leu
305                 310                 315                 320

Arg Asp Gln Leu Ala Leu Arg Ala Leu Glu Glu Ala Leu Glu Gln Gly
                325                 330                 335

Gln Ser Leu Gly Pro Val Glu Pro Leu Asp Gly Pro Ala Gly Ala Val
            340                 345                 350

Leu Glu Cys Leu Val Leu Ser Ser Gly Met Leu Val Pro Glu Leu Ala
        355                 360                 365

Ile Pro Val Val Tyr Leu Leu Gly Ala Leu Thr Met Leu Ser Glu Thr
    370                 375                 380

Gln His Lys Leu Leu Ala Glu Ala Leu Glu Ser Gln Thr Leu Leu Gly
385                 390                 395                 400

Pro Leu Glu Leu Val Gly Ser Leu Leu Glu Gln Ser Ala Pro Trp Gln
                405                 410                 415

Glu Arg Ser Thr Met Ser Leu Pro Pro Gly Leu Leu Gly Asn Ser Trp
            420                 425                 430

Gly Glu Gly Ala Pro Ala Trp Val Leu Leu Asp Glu Cys Gly Leu Glu
        435                 440                 445

Leu Gly Glu Asp Thr Pro His Val Cys Trp Glu Pro Gln Ala Gln Gly
    450                 455                 460

Arg Met Cys Ala Leu Tyr Ala Ser Leu Ala Leu Leu Ser Gly Leu Ser
465                 470                 475                 480

Gln Glu Pro His

<210> SEQ ID NO 40
<211> LENGTH: 487
<212> TYPE: PRT
<213> ORGANISM: Mus musculus
<220> FEATURE:
<221> NAME/KEY: SITE
<222> LOCATION: (1)..(487)
<223> OTHER INFORMATION: gasdermin-D [Mus musculus], NP_081236.1

<400> SEQUENCE: 40

Met Pro Ser Ala Phe Glu Lys Val Val Lys Asn Val Ile Lys Glu Val
1               5                   10                  15

Ser Gly Ser Arg Gly Asp Leu Ile Pro Val Asp Ser Leu Arg Asn Ser
                20                  25                  30

Thr Ser Phe Arg Pro Tyr Cys Leu Leu Asn Arg Lys Phe Ser Ser Ser
            35                  40                  45

Arg Phe Trp Lys Pro Arg Tyr Ser Cys Val Asn Leu Ser Ile Lys Asp
    50                  55                  60

Ile Leu Glu Pro Ser Ala Pro Glu Pro Glu Pro Glu Cys Phe Gly Ser
65                  70                  75                  80

Phe Lys Val Ser Asp Val Val Asp Gly Asn Ile Gln Gly Arg Val Met
                85                  90                  95

Leu Ser Gly Met Gly Glu Gly Lys Ile Ser Gly Gly Ala Ala Val Ser
            100                 105                 110

```
Asp Ser Ser Ser Ala Ser Met Asn Val Cys Ile Leu Arg Val Thr Gln
            115                 120                 125
Lys Thr Trp Glu Thr Met Gln His Glu Arg His Leu Gln Gln Pro Glu
130                 135                 140
Asn Lys Ile Leu Gln Gln Leu Arg Ser Arg Gly Asp Asp Leu Phe Val
145                 150                 155                 160
Val Thr Glu Val Leu Gln Thr Lys Glu Glu Val Gln Ile Thr Glu Val
            165                 170                 175
His Ser Gln Glu Gly Ser Gly Gln Phe Thr Leu Pro Gly Ala Leu Cys
            180                 185                 190
Leu Lys Gly Glu Gly Lys Gly His Gln Ser Arg Lys Lys Met Val Thr
            195                 200                 205
Ile Pro Ala Gly Ser Ile Leu Ala Phe Arg Val Ala Gln Leu Leu Ile
            210                 215                 220
Gly Ser Lys Trp Asp Ile Leu Leu Val Ser Asp Glu Lys Gln Arg Thr
225                 230                 235                 240
Phe Glu Pro Ser Ser Gly Asp Arg Lys Ala Val Gly Gln Arg His His
            245                 250                 255
Gly Leu Asn Val Leu Ala Ala Leu Cys Ser Ile Gly Lys Gln Leu Ser
            260                 265                 270
Leu Leu Ser Asp Gly Ile Asp Glu Glu Leu Ile Glu Ala Ala Asp
            275                 280                 285
Phe Gln Gly Leu Tyr Ala Glu Val Lys Ala Cys Ser Ser Glu Leu Glu
            290                 295                 300
Ser Leu Glu Met Glu Leu Arg Gln Gln Ile Leu Val Asn Ile Gly Lys
305                 310                 315                 320
Ile Leu Gln Asp Gln Pro Ser Met Glu Ala Leu Glu Ala Ser Leu Gly
            325                 330                 335
Gln Gly Leu Cys Ser Gly Gly Val Glu Pro Leu Asp Gly Pro Ala
            340                 345                 350
Gly Cys Ile Leu Glu Cys Leu Val Leu Asp Ser Gly Glu Leu Val Pro
            355                 360                 365
Glu Leu Ala Ala Pro Ile Phe Tyr Leu Gly Ala Leu Ala Val Leu
            370                 375                 380
Ser Glu Thr Gln Gln Gln Leu Leu Ala Lys Ala Leu Glu Thr Thr Val
385                 390                 395                 400
Leu Ser Lys Gln Leu Glu Leu Val Lys His Val Leu Glu Gln Ser Thr
            405                 410                 415
Pro Trp Gln Glu Gln Ser Ser Val Ser Leu Pro Thr Val Leu Leu Gly
            420                 425                 430
Asp Cys Trp Asp Glu Lys Asn Pro Thr Trp Val Leu Leu Glu Glu Cys
            435                 440                 445
Gly Leu Arg Leu Gln Val Glu Ser Pro Gln Val His Trp Glu Pro Thr
            450                 455                 460
Ser Leu Ile Pro Thr Ser Ala Leu Tyr Ala Ser Leu Phe Leu Leu Ser
465                 470                 475                 480
Ser Leu Gly Gln Lys Pro Cys
            485

<210> SEQ ID NO 41
<211> LENGTH: 2326
<212> TYPE: DNA
<213> ORGANISM: Homo sapiens
```

```
<220> FEATURE:
<221> NAME/KEY: misc_feature
<223> OTHER INFORMATION: Homo sapiens gasdermin D (GSDMD), transcript
      variant 2, mRNA, NM_001166237.1

<400> SEQUENCE: 41
cttccttgga gccccgccgc ccgccgctca ctctgcacac gcagcagaag ggacgtggtg      60
ttccccaggc tctggccccc caggacctgc gcggatctgg cccagggcgc ctcgccgact     120
tccgtaaact gggcggaggg atgaaccccg acccagggga cggaggcgct cgccctctcg     180
ctgcagggtt ctgccctcaa cacttctggc cccgcctgtg aatggggggcc ggagcgatgg    240 ggcggggccg gcctccctcc ctcctcccag gctgacctct gccctccttc gagcacttcc     300
cgttcggggt gatgattgaa gaactgagtg tggacagagc acctgtcctc gccagcgccc     360
agctggaagc tgagttattt gtggctgcag cattccaacg cacacaccac cagaaatccc     420
cttcagcata ctggcctcag acctaccagg gcagagacct tgtcttgttt gctgctagaa     480
cccaggatcg ctggaaaatc acctagcagc agccaggtgc ggtgactcac gcctgtaatc     540
ccagcacttt ggaaggccaa ggcgggtgga tagcaaggtc aagagatcga gaccagcctg     600
gccaacatgc tctgggcacc tccagctcct gctcgccgga cggctcccag ggagagcaga     660
cgcgccagac gcgccaccct cggggcgccg acggtcacgg agcatggggt cggcctttga     720
gcgggtagtc cggagagtgg tccaggagct ggaccatggt ggggagttca tccctgtgac     780
cagcctgcag agctccactg gcttccagcc ctactgcctg gtggttagga agccctcaag     840
ctcatggttc tggaaacccc gttataagtg tgtcaacctg tctatcaagg acatcctgga     900
gccggatgcc gcggaaccag acgtgcagcg tggcaggagc ttccacttct acgatgccat     960
ggatgggcag atacagggca gcgtggagct ggcagcccca ggacaggcaa agatcgcagg    1020
cggggccgcg gtgtctgaca gctccagcac ctcaatgaat gtgtactcgc tgagtgtgga    1080
ccctaacacc tggcagactc tgctccatga gaggcacctg cggcagccag aacacaaagt    1140
cctgcagcag ctgcgcagcc gcggggacaa cgtgtacgtg gtgactgagg tgctgcagac    1200
acagaaggag gtggaagtca cgcgcaccca aagcgggag ggctcgggcc ggttttccct     1260
gcccggagcc acgtgcttgc agggtgaggg ccagggccat ctgagccaga agaagacggt    1320
caccatcccc tcaggcagca ccctcgcatt ccgggtggcc cagctggtta ttgactctga    1380
cttggacgtc cttctcttcc cggataagaa gcagaggacc ttccagccac ccgcgacagg    1440
ccacaagcgt tccacgagcg aaggcgcctg gccacagctg ccctctggcc tctccatgat    1500
gaggtgcctc cacaacttcc tgacagatgg ggtccctgcg ggggggcgt tcactgaaga     1560 cttccagggc ctacgggcag aggtggagac catctccaag gaactggagc ttttggacag    1620
agagctgtgc cagctgctgc tggagggcct ggaggggtg ctgcgggacc agctggccct     1680
gcgagccttg gaggaggcgc tggagcaggg ccagagcctt gggccggtgg agccctgga     1740 cggtccagca ggtgctgtcc tggagtgcct ggtgttgtcc tccggaatgc tggtgccgga    1800
actcgctatc cctgttgtct acctgctggg ggcactgacc atgctgagtg aaacgcagca    1860
caagctgctg gcgcaggcgc tggagtcgca gaccctgttg gggccgctcg agctggtggg    1920
cagcctcttg gagcagagtg cccgtggca ggagcgcagc accatgtccc tgccccccgg     1980
gctcctgggg aacagctggg gcgaaggagc accggcctgg gtcttgctgg acgagtgtgg    2040
cctagagctg ggggaggaca ctccccacgt gtgctgggag ccgcaggccc agggccgcat    2100
gtgtgcactc tacgcctccc tggcactgct atcaggactg agccaggagc cccactagcc    2160
```

| | |
|---|---:|
| tgtgcccggg catggcctgg cagctctcca gcagggcaga gtgtttgccc accagctgct | 2220 |
| agccctagga aggccaggag cccagtagcc atgtggccag tctaccatgg ggcccaggag | 2280 |
| ttggggaaac acaataaagg tggcatacga aggaaaaaaa aaaaaa | 2326 |

<210> SEQ ID NO 42
<211> LENGTH: 1776
<212> TYPE: DNA
<213> ORGANISM: Mus musculus
<220> FEATURE:
<221> NAME/KEY: misc_feature
<223> OTHER INFORMATION: Mus musculus gasdermin D (Gsdmd), mRNA, NM_026960.4

<400> SEQUENCE: 42

| | |
|---|---:|
| gtgtcctgcc gcctgagttc cgctcttggt cgtggctccc gttgctcccg ggttgagcag | 60 |
| acaatagacc cctccccggc atcccagcag gtcctcgctt cgcttggtgg acccagatac | 120 |
| ctcggcaggg gtgaaaaatc gaggaccatg ccatcggcct ttgagaaagt ggtcaagaat | 180 |
| gtgatcaagg aggtaagcgg cagcagaggc gatctcattc cggtggacag cctgcggaac | 240 |
| tccaccagct tcaggcccta ctgccttctg aacaggaaat tttcaagctc aaggttctgg | 300 |
| aaaccccgtt attcatgtgt caacctgtca atcaaggaca tcctggagcc cagtgctcca | 360 |
| gaaccagaac cggagtgttt tggctccttc aaagtctctg atgtcgtcga tgggaacatt | 420 |
| cagggcagag tgatgttgtc aggcatggga aagggaaaa tttctggtgg ggctgcagtg | 480 |
| tctgacagtt ccagtgcctc catgaatgtg tgtatactgc gtgtgactca aagacctgg | 540 |
| gagaccatgc agcatgaaag gcaccttcag cagcctgaga acaaaatcct gcaacagctt | 600 |
| cggagtcgtg gggatgacct gtttgtggtg accgaggtgc tgcagacaaa ggaggaagtg | 660 |
| cagatcactg aggtccacag ccaagagggc tcaggccagt ttacgctgcc tggagcttta | 720 |
| tgcttgaagg gtgaaggcaa gggccaccaa agccggaaga gatggtgac cattcctgca | 780 |
| ggcagcatcc tggcattccg agtggcccaa ctgcttattg gctctaaatg ggatatcctt | 840 |
| ctcgtctcag atgagaaaca gaggaccttt gagccctcct caggtgacag aaaagcagtg | 900 |
| ggccagaggc accatggcct caatgtgctt gctgcgcttt gttccatcgg aaagcagctc | 960 |
| agtctcctgt cagatgggat tgatgaggag gaattaattg aggcggcaga cttccagggc | 1020 |
| ctgtatgctg aggtgaaggc ttgctcctca gaactggaga gcttgaaat ggagttgaga | 1080 |
| caacagatac tggtgaacat cggaaagatt ttacaggacc agcccagcat ggaagcctta | 1140 |
| gaggcctcac tagggcaggg cctgtgcagt ggcggccagg tggagcctct ggacggccca | 1200 |
| gctggctgca tccttgagtg tctggtgctt gactctggag aactggtgcc ggaactcgca | 1260 |
| gcccctatct tctacctgct gggagcactg gctgtgctga gtgaaaccca gcagcagctg | 1320 |
| ctagctaagg ctctggagac aacggtgctg tcaaagcagc tggagttggt gaagcacgtc | 1380 |
| ttggaacaga gcaccccgtg gcaggagcag agttctgtgt ccctgcccac cgtgctcctt | 1440 |
| ggggactgct gggatgaaaa gaatcccacc tgggtcttgc tagaagaatg tggcctaagg | 1500 |
| ctgcaggtag aatcccccca ggtgcactgg gaaccaacgt ctctgatccc cacaagtgcg | 1560 |
| ctctatgcct ccctgttcct attgtcaagt ctaggccaga aaccttgtta gcctgtgggc | 1620 |
| ctcccttccc acaacatctc catgtcctac cctccagcca aggtagaatc ttgccaagcc | 1680 |
| tagcctttgg gaagccaaga accatactca gtcacagggt tataatgcac tgagatccag | 1740 |
| aagtttgggaa aactcaataa atgtacaaag gaaagc | 1776 |

```
<210> SEQ ID NO 43
<211> LENGTH: 496
<212> TYPE: PRT
<213> ORGANISM: Homo sapiens
<220> FEATURE:
<221> NAME/KEY: SITE
<222> LOCATION: (1)..(496)
<223> OTHER INFORMATION: Non-syndromic hearing impairment protein 5
      (DFNA5) isoform a [Homo sapiens], NP_004394.1

<400> SEQUENCE: 43

Met Phe Ala Lys Ala Thr Arg Asn Phe Leu Arg Glu Val Asp Ala Asp
1               5                   10                  15

Gly Asp Leu Ile Ala Val Ser Asn Leu Asn Asp Ser Asp Lys Leu Gln
            20                  25                  30

Leu Leu Ser Leu Val Thr Lys Lys Arg Phe Trp Cys Trp Gln Arg
        35                  40                  45

Pro Lys Tyr Gln Phe Leu Ser Leu Thr Leu Gly Asp Val Leu Ile Glu
    50                  55                  60

Asp Gln Phe Pro Ser Pro Val Val Glu Ser Asp Phe Val Lys Tyr
65                  70                  75                  80

Glu Gly Lys Phe Ala Asn His Val Ser Gly Thr Leu Glu Thr Ala Leu
                85                  90                  95

Gly Lys Val Lys Leu Asn Leu Gly Gly Ser Ser Arg Val Glu Ser Gln
            100                 105                 110

Ser Ser Phe Gly Thr Leu Arg Lys Gln Glu Val Asp Leu Gln Gln Leu
        115                 120                 125

Ile Arg Asp Ser Ala Glu Arg Thr Ile Asn Leu Arg Asn Pro Val Leu
130                 135                 140

Gln Gln Val Leu Glu Gly Arg Asn Glu Val Leu Cys Val Leu Thr Gln
145                 150                 155                 160

Lys Ile Thr Thr Met Gln Lys Cys Val Ile Ser Glu His Met Gln Val
                165                 170                 175

Glu Glu Lys Cys Gly Gly Ile Val Gly Ile Gln Thr Lys Thr Val Gln
            180                 185                 190

Val Ser Ala Thr Glu Asp Gly Asn Val Thr Lys Asp Ser Asn Val Val
        195                 200                 205

Leu Glu Ile Pro Ala Ala Thr Thr Ile Ala Tyr Gly Val Ile Glu Leu
210                 215                 220

Tyr Val Lys Leu Asp Gly Gln Phe Glu Phe Cys Leu Leu Arg Gly Lys
225                 230                 235                 240

Gln Gly Gly Phe Glu Asn Lys Lys Arg Ile Asp Ser Val Tyr Leu Asp
                245                 250                 255

Pro Leu Val Phe Arg Glu Phe Ala Phe Ile Asp Met Pro Asp Ala Ala
            260                 265                 270

His Gly Ile Ser Ser Gln Asp Gly Pro Leu Ser Val Leu Lys Gln Ala
        275                 280                 285

Thr Leu Leu Leu Glu Arg Asn Phe His Pro Phe Ala Glu Leu Pro Glu
290                 295                 300

Pro Gln Gln Thr Ala Leu Ser Asp Ile Phe Gln Ala Val Leu Phe Asp
305                 310                 315                 320

Asp Glu Leu Leu Met Val Leu Glu Pro Val Cys Asp Asp Leu Val Ser
                325                 330                 335

Gly Leu Ser Pro Thr Val Ala Val Leu Gly Glu Leu Lys Pro Arg Gln
            340                 345                 350
```

Gln Gln Asp Leu Val Ala Phe Leu Gln Leu Val Gly Cys Ser Leu Gln
            355                 360                 365

Gly Gly Cys Pro Gly Pro Glu Asp Ala Gly Ser Lys Gln Leu Phe Met
    370                 375                 380

Thr Ala Tyr Phe Leu Val Ser Ala Leu Ala Glu Met Pro Asp Ser Ala
385                 390                 395                 400

Ala Ala Leu Leu Gly Thr Cys Cys Lys Leu Gln Ile Ile Pro Thr Leu
            405                 410                 415

Cys His Leu Leu Arg Ala Leu Ser Asp Asp Gly Val Ser Asp Leu Glu
            420                 425                 430

Asp Pro Thr Leu Thr Pro Leu Lys Asp Thr Glu Arg Phe Gly Ile Val
            435                 440                 445

Gln Arg Leu Phe Ala Ser Ala Asp Ile Ser Leu Glu Arg Leu Lys Ser
450                 455                 460

Ser Val Lys Ala Val Ile Leu Lys Asp Ser Lys Val Phe Pro Leu Leu
465                 470                 475                 480

Leu Cys Ile Thr Leu Asn Gly Leu Cys Ala Leu Gly Arg Glu His Ser
            485                 490                 495

<210> SEQ ID NO 44
<211> LENGTH: 512
<212> TYPE: PRT
<213> ORGANISM: Mus musculus
<220> FEATURE:
<221> NAME/KEY: SITE
<222> LOCATION: (1)..(512)
<223> OTHER INFORMATION: Non-syndromic hearing impairment protein 5
      homolog [Mus musculus], NP_061239.1

<400> SEQUENCE: 44

Met Phe Ala Lys Ala Thr Arg Asn Phe Leu Lys Glu Val Asp Ala Gly
1               5                   10                  15

Gly Asp Leu Ile Ser Val Ser His Leu Asn Asp Ser Asp Lys Leu Gln
            20                  25                  30

Leu Leu Ser Leu Val Thr Lys Lys Lys Arg Tyr Trp Cys Trp Gln Arg
        35                  40                  45

Pro Lys Tyr Gln Ile Leu Ser Ala Thr Leu Glu Asp Val Leu Thr Glu
    50                  55                  60

Gly His Cys Leu Ser Pro Val Val Glu Ser Asp Phe Val Lys Tyr
65                  70                  75                  80

Glu Ser Lys Cys Glu Asn His Lys Ser Gly Ala Ile Gly Thr Val Val
                85                  90                  95

Gly Lys Val Lys Leu Asn Val Gly Gly Lys Gly Val Val Glu Ser His
            100                 105                 110

Ser Ser Phe Gly Thr Leu Arg Lys Gln Glu Val Asp Val Gln Gln Leu
        115                 120                 125

Ile Gln Asp Ala Val Lys Arg Thr Val Asn Met Asp Asn Leu Val Leu
    130                 135                 140

Gln Gln Val Leu Glu Ser Arg Asn Glu Val Leu Cys Val Leu Thr Gln
145                 150                 155                 160

Lys Ile Met Thr Thr Gln Lys Cys Val Ile Ser Glu His Val Gln Ser
                165                 170                 175

Glu Glu Thr Cys Gly Gly Met Val Gly Ile Gln Thr Lys Thr Ile Gln
            180                 185                 190

Val Ser Ala Thr Glu Asp Gly Thr Val Thr Thr Asp Thr Asn Val Val
        195                 200                 205

```
Leu Glu Ile Pro Ala Ala Thr Thr Ile Ala Tyr Gly Ile Met Glu Leu
210                 215                 220

Phe Val Lys Gln Asp Gly Gln Phe Glu Phe Cys Leu Leu Gln Gly Lys
225                 230                 235                 240

His Gly Gly Phe Glu His Glu Arg Lys Leu Asp Ser Val Tyr Leu Asp
                245                 250                 255

Pro Leu Ala Tyr Arg Glu Phe Ala Phe Leu Asp Met Leu Asp Gly Gly
                260                 265                 270

Gln Gly Ile Ser Ser Gln Asp Gly Pro Leu Arg Val Val Lys Gln Ala
            275                 280                 285

Thr Leu His Leu Glu Arg Ser Phe His Pro Phe Ala Val Leu Pro Ala
290                 295                 300

Gln Gln Gln Arg Ala Leu Phe Cys Val Leu Gln Lys Ile Leu Phe Asp
305                 310                 315                 320

Glu Glu Leu Leu Arg Ala Leu Glu Gln Val Cys Asp Asp Val Ala Gly
                325                 330                 335

Gly Leu Trp Ser Ser Gln Ala Val Leu Ala Met Glu Glu Leu Thr Asp
                340                 345                 350

Ser Gln Gln Gln Asp Leu Thr Ala Phe Leu Gln Leu Val Gly Tyr Arg
            355                 360                 365

Ile Gln Gly Glu His Pro Gly Pro Gln Asp Glu Val Ser Asn Gln Lys
370                 375                 380

Leu Phe Ala Thr Ala Tyr Phe Leu Val Ser Ala Leu Ala Glu Met Pro
385                 390                 395                 400

Asp Asn Ala Thr Val Phe Leu Gly Thr Cys Cys Lys Leu His Val Ile
                405                 410                 415

Ser Ser Leu Cys Cys Leu Leu His Ala Leu Ser Asp Asp Ser Val Cys
                420                 425                 430

Asp Phe His Asn Pro Thr Leu Ala Pro Leu Arg Asp Thr Glu Arg Phe
            435                 440                 445

Gly Ile Val Gln Arg Leu Phe Ala Ser Ala Asp Ile Ala Leu Glu Arg
450                 455                 460

Met Gln Phe Ser Ala Lys Ala Thr Ile Leu Lys Asp Ser Cys Ile Phe
465                 470                 475                 480

Pro Leu Ile Leu His Ile Thr Leu Ser Gly Leu Ser Thr Leu Ser Lys
                485                 490                 495

Glu His Glu Glu Glu Leu Cys Gln Ser Gly His Ala Thr Gly Gln Asp
            500                 505                 510

<210> SEQ ID NO 45
<211> LENGTH: 2520
<212> TYPE: DNA
<213> ORGANISM: Homo sapiens
<220> FEATURE:
<221> NAME/KEY: misc_feature
<223> OTHER INFORMATION: Homo sapiens deafness, autosomal dominant 5
      (DFNA5), transcript variant 1, mRNA, NM_004403.2

<400> SEQUENCE: 45
aggagcttag agtggagttt acaggaatga atcactgatt agcggcaggc ctaagtgtgg    60
gcactgtcgc accacacacc cagatactac tccaggcacg ggcattaggg gctcccacag   120
gctggacagg ccttggactt tcctggttga accgtgaggc cgcggtgtca gtccacactc   180
cactgtgggt ggcggggttcg gccccgcgag gaggcgccgc tctcaaaccc cacggtcccg   240
cgcagcgaag aggcgaggcg gccgcggaag gcaggcgcag cccactcttc ccgagaggcc   300
```

| | | |
|---|---|---|
| ccgacatctc ccggataatc tggagctttc aaaatgtttg ccaaagcaac caggaatttt | 360 |
| cttagagaag ttgatgctga tggtgacctg attgcagtat caaatctgaa tgactctgat | 420 |
| aagttacagc ttctaagtct ggtgacaaaa aagaagagat tctggtgctg gcagagaccc | 480 |
| aagtaccagt ttttatccct cacccttggc gatgtactca tagaagacca atttccgagt | 540 |
| ccagtggtcg tggagtcgga ctttgtgaaa tacgagggca gtttgcaaa ccacgtgagt | 600 |
| ggaaccctgg agactgcact ggggaaggtc aagctgaacc tgggggggcag cagccgcgta | 660 |
| gagagccagt cttcatttgg aaccctgagg aagcaggagg tggatttgca gcagctcatc | 720 |
| agagactctg ccgagagaac aataaatctg agaaaccctg tgctccagca ggtgctggaa | 780 |
| ggaaggaatg aggtcctgtg cgttttgaca cagaagatca cgacgatgca gaagtgtgtg | 840 |
| atctctgagc acatgcaggt cgaggagaag tgtggtggca tcgtgggcat ccagaccaag | 900 |
| acggtgcagg tgtcagcgac ggaggatggg aatgtcacca aggactccaa cgtggtgctg | 960 |
| gagatcccag ctgccaccac cattgcctac ggtgtcattg agttatacgt gaaactggac | 1020 |
| ggccagttcg agttctgcct tctccgaggg aagcaaggtg gcttcgagaa caagaagaga | 1080 |
| attgactctg tctacctgga ccccctggtc tttcgagagt ttgcattcat agacatgcca | 1140 |
| gatgctgcgc atgggatatc ttcccaggat ggaccattaa gtgttttaaa gcaagcgacc | 1200 |
| ctgctcctgg agaggaattt ccatccattt gcggagctgc ctgagccaca acagacagct | 1260 |
| ttgagtgaca tcttccaggc ggtcctattt gatgatgaac tactcatggt cctggaacca | 1320 |
| gtgtgcgatg acctggtcag cggcctctcg cccacagtgg cggtgctggg ggagctgaag | 1380 |
| ccccggcagc agcaggacct tgtggccttc ctgcagctgg tggggtgcag cttacagggt | 1440 |
| gggtgtccgg gccccgagga tgcaggcagc aagcagctgt ttatgacagc ctacttcttg | 1500 |
| gtcagtgccc tcgcagaaat gccagatagc gcagcagctc tgctgggcac ttgctgcaaa | 1560 |
| ctccagatca ttcccacact gtgccacttg cttcgtgctc tgtctgatga tggagtatct | 1620 |
| gatcttgaag acccaacctt gactcccctg aaagatacag aaaggtttgg gattgtgcag | 1680 |
| cgcttgtttg cctcagctga cattagtctg gagagactga agtcatctgt gaaagctgtc | 1740 |
| attctgaagg actctaaagt cttcccactg cttctttgta taaccctgaa tggactctgt | 1800 |
| gctttaggca gagaacattc atgatgtcat atgtgaacta gaagtacgtg ttactggcca | 1860 |
| aggctatttt tcagaactgt taaaggtcat atgcacgtta aaagttgacc aatgaaatga | 1920 |
| atttacagaa cagtttaaga agtggtgaca ttttgcatga tgaatgacct gacttttagc | 1980 |
| caccaggtac tctttaaaca gttttcctta tcagaggccc tcctgtgctg gtgacccagc | 2040 |
| atctgagtta ggttccagca tgtaaagagc tgggagggcg gagaattctt agcatacatt | 2100 |
| cagacgtttt ttctgcacaa taataagtcc atctgtcact tgcattccac tttttgttac | 2160 |
| atagaaagag tctgaccctt taatccaaaa ggtcttttta cattgtgaat gctgtgggaa | 2220 |
| ggcaatttct ctgcacacaa gaggctacgt tttggaagtg atgtatgtta tttgatgact | 2280 |
| gaaaatgaac tgtaaatgct cctagagtat attcctctgc tgaacaaaat taaacttcaa | 2340 |
| aaaaatctaa cagtaacaca cccctgcttg ggaccctagc tatatgcatt ttatgtgacc | 2400 |
| ttgccatgct tcagtgaaca tactaattct atgtctagca catgttgatt tcctatgtat | 2460 |
| tctgggtatt ctattaaagg aaactttgaa ctatgaaaaa aaaaaaaaaa aaaaaaaaa | 2520 |

<210> SEQ ID NO 46
<211> LENGTH: 2133
<212> TYPE: DNA
<213> ORGANISM: Mus musculus
<220> FEATURE:
<221> NAME/KEY: misc_feature
<223> OTHER INFORMATION: Mus musculus deafness, autosomal dominant 5
(human) (Dfna5), mRNA, NM_018769.3

<400> SEQUENCE: 46

```
agaacggagc gtgcaggacg gagaggcggc gcgcggtttt tcaggtaatc tcaacccgac      60
aaaatgtttg ccaaagcaac tcgaaatttt cttaaagaag ttgatgctgg aggagacctg     120
atttcagtct cacacttgaa cgactctgac aagctgcaac ttctaagtct ggtgaccaaa     180
aagaagagat actggtgctg gcagagaccc aagtaccaga ttttatctgc caccctggaa     240
gatgtactca cagaagggca ctgtctcagt ccagtggttg tggagtcaga cttcgtgaaa     300
tacgagagca agtgtgagaa ccataagagc ggggctattg gacagtcgt ggggaaggtc      360
aagctgaacg ttggtggcaa aggcgtggtg gagagtcact cttcgtttgg aaccctgagg     420
aagcaggagg tggacgtgca gcagctcatc caggatgccg tcaagagaac agttaatatg     480
gacaacctgg tacttcagca ggtgctagag agcaggaacg aggtcctgtg tgtgctgacg     540
cagaagatca tgaccacgca gaagtgcgtg atttctgagc atgtgcagtc ggaggagacg     600
tgtggaggca tggtggggat ccagaccaag actatacagg tgtcagcaac ggaggatggg     660
acggtcacca cggacaccaa tgtagtgctg agatccctg ctgccaccac cattgcctat      720
ggcatcatgg agctgtttgt gaaacaagat ggccagtttg aattctgcct cctccaaggg     780
aaacatggtg gcttcgagca tgagaggaaa ctagactctg tctacttgga ccccctggcc     840
tacagagagt tcgcctttct ggacatgctg gatggggtc aagggatctc ttcgcaggac      900
gggcccctac gagttgtaaa acaagcaacc ctgcacctag agaggagttt ccatcccttt     960
gcggtgttac ctgcccagca gcagagggcg ctgttctgtg tcctgcagaa aatcctgttt    1020
gatgaagaac tccttcgggc cctggagcaa gtgtgtgatg atgtggctgg tggtctctgg    1080
tcctcacagg ctgtattggc aatggaggag ctgaccgaca gtcagcagca ggacctcaca    1140
gccttcttgc agctggtggg atacaggata caaggagagc atcctggccc acaggatgag    1200
gtcagcaacc agaagctctt tgcaacagcc tacttcctgg tcagcgcact agcagaaatg    1260
cctgataatg ccacagtttt cctggggact tgctgcaaac tccatgttat ttcttcgctg    1320
tgctgcttgc tccatgctct gtctgatgac agcgtgtgtg attttcacaa ccccaccttg    1380
gctcctctga gagacacaga gaggtttggc atcgtgcagc gattgtttgc ctctgctgac    1440
attgccctgg agaggatgca gttttctgcg aaagccacca tcctgaagga ctcttgcatc    1500
ttcccgctaa ttcttcacat cactctaagt gggctcagca tctaagcaa agagcatgag     1560
gaagagcttt gtcagtcagg acatgctaca ggtcaagact agctacttttt caggattgag    1620
aaactacttt gggattttgg gcccaagcag gttcagtctg ccagtgaatt ccagtgcacc    1680
tcagaggtgg tgtctttgtg aatggctgcg agcgttgtca atgggttatt ctcatcagag    1740
gcccactgca ctgacactgg agtcactgag gaagaaccaa cctgtcagtc actttatctt    1800
ccactcttat ctgatgtaca aaagcagaag agtctcagat tttacttcag agtccatcat    1860
aagctgggaa tgcaacaggg aagcaatttc cttcccatcc ttcagacatg ctgtacacta    1920
ctgggtgact gggaaaccag aaatgctact tgagtacata aaacaattat agtaagaaca    1980
tctaatttga cccacctcaa catgagaact taaatatatt cctcttatt gactttgtta     2040
tgctttaatg aacatattat gtctggggca attccagtgc gttctgggaa tttgtcacat    2100
gttgcaattt ctattaaaag caattctgaa cta                                 2133
```

<210> SEQ ID NO 47
<211> LENGTH: 1172
<212> TYPE: DNA
<213> ORGANISM: Artificial Sequence
<220> FEATURE:
<223> OTHER INFORMATION: AAV 2/8 vector part 1

<400> SEQUENCE: 47

| | | | | | |
|---|---|---|---|---|---|
| cttaattagg | ctgcgcgctc | gctcgctcac | tgaggccgcc | cgggcaaagc | ccgggcgtcg | 60 |
| ggcgaccttt | ggtcgcccgg | cctcagtgag | cgagcgagcg | cgcagagagg | gagtggccaa | 120 |
| ctccatcact | aggggttcct | tgtagttaat | gattaacccg | ccatgctact | tatctaccag | 180 |
| ggtaatgggg | atcctctaga | actatagcta | gtcgacattg | attattgact | agttattaat | 240 |
| agtaatcaat | tacggggtca | ttagttcata | gcccatatat | ggagttccgc | gttacataac | 300 |
| ttacggtaaa | tggcccgcct | ggctgaccgc | ccaacgaccc | ccgcccattg | acgtcaataa | 360 |
| tgacgtatgt | tcccatagta | acgccaatag | ggactttcca | ttgacgtcaa | tgggtggact | 420 |
| atttacggta | aactgcccac | ttggcagtac | atcaagtgta | tcatatgcca | agtacgcccc | 480 |
| ctattgacgt | caatgacggt | aaatggcccg | cctggcatta | tgcccagtac | atgaccttat | 540 |
| gggactttcc | tacttggcag | tacatctacg | tattagtcat | cgctattacc | atgtcgaggc | 600 |
| cacgttctgc | ttcactctcc | ccatctcccc | ccctcccca | ccccaatttt | tgtatttatt | 660 |
| tattttttaa | ttattttgtg | cagcgatggg | ggcgggggg | ggggcgcgc | gccaggcggg | 720 |
| gcggggcggg | gcgaggggcg | gggcggggcg | aggcggagag | gtgcggcggc | agccaatcag | 780 |
| agcggcgcgc | tccgaaagtt | tccttttatg | gcgaggcggc | ggcggcggcg | gccctataaa | 840 |
| aagcgaagcg | cgcggcgggc | gggagcaagc | tttattgcgg | tagtttatca | cagttaaatt | 900 |
| gctaacgcag | tcagtgcttc | tgacacaaca | gtctcgaact | taagctgcag | aagttggtcg | 960 |
| tgaggcactg | ggcaggtaag | tatcaaggtt | acaagacagg | tttaaggaga | ccaatagaaa | 1020 |
| ctgggcttgt | cgagacagag | aagactcttg | cgtttctgat | aggcacctat | tggtcttact | 1080 |
| gacatccact | ttgcctttct | ctccacaggt | gtccactccc | agttcaatta | cagctcttaa | 1140 |
| ggctagagta | cttaatacga | ctcsactata | gg | | | 1172 |

<210> SEQ ID NO 48
<211> LENGTH: 3231
<212> TYPE: DNA
<213> ORGANISM: Artificial Sequence
<220> FEATURE:
<223> OTHER INFORMATION: AAV 2/8 vector part 2

<400> SEQUENCE: 48

| | | | | | |
|---|---|---|---|---|---|
| taagaattca | cgcgtggtac | ctctagagtc | gacccgggcg | gcctcgagga | cggggtgaac | 60 |
| tacgcctgag | gatccgatct | ttttccctct | gccaaaaatt | atggggacat | catgaagccc | 120 |
| cttgagcatc | tgacttctgg | ctaataaagg | aaatttattt | tcattgcaat | agtgtgttgg | 180 |
| aattttttgt | gtctctcact | cggaagcaat | tcgttgatct | gaatttcgac | cacccataat | 240 |
| acccattacc | ctggtagata | agtagcatgg | cgggttaatc | attaactaca | aggaacccct | 300 |
| agtgatggag | ttggccactc | cctctctgcg | cgctcgctcg | ctcactgagg | ccgggcgacc | 360 |
| aaaggtcgcc | cgacgcccgg | gctttgcccg | ggcggcctca | gtgagcgagc | gagcgcgcag | 420 |
| ccttaattaa | cctaattcac | tggccgtcgt | tttacaacgt | cgtgactggg | aaaaccctgg | 480 |
| cgttacccaa | cttaatcgcc | ttgcagcaca | tccccctttc | gccagctggc | gtaatagcga | 540 |
| agaggcccgc | accgatcgcc | cttcccaaca | gttgcgcagc | ctgaatggcg | aatgggacgc | 600 |

```
gccctgtagc ggcgcattaa gcgcggcggg tgtggtggtt acgcgcagcg tgaccgctac      660
acttgccagc gccctagcgc ccgctccttt cgctttcttc ccttcctttc tcgccacgtt      720
cgccggcttt ccccgtcaag ctctaaatcg ggggctccct ttagggttcc gatttagtgc      780
tttacggcac ctcgacccca aaaaacttga ttagggtgat ggttcacgta gtgggccatc      840
gccctgatag acggtttttc gcccttttgac gttggagtcc acgttcttta atagtggact      900
cttgttccaa actggaacaa cactcaaccc tatctcggtc tattcttttg atttataagg      960
gattttgccg atttcggcct attggttaaa aaatgagctg atttaacaaa aatttaacgc     1020
gaattttaac aaaatattaa cgcttacaat ttaggtggca cttttcgggg aaatgtgcgc     1080 ggaacccta tttgtttatt tttctaaata cattcaaata tgtatccgct catgagacaa      1140
taaccctgat aaatgcttca ataatattga aaaggaaga gtatgagtat tcaacatttc      1200
cgtgtcgccc ttattccctt ttttgcggca ttttgccttc ctgttttgc tcacccagaa      1260 acgctggtga agtaaaaga tgctgaagat cagttgggtg cacgagtggg ttacatcgaa      1320
ctggatctca acagcggtaa gatccttgag agttttcgcc ccgaagaacg ttttccaatg     1380
atgagcactt ttaaagttct gctatgtggc gcggtattat cccgtattga cgccgggcaa     1440
gagcaactcg gtcgccgcat acactattct cagaatgact tggttgagta ctcaccagtc     1500
acagaaaagc atcttacgga tggcatgaca gtaagagaat tatgcagtgc tgccataacc     1560
atgagtgata acactgcggc caacttactt ctgacaacga tcggaggacc gaaggagcta     1620 accgctttt tgcacaacat ggggatcat gtaactcgcc ttgatcgttg ggaaccggag      1680
ctgaatgaag ccataccaaa cgacgagcgt gacaccacga tgcctgtagc aatggcaaca     1740
acgttgcgca aactattaac tggcgaacta cttactctag cttcccggca acaattaata     1800
gactggatgg aggcggataa agttgcagga ccacttctgc gctcggccct tccggctggc     1860
tggtttattg ctgataaatc tggagccggt gagcgtgggt ctcgcggtat cattgcagca     1920
ctggggccag atggtaagcc ctcccgtatc gtagttatct acacgacggg gagtcaggca     1980
actatggatg aacgaaatag acagatcgct gagataggtg cctcactgat taagcattgg     2040
taactgtcag accaagttta ctcatatata ctttagattg atttaaaact tcatttttaa     2100
tttaaaagga tctaggtgaa gatccttttt gataatctca tgaccaaaat cccttaacgt     2160
gagttttcgt tccactgagc gtcagacccc gtagaaaaga tcaaaggatc ttcttgagat     2220
cctttttttc tgcgcgtaat ctgctgcttg caaacaaaaa aaccaccgct accagcggtg     2280
gtttgtttgc cggatcaaga gctaccaact cttttccga aggtaactgg cttcagcaga      2340
gcgcagatac caaatactgt tcttctagtg tagccgtagt taggccacca cttcaagaac     2400
tctgtagcac cgcctacata cctcgctctg ctaatcctgt taccagtggc tgctgccagt     2460
ggcgataagt cgtgtcttac cgggttggac tcaagacgat agttaccgga taaggcgcag     2520
cggtcgggct gaacggggg ttcgtgcaca cagcccagct tggagcgaac gacctacacc      2580
gaactgagat acctacagcg tgagctatga gaaagcgcca cgcttcccga agggagaaag     2640
gcggacaggt atccggtaag cggcagggtc ggaacaggag agcgcacgag ggagcttcca     2700
gggggaaacg cctggtatct ttatagtcct gtcgggtttc gccacctctg acttgagcgt     2760
cgatttttgt gatgctcgtc agggggggcgg agcctatgga aaaacgccag caacgcggcc     2820 ttttacggt tcctggcctt ttgctggcct tttgctcaca tgttctttcc tgcgttatcc      2880
cctgattctg tggataaccg tattaccgcc tttgagtgag ctgataccgc tcgccgcagc     2940
cgaacgaccg agcgcagcga gtcagtgagc gaggaagcgg aagagcgccc aatacgcaaa     3000
```

```
ccgcctctcc ccgcgcgttg gccgattcat taatgcagct ggcacgacag gtttcccgac    3060
tggaaagcgg gcagtgagcg caacgcaatt aatgtgagtt agctcactca ttaggcaccc    3120
caggctttac actttatgct tccggctcgt atgttgtgtg gaattgtgag cggataacaa    3180
tttcacacag gaaacagcta tgaccatgat tacgccagat ttaattaagg c             3231
```

<210> SEQ ID NO 49
<211> LENGTH: 461
<212> TYPE: PRT
<213> ORGANISM: Homo sapiens
<220> FEATURE:
<221> NAME/KEY: misc_feature
<223> OTHER INFORMATION: Human SANS protein

<400> SEQUENCE: 49

```
Met Asn Asp Gln Tyr His Arg Ala Ala Arg Asp Gly Tyr Leu Glu Leu
1               5                   10                  15

Leu Lys Glu Ala Thr Arg Lys Glu Leu Asn Ala Pro Asp Glu Asp Gly
                20                  25                  30

Met Thr Pro Thr Leu Trp Ala Ala Tyr His Gly Asn Leu Glu Ser Leu
            35                  40                  45

Arg Leu Ile Val Ser Arg Gly Gly Asp Pro Asp Lys Cys Asp Ile Trp
    50                  55                  60

Gly Asn Thr Pro Leu His Leu Ala Ala Ser Asn Gly His Leu His Cys
65                  70                  75                  80

Leu Ser Phe Leu Val Ser Phe Gly Ala Asn Ile Trp Cys Leu Asp Asn
                85                  90                  95

Asp Tyr His Thr Pro Leu Asp Met Ala Ala Met Lys Gly His Met Glu
                100                 105                 110

Cys Val Arg Tyr Leu Asp Ser Ile Ala Ala Lys Gln Ser Ser Leu Asn
            115                 120                 125

Pro Lys Leu Val Gly Lys Leu Lys Asp Lys Ala Phe Arg Glu Ala Glu
    130                 135                 140

Arg Arg Ile Arg Glu Cys Ala Lys Leu Gln Arg Arg His His Glu Arg
145                 150                 155                 160

Met Glu Arg Arg Tyr Arg Arg Glu Leu Ala Glu Arg Ser Asp Thr Leu
                165                 170                 175

Ser Phe Ser Ser Leu Thr Ser Ser Thr Leu Ser Arg Arg Leu Gln His
            180                 185                 190

Leu Ala Leu Gly Ser His Leu Pro Tyr Ser Gln Ala Thr Leu His Gly
    195                 200                 205

Thr Ala Arg Gly Lys Thr Lys Met Gln Lys Lys Leu Glu Arg Arg Lys
210                 215                 220

Gln Gly Gly Glu Gly Thr Phe Lys Val Ser Glu Asp Gly Arg Lys Ser
225                 230                 235                 240

Ala Arg Ser Leu Ser Gly Leu Gln Leu Gly Ser Asp Val Met Phe Val
                245                 250                 255

Arg Gln Gly Thr Tyr Ala Asn Pro Lys Glu Trp Gly Arg Ala Pro Leu
            260                 265                 270

Arg Asp Met Phe Leu Ser Asp Glu Asp Ser Val Ser Arg Ala Thr Leu
    275                 280                 285

Ala Ala Glu Pro Ala His Ser Glu Val Ser Asp Ser Gly His Asp
    290                 295                 300

Ser Leu Phe Thr Arg Pro Gly Leu Gly Thr Met Val Phe Arg Arg Asn
305                 310                 315                 320
```

-continued

```
Tyr Leu Ser Ser Gly Leu His Gly Leu Gly Arg Glu Asp Gly Gly Leu
            325                 330                 335

Asp Gly Val Gly Ala Pro Arg Gly Arg Leu Gln Ser Ser Pro Ser Leu
            340                 345                 350

Asp Asp Asp Ser Leu Gly Ser Ala Asn Ser Leu Gln Asp Arg Ser Cys
            355                 360                 365

Gly Glu Glu Leu Pro Trp Asp Glu Leu Asp Leu Gly Leu Asp Glu Asp
    370                 375                 380

Leu Glu Pro Glu Thr Ser Pro Leu Glu Thr Phe Leu Ala Ser Leu His
385                 390                 395                 400

Met Glu Asp Phe Ala Ala Leu Leu Arg Gln Glu Lys Ile Asp Leu Glu
            405                 410                 415

Ala Leu Met Leu Cys Ser Asp Leu Asp Leu Arg Ser Ile Ser Val Pro
            420                 425                 430

Leu Gly Pro Arg Lys Lys Ile Leu Gly Ala Val Arg Arg Arg Arg Gln
            435                 440                 445

Ala Met Glu Arg Pro Pro Ala Leu Glu Asp Thr Glu Leu
    450                 455                 460
```